(12) United States Patent
Musicki et al.

(10) Patent No.: US 10,457,637 B2
(45) Date of Patent: Oct. 29, 2019

(54) BENZENESULFONAMIDE DERIVATIVES AS INVERSE AGONISTS OF RETINOID-RELATED ORPHAN RECEPTOR GAMMA (RORγ(T))

(71) Applicant: GALDERMA RESEARCH & DEVELOPMENT, Biot (FR)

(72) Inventors: Branislav Musicki, Nice (FR); Claire Bouix-Peter, Vallauris (FR); Gilles Ouvry, Biot (FR); Etienne Thoreau, Saint Vallier de Thiey (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/537,667

(22) PCT Filed: Dec. 18, 2015

(86) PCT No.: PCT/EP2015/080687
§ 371 (c)(1),
(2) Date: Jun. 19, 2017

(87) PCT Pub. No.: WO2016/097389
PCT Pub. Date: Jun. 23, 2016

(65) Prior Publication Data
US 2018/0170869 A1    Jun. 21, 2018

(30) Foreign Application Priority Data
Dec. 19, 2014 (FR) ...................................... 14 63034
Jul. 10, 2015  (FR) ...................................... 15 56629

(51) Int. Cl.
| | |
|---|---|
| *C07C 311/29* | (2006.01) |
| *C07D 417/06* | (2006.01) |
| *C07D 309/06* | (2006.01) |
| *C07D 309/04* | (2006.01) |
| *C07D 307/93* | (2006.01) |
| *C07D 261/08* | (2006.01) |
| *C07D 211/22* | (2006.01) |
| *C07D 211/46* | (2006.01) |
| *C07D 213/30* | (2006.01) |
| *C07D 279/16* | (2006.01) |
| *C07D 305/06* | (2006.01) |
| *C07D 305/08* | (2006.01) |
| *C07D 335/02* | (2006.01) |
| *C07D 309/12* | (2006.01) |
| *C07D 333/48* | (2006.01) |
| *C07D 207/26* | (2006.01) |
| *C07D 309/08* | (2006.01) |
| *C07D 263/20* | (2006.01) |
| *C07D 263/24* | (2006.01) |
| *C07D 271/08* | (2006.01) |
| *C07D 295/096* | (2006.01) |
| *C07D 211/76* | (2006.01) |
| *C07D 211/96* | (2006.01) |

(Continued)

(52) U.S. Cl.
CPC ............ *C07D 207/26* (2013.01); *A61P 17/10* (2018.01); *C07C 311/29* (2013.01); *C07C 381/10* (2013.01); *C07D 211/22* (2013.01); *C07D 211/46* (2013.01); *C07D 211/76* (2013.01); *C07D 211/96* (2013.01); *C07D 213/30* (2013.01); *C07D 261/08* (2013.01); *C07D 263/20* (2013.01); *C07D 263/24* (2013.01); *C07D 271/08* (2013.01); *C07D 279/16* (2013.01); *C07D 295/096* (2013.01); *C07D 305/06* (2013.01); *C07D 305/08* (2013.01); *C07D 307/93* (2013.01); *C07D 309/04* (2013.01); *C07D 309/06* (2013.01); *C07D 309/08* (2013.01); *C07D 309/12* (2013.01); *C07D 333/48* (2013.01); *C07D 335/02* (2013.01); *C07D 417/06* (2013.01)

(58) Field of Classification Search
CPC .. C07D 417/06; C07D 309/06; C07D 309/04; C07D 307/93; C07D 261/08; C07D 211/22; C07D 211/46; C07D 213/30; C07D 279/16; C07D 305/06; C07D 305/08; C07D 335/02; C07D 309/12; C07D 333/48; C07C 311/29
See application file for complete search history.

(56) References Cited

U.S. PATENT DOCUMENTS

2008/0004288 A1    1/2008   Santhakumar et al.

FOREIGN PATENT DOCUMENTS

| WO | WO-2006/052190 A1 | 5/2006 |
| WO | WO-2011/137089 A1 | 11/2011 |

(Continued)

OTHER PUBLICATIONS

International Search Report dated Mar. 3, 2016 corresponding to International Patent Application No. PCT/EP2015/080687 (with English translation), 4 pages.

(Continued)

*Primary Examiner* — Bruck Kifle
(74) *Attorney, Agent, or Firm* — Foley & Lardner LLP; Sunit Talapatra

(57) ABSTRACT

Benzenesulfonamide derivatives of formula (I), the pharmaceutically acceptable addition salts thereof, the hydrates and/or solvates thereof, and the use of same as inverse agonist of retinoid-related orphan receptor gamma (RORγt) are described. A pharmaceutical composition including such compounds, as well as the use thereof for the topical and/or oral treatment of RORγt receptor-medicated inflammatory diseases, in particular acne, psoriasis and/or atopic dermatitis are also described.

15 Claims, No Drawings

(51) Int. Cl.
*C07C 381/10* (2006.01)
*A61P 17/10* (2006.01)

(56) References Cited

FOREIGN PATENT DOCUMENTS

WO 2013/160418 A1 10/2013
WO 2014/090712 A1 6/2014

OTHER PUBLICATIONS

Chemical Abstracts Registry No. 1328091-23-1, indexed in the Registry file on STN CAS Online on Sep. 4, 2011. (Year : 2011).
Chemical Abstracts Registry No. 914244-66-9, indexed in the Registry file on STN CAS Online on Nov. 29, 2006. (Year : 2006).
Chemical Abstracts Registry No. 924168-33-2, indexed in the Registry file on STN CAS Online on Mar. 1, 2007. (Year : 2007).
Chemical Abstracts Registry No. 950052-33-2, indexed in the Registry file on STN CAS Online on Oct. 10, 2007. (Year : 2007).
Zhang et al. "Discovery of 2-oxo-1, 2-dihydrobenzo [cd] indole-6-sulfonamide derivatives as new RORγ inhibitors using virtual screening, synthesis and biological evaluation", European Journal of Medicinal Chemistry 78 (2014): 431-441.

BENZENESULFONAMIDE DERIVATIVES AS INVERSE AGONISTS OF RETINOID-RELATED ORPHAN RECEPTOR GAMMA (RORγ(T))

CROSS-REFERENCE TO PRIOR APPLICATIONS

This application is a National Stage of PCT/EP2015/080687, filed Dec. 18, 2015, and designating the United States (published Jun. 23, 20165, as WO 2016/097389 A1), which claims priority under 35 U.S.C. § 119 to French Patent Application No. 1463034, Dec. 19, 2014 and French Patent Application No. 1556629, filed Jul. 10, 2015, each hereby expressly incorporated by reference in its entirety and each assigned to the assignee hereof.

The present invention relates to particular sulfonamide derivatives, to the pharmaceutically acceptable addition salts thereof, hydrates thereof and/or solvates thereof, and also to the use thereof as inverse agonist of the retinoid-related orphan receptor gamma RORγt.

The invention also relates to a pharmaceutical composition comprising such compounds and also to the use thereof for the topical and/or oral treatment of inflammatory diseases mediated by the RORγt receptors, especially acne, atopic dermatitis and/or psoriasis.

The nuclear receptors form a large family (known as a superfamily) of transcription factors which correspond to proteins that are capable of being activated by a ligand, of binding to specific DNA sequences and of regulating the transcription of target genes. Thus, these receptors are involved in the regulation of a wide variety of biological functions, including growth, development, reproduction, differentiation and metabolism in a multitude of living organisms.

The first members of this superfamily that were identified and described in the scientific literature are the nuclear receptors of steroid hormones such as the glucocorticoid receptors and the estrogen receptors. This superfamily also comprises among its members many receptors for which no ligand has been identified. These nuclear receptors are known as "orphan receptors".

Retinoid-related orphan receptors thus constitute a subfamily of nuclear receptors. This subfamily is composed of three members each having an intrinsic expression profile: ROR alpha (known as RORα), ROR beta (known as RORβ) and ROR gamma (known as RORγ). Two isoforms of the orphan receptors RORγ have already been identified, namely RORγ1, which is expressed in a variety of tissues such as the thymus, the kidneys, muscles and the liver, and RORγ2 (also known as RORγt), which is expressed exclusively in the cells of the immune system.

In particular, the receptor RORγt plays an important regulating role in cell differentiation of the Th17 lymphocytes which correspond to helper T lymphocytes whose function is to ensure the defense of the body against a large number of extracellular pathogens such as bacteria and fungal infections.

However, it has been demonstrated that the Th17 lymphocytes are also involved in a wide variety of inflammatory disorders, such as acne, and of autoimmune diseases such as psoriasis, rheumatoid arthritis or multiple sclerosis (Peck A, Mellins E D. Precarious balance; Th17 cells in host defense. Infect. Immun. 2010 January; 78(1): 32-8; Suarez-Farinas: J. Allergy Clin. Immunol. 2014; J. Invest. Dermatol. 2008, 128(11), 2625).

Specifically, the Th17 lymphocytes produce numerous cytokines which have distinct profiles, such as interleukin-17A (IL-17A), interleukin-17F (IL-17F), interleukin-26 (IL-26), interleukin-21 (IL-21), interleukin-22 (IL-22) and TNFα, the development, survival and proliferation of which depend on interleukin-23 (IL-23). These cytokines are capable of activating different types of effector cells, such as keratinocytes, thus leading to their hyperproliferation and to the additional production of pro-inflammatory cytokines, chemokines and antimicrobial peptides, which in turn recruit and activate other immune system cells in the inflamed skin, which may lead to amplification of the immune response.

Thus, activation of the Th17 lymphocytes is responsible for the recruitment of cytokines, especially of interleukin-17 (IL17), and of other types of pro-inflammatory cells, which will lead to the mediation of inflammatory disorders such as acne and/or of autoimmune diseases such as psoriasis.

Experiments conducted on mice show that a decrease in the level of expression of the RORγt receptor leads to a decrease in the activity of the Th17 lymphocytes, which consequently makes it possible to greatly reduce the expression of interleukin-17 (IL-17) (Ivanov I I, McKenzie B S, Zhou L, Tadokoro C E, Lepelley A, Lafaille J J, Cua D J, Littman D R: Cell 2006, 126, 1121-1133) and to efficiently treat inflammatory disorders and autoimmune diseases mediated by these cytokines, especially those for which high levels of interleukin-17 (IL-17) are detected.

To this end, patent application WO 2013/160 418 describes sulfonamide compounds as inverse agonists of the RORγt receptor in order to be able to treat inflammatory disorders and autoimmune diseases. Similarly, other compounds have also been developed as inverse agonists of the RORγt receptor, such as those described in patent applications WO 2014/090 712, WO 2014/008 214, WO 2013/169 588, WO 2013/160 419, WO 2013/1 002 027, WO 2013/092 939, WO 2013/092 941, WO 2013/085 890 and WO 2012/100 732.

There is thus a real need to develop novel compounds as inverse agonists of the RORγt receptor in order to be able to efficiently treat diseases mediated by such a receptor, especially inflammatory disorders such as acne, and/or autoimmune diseases such as psoriasis and atopic dermatitis.

This aim is achieved by means of the use of particular sulfonamide derivatives as described below, which make it possible to modulate the activity of the RORγt receptor and consequently to efficiently treat inflammatory disorders and autoimmune diseases of certain pathologies.

One subject of the present invention is thus one or more compounds of formula (I), the pharmaceutically acceptable addition salts thereof, hydrates thereof and/or solvates thereof:

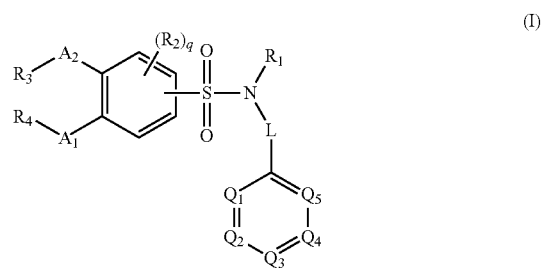

in which formula (I):

q denotes zero or a natural integer ranging from 1 to 3,

L represents a single bond or a methylene group $CH_2$, $R^1$ represents a linear or branched $C_3$-$C_5$ alkyl radical, a $C_3$-$C_5$ cycloalkyl radical, a linear or branched $C_2$-$C_5$ alkenyl radical, a ($C_1$)alkyl($C_3$-$C_5$)cycloalkyl radical, a $C_4$-$C_5$ heterocycloalkyl radical, a ($C_1$)alkyl($C_4$-$C_5$)heterocycloalkyl radical, $R_2$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a cyano group —CN; the alkyl, alkenyl and alkoxy radicals possibly being substituted with one or more halogen atoms, $R^3$ represents a hydrogen atom, a $C_1$-$C_3$ alkyl radical or an amino —$NH_2$ radical, $R^4$ represents a hydrogen atom or a group $(CHR^5)_n$—$(Z)_o$—$(CHR'^5)_p$—$R^6$, n, o and p, which may be identical or different, denote zero or a natural integer ranging from 1 to 3, Z represents a divalent group chosen from —$CH_2$—, —NH— and —O—, $R^5$ and $R'^5$, which may be identical or different, represent a hydrogen atom, a methyl radical —$CH_3$, a hydroxyl radical —OH, a $C_1$ hydroxyalkyl radical, a carboxylic radical —COOH, $R^6$ represents:
  a hydrogen atom or a halogen atom,
  a heterocycloalkyl radical optionally substituted with one or more halogen atoms, one or more linear or branched $C_1$-$C_3$ alkyl groups, one or more —OH groups, one or more carbonyl functions =O, one or more linear or branched $C_1$-$C_4$ hydroxyalkyl groups, a pyrrolidine ring, one or more amino groups, one or more groups —C(=O)$R^7$, one or more groups $S(=O)_2R^7$; $R^7$ representing a linear or branched $C_1$-$C_3$ alkyl radical, a hydroxyl radical —OH, a linear or branched $C_1$-$C_4$ alkoxy radical, or an amino radical $N(R^{7a})(R^{7b})$; with $R^{7a}$ and $R^{7b}$, which may be identical or different, denoting a hydrogen atom, a linear or branched $C_1$-$C_3$ alkyl radical or a cyclopropyl radical,
  a $C_3$-$C_6$ cycloalkyl radical optionally substituted with one or more —OH groups,
  an aromatic or heteroaromatic radical optionally substituted with one or more halogen atoms, one or more linear or branched $C_1$-$C_3$ alkyl groups optionally substituted with one or more halogen atoms, one or more $C_1$-$C_3$ alkoxy groups, one or more amino groups —$NR^{11}R^{12}$, one or more groups —$COR^{11}$, a carbonyl function (=O), one or more groups —$OR^{11}$, one or more $C_1$-$C_4$ hydroxyalkyl groups, one or more groups —$COOR^{11}$, one or more amido groups —$CONR^{11}R^{12}$, one or more groups —$SOR^{11}$, one or more groups —$SO_2R^{11}$, one or more groups —$NHCOR^{11}$, one or more groups —$NHCOOR^{11}$, one or more groups —$SO_2NR^{11}R^{12}$ or one or more —CN groups; $R^{11}$ and $R^{12}$, which may be identical or different, representing a hydrogen atom or a linear or branched $C_1$-$C_3$ alkyl radical optionally substituted with one or more halogen atoms;

$A_1$ represents a divalent group chosen from —$NR^a$—, —O—, —S—, —SO—, —$SO_2$—, —SO(=NH)$^-$, —$CH_2$—, —C=C—, —CH($R^a$)—;

$A_2$ represents a single bond or a divalent group chosen from —S—, —SO—, —$SO_2$—, —SO(=N—$R^b$)—, —CH(OH)—, —C(=O)O—;

given that:
  when $A_1$ represents one of the divalent groups chosen from: —$NR^a$—, —O—, —$CH_2$—, —C=C— and —CH($R^a$), then $A_2$ does not represent the divalent group —CH(OH)— and —C(=O)O— and $R_3$ does not represent a hydrogen atom, an amino radical —$NH_2$ or a $C_1$-$C_3$ alkyl radical,
  when $A_2$ represents a single bond and $R_3$ represents a hydrogen atom, then $A_1$ represents one of the divalent groups chosen from: —SO— and —SO(=NH)—, $R^a$ represents a hydrogen atom, a linear or branched $C_1$-$C_3$ alkyl radical or an acetyl radical —C(=O)$CH_3$, $R^b$ represents a hydrogen atom, a linear or branched $C_1$-$C_3$ alkyl radical or a cyclopropyl group, $Q_1$, $Q_2$, $Q_3$, $Q_4$ and $Q_5$, which may be identical or different, represent a nitrogen atom or a group —$CR'_2$, when $A_2$ represents a divalent group chosen from —S—, —SO, —$SO_2$— and —SO(=N—$R^b$)—, then $R^a$ and $R^3$ can form, together with the carbon atoms to which they are attached, a heterocycloalkyl group which may be optionally substituted with one or more carbonyl functions, one or more $C_1$-$C_3$ alkyl radicals, when $A_1$ represents —$NR^a$—, then $R^a$ and $R^4$ can form, together with the nitrogen atom to which they are attached, a $C_2$-$C_{10}$ heterocycloalkyl group optionally comprising 1 to 3 heteroatoms chosen from a sulfur atom, a nitrogen atom and an oxygen atom; said heterocycloalkyl group being optionally substituted with at least one radical $R^{14}$, $R^{14}$ represents a linear or branched $C_1$-$C_3$ alkyl radical, a linear or branched $C_1$-$C_3$ alkoxy radical, a halogen atom, a hydroxyl group —OH, a cyano group —CN, a group —$CONR^{15}R^{16}$, a group —$SO_2R^{15}$, a group —$COR^{15}$ or an amino group —$NR^{15}R^{16}$; $R^{15}$ and $R^{16}$, which may be identical or different, representing a hydrogen atom or a linear or branched $C_1$-$C_3$ alkyl radical.

In other words, in accordance with formula (I):
  when $A_1$ represents one of the following divalent groups: —$NR^a$—, —O—, —$CH_2$—, —C=C— or —CH($R^a$), then $A_2$ does not represent a single bond or a divalent group: —CH(OH)— or —C(=O)O—,
  when $A_2$-$R_3$ represents a hydrogen atom, then $A_1$ represents one of the following divalent groups: —SO— and —SO(=NH).

The compounds according to the invention correspond to sulfonamide derivatives and preferably to sulfur-based sulfonamide derivatives which comprise in their structure at least one sulfonamide group $SO_2$—N and at least one sulfur atom.

The compounds according to the invention make it possible to modulate, i.e. to inhibit, the activity of the RORγt receptor.

A subject of the present invention is also the compound(s) as defined previously, as medicament and cosmetic.

Another subject of the invention relates to the compound(s) as defined previously for its use in the treatment of diseases mediated by the RORγt receptor, especially inflammatory disorders and/or autoimmune diseases mediated by the RORγt receptor.

Moreover, the invention also relates to a pharmaceutical composition comprising, in a pharmaceutically acceptable medium, one or more compounds of formula (I) as defined previously, pharmaceutically acceptable addition salts thereof, hydrates thereof and/or solvates thereof.

The present invention also relates to the pharmaceutical composition as described previously, for its use for treating diseases mediated by the RORγt receptor, especially inflammatory disorders and/or autoimmune diseases.

Finally, the invention relates to a method for treating diseases mediated by the RORγt receptor, comprising the administration, especially topically or orally, of a therapeutically effective amount of one or more compounds as defined above to a patient.

Other subjects, characteristics, aspects and advantages of the invention will emerge even more clearly on reading the description and the examples that follow.

Preferably, the compound(s) of formula (I) are sulfur-based sulfonamides.

Preferably, the compound(s) of formula (I) according to the invention are chosen from the compound(s) of formulae (Ia) and/or (Ib):

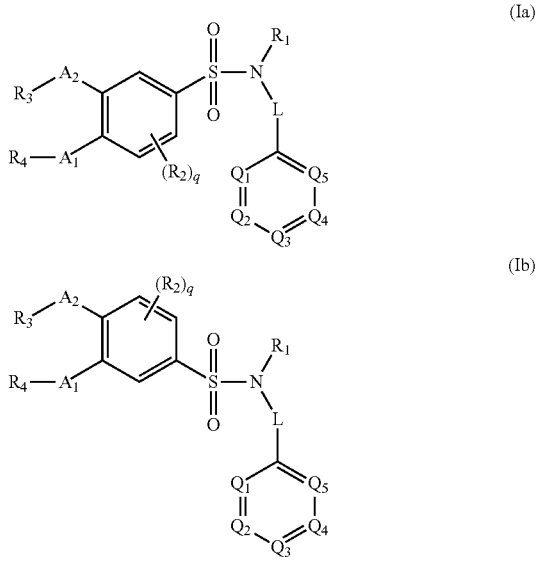

in which formulae (Ia) and (Ib) $R^1$, $R_2$, $R'_2$, $R^3$, $R^4$, $R^5$, $R'^5$, $R^6$, $R^7$, $R^{7a}$, $R^{7b}$, $R^{11}$, $R^{12}$, $R^{14}$, $R^{15}$, $R^{16}$, $R^a$, $R^b$, Z, $Q_1$, $Q_2$, $Q_3$, $Q_4$, $Q_5$, $A_1$, $A_2$, L and the indices q, n, o and p have the same meanings as in formula (I) described previously.

According to one embodiment, in formulae (I), (Ia) and (Ib), L represents a single bond.

According to another embodiment, in formulae (I), (Ia) and (Ib), L represents a methylene group —$CH_2$.

Preferentially, in formulae (I), (Ia) and (Ib), L represents a single bond.

According to one embodiment, in formulae (I), (Ia) and (Ib), $R^1$ represents a linear or branched $C_3$-$C_5$ and especially a branched $C_4$ alkyl radical.

According to one embodiment, in formulae (I), (Ia) and (Ib), $R^1$ represents a $C_3$-$C_5$ cycloalkyl radical.

According to one embodiment, in formulae (I), (Ia) and (Ib), $R^1$ represents a linear or branched $C_2$-$C_5$ alkenyl radical.

According to one embodiment, in formulae (I), (Ia) and (Ib), $R^1$ represents a ($C_1$)alkyl($C_3$-$C_5$)cycloalkyl radical.

According to one embodiment, in formulae (I), (Ia) and (Ib), $R^1$ represents a $C_4$-$C_5$ heterocycloalkyl radical.

According to one embodiment, in formulae (I), (Ia) and (Ib), $R^1$ represents a ($C_1$)alkyl($C_4$-$C_5$)heterocycloalkyl radical.

Preferentially, $R^1$ represents a linear or branched $C_3$-$C_5$, especially branched, and even more preferentially a branched $C_4$ alkyl radical.

According to one embodiment, in formulae (I), (Ia) and (Ib), $R^3$ represents a hydrogen atom.

According to one embodiment, in formulae (I), (Ia) and (Ib), $R^3$ represents a linear or branched $C_1$-$C_3$, and especially $C_1$, alkyl radical.

According to one embodiment, in formulae (I), (Ia) and (Ib), $Q_1$, $Q_2$, $Q_4$ and $Q_5$, which may be identical or different, represent a group —$CR'_2$, with $R'_2$ possibly representing a hydrogen atom or a linear or branched $C_1$-$C_5$ alkyl radical.

Preferably, in formulae (I), (Ia) and (Ib), $Q_3$ represents a group —$CR'_2$ with $R'_2$ representing a linear or branched $C_1$-$C_5$ and especially a $C_2$ alkyl radical.

Preferably, $Q_1$, $Q_2$, $Q_4$ and $Q_5$, which may be identical or different, represent a group —$CR'_2$, with $R'_2$ representing a hydrogen atom.

In accordance with a preferential mode, $Q_3$ represents a group —$CR'_2$ with $R'_2$ representing a linear or branched $C_1$-$C_5$ and especially $C_2$ alkyl radical, and $Q_1$, $Q_2$, $Q_4$ and $Q_5$, which may be identical or different, represent a group —$CR'_2$, with $R'_2$ representing a hydrogen atom.

According to one embodiment, in formulae (I), (Ia) and (Ib), the index q corresponds to zero.

Preferably, in formulae (I), (Ia) and (Ib), $A_2$ represents a divalent group chosen from —SO—, —$SO_2$— and —SO(=N—$R^b$)—.

According to one embodiment, in formulae (I), (Ia) and (Ib), $A_2$ represents the divalent group —SO—.

According to one embodiment, in formulae (I), (Ia) and (Ib), $A_2$ represents the divalent group —$SO_2$—.

According to one embodiment, in formulae (I), (Ia) and (Ib), $A_2$ represents the divalent group —SO(=N—$R^b$)—.

According to one embodiment, in formulae (I), (Ia) and (Ib), $A_2$ represents the divalent group —CH(OH)—.

According to one embodiment, in formulae (I), (Ia) and (Ib), $A_2$ represents a single bond.

Preferentially, in formulae (I), (Ia) and (Ib), $A_2$ represents the divalent group —SO(=N—$R^b$)— with $R^b$ representing a hydrogen atom.

Preferably, in formulae (I), (Ia) and (Ib), $A_1$ represents a divalent group chosen from the groups —$NR^a$— and —CH($R^a$)—.

According to one embodiment, in formulae (I), (Ia) and (Ib), $A_1$ represents the divalent group —$NR^a$—.

According to one embodiment, in formulae (I), (Ia) and (Ib), $A_1$ represents the divalent group —O—.

According to one embodiment, in formulae (I), (Ia) and (Ib), $A_1$ represents the divalent group —SO—.

According to one embodiment, in formulae (I), (Ia) and (Ib), $A_1$ represents the divalent group —S—.

According to one embodiment, in formulae (I), (Ia) and (Ib), $A_1$ represents the divalent group —$SO_2$—.

According to one embodiment, in formulae (I), (Ia) and (Ib), $A_1$ represents the divalent group —SO(=NH)—.

According to one embodiment, in formulae (I), (Ia) and (Ib), $A_1$ represents the divalent group —$CH_2$—.

According to one embodiment, in formulae (I), (Ia) and (Ib), $A_1$ represents the divalent group —C≡C—.

According to one embodiment, in formulae (I), (Ia) and (Ib), $A_1$ represents the divalent group —CH($R^a$)—.

Preferentially, in formulae (I), (Ia) and (Ib), $A_1$ represents the divalent group —O—, —S— or —SO—, and even more preferentially the divalent group —O—.

According to one embodiment, in formulae (I), (Ia) and (Ib), the indices n, o and p, which may be identical or different, denote zero.

According to one embodiment, in formulae (I), (Ia) and (Ib), the indices n, o and p, which may be identical or different, denote a natural integer ranging from 1 to 3.

According to one embodiment, the indices n and o denote 1 and the index p denotes zero.

According to one embodiment, the indices n and p denote zero and the index o denotes 1.

According to one embodiment, in formulae (I), (Ia) and (Ib), Z represents a methylene group —CH$_2$—.

According to one embodiment, in formulae (I), (Ia) and (Ib), Z represents a divalent group —O—.

According to one embodiment, in formulae (I), (Ia) and (Ib), Z represents a divalent group —NH—.

Preferably, $R^4$ is other than a hydrogen atom.

According to one embodiment, in formulae (I), (Ia) and (Ib), $R^4$ represents a group Z—$R^6$, with Z having the meaning described previously.

According to one embodiment, in formulae (I), (Ia) and (Ib), $R^4$ represents a group —C$_2$—$R^6$.

According to one embodiment, in formulae (I), (Ia) and (Ib), $R^4$ represents a group —O—$R^6$.

According to one embodiment, in formulae (I), (Ia) and (Ib), $R^4$ represents a group —NH—$R^6$.

Thus, in formulae (I), (Ia) and (Ib), $R^4$ is chosen from the groups —CH$_2$—$R^6$, —O—$R^6$ or —NH—$R^6$.

According to one embodiment, in formulae (I), (Ia) and (Ib), $R^6$ represents a monocyclic, bicyclic or spiro bicyclic heterocyclic group.

According to one embodiment, $R^6$ represents a heterocycloalkyl radical, preferably chosen from:

in which:

$R_7$ represents a linear or branched $C_1$-$C_3$ alkyl radical, a hydroxyl radical —OH, a $C_1$-$C_3$ alkoxy radical or an amino radical N($R^{7a}$)($R^{7b}$), $R^{7a}$ and $R^{7b}$, which may be identical or different, denote a hydrogen atom, a linear or branched $C_1$-$C_3$ alkyl radical or a cyclopropyl radical, $R_8$ and $R_9$, which may be identical or different, represent a hydrogen atom, a linear or branched $C_1$-$C_3$ alkyl radical, a hydroxyl group —OH, a carbonyl group, a ($C_1$)hydroxyalkyl radical (CH$_2$OH), an amino group —NH$_2$, $R_8$ and $R_9$ can form, together with the carbon atoms to which they are attached, a 5- to 7-membered carbocyclic ring.

According to one embodiment, in formulae (I), (Ia) and (Ib), $R^6$ represents an aromatic or heteroaromatic radical preferably chosen from:

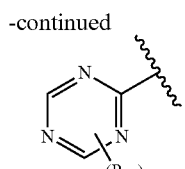
and
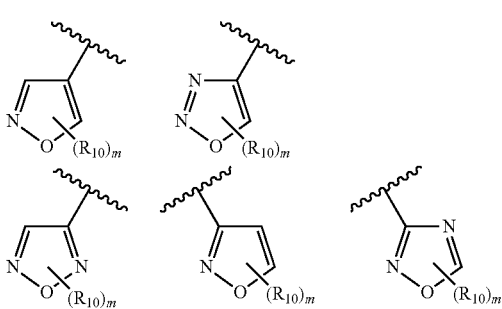

in which:
R$_{10}$ represents a hydrogen atom or a halogen atom; a linear or branched C$_1$-C$_3$ alkyl radical optionally substituted with one or more halogen atoms; a carbonyl function C(=O), a group OR$^{11}$, a C$_1$-C$_4$ hydroxyalkyl group, an amino group —NR$^{11}$R$^{12}$, a group —COR$^{11}$, a group —COOR$^{11}$, an amido group —CONR$^{11}$R$^{12}$, a group —SOR$^{11}$, a group —SO$_2$R$^{11}$, a group —NH-COR$^{11}$, a group —NHCOOR$^{11}$, a group —SO$_2$NR$^{11}$R$^{12}$ or a cyano group —CN, R$^{11}$ and R$^{12}$, which may be identical or different, represent a hydrogen atom or a linear or branched C$_1$-C$_3$ alkyl radical optionally substituted with one or more halogen atoms, m denotes zero or a natural integer ranging from 1 to 3.

Preferentially, R$^6$ represents an aromatic or heteroaromatic radical as defined previously, optionally substituted with one or more methyl groups —CH$_3$, one or more methoxy groups —OCH$_3$, one or more hydroxyl groups —OH, one or more amino groups —NH$_2$, one or more —CH$_2$OH groups, one or more cyano groups —CN, one or more halogen atoms, one or more carbonyl functions.

According to one embodiment, R$^6$ represents a hydrogen atom.

According to one embodiment, R$^6$ represents a C$_3$-C$_6$ cycloalkyl radical.

According to one embodiment, R$_8$ and R$_9$ represent a hydrogen atom.

According to one embodiment, R$_8$ and R$_9$ represent a linear or branched C$_1$-C$_3$ alkyl radical.

According to one embodiment, in formulae (I), (Ia) and (Ib), when A$_2$ represents a divalent group chosen from —SO, —SO$_2$—, —SO(=N—R$^b$)—, then A$_1$ represents a divalent group chosen from the groups —NR$^a$— and —CH(R$^a$)— and R$^a$ and R$_3$ form, together with the carbon atoms to which they are attached, a 5- or 6-membered heterocycloalkyl group optionally substituted with one or more carbonyl functions, one or more halogen atoms or one or more C$_1$-C$_2$ alkyl radicals.

In accordance with this embodiment, R$^a$ and R$_3$ form, together with the carbon atoms to which they are attached, an unsubstituted 5- or 6-membered heterocycloalkyl group.

In accordance with this embodiment, A$_2$ preferentially represents —SO$_2$—.

In accordance with this embodiment, A$_2$ preferentially represents —SO—.

In accordance with this embodiment, A$_2$ preferentially represents SO(=N—R$^b$)— with R$^b$ preferably representing a hydrogen atom or a linear or branched C$_1$-C$_3$ alkyl radical.

According to another embodiment, in formulae (I), (Ia) and (Ib), when A$_2$ represents a divalent group chosen from —SO, —SO$_2$—, —SO(=N—R$^b$)—, then A$_1$ represents a divalent group chosen from the divalent groups —NR$^a$—, —O—, —CH$_2$—, —C=C— and —CH(R$^a$).

In accordance with this embodiment, R$^a$ and R$_3$ do not form, together with the carbon atoms to which they are attached, a 5- or 6-membered heterocycloalkyl group.

According to one embodiment, when A$_1$ represents —NR$^a$—, then R$^a$ and R$^4$ form, together with the nitrogen atom to which they are attached, a C$_2$-C$_{10}$ heterocycloalkyl group optionally comprising 1 to 3 heteroatoms chosen from a sulfur atom, a nitrogen atom and an oxygen atom; said heterocycloalkyl group being optionally substituted with at least one radical R$^{14}$ as defined in formula (I) described previously.

In particular, the C$_2$-C$_{10}$ heterocycloalkyl group may be a monocyclic, bicyclic or spiro bicyclic group.

Preferably, the heterocycloalkyl group is optionally substituted with one, two or three radicals R$^{14}$ as defined previously.

Preferably, the compound(s) according to the invention are chosen from the compounds of formula (II) and also the pharmaceutically acceptable addition salts thereof, hydrates thereof and/or solvates thereof:

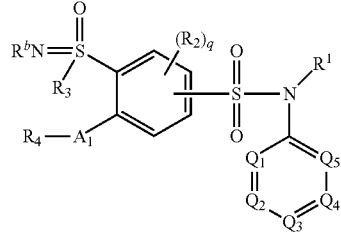

(II)

in which formula (II):
R$^3$ represents a C$_1$-C$_3$ alkyl radical,
R$^1$, R$_2$, R'$_2$, R$^3$, R$^4$, R$^5$, R'$^5$, R$^6$, R$^7$, R$^{7a}$, R$^{7b}$, R$_8$, R$_9$, R$_{10}$, R$^{11}$, R$^{12}$, R$^a$, R$^b$Z, Q$_1$, Q$_2$, Q$_3$, Q$_4$, Q$_5$, A$_1$, and the indices q, m, n, o and p have the same meanings as those indicated previously.

Preferably, R$^b$ represents a hydrogen atom or a C$_1$ alkyl radical.

Preferentially, R$^b$ represents a hydrogen atom.
Preferably, R$^3$ represents a C$_1$ alkyl radical.
Preferably, R$^1$ represents a branched C$_3$ alkyl radical.
Preferentially, R$^4$ represents a group (CHR$^5$)$_n$—(Z)$_o$—(CHR'$^5$)$_p$—R$^6$ with R$^6$ preferably corresponding to an aromatic or heteroaromatic radical, a cycloalkyl radical or a heterocyclic radical as defined above in formula (I) or as previously.

Preferably, Q$^1$-Q$^2$ and Q$^4$-Q$^5$ correspond to a group —CR$^2$ with R$^2$ denoting a hydrogen atom and Q$^3$ corresponds to a group —CR$^2$ with R$^2$ denoting a linear or branched C$_1$-C$_5$ and preferably C$_2$ alkyl radical.

Preferably, Q$^1$ and Q$^3$, which may be identical or different, correspond to a group —CR'$_2$ with R'$_2$ denoting a hydrogen atom or a linear or branched C$_1$-C$_5$ and preferably C$_2$ alkyl radical.

In accordance with one embodiment, preferably, $R^1$ represents a linear or branched $C_3$-$C_5$ alkyl radical and $R^b$ represents a hydrogen atom.

Preferably, the compound(s) according to the invention are chosen from the compounds of formula (III) and also the pharmaceutically acceptable addition salts thereof, hydrates thereof and/or solvates thereof:

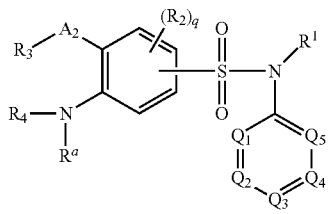

(III)

in which formula (III):
$R^1$, $R_2$, $R'_2$, $R^3$, $R^b$, $Q_1$, $Q_2$, $Q_3$, $Q_4$, $Q_5$, $A_2$ and the index q have the same meanings as in formula (I) described previously, $R^a$ and $R_4$ form, together with the nitrogen atom to which they are attached, a $C_2$-$C_{10}$ heterocycloalkyl group optionally comprising 1 to 3 heteroatoms chosen from a sulfur atom, a nitrogen atom and an oxygen atom; said heterocycloalkyl group being optionally substituted with at least one radical $R^{14}$ $R^{14}$ represents a linear or branched $C_1$-$C_3$ alkyl radical, a linear or branched $C_1$-$C_3$ alkoxy radical, a halogen atom, a hydroxyl group —OH, a cyano group —CN, a group —$CONR^{15}R^{16}$, a group —$SO_2R^{15}$, a group —$COR^{15}$ or an amino group —$NR^{15}R^{16}$; $R^{15}$ and $R^{16}$, which may be identical or different, representing a hydrogen atom or a linear or branched $C_1$-$C_3$ alkyl radical.

In particular, the $C_2$-$C_{10}$ heterocycloalkyl group may be a monocyclic, bicyclic or spiro bicyclic group.

The compounds of formulae (I), (II), (III), (Ia) and (Ib) may be in the form of pharmaceutically acceptable salts. Examples of pharmaceutically acceptable salts are described in Berge et al., 1977, "Sels pharmaceutiquement acceptables" [Pharmaceutically acceptable salts], J. Pharm. Sci., Vol. 66, pages 1-19.

In particular, when the compounds of formula according to the invention are in the form of salts, then the electrical neutrality of said compounds is ensured by an external cationic counterion Y which may be organic or mineral.

Y may be chosen from suitable inorganic cations such as alkali metal ions, especially $Na^+$, $K^+$, alkaline-earth metal ions, especially $Ca^{2+}$, $Mg^{2+}$, or alternatively other cations such as the aluminum ion $Al^{3+}$.

Y may be chosen from suitable organic cations such as the ammonium ion $NH_4^+$, substituted ammonium ions such as $NH_3R^+$, $NHR_2^+$, $NR_4^+$ with R representing a $C_1$-$C_4$ alkyl radical.

In particular, the substituted ammonium ions are those chosen from derivatives of ethylamine, diethylamine, dicyclohexylamine, trimethylamine, butylamine, ethylenediamine, ethanolamine, diethanolamine, piperazine, benzylamine, phenylbenzylamine, choline, melglumine and tromethamine, and amino acids such as lysine and arginine.

An example of a quaternary ammonium ion may be the ion $N^+(CH_3)_4$.

The compound(s) according to the invention may be in the form of the solvates thereof.

For the purposes of the present invention, the term "solvate" means a complex of solute (i.e. the compound according to the invention or the salt of said compound) and of solvent.

If the solvent is water, then the solvate may suitably be considered as a hydrate, for example, a hemihydrate, a monohydrate, a dihydrate, a trihydrate, etc.

For example, the solvates and/or hydrates may be obtained directly at the end of the synthetic process, the target compound being isolated in the form of a hydrate, for example a monohydrate or hemihydrate, or in the form of a solvate of the reaction and/or purification solvent.

Unless otherwise indicated, any reference to a compound according to the invention also includes the solvate or the hydrate of the corresponding compound.

Typical processes for the preparation and identification of hydrates and solvates are well known to those skilled in the art: see, for example, pages 202-209 of K J Guillory, "Generation of Polymorphs, Hydrates, Solvates, and Amorphous Solids" in Polymorphism in Pharmaceutical Solids, edition. Harry G. Britain, Vol. 95, Marcel Dekker, Inc., New York, 1999.

The hydrates and solvates may be isolated and characterized via methods known in the art, such as thermogravimetric analysis (TGA), TGA-mass spectroscopy, TGA-infrared spectroscopy, x-ray powder diffraction, Karl Fischer titration, high-resolution x-ray diffraction, and the like.

Preferably, the compound(s) of formula (I) are chosen from the following compounds as described in the tables below, and also the pharmaceutically acceptable addition salts thereof, hydrates thereof and/or solvates thereof:

TABLE 1

| | | IC50 hRORg | IC50 hCD4/IL17 |
|---|---|---|---|
| 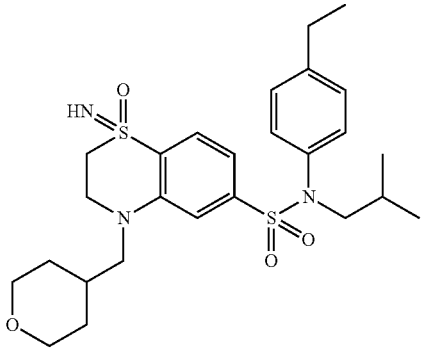 [SMILES: CCc1ccc(N(CC(C)C)S(=O)(=O)c2ccc3c(c2)N(CC2CCOCC2)CCS3(=N)=O)cc1] | imino-1-oxo-4-(tetrahydropyran-4-ylmethyl)-1,2,3,4-tetrahydro-1$\lambda^6$-benzo[1,4]thiazine-7-sulfonic acid (4-ethylphenyl)isobutylamide compound 1 | C | ND |
| 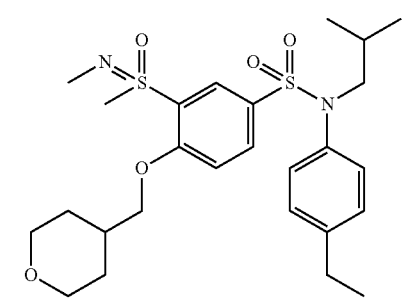 [SMILES: CCc1ccc(N(CC(C)C)S(=O)(=O)c2ccc(OCC3CCOCC3)c(S(C)(=O)=NC)c2)cc1] | N-(4-ethylphenyl)-N-isobutyl-3-methanesulfinyl-4-(tetrahydropyran-4-ylmethoxy)benzene-N-methylsulfoximine compound 2 | B | ND |
| 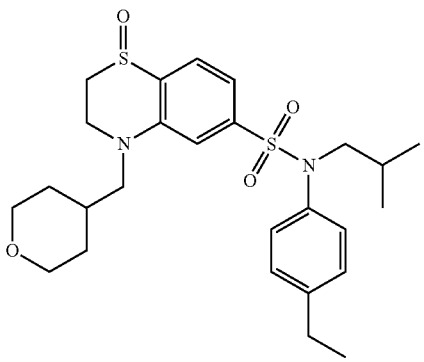 [SMILES: CCc1ccc(N(CC(C)C)S(=O)(=O)c2ccc3c(c2)N(CC2CCOCC2)CCS3=O)cc1] | 1-oxo-4-(tetrahydropyran-4-ylmethyl)-1,2,3,4-tetrahydro-1$\lambda^4$-benzo[1,4]thiazine-7-sulfonic acid compound 3 | C | ND |
| 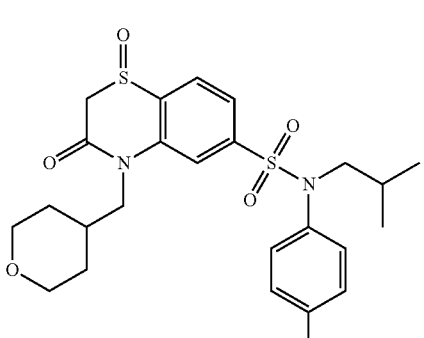 | 1,3-dioxo-4-(tetrahydropyran-4-ylmethyl)-1,2,3,4-tetrahydro-1$\lambda^4$-benzo[1,4]thiazine-6-sulfonic acid (4-ethylphenyl)isobutylamide compound 4 | C | ND |

TABLE 1-continued

| | | | IC50 hRORg | IC50 hCD4/IL17 |
|---|---|---|---|---|
| 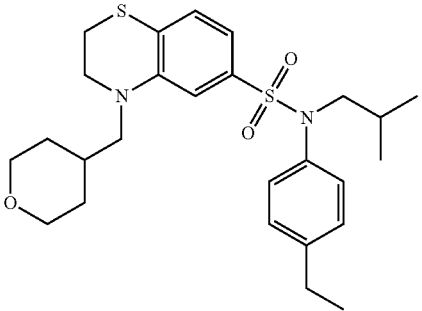 [SMILES: CCc1ccc(N(CC(C)C)S(=O)(=O)c2ccc3c(c2)N(CC2CCOCC2)CCS3)cc1] | | 4-(tetrahydropyran-4-ylmethyl)-3,4-dihydro-2H-benzo[1,4]thiazine-6-sulfonic acid (4-ethylphenyl)isobutylamide compound 6 | C | ND |
| 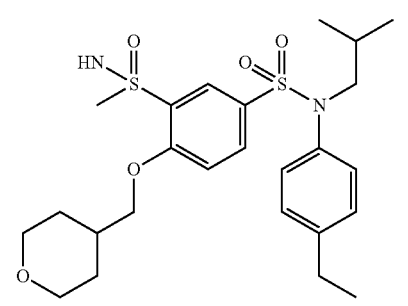 | | N-(4-ethylphenyl)-N-isobutyl-3-methanesulfonoximino-4-(tetrahydropyran-4-ylmethoxy)benzene-sulfonamide compound 26 | A | A |
| 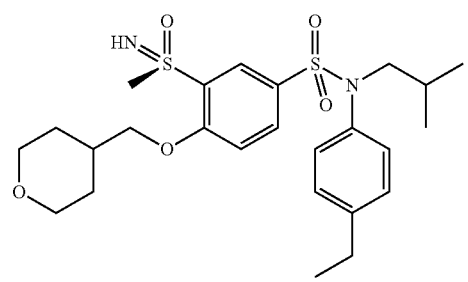 | Chiral | N-(4-ethylphenyl)-N-isobutyl-3-methanesulfoximino-4-(tetrahydropyran-4-ylmethoxy)benzene-sulfonamide compound 7 (enantiomer A of compound 26) | A | A |
| 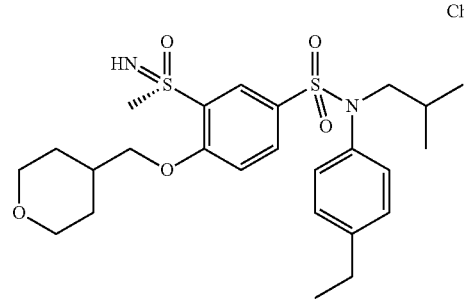 | Chiral | N-(4-ethylphenyl)-N-isobutyl-3-methanesulfoximino-4-(tetrahydropyran-4-ylmethoxy)benzene-sulfonamide compound 8 (enantiomer B of compound 26) | A | A |
| 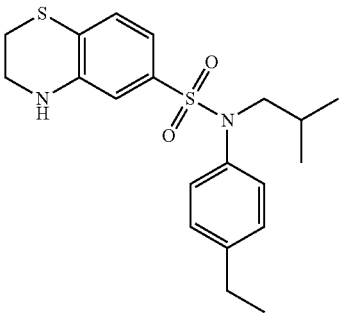 [SMILES: CCc1ccc(N(CC(C)C)S(=O)(=O)c2ccc3c(c2)NCCS3)cc1] | | 3,4-dihydro-2H-benzo[1,4]thiazine-6-sulfonic acid (4-ethylphenyl)isobutylamide compound 9 | C | ND |

TABLE 1-continued

| | | IC50 hRORg | IC50 hCD4/IL17 |
|---|---|---|---|
| 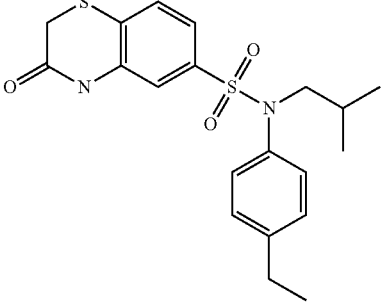 | 3-oxo-3,4-dihydro-2H-benzo[1,4]thiazine-6-sulfonic acid (4-ethylphenyl)isobutylamide compound 10 | C | ND |
| 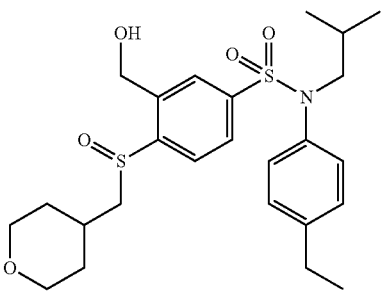 [SMILES: CCc1ccc(N(CC(C)C)S(=O)(=O)c2ccc(S(=O)CC3CCOCC3)c(CO)c2)cc1] | N-(4-ethylphenyl)-3-hydroxymethyl-N-isobutyl-4-(tetrahydropyran-4-ylmethanesulfinyl)benzene-sulfonamide compound 15 | B | ND |
| 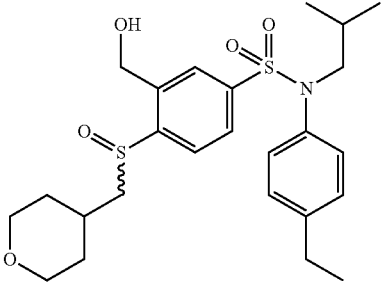 [SMILES: CCc1ccc(N(CC(C)C)S(=O)(=O)c2ccc(S(=O)CC3CCOCC3)c(CO)c2)cc1] | N-(4-ethylphenyl)-3-hydroxymethyl-N-isobutyl-4-(tetrahydropyran-4-ylmethanesulfinyl)benzene-sulfonamide compound 11 (enantiomer A of compound 15) | B | ND |
| 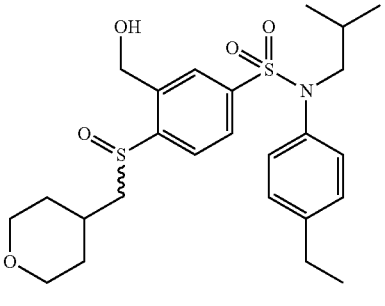 [SMILES: CCc1ccc(N(CC(C)C)S(=O)(=O)c2ccc(S(=O)CC3CCOCC3)c(CO)c2)cc1] | N-(4-ethylphenyl)-3-hydroxymethyl-N-isobutyl-4-(tetrahydropyran-4-ylmethanesulfinyl)benzene-sulfonamide compound 12 (enantiomer B of compound 15) | B | ND |
| 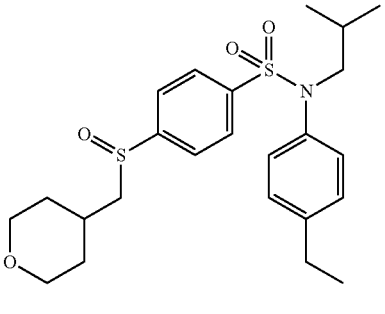 [SMILES: CCc1ccc(N(CC(C)C)S(=O)(=O)c2ccc(S(=O)CC3CCOCC3)cc2)cc1] | N-(4-ethylphenyl)-N-isobutyl-4-(tetrahydropyran-4-ylmethanesulfinyl)benzene-sulfonamide compound 29 | B | B |

TABLE 1-continued

| | | IC50 hRORg | IC50 hCD4/IL17 |
|---|---|---|---|
| 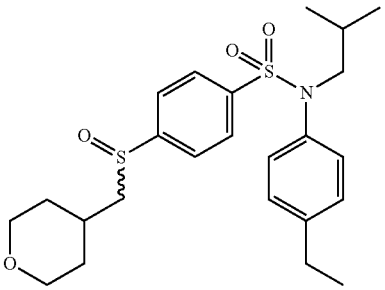 [SMILES: CCc1ccc(N(CC(C)C)S(=O)(=O)c2ccc(S(=O)CC3CCOCC3)cc2)cc1] | N-(4-ethylphenyl)-N-isobutyl-4-(tetrahydropyran-4-ylmethanesulfinyl)benzene-sulfonamide compound 13 (enantiomer A of compound 29) | B | B |
| 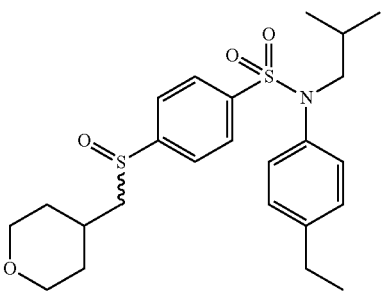 [SMILES: CCc1ccc(N(CC(C)C)S(=O)(=O)c2ccc(S(=O)CC3CCOCC3)cc2)cc1] | N-(4-ethylphenyl)-N-isobutyl-4-(tetrahydropyran-4-ylmethanesulfinyl)benzene-sulfonamide compound 14 (enantiomer B of compound 29) | B | B |
| 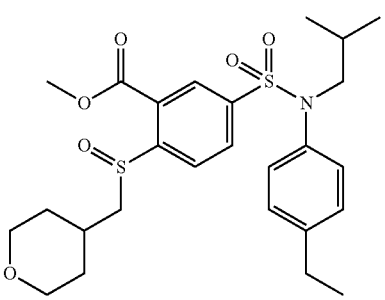 [SMILES: CCc1ccc(N(CC(C)C)S(=O)(=O)c2ccc(S(=O)CC3CCOCC3)c(C(=O)OC)c2)cc1] | methyl 5-[(4-ethylphenyl)isobutylsulfa-moyl]-2-(tetrahydropyran-4-ylmethanesulfinyl)benzoate compound 16 | C | ND |
| 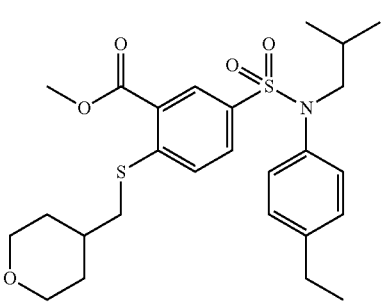 | methyl 5-[(4-ethylphenyl)isobutylsulfa-moyl]-2-(tetrahydropyran-4-ylmethylsulfanyl)benzoate compound 17 | C | ND |
| 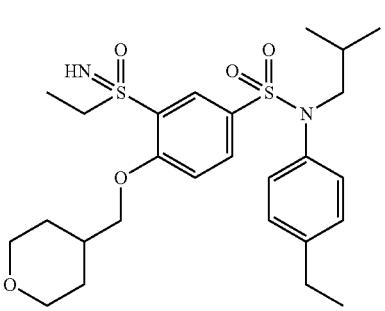 | N-(4-ethylphenyl)-N-isobutyl-3-ethanesulfoximino-4-(tetrahydropyran-4-ylmethoxy)benzene-sulfonamide compound 18 | A | A |

TABLE 1-continued

| | | | IC50 hRORg | IC50 hCD4/IL17 |
|---|---|---|---|---|
| 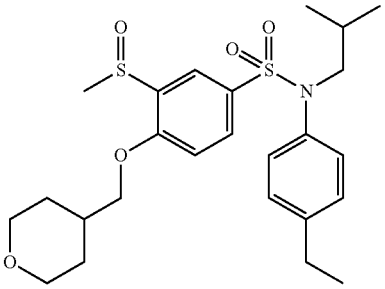 | | N-(4-ethylphenyl)-N-isobutyl-3-methanesulfinyl-4-(tetrahydropyran-4-ylmethoxy)benzene-sulfonamide compound 27 | A | A |
| 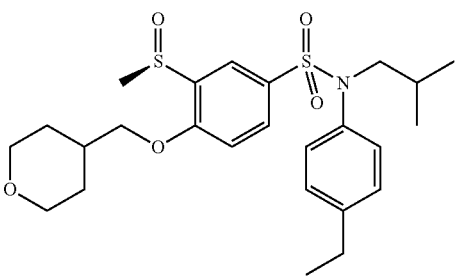 | Chiral | N-(4-ethylphenyl)-N-isobutyl-3-methanesulfinyl-4-(tetrahydropyran-4-ylmethoxy)benzene-sulfonamide compound 19 (enantiomer A of compound 27) | B | A |
| 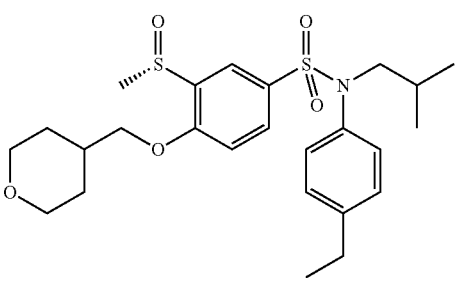 | Chiral | N-(4-ethylphenyl)-N-isobutyl-3-methanesulfinyl-4-(tetrahydropyran-4-ylmethoxy)benzene-sulfonamide compound 20 (enantiomer B of compound 27) | B | B |
| 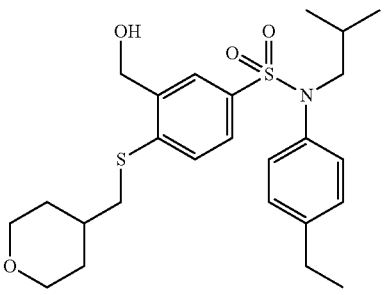 [SMILES: CCc1ccc(N(CC(C)C)S(=O)(=O)c2ccc(SCC3CCOCC3)c(CO)c2)cc1] | | N-(4-ethylphenyl)-3-hydroxymethyl-N-isobutyl-4-(tetrahydropyran-4-ylmethylsulfanyl)benzene-sulfonamide compound 21 | B | A |
| 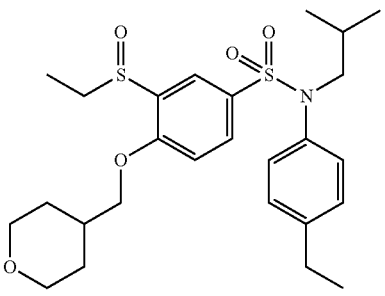 [SMILES: CCc1ccc(N(CC(C)C)S(=O)(=O)c2ccc(OCC3CCOCC3)c(S(=O)CC)c2)cc1] | | ethanesulfinyl-N-(4-ethylphenyl)-N-isobutyl-4-(tetrahydropyran-4-ylmethoxy)benzene-sulfonamide compound 22 | B | B |

TABLE 1-continued

| | | IC50 hRORg | IC50 hCD4/IL17 |
|---|---|---|---|
| 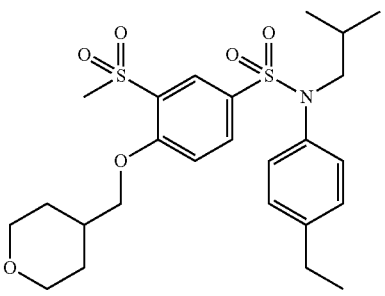 | N-(4-ethylphenyl)-N-isobutyl-3-methanesulfonyl-4-(tetrahydropyran-4-ylmethoxy)benzene-sulfonamide compound 24 | B | A |
| 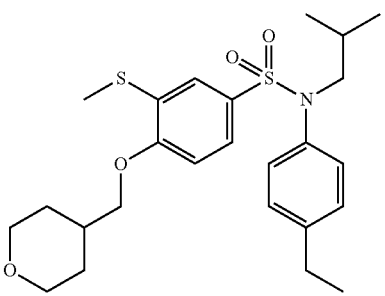 [SMILES: CCc1ccc(N(CC(C)C)S(=O)(=O)c2ccc(OCC3CCOCC3)c(SC)c2)cc1] | N-(4-ethylphenyl)-N-isobutyl-3-methylsulfanyl-4-(tetrahydropyran-4-ylmethoxy)benzene-sulfonamide compound 25 | B | B |
| 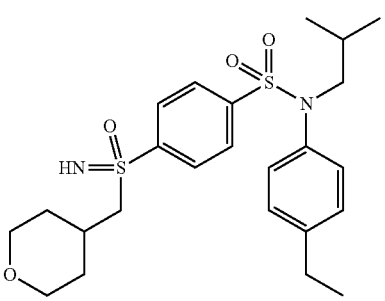 [SMILES: CCc1ccc(N(CC(C)C)S(=O)(=O)c2ccc(S(=N)(=O)CC3CCOCC3)cc2)cc1] | N-(4-ethylphenyl)-N-isobutyl-4-(tetrahydropyran-4-ylmethanesulfoximimyl)benzene-sulfonamide compound 28 | C | ND |

TABLE 2

| | | IC50 hRORg | IC50 hCD4/IL17 |
|---|---|---|---|
| 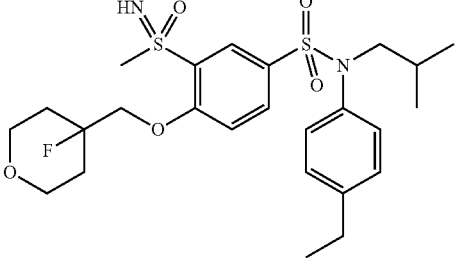 | N-(4-ethylphenyl)-4-((4-fluorotetrahydro-2H-pyran-4-yl)methoxy)-N-isobutyl-3-(S-methylsulfonimidoyl)benzene-sulfonamide compound 30 | A | A |
| 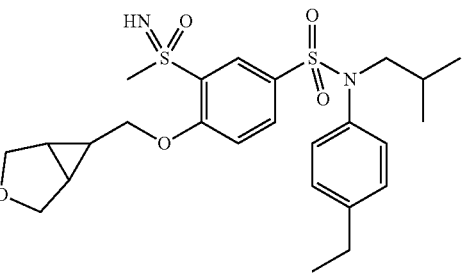 | 4-((3-oxabicyclo[3.1.0]hexan-6-yl)methoxy)-N-(4-ethylphenyl)-N-isobutyl-3-(S-methylsulfonimidoyl)benzene-sulfonamide compound 31 | A | ND |

TABLE 2-continued

| | | IC50 hRORg | IC50 hCD4/IL17 |
|---|---|---|---|
| 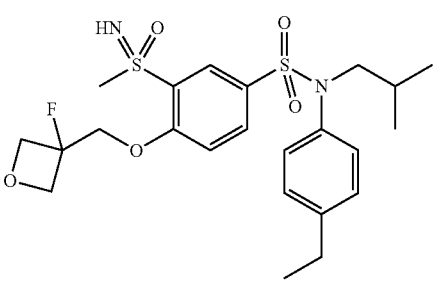 [SMILES: CCc1ccc(N(CC(C)C)S(=O)(=O)c2ccc(OCC3(F)COC3)c(S(C)(=N)=O)c2)cc1] | N-(4-eethylphenyl)-4-((3-fluorooxetan-3-yl)methoxy)-N-isobutyl-3-(S-methylsulfonimidoyl)benzenesulfonamide compound 32 | C | ND |
| 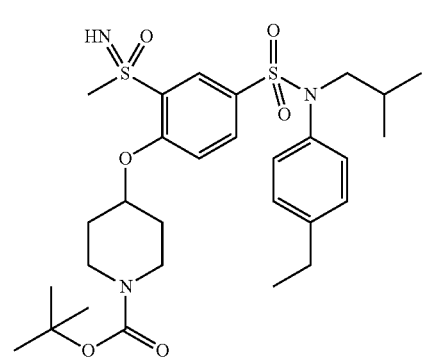 [SMILES: CCc1ccc(N(CC(C)C)S(=O)(=O)c2ccc(OC3CCN(C(=O)OC(C)(C)C)CC3)c(S(C)(=N)=O)c2)cc1] | tert-butyl 4-(4-(N-(4-ethylphenyl)-N-isobutylsulfamoyl)-2-(S-methylsulfonimidoyl)phenoxy)piperidine-1-carboxylate compound 33 | C | ND |
| 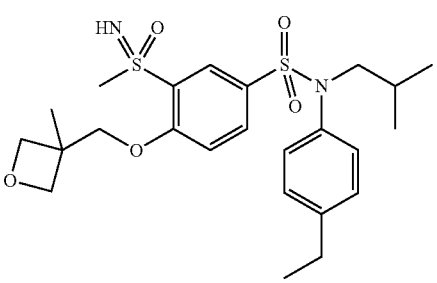 [SMILES: CCc1ccc(N(CC(C)C)S(=O)(=O)c2ccc(OCC3(C)COC3)c(S(C)(=N)=O)c2)cc1] | N-(4-ethylphenyl)-N-isobutyl-4-((3-methyloxetan-3-yl)methoxy)-3-(S-methylsulfonimidoyl)benzenesulfonamide compound 34 | C | ND |
| 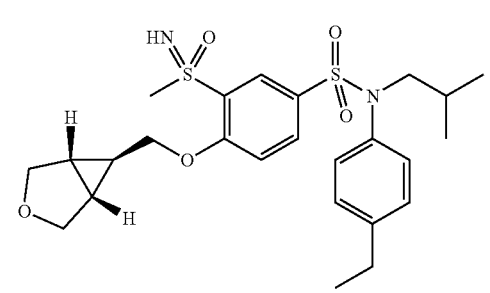 [SMILES: CCc1ccc(N(CC(C)C)S(=O)(=O)c2ccc(OC[C@H]3[C@@H]4COC[C@@H]43)c(S(C)(=N)=O)c2)cc1] | 4-(((1R,5S,6R)-3-oxabicyclo[3.1.0]hexan-6-yl)methoxy)-N-(4-ethylphenyl)-N-isobutyl-3-(S-methylsulfonimidoyl)benzenesulfonamide compound 35 | A | ND |
| 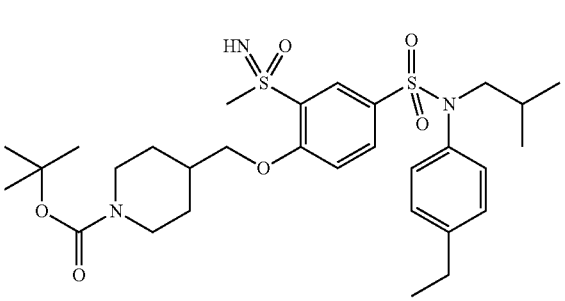 [SMILES: CCc1ccc(N(CC(C)C)S(=O)(=O)c2ccc(OCC3CCN(C(=O)OC(C)(C)C)CC3)c(S(C)(=N)=O)c2)cc1] | tert-butyl 4-((4-(N-(4-ethylphenyl)-N-isobutylsulfamoyl)-2-(S-methylsulfonimidoyl)phenoxy)methyl)piperidine-1-carboxylate compound 36 | C | ND |

TABLE 2-continued

| | | IC50 hRORg | IC50 hCD4/IL17 |
|---|---|---|---|
| 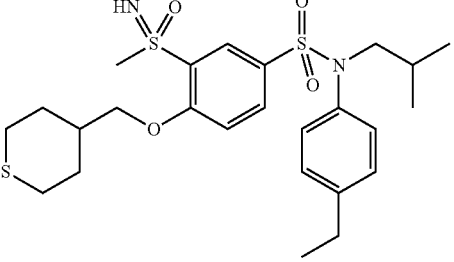 | N-(4-ethylphenyl)-N-isobutyl-3-(S-methylsulfonomidoyl)-4-(pyridin-4-ylmethoxy)benzene-sulfonamide compound 37 | A | ND |
| 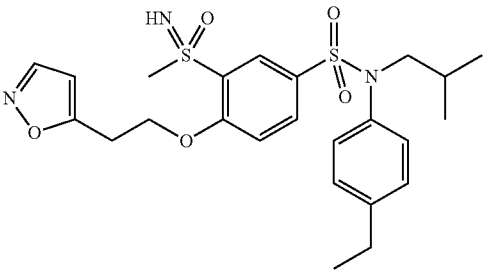 [SMILES: CCc1ccc(N(CC(C)C)S(=O)(=O)c2ccc(OCCc3ccno3)c(S(C)(=N)=O)c2)cc1] | N-(4-ethylphenyl)-N-isobutyl-4-(2-(isoxazol-5-yl)ethoxy)-3-(S-methylsulfonimidoyl)benzene-sulfonamide compound 38 | C | ND |
| 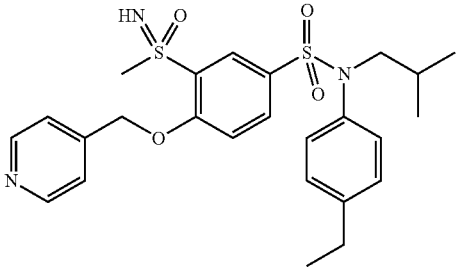 [SMILES: CCc1ccc(N(CC(C)C)S(=O)(=O)c2ccc(OCc3ccncc3)c(S(C)(=N)=O)c2)cc1] | N-(4-ethylphenyl)-N-isobutyl-3-(S-methylsulfonimidoyl)-4-(pyridin-4-ylmethoxy)benzene-sulfonamide compound 39 | C | ND |
| 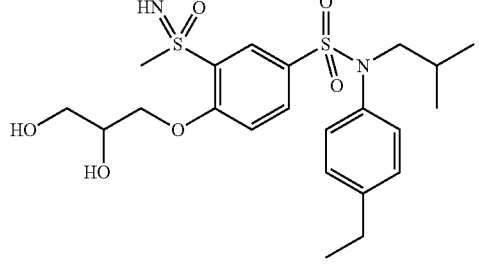 | 4-(2,3-dihydroxypropoxy)-N-(4-ethylphenyl)-N-isobutyl-3-(S-methylsulfonimidoyl)benzene-sulfonamide compound 40 | C | ND |
| 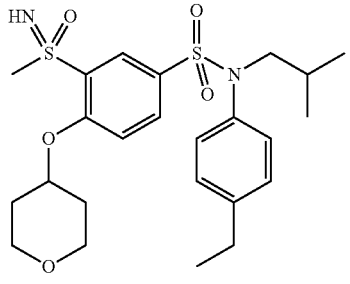 | N-(4-ethylphenyl)-N-isobutyl-3-(S-methylsulfonimidoyl)-4-((tetrahydro-2H-pyran-4-yl)oxy)benzenesulfonamide compound 42 | C | ND |

TABLE 2-continued

| | | IC50 hRORg | IC50 hCD4/IL17 |
|---|---|---|---|
| | 4-((2,6-dimethylpyridin-4-yl)methoxy)-N-(4-ethylphenyl)-N-isobutyl-3-(S-methylsulfonimidoyl)benzenesulfonamide compound 43 | C | ND |
| | 4-((2,4-difluorobenzyl)oxy)-N-(4-ethylphenyl)-N-isobutyl-3-(S-methylsulfonimidoyl)benzenesulfonamide compound 45 | C | ND |
| | N-(4-ethylphenyl)-N-isobutyl-3-(S-methylsulfonimidoyl)-4-(piperidin-4-ylmethoxy)benzenesulfonamide N-(4-ethylphenyl)-N-isobutyl-3-(S-methylsulfonimidoyl)-4-(piperiidn-4-ylmethoxy)benzenesulfonamide compound 46 | C | ND |
| | 4-((1-acetylpiperidin-4-yl)oxy)-N-(4-ethylphenyl)-N-isobutyl-3-(S-methylsulfonimidoyl)benzenesulfonamide compound 47 | C | ND |
| | N-(4-ethylphenyl)-N-isobutyl-3-(S-methylsulfonimidoyl)-4-((1-(methylsulfonyl)piperidin-4-yl)oxy)benzenesulfonamide compound 48 | C | ND |

TABLE 2-continued

| Structure | Name | IC50 hRORg | IC50 hCD4/IL17 |
|---|---|---|---|
| | N-(4-ethylphenyl)-N-isobutyl-3-(S-methylsulfonimidoyl)-4-(piperidin-4-ylmethoxy)benzene-sulfonamide compound 49 | C | ND |
| | 4-((1-acetylpiperidin-4-yl)methoxy)-N-(4-ethylphenyl)-N-isobutyl-3-(S-methylsulfonimidoyl)benzene-sulfonamide compound 50 | C | ND |
| | N-(4-ethylphenyl)-N-isobutyl-3-(S-methylsulfonimidoyl)-4-((1-(methylsulfonylpiperidin-4-yl)methoxy)benzene-sulfonamide compound 51 | C | ND |
| | N-(4-ethylphenyl)-N-isobutyl-3-(S-methysulfonimidoyl)-4-[(tetrahydropyran-4-ylmethyl)amino]benzene-sulfonamide compound 52 | A | A |
| | N-(4-ethylphenyl)-N-isobutyl-4-(methyl((tetrahydro-2H-pyran-4-yl)methyl)amino)-3-(S-methylsulfonimidoyl)benzene-sulfonamide compound 53 | A | A |

TABLE 2-continued

| | | IC50 hRORg | IC50 hCD4/IL17 |
|---|---|---|---|
| 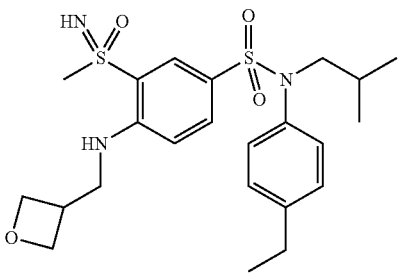 [SMILES: CCc1ccc(N(CC(C)C)S(=O)(=O)c2ccc(NCC3COC3)c(S(C)(=N)=O)c2)cc1] | N-(4-ethylphenyl)-N-isobutyl-3-(S-methylsulfonimidoyl)-4-((oxetan-3-ylmethyl)amino)benzene-sulfonamide compound 54 | B | ND |
| 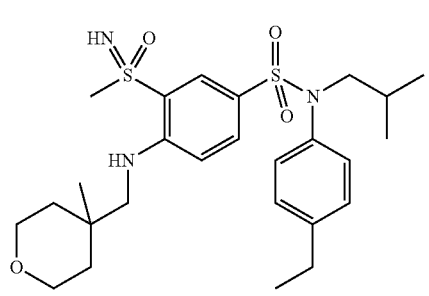 [SMILES: CCc1ccc(N(CC(C)C)S(=O)(=O)c2ccc(NCC3(C)CCOCC3)c(S(C)(=N)=O)c2)cc1] | N-(4-ethylphenyl)-N-isobutyl-3-(S-methylsulfonimidoyl)-4-(((4-methyltetrahydro-2H-pyran-4-yl)methyl)amino)benzene-sulfonamide compound 55 | A | A |
| 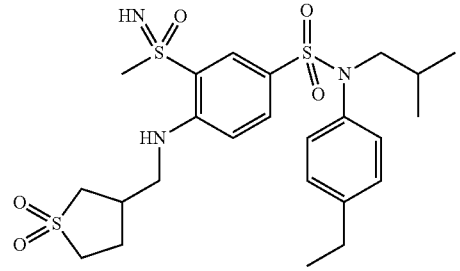 | 4-(((1,1-dioxidotetrahydrothiophen-3-yl)methyl)amino)-N-(4-ethylphenyl)-N-isobutyl-3-(S-methylsulfonimidoyl)benzene-sulfonamide compund 56 | B | ND |
| 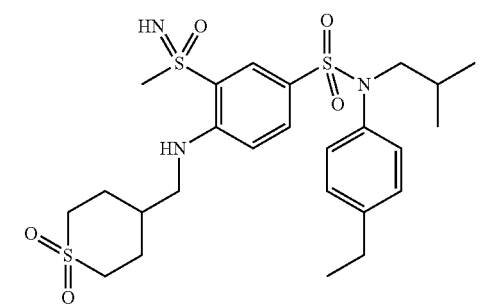 [SMILES: CCc1ccc(N(CC(C)C)S(=O)(=O)c2ccc(NCC3CCS(=O)(=O)CC3)c(S(C)(=N)=O)c2)cc1] | 4-(((1,1-dioxidotetrahydro-2H-thiopyran-4-yl)methyl)amino)-N-(4-ethylphenyl)-N-isobutyl-3-(S-methylsulfonimidoyl)benzene-sulfonamide compound 57 | C | ND |
| 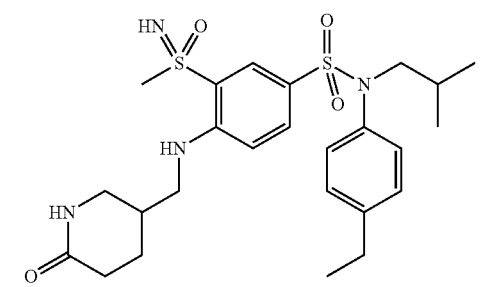 [SMILES: CCc1ccc(N(CC(C)C)S(=O)(=O)c2ccc(NCC3CCC(=O)NC3)c(S(C)(=N)=O)c2)cc1] | N-(4-ethylphenyl)-N-isobutyl-3-(S-methylsulfonimidoyl)-4-(((6-oxopiperidin-3-yl)methyl)amino)benzene-sulfonamide compound 58 | C | ND |

TABLE 2-continued

| | | IC50 hRORg | IC50 hCD4/IL17 |
|---|---|---|---|
| 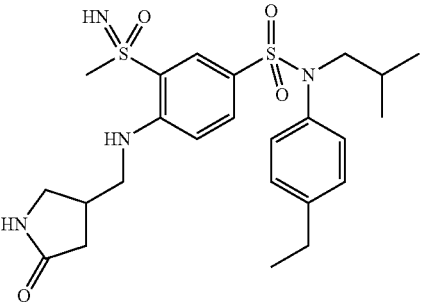 | N-(4-ethylphenyl)-N-isobutyl-3-(S-methylsulfonimidoyl)-4-(((5-oxopyrrolidin-3-yl)methyl)amino)benzene-sulfonamide compound 59 | B | B |
| 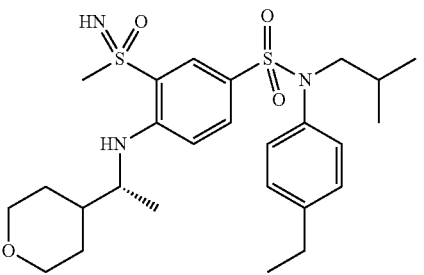 [SMILES: CCc1ccc(N(CC(C)C)S(=O)(=O)c2ccc(N[C@H](C)C3CCOCC3)c(S(C)(=N)=O)c2)cc1] | N-(4-ethylphenyl)-N-isobutyl-3-(S-methylsulfonimidoyl)-4-(((R)-1-(tetrahydro-2H-pyran-4-yl)ethyl)amino)benzene-sulfonamide compound 60 | B | ND |
| 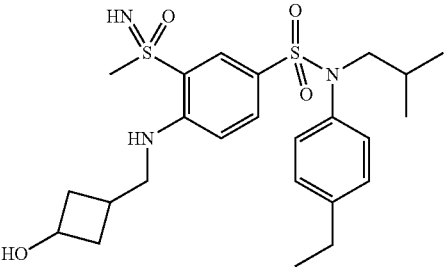 [SMILES: CCc1ccc(N(CC(C)C)S(=O)(=O)c2ccc(NCC3CC(O)C3)c(S(C)(=N)=O)c2)cc1] | N-(4-ethylphenyl)-4-(((3-hydroxycyclobutyl)methyl)amino)-N-isobutyl-3-(S-methylsulfonimidoyl)benzene-sulfonamide compound 61 | A | A |
| 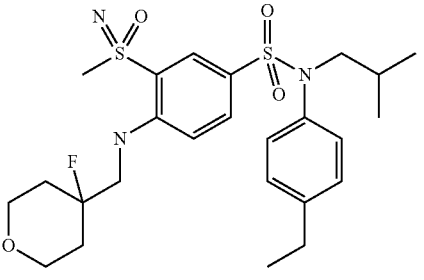 [SMILES: CCc1ccc(N(CC(C)C)S(=O)(=O)c2ccc(NCC3(F)CCOCC3)c(S(C)(=N)=O)c2)cc1] | N-(4-ethylphenyl)-4-(((4-fluorotetrahydro-2H-pyran-4-yl)methyl)amino)-N-isobutyl-3-(S-methylsulfonimidoyl)benzene-sulfonamide compound 62 | A | A |
| 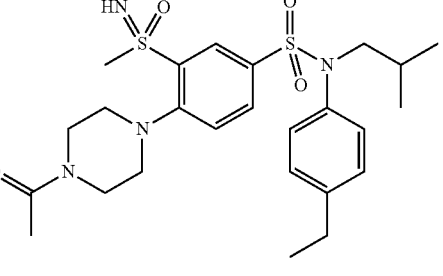 | 4-(4-acetylpiperazin-1-yl)-N-(4-ethylphenyl)-N-isobutyl-3-(S-methylsulfonimidoyl)benzene-sulfonamide compound 63 | B | C |

TABLE 2-continued

| | | IC50 hRORg | IC50 hCD4/IL17 |
|---|---|---|---|
| | N-(4-ethylphenyl)-N-isobutyl-3-(S-methylsulfonimidoyl)-4-((pyridin-4-ylmethyl)amino)benzene-sulfonamide compound 64 | A | A |
| | N-(4-ethylphenyl)-N-isobutyl-3-(S-methylsulfonimidoyl)-4-(2-morpholinoethyl)benzene-sulfonamide compound 65 | B | B |
| | 4-(tetrahydropyran-4-ylmethoxy)benzene-1,3-disulfonic acid 3-amide 1-[(4-ethylphenyl)isobutylamide] compound 66 | A | A |
| | 4-[(tetrahydropyran-4-ylmethyl)amino]benzene-1,3-disulfonic acid 3-amide 1-[(4-ethylphenyl)isobutylamide] compound 67 | B | ND |
| | N-(4-ethylphenyl)-N-isobutyl-4-(tetrahydropyran-4-ylmethylsulfanyl)benzene-sulfonamide compound 68 | B | B |

TABLE 2-continued

| | | IC50 hRORg | IC50 hCD4/IL17 |
|---|---|---|---|
| 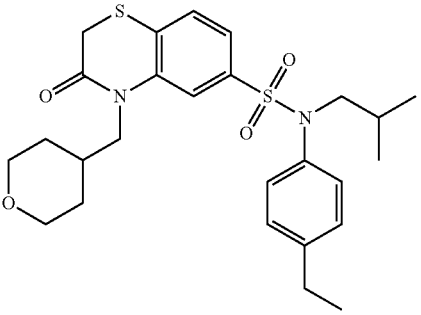 [SMILES: CCc1ccc(N(CC(C)C)S(=O)(=O)c2ccc3c(c2)N(CC2CCOCC2)C(=O)CS3)cc1] | 3-oxo-4-(tetrahydropyran-4-ylmethyl)-3,4-dihydro-2H-benzo[1,4]thiazine-7-sulfonic acid (4-ethylphenyl)isobutylamide compound 70 | C | ND |
| 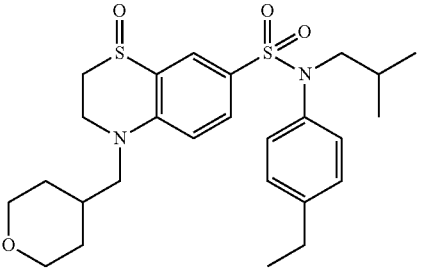 [SMILES: CCc1ccc(N(CC(C)C)S(=O)(=O)c2ccc3c(c2)S(=O)CCN3CC2CCOCC2)cc1] | 1-oxo-4-(tetrahydropyran-4-ylmethyl)-1,2,3,4-tetrahydro-1$\lambda^4$-benzo[1,4]thiazine-7-sulfonic acid (4-ethylphenyl)isobutylamide compound 71 | C | ND |
| 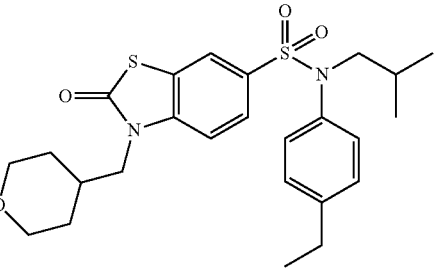 | 3-oxo-4-(tetrahydropyran-4-ylmethyl)-3,4-dihydro-2H-benzo[1,4]thiazine-7-sulfonic acid (4-ethylphenyl)isobutylamide compound 72 | B | ND |
| 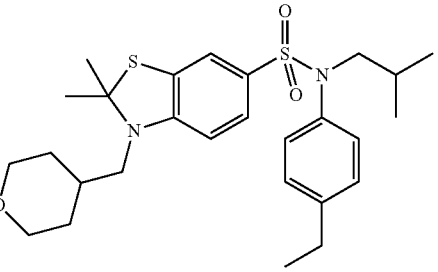 | 2,2-dimethyl-3-(tetrahydropyran-4-ylmethyl)-2,3-dihydrobenzothiazole-6-sulfonic acid (4-ethylphenyl)isobutylamide compound 73 | C | ND |
| 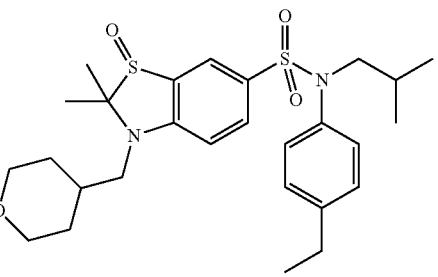 | 2,2-dimethyl-1-oxo-3-(tetrahydropyran-4-ylmethyl)-2,3-dihydro-1H-1$\lambda^4$-benzothiazole-6-sulfonic acid (4-ethylphenyl)isobutylamide compound 74 | B | ND |

TABLE 2-continued

| | | IC50 hRORg | IC50 hCD4/IL17 |
|---|---|---|---|
| 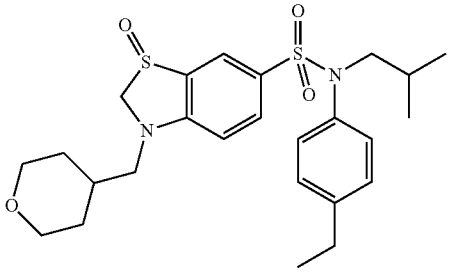 [SMILES: CCc1ccc(N(CC(C)C)S(=O)(=O)c2ccc3c(c2)S(=O)CN3CC2CCOCC2)cc1] | 1-oxo-3-(tetrahydropyran-4-ylmethyl)-2,3-dihydro-1H-1λ⁴-benzothiazole-6-sulfonic acid (4-ethylphenyl)isobutylamide compound 75 | C | ND |
| 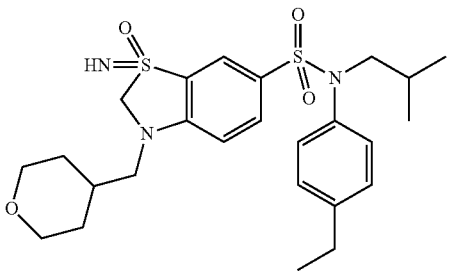 [SMILES: CCc1ccc(N(CC(C)C)S(=O)(=O)c2ccc3c(c2)S(=N)(=O)CN3CC2CCOCC2)cc1] | 1-imino-1-oxo-3-(tetrahydropyran-4-ylmethyl)-2,3-dihydro-1H-1λ⁶-benzothiazole-6-sulfonic acid (4-ethylphenyl)isobutylamide compound 76 | C | ND |
| 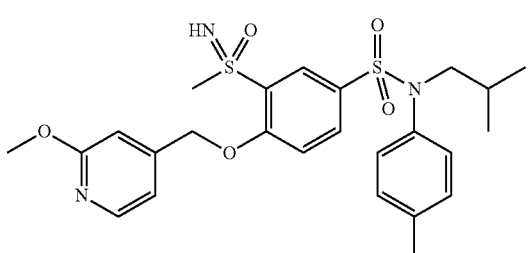 | N-(4-ethylphenyl)-N-isobutyl-4-((2-methoxypyridin-4-yl)methoxy)-3-(S-methylsulfonimidoyl)benzene-sulfonamide compound 77 | C | ND |
| 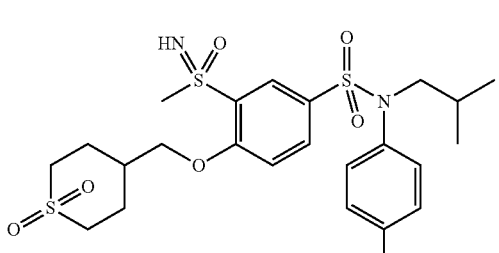 | N-(4-ethylphenyl)-N-isobutyl-4-((2-methoxypyridin-4-yl)methoxy)-3-(S-methylsulfonimidoyl)benzene-sulfonamide compound 78 | C | ND |
| 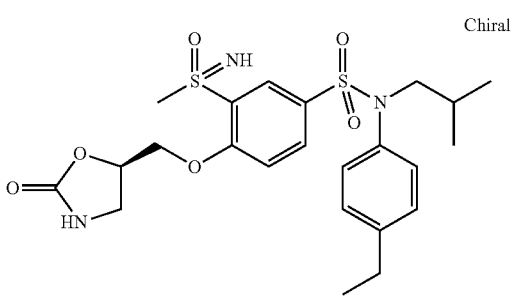 [SMILES: CCc1ccc(N(CC(C)C)S(=O)(=O)c2ccc(OC[C@H]3CNC(=O)O3)c(S(C)(=N)=O)c2)cc1] Chiral | N-(4-ethylphenyl)-N-isobutyl-3-(S-methylsulfonimidoyl)-4-(((R)-2-oxooxazolidin-5-yl)methoxy)benzene-sulfonamide compound 79 | C | ND |

TABLE 2-continued

| | | IC50 hRORg | IC50 hCD4/IL17 |
|---|---|---|---|
| 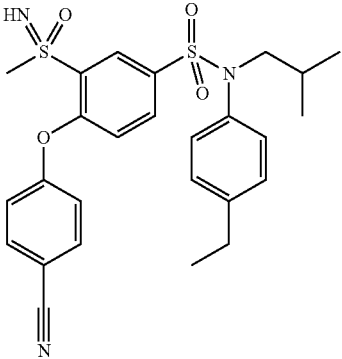 [SMILES: CCc1ccc(N(CC(C)C)S(=O)(=O)c2ccc(Oc3ccc(C#N)cc3)c(S(C)(=N)=O)c2)cc1] | 4-(4-cyanophenoxy)-N-(4-ethylphenyl)-N-isobutyl-3-(S-methylsulfonimidoyl)benzene-sulfonamide compound 80 | C | ND |
| 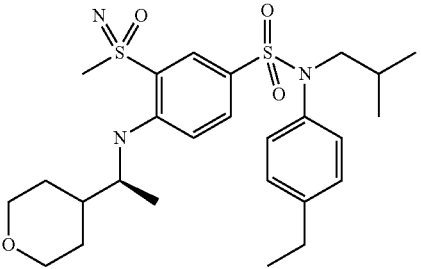 [SMILES: CCc1ccc(N(CC(C)C)S(=O)(=O)c2ccc(N[C@@H](C)C3CCOCC3)c(S(C)(=N)=O)c2)cc1] | N-(4-ethylphenyl)-N-isobutyl-3-(S-methylsulfonimidoyl)-4-(((S)-1-(tetrahydro-2H-pyran-4-yl)ethyl)amino)benzene-sulfonamide compound 81 | B | ND |
| 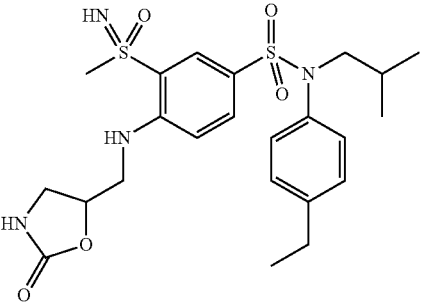 | N-(4-ethylphenyl)-N-isobutyl-3-(S-methylsulfonimidoyl)-4-(((2-oxooxazolidin-5-yl)methyl)amino)benzene-sulfonamide compound 82 | B | ND |
| 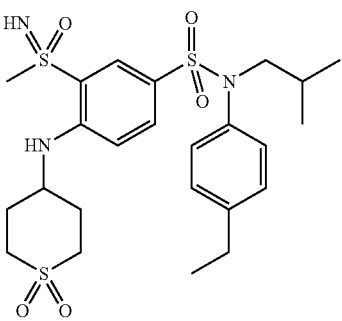 [SMILES: CCc1ccc(N(CC(C)C)S(=O)(=O)c2ccc(NC3CCS(=O)(=O)CC3)c(S(C)(=N)=O)c2)cc1] | 4-((1,1-dioxidotetrahydro-2H-thiopyran-4-yl)amino)-N-(4-ethylphenyl)-N-isobutyl-3-(S-methylsulfonimidoyl)benzene-sulfonamide compound 83 | C | ND |
| 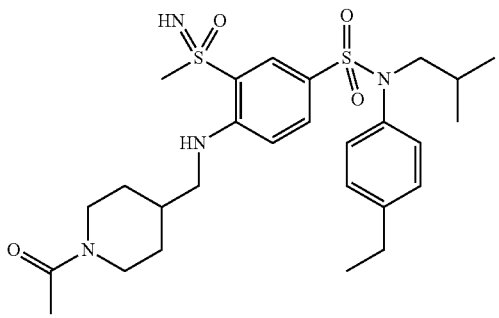 [SMILES: CCc1ccc(N(CC(C)C)S(=O)(=O)c2ccc(NCC3CCN(C(C)=O)CC3)c(S(C)(=N)=O)c2)cc1] | 4-(((1-acetylpiperidin-4-yl)methyl)amino)-N-(4-ethylphenyl)-N-isobutyl-3-(S-methylsulfonimidoyl)benzenesulfonamide compound 84 | C | ND |

TABLE 2-continued

| | | IC50 hRORg | IC50 hCD4/IL17 |
|---|---|---|---|
| 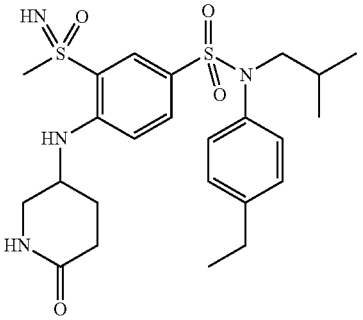 [SMILES: CCc1ccc(N(CC(C)C)S(=O)(=O)c2ccc(NC3CCC(=O)NC3)c(S(C)(=N)=O)c2)cc1] | N-(4-ethylphenyl)-N-isobutyl-3-(S-methylsulfonimidoyl)-4-((6-oxopiperidin-3-yl)amino)benzene-sulfonamide compound 85 | C | ND |
| 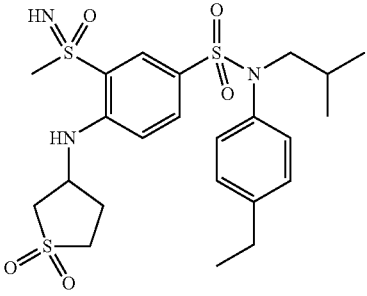 [SMILES: CCc1ccc(N(CC(C)C)S(=O)(=O)c2ccc(NC3CCS(=O)(=O)C3)c(S(C)(=N)=O)c2)cc1] | 4-((1,1-dioxidotetrahydrothio-phen-3-yl)amino)-N-(4-ethylphenyl)-N-isobuytl-3-(S-methylsulfonimidoyl)benzenesulfonamide compound 86 | B | ND |
| 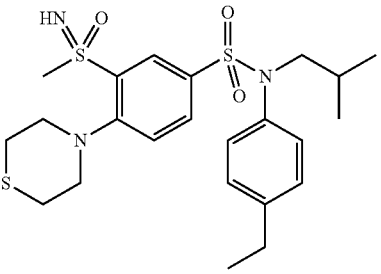 [SMILES: CCc1ccc(N(CC(C)C)S(=O)(=O)c2ccc(N3CCSCC3)c(S(C)(=N)=O)c2)cc1] | N-(4-ethylphenyl)-N-isobutyl-3-(S-methylsulfonimidoyl)-4-thiomorpholinobenzene-sulfonamide compound 87 | A | A |
| 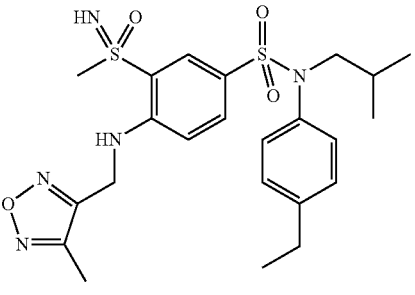 [SMILES: CCc1ccc(N(CC(C)C)S(=O)(=O)c2ccc(NCc3nonc3C)c(S(C)(=N)=O)c2)cc1] | N-(4-ethylphenyl)-N-isobutyl-4-(((4-methyl-1,2,5-oxadiazol-3-yl)methyl)amino)-3-(S-methylsulfonimidoyl)benzenesulfonamide compound 88 | C | ND |
| 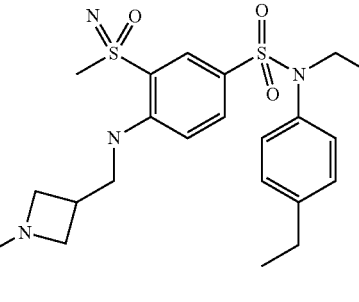 | methyl 3-(((4-(N-(4-ethylphenyl)-N-isobutylsulfamoyl)-2-(S-methylsulfonimidoyl)phenyl)amino)methyl)azetidine-1-carboxylate compound 89 | C | ND |

TABLE 2-continued

| | | IC50 hRORg | IC50 hCD4/IL17 |
|---|---|---|---|
| 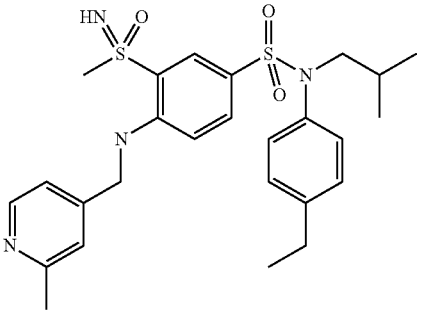 [SMILES: CCc1ccc(N(CC(C)C)S(=O)(=O)c2ccc(NCc3ccnc(C)c3)c(S(C)(=N)=O)c2)cc1] | N-(4-ethylphenyl)-N-isobutyl-4-(((2-methylpyridin-4-yl)methyl)amino)-3-(S-methylsulfonimidoyl)benzene-sulfonamide compound 90 | C | ND |
| 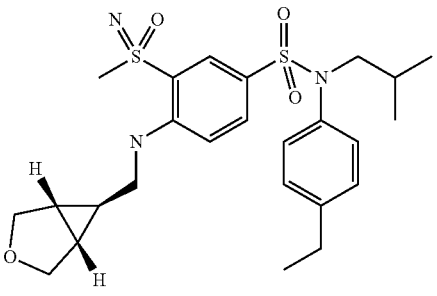 [SMILES: CCc1ccc(N(CC(C)C)S(=O)(=O)c2ccc(NC[C@@H]3[C@H]4COC[C@@H]34)c(S(C)(=N)=O)c2)cc1] | 4-((((1R,5S,6S)-3-oxabicyclo[3.1.0]hexan-6-yl)methyl)amino)-N-(4-ethylphenyl)-N-isobutyl-3-(S-methylsulfonimidoyl)benzene-sulfonamide compound 91 | A | A |
| 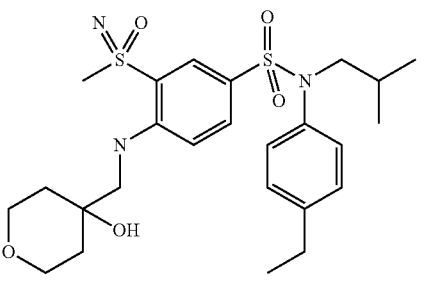 [SMILES: CCc1ccc(N(CC(C)C)S(=O)(=O)c2ccc(NCC3(O)CCOCC3)c(S(C)(=N)=O)c2)cc1] | N-(4-ethylphenyl)-4-(((4-hydroxytetrahydro-2H-pyran-4-yl)methyl)amino)-N-isobutyl-3-(S-methylsulfonimidoyl)benzenesulfonamide compound 92 | B | B |
| 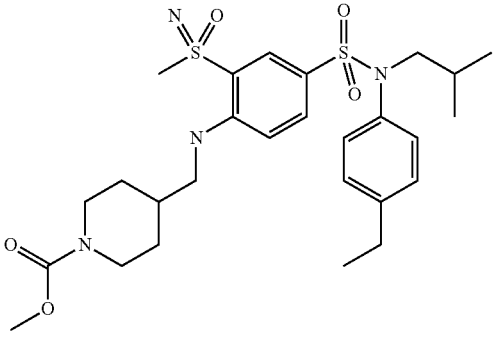 [SMILES: CCc1ccc(N(CC(C)C)S(=O)(=O)c2ccc(NCC3CCN(C(=O)OC)CC3)c(S(C)(=N)=O)c2)cc1] | methyl 4-(((4-(N-(4-ethylphenyl)-N-isobutylsulfamoyl)-2-(S-methylsulfonimidoyl)phenyl)amino)methyl)piperidine-1-carboxylate compound 93 | C | ND |

TABLE 2-continued

| | | IC50 hRORg | IC50 hCD4/IL17 |
|---|---|---|---|
| 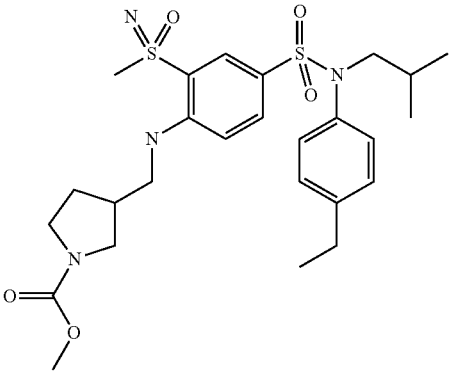 [SMILES: CCc1ccc(N(CC(C)C)S(=O)(=O)c2ccc(NCC3CCN(C(=O)OC)C3)c(S(C)(=N)=O)c2)cc1] | methyl 3-(((4-(N-(4-ethylphenyl)-N-isobutylsulfamoyl)-2-(S-methylsulfonimidoyl)phenyl)amino)methyl)pyrrolidine-1-carboxylate compound 94 | C | ND |
| 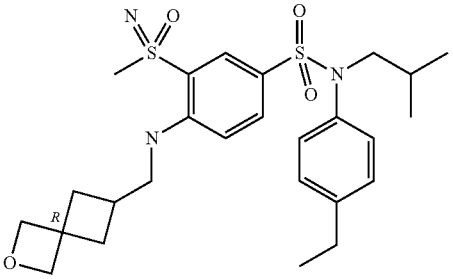 | 4-(((2-oxaspiro[3.3]heptan-6-yl)methyl)amino)-N-(4-ethylphenyl)-N-isobutyl-3-(S-methylsulfonimidoyl)benzene-sulfonamide compound 95 | B | B |
| 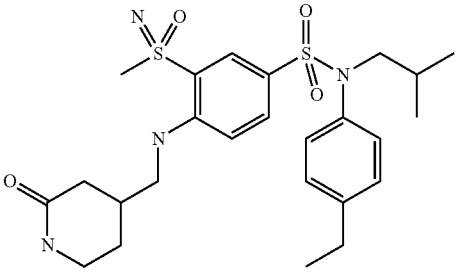 [SMILES: CCc1ccc(N(CC(C)C)S(=O)(=O)c2ccc(NCC3CCNC(=O)C3)c(S(C)(=N)=O)c2)cc1] | 4-N-(4-ethylphenyl)-N-isobutyl-3-(S-methylsulfonimidoyl)-4-(((2-oxopiperidin-4-yl)methyl)amino)benzene-sulfonamide compound 96 | C | ND |
| 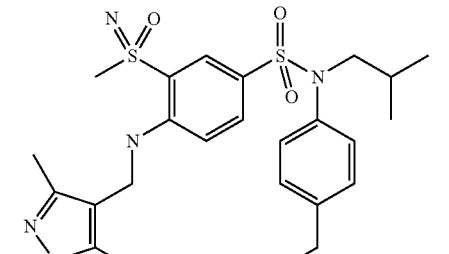 | 4-(((3,5-dimethylisoxazol-4-yl)methyl)amino)-N-(4-ethylphenyl)-N-isobutyl-3-(S-methylsulfonimidoyl)benzene-sulfonamide compound 97 | B | ND |
| 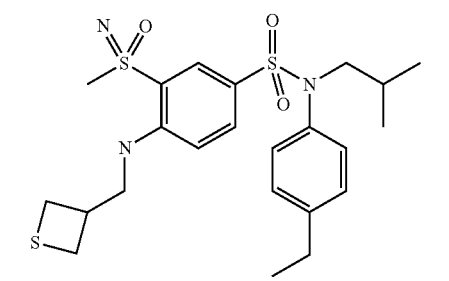 [SMILES: CCc1ccc(N(CC(C)C)S(=O)(=O)c2ccc(NCC3CSC3)c(S(C)(=N)=O)c2)cc1] | N-(4-ethylphenyl)-N-isobutyl-3-(S-methylsulfonimidoyl)-4-((thietan-3-ylmethyl)amino)benzene-sulfonamide compound 99 | A | A |

TABLE 2-continued

| | | | IC50 hRORg | IC50 hCD4/IL17 |
|---|---|---|---|---|
| 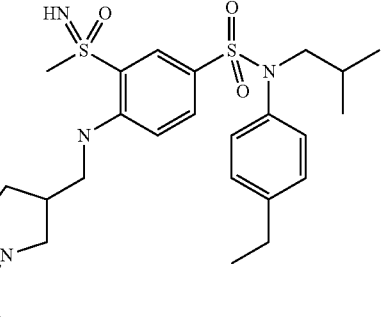 | | 4-(((1-acetylpyrrolidin-3-yl)methyl)amino)-N-(4-ethylphenyl)-N-isobutyl-3-(S-methylsulfonimidoyl)benzene-sulfonamide compound 100 | C | ND |
| 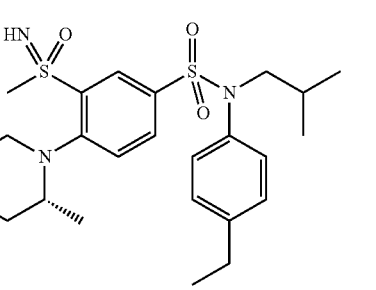 | | N-(4-ethylphenyl)-N-isobutyl-4-((R)-3-methylmorpholino)-3-(S-methylsulfonimidoyl)benzene-sulfonamide compound 103 | C | C |
| 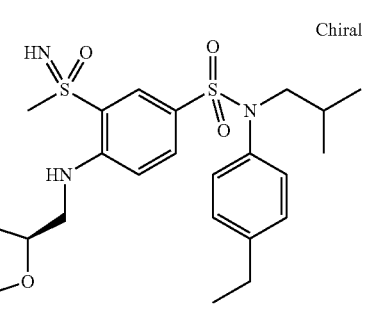 | Chiral | N-(4-ethylphenyl)-N-isobutyl-3-(S-methylsulfonimidoyl)-4-((((R)-2-oxooxazolidin-5-yl)methyl)amino)benzene-sulfonamide compound 105 | C | ND |
| 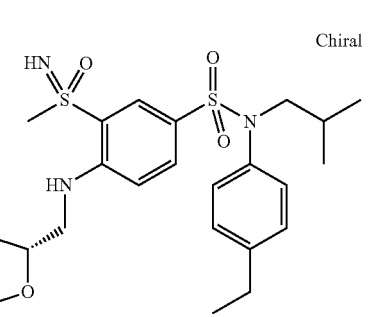 | Chiral | N-(4-ethylphenyl)-N-isobutyl-3-(S-methylsulfonimidoyl)-4-((((S)-2-oxooxazolidin-5-yl)methyl)amino)benzene-sulfonamide compound 106 | C | ND |
| 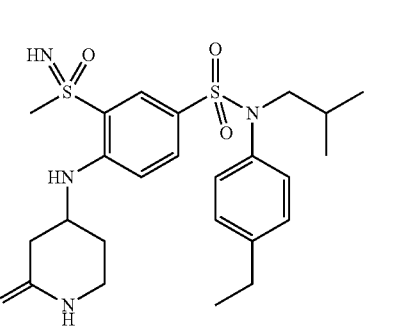 | | N-(4-ethylphenyl)-N-isobutyl-3-(S-methylsulfonimidoyl)-4-((2-oxopiperidin-4-yl)amino)benzene-sulfonamide compound 107 | C | ND |

TABLE 2-continued

| | | IC50 hRORg | IC50 hCD4/IL17 |
|---|---|---|---|
| | N-(4-ethylphenyl)-N-isobutyl-3-(S-methylsulfonimidoyl)-4-(2-oxa-6-azaspiro[3.5]nonan-6-yl)benzenesulfonamide compound 109 | C | ND |
| | tert-butyl 6-(4-(N-(4-ethylphenyl)-N-isobutylsulfamoyl)-2-(S-methylsulfonimidoyl)phenyl)-2,6-diazaspiro[3.3]heptane-2-carboxylate compound 110 | C | ND |
| | N-(4-ethylphenyl)-N-isobutyl-3-(S-methylsulfonimidoyl)-4-(2-oxa-6-azaspiro[3.3]heptan-6-yl)benzenesulfonamide compound 111 | A | ND |
| | N-(4-ethylphenyl)-N-isobutyl-3-(S-methylsulfonimidoyl)-4-(2-oxa-6-azaspiro[3.4]octan-6-yl)benzenesulfonamide compound 112 | B | A |
| | 4-(2,2-dioxido-2-thia-6-azaspiro[3.3]heptan-6-yl)-N-(4-ethylphenyl)-N-isobutyl-3-(S-methylsulfonimidoyl)benzenesulfonamide compound 113 | B | B |

TABLE 2-continued

| | | | IC50 hRORg | IC50 hCD4/IL17 |
|---|---|---|---|---|
| 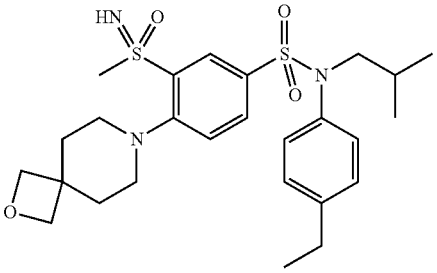 [SMILES: CCc1ccc(N(CC(C)C)S(=O)(=O)c2ccc(N3CCC4(CC3)COC4)c(S(C)(=N)=O)c2)cc1] | | N-(4-ethylphenyl)-N-isobutyl-3-(S-methylsulfonimidoyl)-4-(2-oxa-7-azaspiro[3.5]nonan-7-yl)benzenesulfonamide compound 114 | B | B |
| 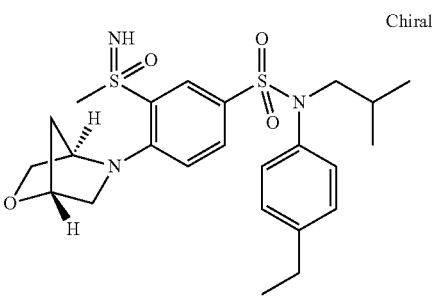 [SMILES: CCc1ccc(N(CC(C)C)S(=O)(=O)c2ccc(N3C[C@H]4C[C@@H]3CO4)c(S(C)(=N)=O)c2)cc1] | Chiral | 4-((1R,4R)-2-oxa-5-azabicyclo[2.2.1]heptan-5-yl)-N-(4-ethylphenyl)-N-isobutyl-3-(S-methylsulfonimidoyl)benzenesulfonamide compound 115 | B | ND |
| 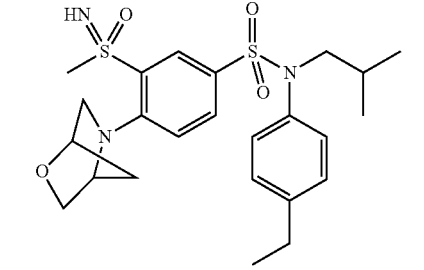 [SMILES: CCc1ccc(N(CC(C)C)S(=O)(=O)c2ccc(N3CC4CC3CO4)c(S(C)(=N)=O)c2)cc1] | | 4-((1R,4R)-2-oxa-5-azabicyclo[2.2.1]heptan-5-yl)-N-(4-ethylphenyl)-N-isobutyl-3-(S-methylsulfonimidoyl)benzenesulfonamide compound 117 | B | ND |
| 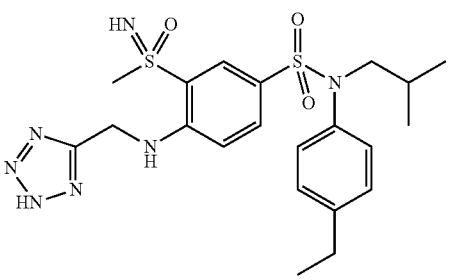 [SMILES: CCc1ccc(N(CC(C)C)S(=O)(=O)c2ccc(NCc3nn[nH]n3)c(S(C)(=N)=O)c2)cc1] | | 4-(((2H-tetrazol-5-yl)methyl)amino)-N-(4-ethylphenyl)-N-isobutyl-3-(S-methylsulfonimidoyl)benzenesulfonamide compound 118 | C | ND |
| 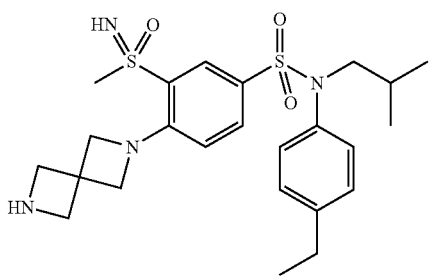 [SMILES: CCc1ccc(N(CC(C)C)S(=O)(=O)c2ccc(N3CC4(CNC4)C3)c(S(C)(=N)=O)c2)cc1] | | -(4-ethylphenyl)-N-isobutyl-3-(S-methylsulfonimidoyl)-4-(2,6-diazaspiro[3.3]heptan-2-yl)benzenesulfonamide compound 121 | C | ND |

TABLE 2-continued

| | | IC50 hRORg | IC50 hCD4/IL17 |
|---|---|---|---|
| 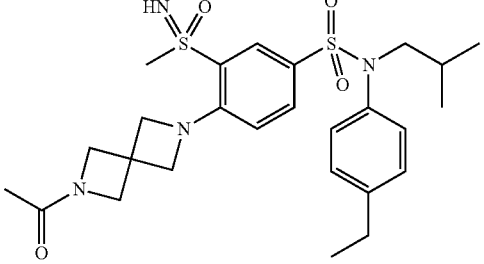 | 4-(6-acetyl-2,6-diazaspiro[3.3]heptan-2-yl)-N-(4-ethylphenyl)-N-isobutyl-3-(S-methylsulfonimidoyl)benzenesulfonamide compound 122 | C | ND |
| 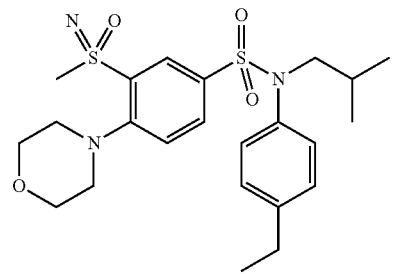 [SMILES: CCc1ccc(N(CC(C)C)S(=O)(=O)c2ccc(N3CCOCC3)c(S(C)(=N)=O)c2)cc1] | N-(4-ethylphenyl)-N-isobutyl-3-(S-methylsulfonimidoyl)-4-morpholinobenzene-sulfonamide compound 123 | A | A |
| 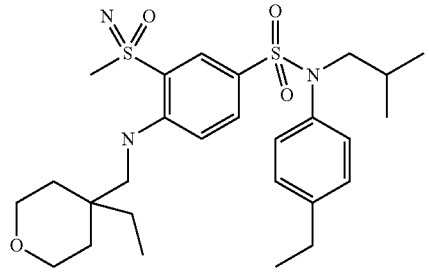 [SMILES: CCc1ccc(N(CC(C)C)S(=O)(=O)c2ccc(NCC3(CC)CCOCC3)c(S(C)(=N)=O)c2)cc1] | N-(4-ethylphenyl)-4-(((4-ethyltetrahydro-2H-pyran-4-yl)methyl)amino)-N-isobutyl-3-(S-methylsulfonimidoyl)benzenesulfonamide compound 124 | A | A |
| 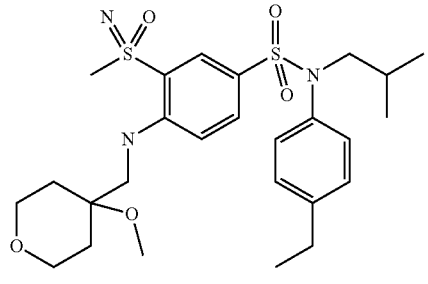 [SMILES: CCc1ccc(N(CC(C)C)S(=O)(=O)c2ccc(NCC3(OC)CCOCC3)c(S(C)(=N)=O)c2)cc1] | N-(4-ethylphenyl)-N-isobutyl-4-(((4-methoxytetrahydro-2H-pyran-4-yl)methyl)amino)-3-(S-methylsulfonimidoyl)benzenesulfonamide compound 125 | B | C |
| 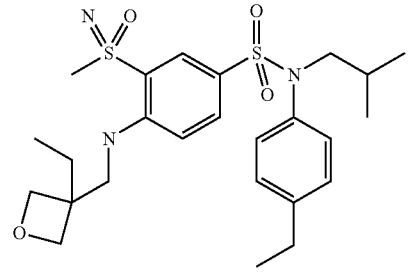 [SMILES: CCc1ccc(N(CC(C)C)S(=O)(=O)c2ccc(NCC3(CC)COC3)c(S(C)(=N)=O)c2)cc1] | 4-(((3-ethyloxetan-3-yl)methyl)amino)-N-(4-ethylphenyl)-N-isobutyl-3-(S-methylsulfonimidoyl)benzenesulfonamide compound 126 | C | ND |

TABLE 2-continued

| | | | IC50 hRORg | IC50 hCD4/IL17 |
|---|---|---|---|---|
| 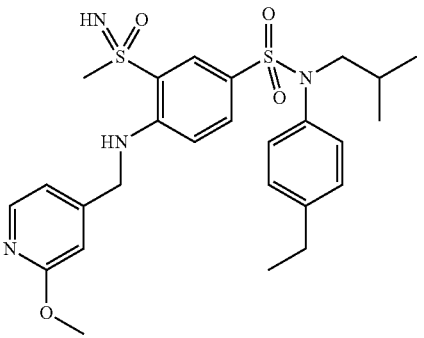 [SMILES: CCc1ccc(N(CC(C)C)S(=O)(=O)c2ccc(NCc3ccnc(OC)c3)c(S(C)(=N)=O)c2)cc1] | N-(4-ethylphenyl)-N-isobutyl-4-(((2-methoxypyridin-4-yl)methyl)amino)-3-(S-methylsulfonimidoyl)benzenesulfonamide compound 127 | | B | B |
| 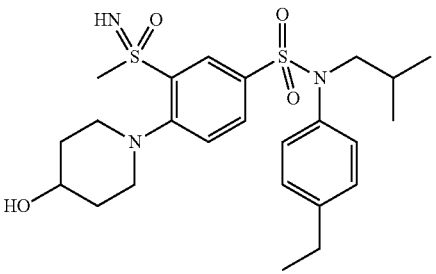 [SMILES: CCc1ccc(N(CC(C)C)S(=O)(=O)c2ccc(N3CCC(O)CC3)c(S(C)(=N)=O)c2)cc1] | N-(4-ethylphenyl)-4-(4-hydroxypiperidin-1-yl)-N-isobutyl-3-(S-methylsulfonimidoyl)benzenesulfonamide compound 128 | | C | C |
| 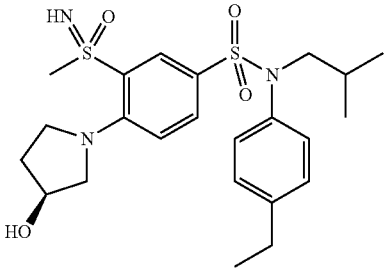 [SMILES: CCc1ccc(N(CC(C)C)S(=O)(=O)c2ccc(N3CC[C@H](O)C3)c(S(C)(=N)=O)c2)cc1] | N-(4-ethylphenyl)-4-((S)-3-hydroxypyrrolidin-1-yl)-N-isobutyl-3-(S-methylsulfonimidoyl)benzenesulfonamide compound 129 | | C | C |
| 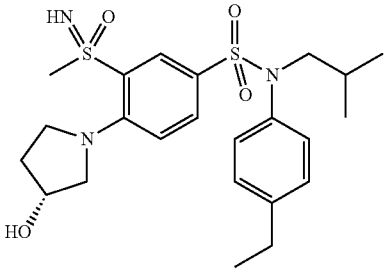 [SMILES: CCc1ccc(N(CC(C)C)S(=O)(=O)c2ccc(N3CC[C@@H](O)C3)c(S(C)(=N)=O)c2)cc1] | N-(4-ethylphenyl)-4-((R)-3-hydroxypyrrolidin-1-yl)-N-isobutyl-3-(S-methylsulfonimidoyl)benzenesulfonamide compound 130 | | C | C |
| 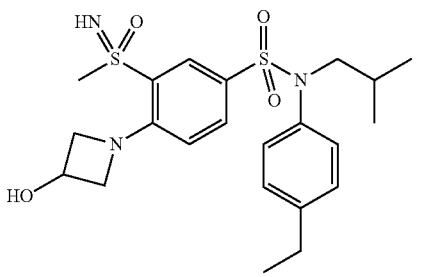 [SMILES: CCc1ccc(N(CC(C)C)S(=O)(=O)c2ccc(N3CC(O)C3)c(S(C)(=N)=O)c2)cc1] | N-(4-ethylphenyl)-4-(3-hydroxyazetidin-1-yl)-N-isobutyl-3-(S-methylsulfonimidoyl)benzenesulfonamide compound 131 | | C | C |

TABLE 2-continued

| | | IC50 hRORg | IC50 hCD4/IL17 |
|---|---|---|---|
| 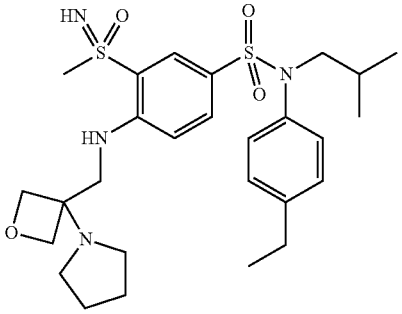 [SMILES: CCc1ccc(N(CC(C)C)S(=O)(=O)c2ccc(NCC3(N4CCCC4)COC3)c(S(C)(=N)=O)c2)cc1] | N-(4-ethylphenyl)-N-isobutyl-3-(S-methylsulfonimidoyl)-4-(((3-(pyrrolidin-1-yl)oxetan-3-yl)methyl)amino)benzene-sulfonamide compound 132 | C | ND |
| 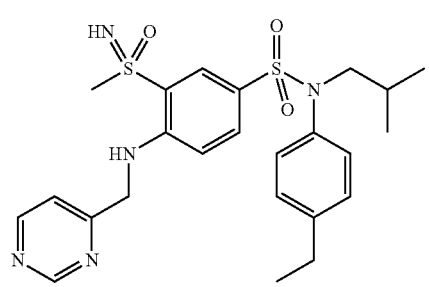 | N-(4-ethylphenyl)-N-isobutyl-3-(S-methylsulfonimidoyl)-4-((pyrimidin-4-ylmethyl)amino)benzene-sulfonamide compound 133 | A | A |
| 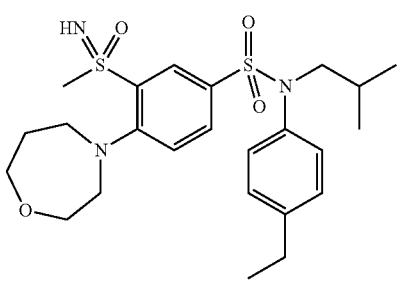 [SMILES: CCc1ccc(N(CC(C)C)S(=O)(=O)c2ccc(N3CCCOCC3)c(S(C)(=N)=O)c2)cc1] | N-(4-ethylphenyl)-N-isobutyl-3-(S-methylsulfonimidoyl)-4-(1,4-oxazepan-4-yl)benzenesulfonamide compound 137 | B | B |
| 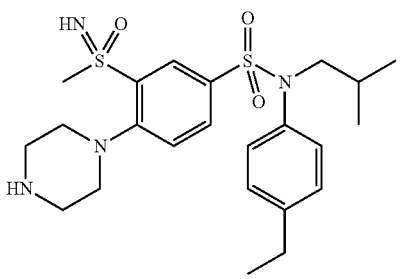 [SMILES: CCc1ccc(N(CC(C)C)S(=O)(=O)c2ccc(N3CCNCC3)c(S(C)(=N)=O)c2)cc1] | N-(4-ethylphenyl)-N-isobutyl-3-(S-methylsulfonimidoyl)-4-(piperazin-1-yl)benzenesulfonamide compound 140 | C | ND |
| 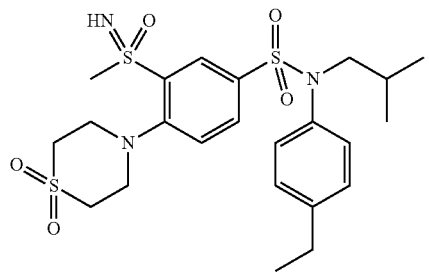 [SMILES: CCc1ccc(N(CC(C)C)S(=O)(=O)c2ccc(N3CCS(=O)(=O)CC3)c(S(C)(=N)=O)c2)cc1] | N-(4-ethylphenyl)-4-(((3-hydroxycyclobutyl)methyl)amino)-N-isobutyl-3-(S-methylsulfonimidoyl)benzenesulfonamide compound 141 | C | ND |

TABLE 2-continued

| | | | IC50 hRORg | IC50 hCD4/IL17 |
|---|---|---|---|---|
| 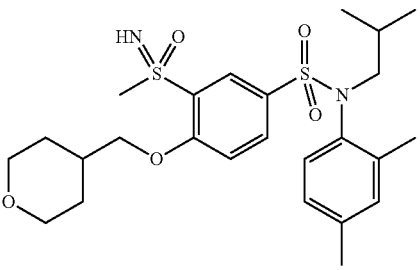 [SMILES: Cc1ccc(N(CC(C)C)S(=O)(=O)c2ccc(OCC3CCOCC3)c(S(C)(=N)=O)c2)c(C)c1] | N-(2,4-dimethylphenyl)-N-isobutyl-3-(S-methylsulfonimidoyl)-4-((tetrahydro-2H-pyran-4-yl)methoxy)benzene-sulfonamide compound 142 | | A | A |
| 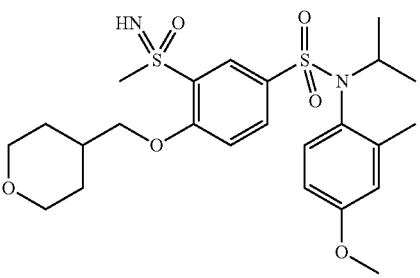 [SMILES: COc1ccc(N(C(C)C)S(=O)(=O)c2ccc(OCC3CCOCC3)c(S(C)(=N)=O)c2)c(C)c1] | N-isopropyl-N-(4-methoxy-2-methylphenyl)-3-(S-methylsulfonimidoyl)-4-((tetrahydro-2H-pyran-4-yl)methoxy)benzene-sulfonamide compound 143 | | B | B |

ND: not determined;
A: IC50 < 100 nM.;
B: IC50 = 100 nM-1 μM;
C: IC50 > 1 μM

In the tables described above, the median inhibitory concentrations $IC_{50}$ for the compounds belonging to formula (I) according to the invention have been given according to the following models:

GAL4-RORγ Transactivation

The RORγ transactivation model was developed from the line HG5LN, which is a HeLa line that stably expresses a luciferase reporter gene controlled by a pentamer of the GAL4 recognition domain of yeast and of a β-globin promoter. The HG5LN line was stably transfected by the DNA-binding domain (DBD) of GAL4 fused to the ROR gamma ligand-binding domain (LBD). Molecules that inhibit the ROR gamma constitutive activity reduce the luciferase expression, thus leading to a reduction in the emitted luminescence.

The cells are seeded in 384-well plates (5000 cells in 45 μL/well of culture medium containing 10% fetal calf serum) and incubated for 4 hours at 37° C., 5% $CO_2$. 5 μL of the test molecules (compounds described in the tables described above) are then added to each well and the plates are incubated for 18 hours at a temperature of 37° C. under 5% of $CO_2$. 20 μL of luciferase substrate (Promega) are added to each well and the luminescence emitted is read by a microplate reader.

The luminescence units ("RLU") are normalized by positive controls ("POS" containing a saturated concentration of benzenesulfonamide, N-(2,2,2-trifluoroethyl)-N-[4-[2,2,2-trifluoro-1-hydroxy-1-(trifluoromethyl)ethyl]phenyl]) and negative controls ("NEG" containing DMSO): % inhibition=((RLU−NEG)*100)/(POS−NEG). The IC50 values are calculated from a 4-parameter logistic model using the XLFit software (IDBS).

I L-17A Secretion

This model allows measurement of the effect of inhibitors on IL-17A secretion by CD4+ cells. The cells are frozen CD4+ cells (STEMCELL, #70026), isolated from peripheral human blood and activated with anti-CD3 and anti-CD28 antibodies. The amount of IL-17a secreted is measured by the TR-FRET (kit HTRF® Human Interleukin 17A (Cisbio, #64H17PEC)) technology.

The cells are rapidly thawed, resuspended in their culture medium (RPMI inactivated 10% FCS) supplemented with soluble anti-CD28 antibodies and seeded (100 000 cells/well) in 96-well plates precoated with anti-CD3 antibodies. The cells are then treated with the ranges of inhibitors to be tested (from 1000 nM to 0.05 nM, 0.1% DMSO). After 4 days of incubation, the HTRF signal is measured using a microplate reader (λexcitation=337 nm, λemission=620/665 nm). The ratios obtained (665/620) are normalized relative to the positive control (cells activated with anti-CD3 and anti-CD28, 0.1% DMSO). The $IC_{50}$ values are calculated from a 4-parameter logistic model using the XLFit software (IDBS).

In the table below, the median inhibitory concentrations $IC_{50}$ for the compounds belonging to formula (I) according to the invention have been given in accordance with the hERG test.

The hERG test makes it possible to study a gene which codes for a protein required for the functioning of heart tissue potassium channels. The patch clamp method on CHO-K1 cells (cells transfected with the hERG gene which has K+ ion activity on the membranes) is used for in vitro prediction of the blocking of hERG (human Ether-a-go-go Related).

The extracellular solution (control) is applied first. The cells (Chinese hamster ovarian cells expressing the Human Ether-a-go-go Related Gene) are stabilized with the extracellular solution for 5 minutes. The cells are incubated for 5 minutes with the molecules from the weakest to the strongest concentration at 0.6% DMSO final.

The method for calculating the inhibition for each concentration: % inhibition=100×(tail current amplitude of the incubated molecule−tail current amplitude of the control vehicle). The result is expressed in the form of an $IC_{50}$ value in μM.

The results are given for the following compounds:

| Compounds | | hERG IC50 |
|---|---|---|
| | N-(4-ethylphenyl)-N-isobutyl-3-methanesulfoximino-4-(tetrahydropyran-4-ylmethoxy)benzenesulfonamide compound 26 | >30 |
| 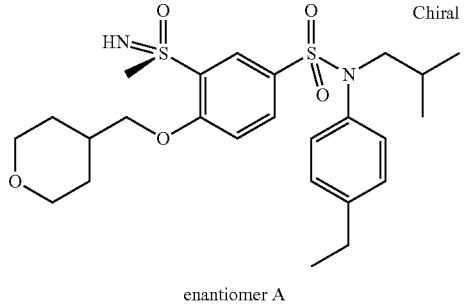 [SMILES: CCc1ccc(N(CC(C)C)S(=O)(=O)c2ccc(OCC3CCOCC3)c([S@](C)(=N)=O)c2)cc1] enantiomer A | compound 7, enantiomer A of compound 26 | >30 |
| 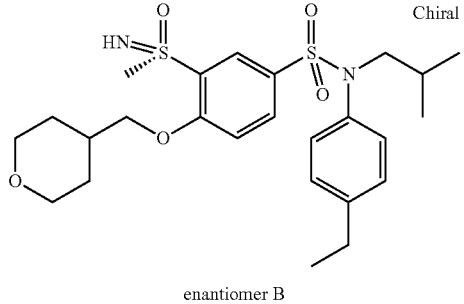 [SMILES: CCc1ccc(N(CC(C)C)S(=O)(=O)c2ccc(OCC3CCOCC3)c([S@@](C)(=N)=O)c2)cc1] enantiomer B | compound 8, enantiomer B of compound 26 | >30 |
| 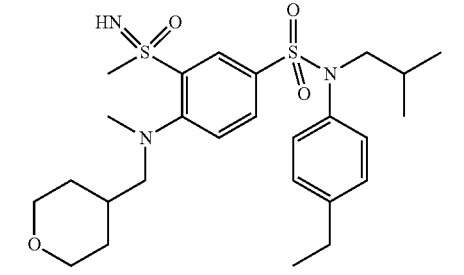 [SMILES: CCc1ccc(N(CC(C)C)S(=O)(=O)c2ccc(N(C)CC3CCOCC3)c(S(C)(=N)=O)c2)cc1] | N-(4-ethylphenyl)-N-isobutyl-4-(methyl((tetrahydro-2H-pyran-4-yl)methyl)amino)-3-(S-methylsulfonimidoyl)benzenesulfonamide compound 53 | 11.8 |
| | N-(4-ethylphenyl)-N-isobutyl-3-(S-methylsulfonimidoyl)-4-(pyridin-4-ylmethoxy)benzenesulfonamide compound 37 | 11.8 |
| 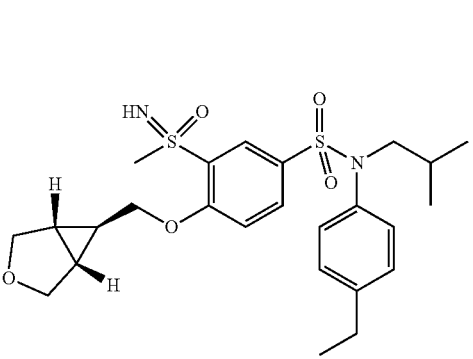 [SMILES: CCc1ccc(N(CC(C)C)S(=O)(=O)c2ccc(OC[C@H]3[C@@H]4COC[C@@H]43)c(S(C)(=N)=O)c2)cc1] | 4-(((1R,5S,6R)-3-oxabicyclo[3.1.0]hexan-6-yl)methoxy)-N-(4-ethylphenyl)-N-isobutyl-3-(S-methylsulfonimidoyl)benzenesulfonamide compound 35 | >30 |
| | N-(4-ethylphenyl)-N-isobutyl-3-(S-methylsulfonimidoyl)-4-(((4-methyltetrahydro-2H-pyran-4-yl)methyl)amino)benzenesulfonamide compound 55 | 14.1 |
| | N-(4-ethylphenyl)-4-(((3-hydroxycyclobutyl)methyl)amino)-N- | 25.7 |

-continued

| Compounds | hERG IC50 |
|---|---|
| isobutyl-3-(S-methylsulfonimidoyl)benzenesulfonamide compound 61 | |
| N-(4-ethylphenyl)-4-(((4-fluorotetrahydro-2H-pyran-4-yl)methyl)amino)-N-isobutyl-3-(S-methylsulfonimidoyl)benzenesulfonamide compound 62 | 16.4 |

Preferentially, the compound(s) of formula (I) according to the invention are chosen from the following compounds:

| Compounds | |
|---|---|
| 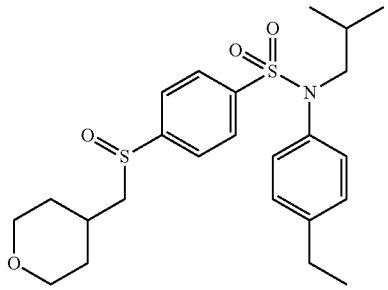 [SMILES: CCc1ccc(N(CC(C)C)S(=O)(=O)c2ccc(S(=O)CC3CCOCC3)cc2)cc1] | N-(4-ethylphenyl)-N-isobutyl-4-(tetrahydropyran-4-ylmethanesulfinyl)benzenesulfonamide compound 29 |
| 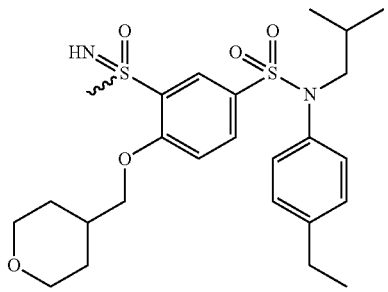 enantiomer A | enantiomer A of compound 7 |
| 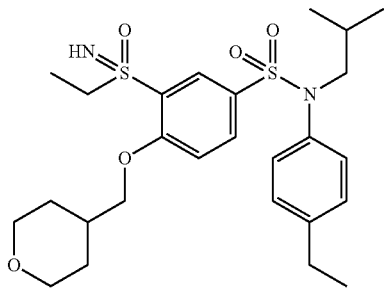 | N-(4-ethylphenyl)-N-isobutyl-3-ethanesulfoximino-4-(tetrahydropyran-4-ylmethoxy)benzenesulfonamide compound 18 |

| Compounds | |
|---|---|
| 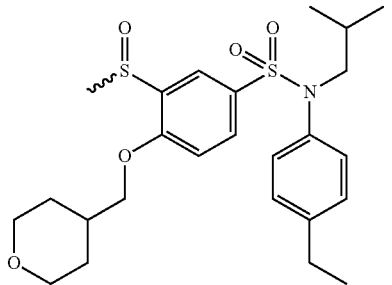<br>enantiomer A | N-(4-ethylphenyl)-N-isobutyl-3-methanesulfinyl-4-(tetrahydropyran-4-ylmethoxy)benzenesulfonamide<br>compound 19 |
| 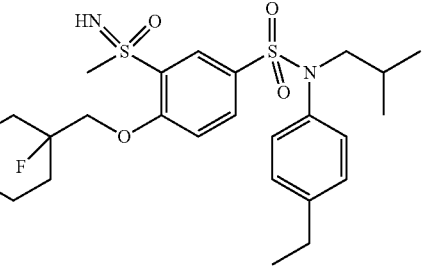 | N-(4-ethylphenyl)-4-((4-fluorotetrahydro-2H-pyran-4-yl)methoxy)-N-isobutyl-3-(S-methylsulfonimidoyl)benzenesulfonamide<br>compound 30 |
| 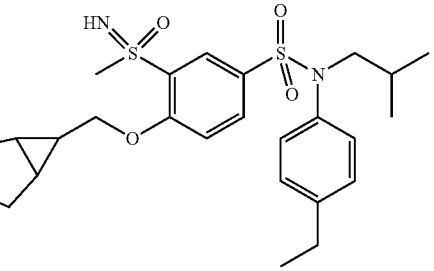 | 4-((3-oxabicyclo[3.1.0]hexan-6-yl)methoxy)-N-(4-ethylphenyl)-N-isobutyl-3-(S-methylsulfonimidoyl)benzenesulfonamide<br>compound 31 |
| 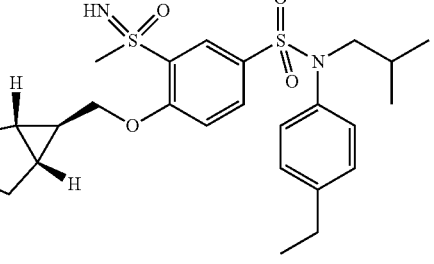 | 4-(((1R,5S,6R)-3-oxabicyclo[3.1.0]hexan-6-yl)methoxy)-N-(4-ethylphenyl)-N-isobutyl-3-(S-methylsulfonimidoyl)benzenesulfonamide<br>compound 35 |
| | N-(4-ethylphenyl)-N-isobutyl-3-(S-methylsulfonimidoyl)-4-(pyridin-4-ylmethoxy)benzenesulfonamide<br>compound 37<br>N-(4-ethylphenyl)-N-isobutyl-3-(S-methylsulfonimidoyl)-4-[(tetrahydropyran-4-ylmethyl)amino]benzenesulfonamide<br>compound 52 |

| Compounds | |
|---|---|
| [structure] | N-(4-ethylphenyl)-N-isobutyl-4-(methyl((tetrahydro-2H-pyran-4-yl)methyl)amino)-3-(S-methylsulfonimidoyl)benzenesulfonamide<br>compound 53 |
| | N-(4-ethylphenyl)-N-isobutyl-3-(S-methylsulfonimidoyl)-4-(((4-methyltetrahydro-2H-pyran-4-yl)methyl)amino)benzenesulfonamide<br>compound 55 |
| | N-(4-ethylphenyl)-4-(((3-hydroxycyclobutyl)methyl)amino)-N-isobutyl-3-(S-methylsulfonimidoyl)benzenesulfonamide<br>compound 61 |
| | N-(4-ethylphenyl)-4-(((4-fluorotetrahydro-2H-pyran-4-yl)methyl)amino)-N-isobutyl-3-(S-methylsulfonimidoyl)benzenesulfonamide<br>compound 62 |
| | :4-(4-acetylpiperazin-1-yl)-N-(4-ethylphenyl)-N-isobutyl-3-(S-methylsulfonimidoyl)benzenesulfonamide<br>compound 63 |
| | N-(4-ethylphenyl)-N-isobutyl-3-(S-methylsulfonimidoyl)-4-((pyridin-4-ylmethyl)amino)benzenesulfonamide<br>compound 64 |

The preferred compound(s) according to the invention have the advantage of having strong biological activity, in particular a median inhibitory concentration IC50 which is less than 100 nM in accordance with the GAL-4 RORγ transactivation test as described previously.

Furthermore, the preferred compound(s) according to the invention have the advantage of having low toxicity.

The invention also relates to the compound(s) as described previously, as medicament and cosmetic.

Preferably, the invention also relates to the compound(s) as described previously, as medicament.

Specifically, the compounds according to the invention have advantageous pharmacological properties, given that said compounds modulate, i.e. inhibit, the activity of the RORγt receptor.

Thus, these properties make the compound(s) of formula (I) as described previously usable as medicament in the treatment of diseases mediated by the RORγt receptor.

Preferably, the compound(s) according to the invention are used in the treatment of inflammatory disorders and/or autoimmune diseases mediated by the RORγt receptor.

More preferentially, the compound(s) according to the invention are used in the treatment of acne, psoriasis and/or atopic dermatitis.

According to one embodiment, compounds (1) to (76) are used in the treatment of acne, psoriasis and/or atopic dermatitis.

Preferably, compounds (7), (8), (18), (19), (26), (30), (31), (35), (37), (52), (53), (55), (61), (62), (63) and (64) are used in the treatment of acne, psoriasis and/or atopic dermatitis.

According to another embodiment, the compounds are used for cosmetic treatment of the skin.

As indicated above, the present invention also relates to a pharmaceutical composition comprising, in a pharmaceutically acceptable medium, one or more compounds of formula (I) as defined previously, pharmaceutically acceptable addition salts thereof, hydrates thereof and/or solvates thereof.

Preferably, the pharmaceutical composition comprises one or more compounds of formula (Ia) and/or (Ib) as defined previously, the pharmaceutically acceptable addition salts thereof, hydrates thereof and/or solvates thereof.

More preferentially, the pharmaceutical composition comprises one or more compounds of formula (Ia) or (Ib) chosen from compounds (1) to (143) defined previously.

Even more preferentially, the pharmaceutical composition comprises one or more compounds of formula (Ia) or (Ib) chosen from compounds (7), (8), (18), (19), (26), (30), (31), (35), (37), (52), (53), (55), (61), (62), (63) and (64).

The pharmaceutical composition according to the invention may be administered orally or topically.

Preferably, the pharmaceutical composition is conditioned in a form that is suitable for topical application.

Via the oral route, the composition may be in the form of tablets, gel capsules, coated tablets, syrups, suspensions, solutions, powders, granules, emulsions, suspensions of microspheres or nanospheres or lipid or polymeric vesicles allowing controlled release.

Via the topical route, the pharmaceutical composition according to the invention is more particularly intended for treating the skin and mucous membranes, and may be in liquid, pasty or solid form, and more particularly in the form of ointments, creams, milks, pomades, powders, impregnated pads, syndets, solutions, gels, sprays, mousses, suspensions, sticks, shampoos or washing bases. It may also be in the form of suspensions of microspheres or nanospheres or lipid or polymeric vesicles or of polymeric or gelled patches allowing controlled release.

The pharmaceutical composition is used for treating inflammatory disorders and/or autoimmune diseases mediated by the RORγt receptor.

More preferentially, the pharmaceutical composition is used in the treatment of acne, psoriasis or atopic dermatitis.

The invention also relates to a process for treating diseases mediated by the RORγt receptor, comprising the administration, especially topically or orally, of a therapeutically effective amount of the pharmaceutical composition as defined above to a patient.

Preferably, the pharmaceutical composition is applied topically.

In accordance with one embodiment, a subject of the present invention is also one or more compounds of formula (II), and also the pharmaceutically acceptable addition salts thereof, hydrates thereof and/or solvates thereof:

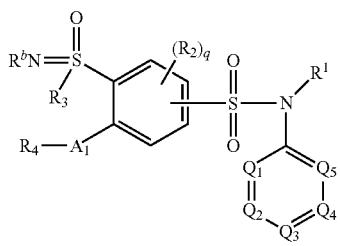

(II)

in which formula (II):
$R_3$ represents a $C_1$-$C_3$ alkyl radical,
$R^1$, $R_2$, $R'_2$, $R^4$, $R^5$, $R'^5$, $R^6$, $R^7$, $R^{7a}$, $R^{7b}$, $R_8$, $R_9$, $R_{10}$, $R^{11}$, $R^{12}$, $R^a$, $R^b$, Z, $Q_1$, $Q_2$, $Q_3$, $Q_4$, $Q_5$, $A_1$ and the indices q, n, m, o and p have the same meanings as in formula (I) described previously.

Preferably, $R^b$ represents a hydrogen atom or a $C_1$ alkyl radical.

Preferentially, $R^b$ represents a hydrogen atom.
Preferably, $R^3$ represents a $C_1$ alkyl radical.
Preferably, $R^1$ represents a linear or branched $C_3$-$C_5$ alkyl radical.

Preferentially, $R^4$ represents a group $(CHR^5)_n$—$(Z)_o$—$(CHR'^5)_p$—$R^6$ with $R^6$ preferably corresponding to an aromatic or heteroaromatic radical, a cycloalkyl radical or a heterocyclic radical as defined above in formula (I) or as previously.

Preferably, $Q^1$-$Q^2$ and $Q^4$-$Q^5$ correspond to a group —$CR'_2$ with $R^2$ denoting a hydrogen atom and $Q^3$ corresponds to a group —$CR'_2$ with $R'_2$ denoting a linear or branched $C_1$-$C_5$ and preferably $C_2$ alkyl radical.

Preferably, $Q^1$ and $Q^3$, which may be identical or different, correspond to a group —$CR'_2$ with $R'_2$ denoting a hydrogen atom or a linear or branched $C_1$-$C_5$ and preferably $C_2$ alkyl radical.

Preferably, the index q is equal to zero.

In particular, when the group $A_1$ represents a divalent group —$NR^a$, then $R^a$ and $R_4$ do not form, together with the nitrogen atom to which they are attached, a $C_2$-$C_{10}$ heterocycloalkyl group as defined in formula (I) described previously.

In accordance with one embodiment, preferably, $R^1$ represents a linear or branched $C_3$-$C_5$ alkyl radical and $R^b$ represents a hydrogen atom.

Preferably, the compound(s) of formula (II) are chosen from the compound(s) of formulae (IIa) and (IIb) below:

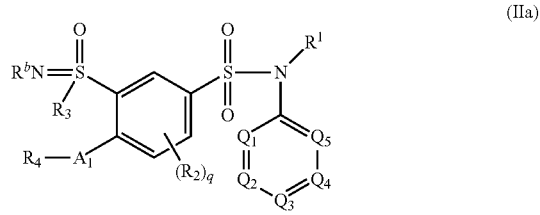

(IIa)

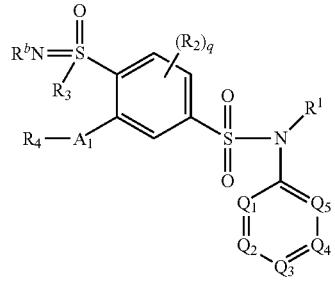

(IIb)

in which formulae (IIa) and (IIb) $R^1$, $R_2$, $R'_2$, $R^3$, $R^4$, $R^5$, $R'^5$, $R^6$, $R^7$, $R^{7a}$, $R^{7b}$, $R_8$, $R_9$, $R_{10}$, $R^{11}$, $R^{12}$, $R^a$, $R^b$, Z, $Q_1$, $Q_2$, $Q_3$, $Q_4$, $Q_5$, $A_1$ and the indices q, m, n, o and p have the same meanings as in formula (II) described previously.

Preferentially, the compound(s) of formula (III) are chosen from the compound(s) of formulae (IIa).

In accordance with this embodiment, the invention also relates to the compound(s) of formula (II), preferably of formulae (IIa) and (IIb), as medicament and cosmetic.

Preferentially, the invention relates to the compound(s) of formula (II), as medicament and cosmetic.

Preferentially, the invention relates to the compound(s) of formula (IIa), as medicament and cosmetic, especially as medicament.

In particular, the invention relates to the compound(s) of formula (II), preferably of formula (IIa), as medicament in the treatment of diseases mediated by the RORγt receptor, preferably the treatment of inflammatory disorders and/or autoimmune diseases mediated by the RORγt receptor.

More preferentially, the compound(s) of formula (II) according to the invention, preferably of formula (IIa), are used in the treatment of acne, psoriasis and/or atopic dermatitis.

In accordance with this embodiment, the present invention also relates to a pharmaceutical composition comprising, in a pharmaceutically acceptable medium, one or more compounds of formula (II) as defined previously, pharmaceutically acceptable addition salts thereof, hydrates thereof and/or solvates thereof.

The pharmaceutical composition is used for treating inflammatory disorders and/or autoimmune diseases mediated by the RORγt receptor, preferably for treating acne, psoriasis or atopic dermatitis.

The invention also relates to a process for treating diseases mediated by the RORγt receptor, comprising the administration, especially topically or orally, of a therapeutically effective amount of the pharmaceutical composition as defined above to a patient, in particular topically.

In accordance with another embodiment, a subject of the present invention is also one or more compounds of formula (III), and also the pharmaceutically acceptable addition salts thereof, hydrates thereof and/or solvates thereof:

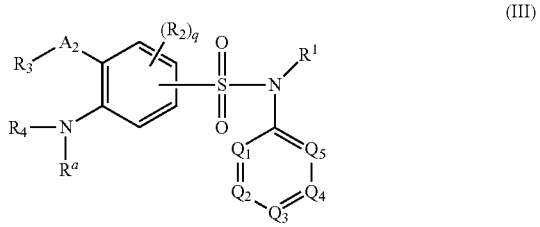

(III)

in which formula (III):

- $R^a$ and $R_4$ form, together with the nitrogen atom to which they are attached, a $C_2$-$C_{10}$ heterocycloalkyl group optionally comprising 1 to 3 heteroatoms chosen from a sulfur atom, a nitrogen atom and an oxygen atom; said heterocycloalkyl group being optionally substituted with at least one radical $R^{14}$,
- $R^{14}$ represents a linear or branched $C_1$-$C_3$ alkyl radical, a linear or branched $C_1$-$C_3$ alkoxy radical, a halogen atom, a hydroxyl group —OH, a cyano group —CN, a group —CONR$^{15}$R$^{16}$, a group —SO$_2$R$^{15}$, a group —COR$^{15}$ or an amino group —NR$^{15}$R$^{16}$; $R^{15}$ and $R^{16}$, which may be identical or different, representing a hydrogen atom or a linear or branched $C_1$-$C_3$ alkyl radical,
- $R^1$, $R_2$, $R'_2$, $R^3$, $R^b$, $Q_1$, $Q_2$, $Q_3$, $Q_4$, $Q_5$, $A_2$ and the index q have the same meanings as in formula (I) described previously.

Thus, $A_2$ does not represent the divalent group —CH(OH)— and —C(=O)O—.

In other words, in formula (III), $A_2$ represents a divalent group chosen from the following groups: —S—, —SO—, SO$_2$—, —SO(=N—R$^b$)—.

Preferably, $A_2$ represents a divalent group —SO(=N—R$^b$)—.

In particular, $R^a$ and $R_4$ form, together with the nitrogen atom to which they are attached, a monocyclic, bicyclic or spiro bicyclic $C_2$-$C_{10}$ heterocycloalkyl group as defined previously.

Preferably, $R^a$ and $R_4$ form, together with the nitrogen atom to which they are attached, a monocyclic or spiro bicyclic, in particular monocyclic, $C_2$-$C_{10}$ heterocycloalkyl group.

Preferably, $R^a$ and $R_4$ form, together with the nitrogen atom to which they are attached, a $C_2$-$C_{10}$ heterocycloalkyl group, said heterocycloalkyl group being optionally substituted with at least one radical $R^{14}$ as defined previously.

Preferably, the heterocycloalkyl group is optionally substituted with one, two or three radicals $R^{14}$ as defined previously.

In particular, the heterocycloalkyl group is substituted with a radical $R^{14}$ Preferably, $Q^1$-$Q^2$ and $Q^4$-$Q^5$ correspond to a group —CR$^2$ with $R^2$ denoting a hydrogen atom and $Q^3$ corresponds to a group —CR'$_2$ with R'$_2$ denoting a linear or branched $C_1$-$C_5$ and preferably $C_2$ alkyl radical.

Preferably, $Q^1$ and $Q^3$, which may be identical or different, correspond to a group —CR'$_2$ with R'$_2$ denoting a hydrogen atom or a linear or branched $C_1$-$C_5$ and preferably $C_2$ alkyl radical.

Preferably, the index q is equal to zero.

According to a particular case, $A_2$ represents a divalent group chosen from —S—, —SO— and SO$_2$—.

Preferably, the compound(s) of formula (III) are chosen from the compound(s) of formulae (IIIa) and (IIIb) below:

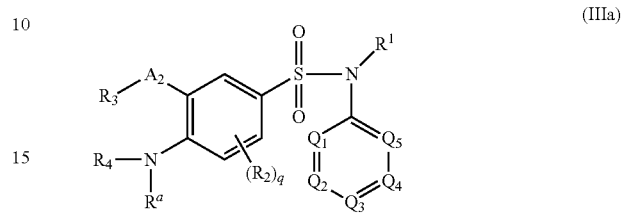

(IIIa)

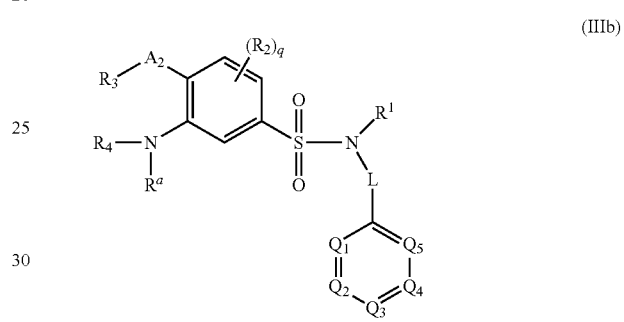

(IIIb)

in which formulae (IIIa) and (IIIb) $R^1$, $R_2$, $R'_2$, $R^3$, $R_4$, $R^a$, $R^b$, $Q_2$, $Q_3$, $Q_4$, $Q_5$, $A_2$ and the index q have the same meanings as in formula (III) described previously.

Preferentially, the compound(s) of formula (III) are chosen from the compound(s) of formulae (IIIa).

Preferably, the invention relates to the compound(s) of formula (III), preferably of formulae (IIIa) and (IIIb), as medicament and cosmetic.

Preferentially, the invention relates to the compound(s) of formula (IIIa), as medicament and cosmetic, especially as medicament.

In particular, the invention relates to the compound(s) of formula (III), preferably of formula (IIIa), as medicament in the treatment of diseases mediated by the RORγt receptor, preferably the treatment of inflammatory disorders and/or autoimmune diseases mediated by the RORγt receptor.

More preferentially, the compound(s) of formula (III), preferably of formula (IIIa), according to the invention are used in the treatment of acne, psoriasis and/or atopic dermatitis.

In accordance with this embodiment, the present invention also relates to a pharmaceutical composition comprising, in a pharmaceutically acceptable medium, one or more compounds of formula (III) as defined previously, pharmaceutically acceptable addition salts thereof, hydrates thereof and/or solvates thereof.

The pharmaceutical composition is used for treating inflammatory disorders and/or autoimmune diseases mediated by the RORγt receptor, preferably for treating acne, psoriasis or atopic dermatitis.

The invention also relates to a process for treating diseases mediated by the RORγt receptor, comprising the administration, especially topically or orally, of a therapeutically effective amount of the pharmaceutical composition as defined above to a patient, in particular topically.

The examples that follow serve to illustrate the invention without, however, being limiting in nature.

EXAMPLES

The standard LCMS method for analyzing the products is as follows: BEH $C_{18}$ standard column (150×2.1 mm, 1.8 μm) solvent: water/acetonitrile 0.1% formic acid.

The preparative HPLC purifications were performed on a $C_{18}$ column using, as eluent: 85% acetonitrile in water/0.1% formic acid.

The apparatus used for the chromatography is a 10-20 peak-solution machine, Chiraltechnologie Ic 25×5 micron column, (eluent phase: supercritical $CO_2$/methanol, flow rate 4 ml/minute).

The standard LCMS method for analyzing the products is as follows: BEH C18 150×2.1 mm, 1 μm column, solvent: water/acetonitrile 0.1% formic acid.

The preparative HPLC purifications were performed on a C18 column using, as eluent: 85% acetonitrile in water/0.1% formic acid.

Part I: Synthesis of the Sulfur-Based Sulfonamides
Via Reaction Scheme 1

Reaction scheme 1:
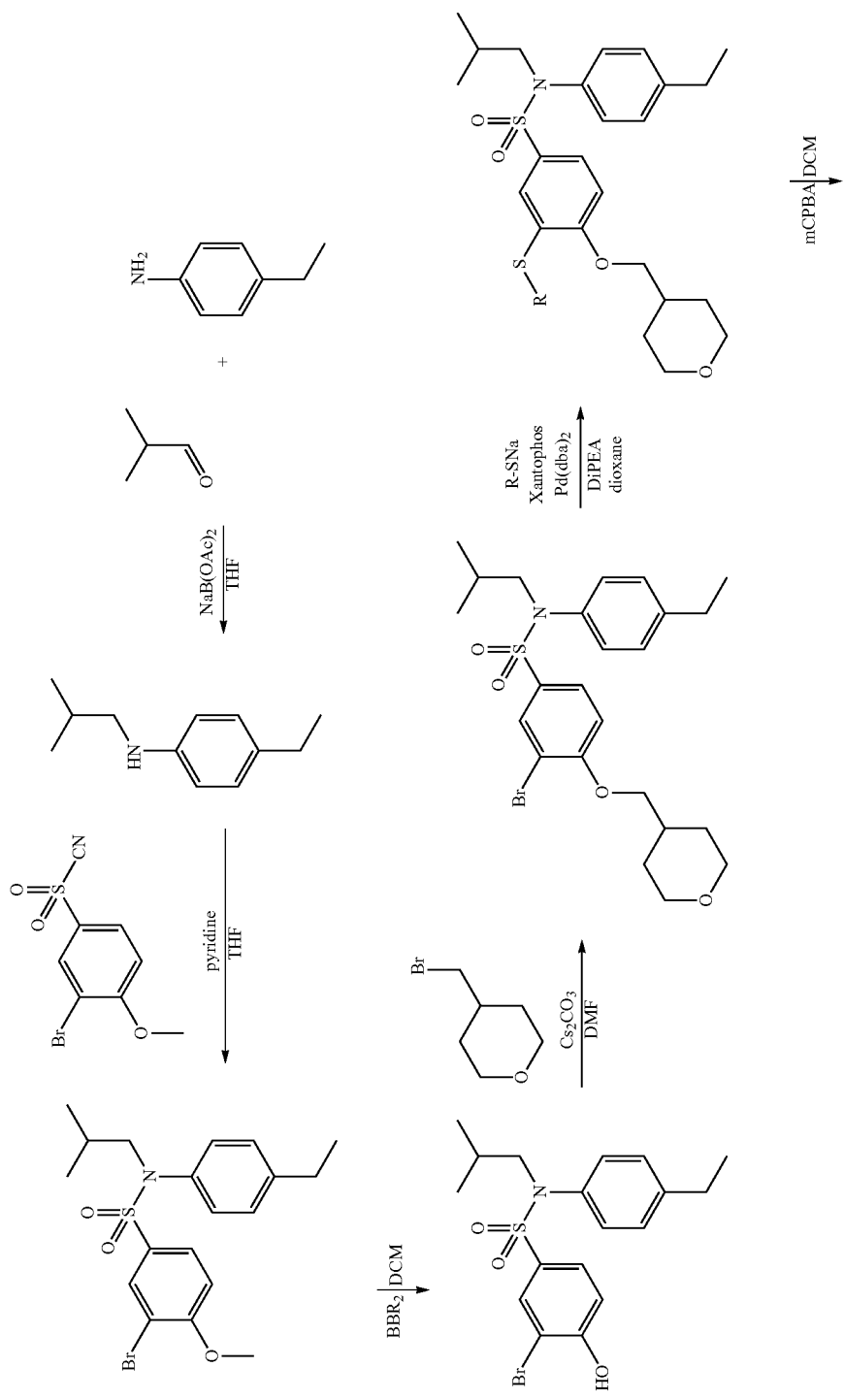

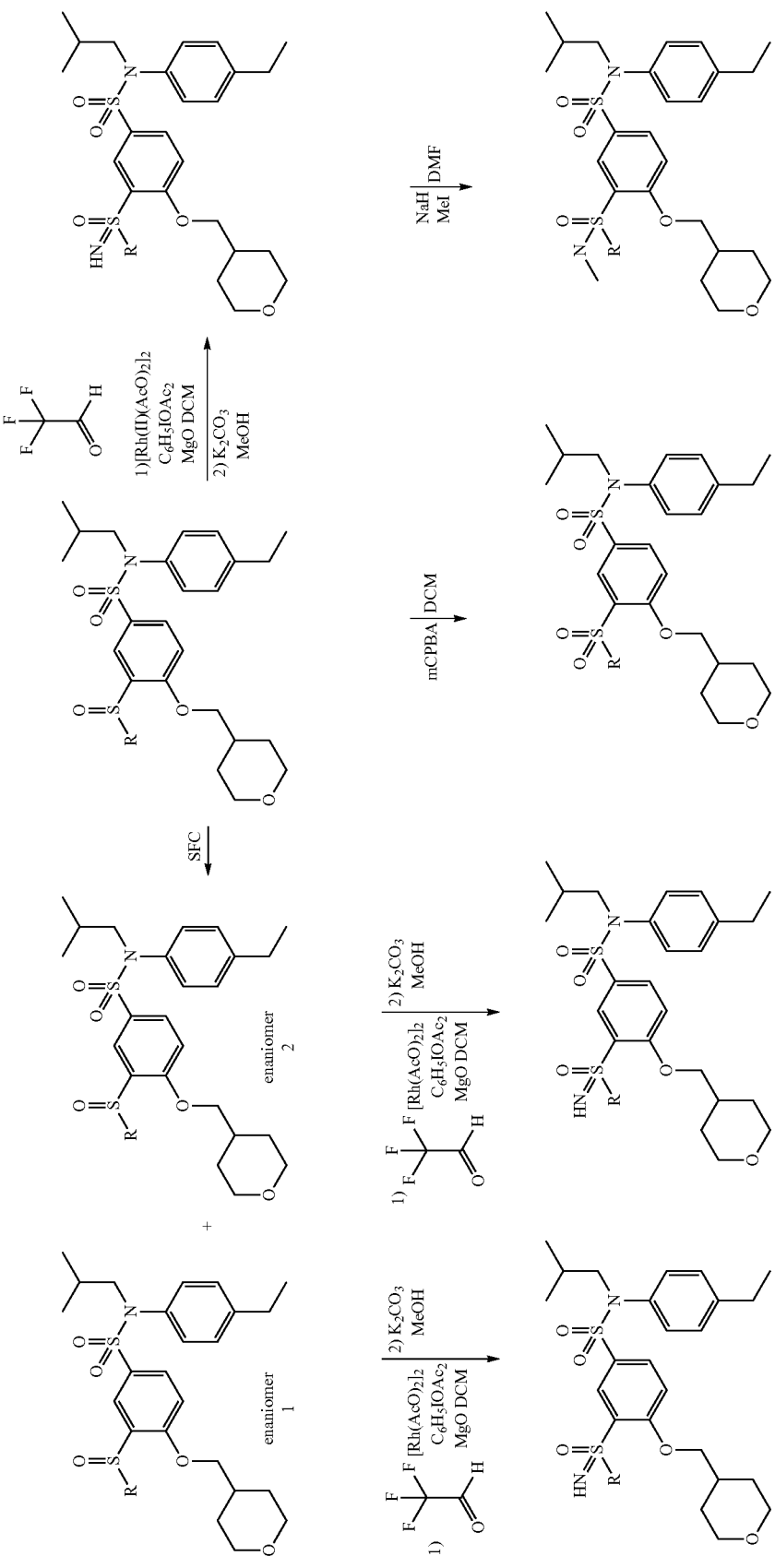

Example 1: Synthesis of N-(4-ethylphenyl)-N-isobutyl-3-methanesulfanyl-4-(tetrahydropyran-4-ylmethoxy)benzenesulfonamide

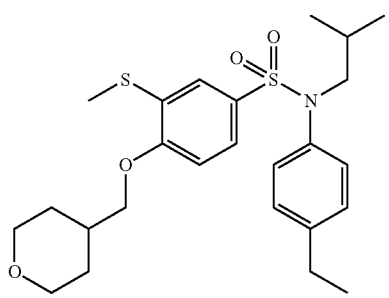

Compound 25

1. Synthesis of Intermediate 1.1

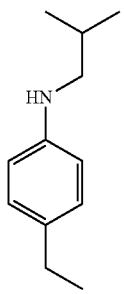

(4-ethylphenyl)isobutylamine

Isobutyraldehyde (6.33 ml; 0.07 mol) in tetrahydrofuran (100 ml) is added to 4-ethylaniline (9.48 ml; 0.08 mol). The mixture is stirred for 2 hours at room temperature. Sodium triacetoxyborohydride (22.04 g; 0.10 mol) is then added. The mixture is stirred overnight at room temperature, water (100 ml) is added and the resulting mixture is extracted with ethyl acetate (2×100 ml).

The organic phases are combined, washed with brine (100 ml), dried over $Na_2SO_4$ and concentrated. The crude product is chromatographed on silica gel (eluent: heptane/dichloromethane from 0 to 50% of dichloromethane). The (4-ethylphenyl)isobutylamine is obtained in the form of an orange oil with a compliant $^1H$ NMR.

MS: [M+H]=179

2. Synthesis of Intermediate 1.2

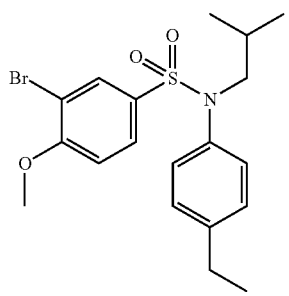 [SMILES: CCc1ccc(N(CC(C)C)S(=O)(=O)c2ccc(OC)c(Br)c2)cc1]

N-(4-ethylphenyl)-N-isobutyl-4-methoxybenzenesulfonamide

3-Bromo-4-methoxybenzenesulfonyl chloride (3.22 g; 11.28 mmol) is added to the (4-ethylphenyl)isobutylamine (2.00 g; 11.28 mmol) and pyridine (5.5 ml; 67.69 mmol) dissolved in tetrahydrofuran (40 ml). The reaction medium is stirred for 4 hours at room temperature, hydrolyzed and extracted with ethyl acetate. The organic phases are combined, washed with saturated $NH_4Cl$ solution and then with brine, dried ($Na_2SO_4$) and concentrated. The crude product is chromatographed on silica gel (eluent: heptane/ethyl acetate, from 0 to 20% of ethyl acetate). The N-(4-ethylphenyl)-N-isobutyl-4-methoxybenzenesulfonamide (1.63 g; 34%) is obtained in the form of a pale yellow oil with a compliant $^1H$ NMR.

MS: [M+H]=426

3. Synthesis of Intermediate 1.3

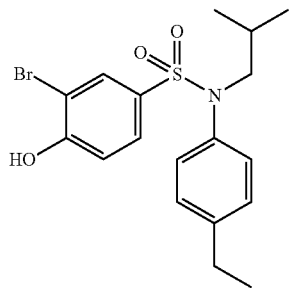 [SMILES: CCc1ccc(N(CC(C)C)S(=O)(=O)c2ccc(O)c(Br)c2)cc1]

3-Bromo-N-(4-ethylphenyl)-4-hydroxy-N-isobutylbenzenesulfonamide 1M boron tribromide in dichloromethane (5.6 ml; 5.63 mmol) is added slowly at a temperature of 0° C. to the 3-bromo-N-(4-ethylphenyl)-N-isobutyl-4-methoxybenzenesulfonamide (1.60 g; 3.75 mmol) dissolved in dichloromethane (32 ml). The reaction medium is allowed to return slowly to room temperature, stirred for 16 hours and hydrolyzed at a temperature of 0° C. and then extracted with dichloromethane. The organic phases are combined, washed with brine, dried ($Na_2SO_4$) and concentrated.

The crude product is chromatographed on silica gel (eluent: heptane/ethyl acetate, from 0 to 30% of ethyl acetate). The 3-bromo-N-(4-ethylphenyl)-4-hydroxy-N- isobutylbenzenesulfonamide (1.41 g; 91%) is obtained in the form of a beige-colored solid with a compliant ¹H NMR.

MS: [M+H]=414

4. Synthesis of Intermediate 1.4

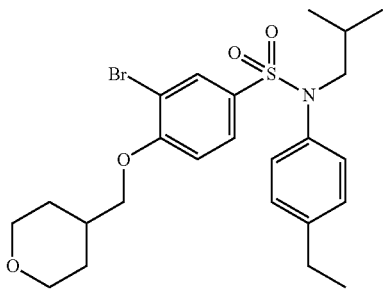 [SMILES: CCc1ccc(N(CC(C)C)S(=O)(=O)c2ccc(OCC3CCOCC3)c(Br)c2)cc1]

N-(4-ethylphenyl)-N-isobutyl-4-(tetrahydropyran-4-ylmethoxy)benzenesulfonamide 4-(Bromomethyl)tetrahydropyran (261 mg; 1.46 mmol) and cesium carbonate (790 mg; 2.43 mmol) are added to the 3-bromo-N-(4-ethylphenyl)-4-hydroxy-N-isobutylbenzenesulfonamide (500 mg; 1.21 mmol) dissolved in N,N-dimethylformamide (10 ml). The reaction medium is stirred for 2 hours at a temperature of 80° C., hydrolyzed and extracted with ethyl acetate. The organic phases are combined, washed with brine, dried ($Na_2SO_4$) and concentrated.

The crude product is chromatographed on silica gel (eluent: heptane/ethyl acetate, from 0 to 30% of ethyl acetate). The N-(4-ethylphenyl)-N-isobutyl-4-(tetrahydropyran-4-ylmethoxy)benzenesulfonamide (598 mg; 97%) is obtained in the form of a white solid with a compliant ¹H NMR.

MS: [M+H]=512

Example 1: Synthesis of Compound 25 According to the Invention

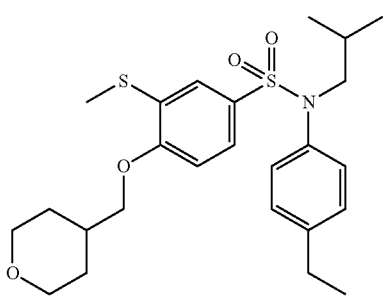 [SMILES: CCc1ccc(N(CC(C)C)S(=O)(=O)c2ccc(OCC3CCOCC3)c(SC)c2)cc1]

Bis(dibenzylideneacetone)palladium(0) (216 mg; 0.38 mmol) is added to a solution, degassed with argon for 15 minutes, of 3-bromo-N-(4-ethylphenyl)-N-isobutyl-4-(tetrahydropyran-4-ylmethoxy)benzenesulfonamide (480 mg; 0.94 mmol), N,N-diisopropylethylamine (490 μl; 2.82 mmol), 4,5-bis(diphenylphosphino)-9,9-dimethylxanthene (45 mg; 0.08 mmol) and sodium methanethiolate (264 mg; 3.76 mmol) in 1,4-dioxane (5 ml). The reaction medium is stirred for 3 hours at a temperature of 110° C., hydrolyzed and extracted with ethyl acetate. The organic phases are combined, washed with brine, dried ($Na_2SO_4$) and concentrated.

The crude product is chromatographed on silica gel (eluent: heptane/ethyl acetate, from 0 to 30% of ethyl acetate). The N-(4-ethylphenyl)-N-isobutyl-3-methylsulfanyl-4-(tetrahydropyran-4-ylmethoxy)benzenesulfonamide (335 g; 71%) is obtained in the form of a pale yellow solid.

¹H NMR (400 MHz, Chloroform-d) δ 7.41 (dd, J=8.4, 2.1 Hz, 1H), 7.19-7.11 (m, 2H), 7.08 (d, J=2.2 Hz, 1H), 7.04-6.95 (m, 2H), 6.83 (d, J=8.5 Hz, 1H), 4.07 (dt, J=11.5, 2.8 Hz, 2H), 3.95 (d, J=6.4 Hz, 2H), 3.49 (td, J=11.9, 2.1 Hz, 2H), 3.27 (d, J=7.3 Hz, 2H), 2.66 (q, J=7.6 Hz, 2H), 2.24-2.10 (m, 1H), 1.87-1.74 (m, 2H), 1.59 (s, 11H), 1.25 (t, J=7.6 Hz, 4H), 0.93 (d, J=6.7 Hz, 7H).

MS: [M+H]=478

Example 2: Synthesis of N-(4-ethylphenyl)-N-isobutyl-3-methanesulfinyl-4-(tetrahydropyran-4-ylmethoxy)benzenesulfonamide

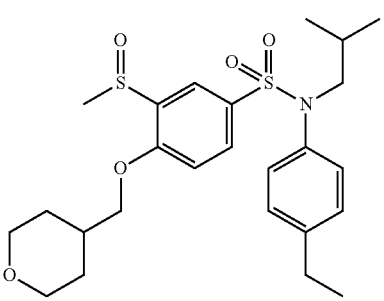

Compound 27

3-Chloroperoxybenzoic acid (0.17 g; 0.75 mmol) is added portionwise to a solution of N-(4-ethylphenyl)-N-isobutyl-3-methylsulfanyl-4-(tetrahydropyran-4-ylmethoxy)benzenesulfonamide (0.40 g; 0.84 mmol) in dichloromethane (8 ml) at 0° C. The reaction medium is stirred for 45 minutes, hydrolyzed with aqueous 10% $Na_2S_2O_3$ solution and extracted with dichloromethane. The organic phase is washed with 1N sodium hydroxide and then dried ($Na_2SO_4$), filtered and concentrated.

The crude product is chromatographed on silica gel (eluent: heptane/ethyl acetate, from 50 to 100% of ethyl acetate). The N-(4-ethylphenyl)-N-isobutyl-3-methanesulfinyl-4-(tetrahydropyran-4-ylmethoxy)benzenesulfonamide (0.24 g; 58%) is obtained in the form of a white solid.

¹H NMR (DMSO-$d_6$) δ: 0.85 (t, J=6.9 Hz, 6H), 1.18 (t, J=7.6 Hz, 3H), 1.28-1.48 (m, 3H), 1.65 (tdd, J=11.5, 4.0, 2.1 Hz, 2H), 2.61 (q, J=7.6 Hz, 2H), 2.74 (s, 3H), 3.21-3.40 (m, 5H), 3.90 (ddd, J=11.5, 4.9, 2.1 Hz, 2H), 4.00-4.15 (m, 2H), 6.94-7.02 (m, 2H), 7.15-7.23 (m, 2H), 7.33-7.35 (m, 1H) 7.64-7.73 (m, 2H)

MS: [M+H]=494

Compound 27: (550 mg; 1.11 mmol) is chromatographed by chiral SFC to separate the two enantiomers (compound 19 and compound 20) below:

Supercritical conditions 100 bar, 70° C.; Chiralpak IC 250×4.6 mm 5μ column]

Example 3: N-(4-ethylphenyl)-N-isobutyl-3-methanesulfinyl-4-(tetrahydropyran-4-ylmethoxy)benzenesulfonamide (Compound 19)—Enantiomer A of Compound 27

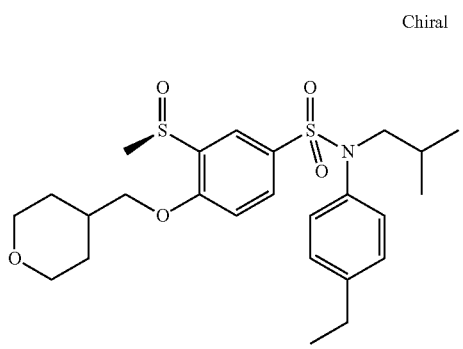 [SMILES: CCc1ccc(N(CC(C)C)S(=O)(=O)c2ccc(OCC3CCOCC3)c([S@@](C)=O)c2)cc1]

(311 mg; 56%) in the form of a white solid $^1$H NMR (Chloroform-d) δ: 0.86-0.96 (m, 6H), 1.23 (t, J=7.6 Hz, 3H), 1.40-1.65 (m, 7H), 1.65-1.87 (m, 2H), 2.11 (s, 1H), 2.63 (q, J=7.6 Hz, 2H), 2.77 (s, 2H), 3.22-3.34 (m, 1H), 3.36-3.45 (m, 1H), 3.48 (dd, J=11.9, 2.2 Hz, 1H), 3.89-4.09 (m, 4H), 6.88 (d, J=8.6 Hz, 1H), 6.94-7.01 (m, 2H), 7.09-7.16 (m, 2H), 7.57 (dd, J=8.6, 2.4 Hz, 1H), 8.16 (d, J=2.3 Hz, 1H)

Retention time (chiral SFC) of 6.0 minutes

Example 4: N-(4-ethylphenyl)-N-isobutyl-3-methanesulfinyl-4-(tetrahydropyran-4-ylmethoxy)benzenesulfonamide (Compound 20)–Enantiomer B of Compound 27

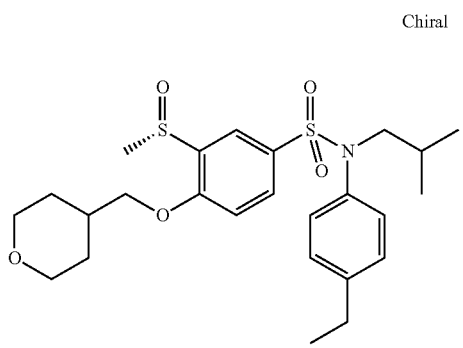 [SMILES: CCc1ccc(N(CC(C)C)S(=O)(=O)c2ccc(OCC3CCOCC3)c([S@](C)=O)c2)cc1]

(240 mg; 44%) in the form of a white solid $^1$H NMR (Chloroform-d) δ: 0.91 (dd, J=13.3, 6.7 Hz, 6H), 1.23 (t, J=7.6 Hz, 4H), 1.39-1.64 (m, 7H), 1.66-1.79 (m, 2H), 2.02-2.20 (m, 1H), 2.63 (q, J=7.7 Hz, 2H), 2.77 (s, 3H), 3.27 (dd, J=12.9, 6.8 Hz, 1H), 3.36-3.52 (m, 3H), 3.87-4.10 (m, 4H), 6.88 (d, J=8.6 Hz, 1H), 6.94-7.02 (m, 2H), 7.09-7.16 (m, 2H), 7.57 (dd, J=8.6, 2.3 Hz, 1H), 8.16 (d, J=2.3 Hz, 1H)

Retention time (chiral SFC) of 9.9 minutes

Example 5: Synthesis of N-(4-ethylphenyl)-N-isobutyl-3-methanesulfoximino-4-(tetrahydropyran-4-ylmethoxy)benzenesulfonamide

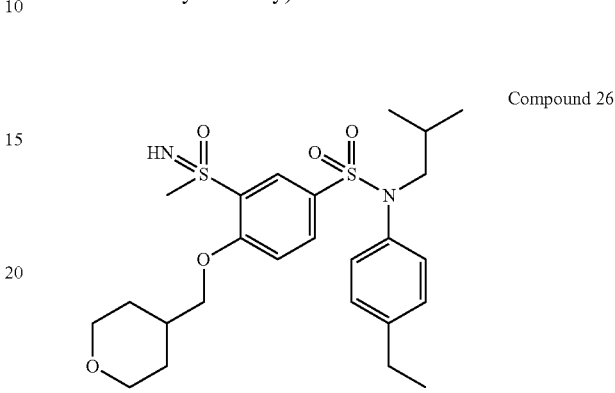

Compound 26

2,2,2-Trifluoroacetamide (0.13 g; 1.16 mmol), magnesium oxide (0.09 g; 2.33 mmol), rhodium(II) acetate dimer (31 mg; 0.07 mmol) and iodobenzene diacetate (0.29 g; 0.89 mmol) are added to a solution, degassed beforehand with argon, of N-(4-ethylphenyl)-N-isobutyl-3-methanesulfinyl-4-(tetrahydropyran-4-ylmethoxy)benzenesulfonamide (0.23 g; 0.47 mmol) in dichloromethane (8 ml). The reaction medium is stirred for 4 hours 30 minutes, filtered through Celite and concentrated.

The residue is diluted in methanol (8 ml) and potassium carbonate (0.32 g; 2.33 mmol) is added. The reaction medium is stirred for 30 minutes, hydrolyzed and extracted with ethyl acetate. The organic phases are combined, dried (Na$_2$SO$_4$), filtered and concentrated.

The crude product is purified by preparative HPLC. The N-(4-ethylphenyl)-N-isobutyl-3-methanesulfoximino-4-(tetrahydropyran-4-ylmethoxy)benzenesulfonamide (0.08 g; 34%) is obtained in the form of a white solid.

$^1$H NMR (DMSO-d$_6$) δ: 0.84 (d, J=4.5 Hz, 3H), 0.86 (d, J=4.4 Hz, 3H), 1.18 (t, J=7.6 Hz, 3H), 1.27-1.58 (m, 3H), 1.66-1.83 (m, 2H), 2.02-2.21 (m, 1H), 2.61 (q, J=7.6 Hz, 2H), 3.19 (d, J=1.2 Hz, 3H), 3.24-3.39 (m, 4H), 3.83-3.96 (m, 2H), 4.11 (dd, J=6.2, 2.5 Hz, 2H), 4.41 (d, J=1.5 Hz, 1H), 7.01 (d, J=8.3 Hz, 2H), 7.21 (d, J=8.4 Hz, 2H), 7.39 (d, J=8.8 Hz, 1H), 7.67 (dd, J=8.8, 2.4 Hz, 1H), 8.00 (d, J=2.4 Hz, 1H)

MS: [M+H]=509

A procedure similar to that applied to compound 26 to obtain compounds 19 and 20 is performed so as to obtain compounds 7 and 8 (enantiomers of compound 26).

Example 6: N-(4-ethylphenyl)-N-isobutyl-3-(methanesulfinyl)-4-(tetrahydropyran-4-ylmethoxy)benzenesulfoximine (Compound 7)—Enantiomer A of Compound 26

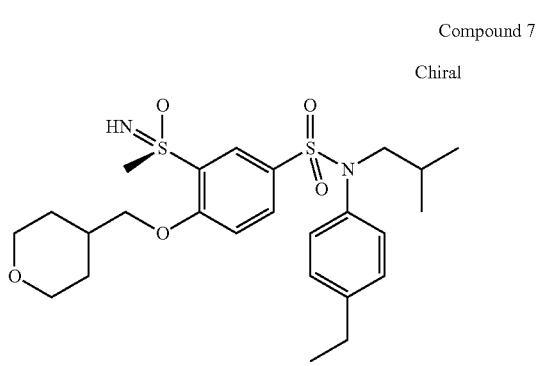

Compound 7
Chiral

Same procedure as for example 3, on example 4 (213 mg; 0.43 mmol). The N-(4-ethylphenyl)-N-isobutyl-3-((S)-methanesulfinyl)-4-(tetrahydropyran-4-ylmethoxy)benzenesulfoximine (20 mg; 9%) is obtained in the form of a beige-colored solid with a compliant ¹H NMR.

MS: [M+H]=509

Example 7: N-(4-ethylphenyl)-N-isobutyl-3-(methanesulfinyl)-4-(tetrahydropyran-4-ylmethoxy)benzenesulfoximine (Compound 8)—Enantiomer B of Compound 26

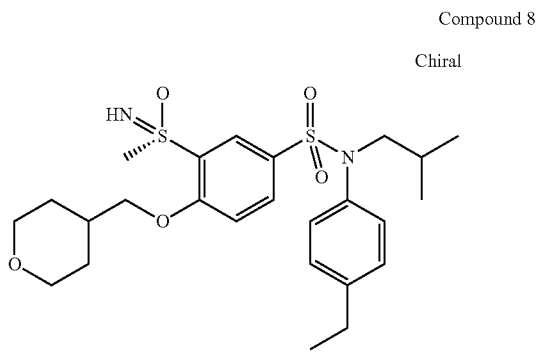

Compound 8
Chiral

Same procedure as for example 3, on example 5 (132 mg; 0.27 mmol). The N-(4-ethylphenyl)-N-isobutyl-3-((R)-methanesulfinyl)-4-(tetrahydropyran-4-ylmethoxy)benzenesulfoximine (11 mg; 9%) is obtained in the form of an off-white solid with a compliant ¹H NMR.

MS: [M+H]=509

Example 8: Synthesis of N-(4-ethylphenyl)-N-isobutyl-3-methanesulfinyl-4-(tetrahydropyran-4-ylmethoxy)benzene-N-methylsulfoximine

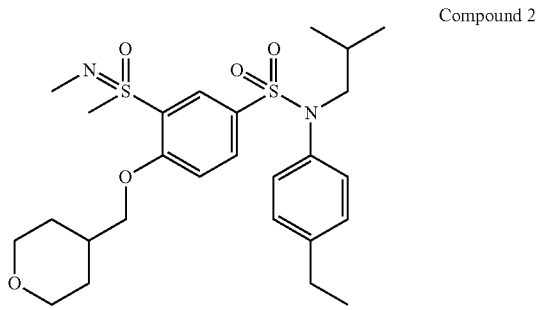 [SMILES: CCc1ccc(N(CC(C)C)S(=O)(=O)c2ccc(OCC3CCOCC3)c(S(C)(=O)=NC)c2)cc1]

Compound 2

60% sodium hydride (9.2 mg; 0.23 mmol) is added portionwise to a solution at 0° C. of N-(4-ethylphenyl)-N-isobutyl-3-(methanesulfinyl)-4-(tetrahydropyran-4-ylmethoxy)benzenesulfoximine (90 mg; 0.18 mmol) in N,N-dimethylformamide (1.8 ml). The reaction medium is stirred for 20 minutes at a temperature of 0° C., and iodomethane (22 µl; 0.35 mmol) is then added dropwise. The reaction medium is stirred for 20 hours at room temperature, hydrolyzed and extracted with ethyl acetate.

The organic phases are combined, washed with brine, dried ($Na_2SO_4$) and concentrated, and the crude product is chromatographed on silica gel (eluent: dichloromethane/methanol from 0 to 5% of methanol).

The N-(4-ethylphenyl)-N-isobutyl-3-methanesulfinyl-4-(tetrahydropyran-4-ylmethoxy)benzene-N-methylsulfoximine (59.3 mg; 64%) is obtained in the form of a white solid.

¹H NMR (DMSO-d6) δ: 0.85 (t, J=7.1 Hz, 6H), 1.17 (t, J=7.6 Hz, 3H), 1.30-1.51 (m, 3H), 1.62-1.71 (m, 1H), 1.80 (ddd, J=13.0, 4.1, 2.0 Hz, 1H), 2.08 (s, 1H), 2.34 (s, 3H), 2.59 (q, J=7.6 Hz, 2H), 3.20 (s, 3H), 3.22-3.41 (m, 8H), 3.90 (ddd, J=11.5, 4.6, 1.9 Hz, 2H), 4.04 (dd, J=9.5, 6.7 Hz, 1H), 4.17 (dd, J=9.3, 5.6 Hz, 1H), 6.93-7.00 (m, 2H), 7.14-7.21 (m, 2H), 7.45 (d, J=8.8 Hz, 1H), 7.74 (d, J=2.4 Hz, 1H), 7.86 (dd, J=8.8, 2.5 Hz, 1H).

MS: [M+H]=523

Example 9: Synthesis of N-(4-ethylphenyl)-N-isobutyl-3-methanesulfonyl-4-(tetrahydropyran-4-ylmethoxy)benzenesulfonamide

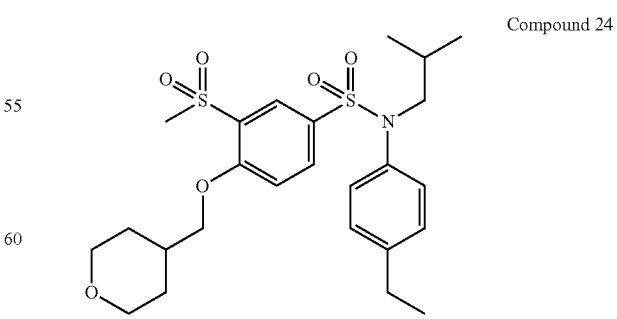

Compound 24

3-Chloroperbenzoic acid (188 mg; 0.84 mmol) is added portionwise at 0° C. to N-(4-ethylphenyl)-N-isobutyl-3-methanesulfanyl-4-(tetrahydropyran-4-ylmethoxy)benzenesulfonamide (200 mg; 0.42 mmol) dissolved in dichloromethane (2 ml). The reaction medium is stirred for 72 hours, hydrolyzed and extracted with ethyl acetate. The organic phases are combined, washed with brine, dried (Na$_2$SO$_4$) and concentrated. The crude product is chromatographed on silica gel (eluent: heptane/ethyl acetate, from 0 to 50% of ethyl acetate). The N-(4-ethylphenyl)-N-isobutyl-3-methanesulfonyl-4-(tetrahydropyran-4-ylmethoxy)benzenesulfonamide (150 mg; 71%) is obtained in the form of a white solid.

$^1$H NMR (400 MHz, DMSO-d6) δ 7.86-7.77 (m, 2H), 7.48 (d, J=8.7 Hz, 1H), 7.24-7.17 (m, 2H), 7.05-6.96 (m, 2H), 4.16 (d, J=6.2 Hz, 2H), 3.95-3.86 (m, 2H), 3.32-3.25 (m, 6H), 2.61 (q, J=7.6 Hz, 2H), 2.16-2.09 (m, 1H), 1.77-1.68 (m, 2H), 1.49-1.34 (m, 3H), 1.18 (t, J=7.6 Hz, 3H), 0.85 (d, J=6.6 Hz, 6H).

MS: [M+H]=510

Example 10: Synthesis of ethanesulfinyl-N-(4-ethylphenyl)-N-isobutyl-4-(tetrahydropyran-4-ylmethoxy)benzenesulfonamide Compound 22

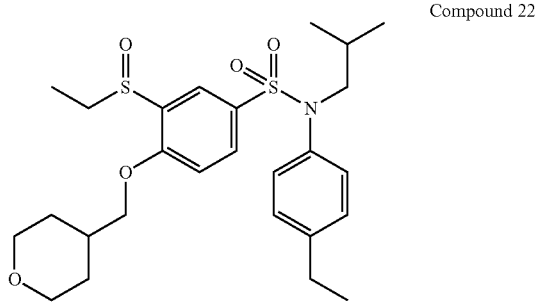 [SMILES: CCc1ccc(N(CC(C)C)S(=O)(=O)c2ccc(OCC3CCOCC3)c(S(=O)CC)c2)cc1]

1. Synthesis of Intermediate 10.1

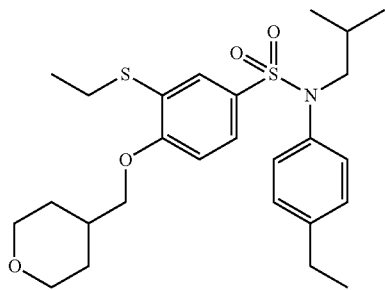 [SMILES: CCSc1cc(S(=O)(=O)N(CC(C)C)c2ccc(CC)cc2)ccc1OCC1CCOCC1]

N-(4-ethylphenyl)-3-ethylsulfanyl-N-isobutyl-4-(tetrahydropyran-4-ylmethoxy)benzenesulfonamide Bis(dibenzylideneacetone)palladium(0) (225 mg; 0.39 mmol) is added to a solution, degassed with argon for 15 minutes, of 3-bromo-N-(4-ethylphenyl)-N-isobutyl-4-(tetrahydropyran-4-ylmethoxy)benzenesulfonamide (500 mg; 0.98 mmol), N,N-diisopropylethylamine (510 µl; 2.94 mmol), 4,5-bis(diphenylphosphino)-9,9-dimethylxanthene (45 mg; 0.08 mmol) and sodium ethanethiolate (91 mg; 1.08 mmol) dissolved in 1,4-dioxane (5 ml). The reaction medium is stirred for 1 hour at 110° C., hydrolyzed and extracted with ethyl acetate. The organic phases are combined, washed with brine, dried (Na$_2$SO$_4$) and concentrated. The crude product is purified by preparative HPLC (C18 column, eluent: from 56% to 62% of acetonitrile in water/0.1% of formic acid). The N-(4-ethylphenyl)-3-ethylsulfanyl-N-isobutyl-4-(tetrahydropyran-4-ylmethoxy)benzenesulfonamide (271 mg; 42%) is obtained in the form of a white solid after trituration in heptane, with a compliant $^1$H NMR.

MS: [M+H]=492

2. Synthesis of Compound 22 According to the Invention

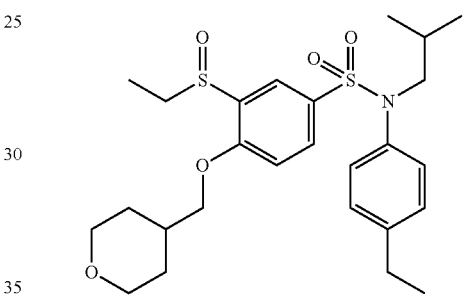

3-Chloroperbenzoic acid (59 mg; 0.26 mmol) is added portionwise at a temperature of 0° C. to N-(4-ethylphenyl)-3-ethanesulfanyl-N-isobutyl-4-(tetrahydropyran-4-ylmethoxy)benzenesulfonamide (260 mg; 0.53 mmol) dissolved in dichloromethane (5 ml). The reaction medium is stirred for 1 hour at room temperature, hydrolyzed with aqueous 10% Na$_2$S$_2$O$_3$ solution and then extracted with dichloromethane. The organic phases are combined, washed with 0.1N sodium hydroxide solution and then with brine, dried (Na$_2$SO$_4$) and concentrated.

The crude product is chromatographed on silica gel (eluent: heptane/ethyl acetate, from 0 to 100% of ethyl acetate). The 3-ethylsulfinyl-N-(4-ethylphenyl)-N-isobutyl-4-(tetrahydropyran-4-ylmethoxy)benzenesulfonamide (125 mg; 47%) is obtained in the form of a white solid.

$^1$H NMR (Chloroform-d) δ: 0.84 (dd, J=13.3, 6.7 Hz, 6H), 1.10 (t, J=7.4 Hz, 3H), 1.15 (t, J=7.6 Hz, 3H), 1.33-1.55 (m, 2H), 1.58-1.72 (m, 2H), 1.94-2.12 (m, 1H), 2.56 (q, J=7.6 Hz, 2H), 2.73 (dq, J=13.4, 7.4 Hz, 1H), 2.99 (dq, J=13.5, 7.4 Hz, 1H), 3.21 (dd, J=12.8, 6.8 Hz, 1H), 3.28-3.45 (m, 3H), 3.84 (dd, J=9.0, 6.3 Hz, 1H), 3.91 (dd, J=9.0, 6.4 Hz, 1H), 3.98 (ddd, J=11.6, 4.6, 1.8 Hz, 2H), 6.81 (d, J=8.7 Hz, 1H), 6.86-6.93 (m, 2H), 7.01-7.08 (m, 2H), 7.50 (dd, J=8.6, 2.4 Hz, 1H), 8.02 (d, J=2.4 Hz, 1H)

MS: [M+H]=508

Example 11: Synthesis of N-(4-ethylphenyl)-N-isobutyl-3-ethanesulfoximine-4-(tetrahydropyran-4-ylmethoxy)benzenesulfonamide

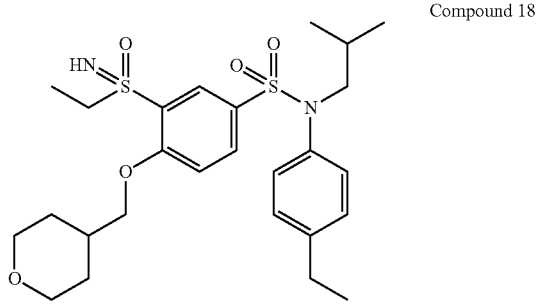 [SMILES: CCc1ccc(N(CC(C)C)S(=O)(=O)c2ccc(OCC3CCOCC3)c(S(=N)(=O)CC)c2)cc1]

Compound 18

2,2,2-Trifluoroacetamide (61 mg; 0.54 mmol), magnesium oxide (44 mg; 1.08 mmol), rhodium(II) acetate (14 mg; 0.03 mmol) and iodobenzene diacetate (133 mg; 0.41 mmol) are added to a solution, degassed beforehand with argon, of 3-ethylsulfinyl-N-(4-ethylphenyl)-N-isobutyl-4-(tetrahydropyran-4-ylmethoxy)benzenesulfonamide (110 mg; 0.22 mmol) in dichloromethane (8 ml). The reaction medium is stirred for 16 hours at room temperature, filtered through Celite and concentrated. The residue obtained is diluted in methanol (8 ml) and potassium carbonate (150 mg; 1.08 mmol) is added. The reaction medium is stirred for 30 minutes, hydrolyzed and extracted with ethyl acetate. The organic phases are combined, washed with brine, dried ($Na_2SO_4$) and concentrated.

The crude product is purified by preparative HPLC (C18 column, eluent: from 56% to 62% of acetonitrile in water/0.1% of formic acid). The N-(4-ethylphenyl)-N-isobutyl-3-ethanesulfoximino-4-(tetrahydropyran-4-ylmethoxy)benzenesulfonamide (23 mg; 20%) is obtained in the form of an off-white solid.

$^1$H NMR (Chloroform-d) δ: 0.93 (dd, J=8.4, 6.6 Hz, 6H), 1.25 (q, J=7.4 Hz, 7H), 1.46-1.69 (m, 6H), 1.86 (ddq, J=11.1, 4.5, 2.2 Hz, 2H), 2.14-2.30 (m, 1H), 2.67 (q, J=7.6 Hz, 2H), 2.75 (s, 1H), 3.28 (dd, J=12.8, 7.0 Hz, 1H), 3.31-3.45 (m, 3H), 3.49 (td, J=11.9, 2.2 Hz, 2H), 4.00-4.12 (m, 4H), 6.96-7.01 (m, 2H), 7.04 (d, J=8.8 Hz, 1H), 7.13-7.20 (m, 2H), 7.73 (dd, J=8.7, 2.4 Hz, 1H), 8.12 (d, J=2.4 Hz, 1H)

MS: [M+H]=523

Part II: Synthesis of the Sulfur-Based Sulfonamides Via Reaction Scheme 2

Reaction scheme 2:

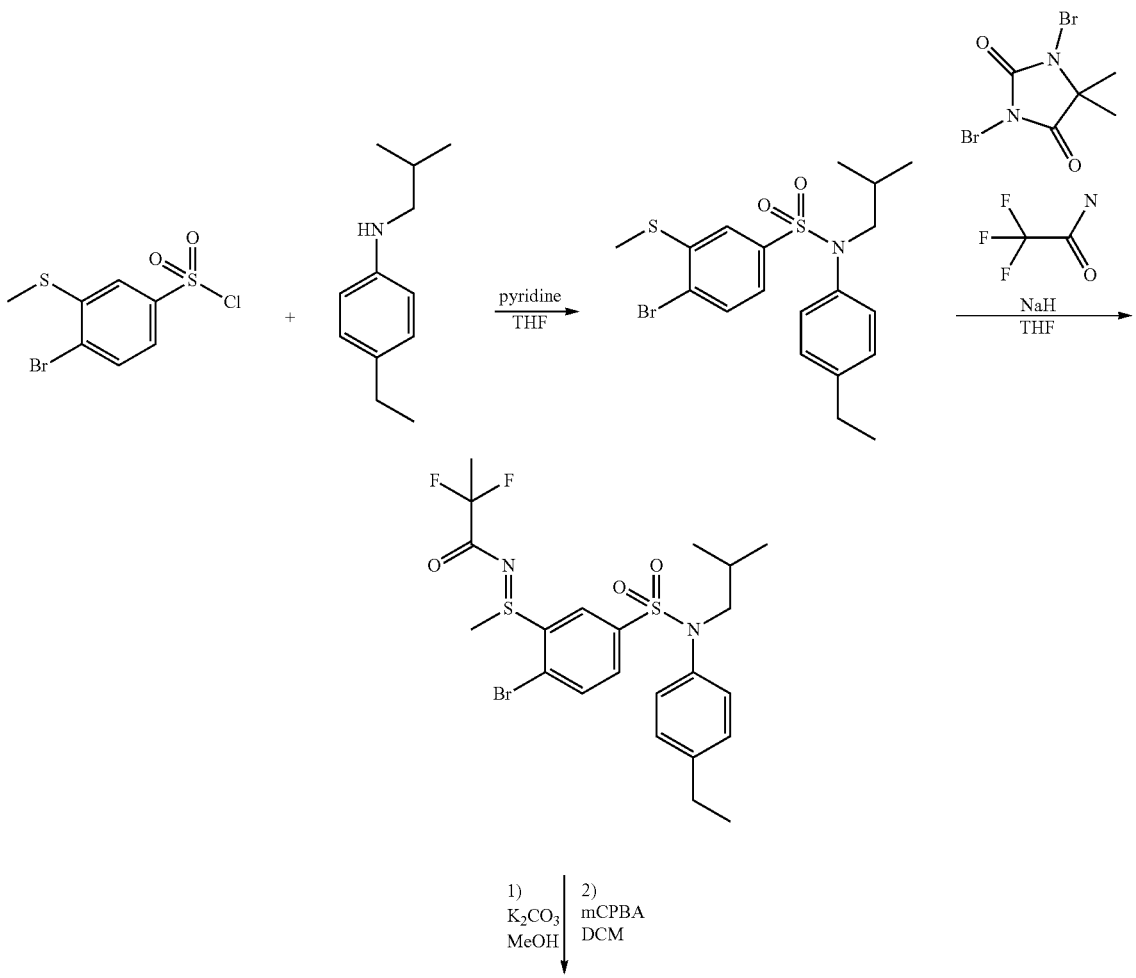

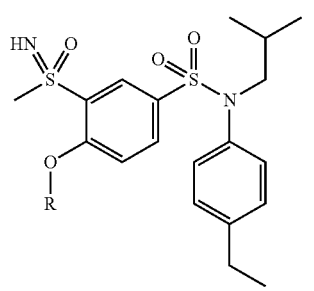 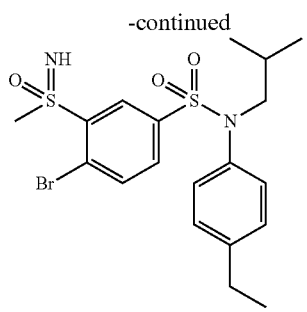 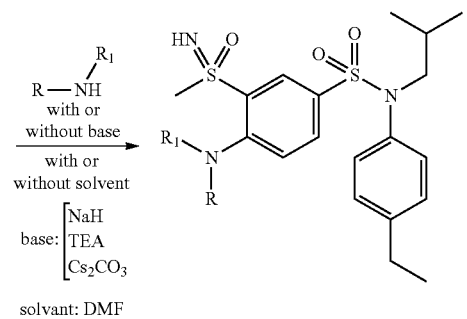

Example 12: Synthesis of N-4-ethylphenyl-4-(((4-fluorotetrahydro-2H-pyran-4-yl)methoxy)-N-isobutyl-3-(S-methylsulfonimidoyl)benzenesulfonamide Compound 30

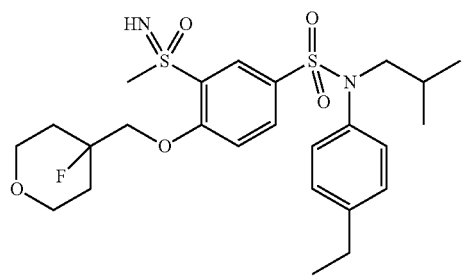

1. Synthesis of Intermediate 12.1

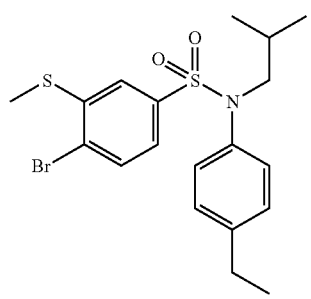 [SMILES: CCc1ccc(N(CC(C)C)S(=O)(=O)c2ccc(Br)c(SC)c2)cc1]

4-bromo-N-(4-ethylphenyl)-N-isobutyl-3-methylsulfanylbenzenesulfonamide

4-Bromo-3-(methylthio)benzene-1-sulfonyl chloride (19.63 g; 61.83 mmol) dissolved in tetrahydrofuran (95 ml) is added to (4-ethylphenyl)isobutylamine (10.96 g; 61.83 mmol) and pyridine (30 ml; 371 mmol) dissolved in tetrahydrofuran (370 ml). The reaction medium is stirred for 16 hours at room temperature and then hydrolyzed and extracted with ethyl acetate. The organic phases are combined, washed with saturated ammonium chloride solution and then with brine, dried (Na$_2$SO$_4$) and concentrated. The crude product is taken up in heptane and suction-filtered.

The 4-bromo-N-(4-ethylphenyl)-N-isobutyl-3-methylsulfanylbenzenesulfonamide (21.31 g; 78%) is obtained in the form of a pale yellow solid with a compliant $^1$H NMR.

MS: [M+H]=444

2. Synthesis of Intermediate 12.2

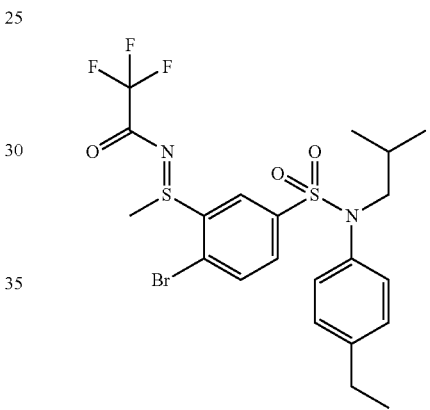

(E)-N-((2-bromo-5-(N-(4-ethylphenyl)-N-isobutylsulfamoyl)phenyl)(methyl)-λ$^4$-sulfanylidene)-2,2,2-trifluoroacetamide 4-Bromo-N-(4-ethylphenyl)-N-isobutyl-3-methylsulfanylbenzenesulfonamide (5.00 g; 11.30 mmol) and 2,2,2-trifluoroacetamide (1.92 g; 16.95 mmol) dissolved in tetrahydrofuran (10 ml) are added slowly to 60% sodium hydride (0.41 g; 10.17 mmol) suspended in tetrahydrofuran (10 ml) at 0-5° C., and 1,3-dibromo-5,5-dimethylhydantoin (4.85 g; 16.95 mmol) dissolved in tetrahydrofuran (25 ml) is added at a temperature of 0-5° C. The medium is stirred for 1 hour at room temperature. The reaction medium is hydrolyzed with 10% citric acid solution and then extracted with ethyl acetate.

The organic phases are combined, washed with 25% sodium sulfite solution and then with brine, dried (Na$_2$SO$_4$) and concentrated. The residue is taken up in ether and suction-filtered. The (E)-N-((2-bromo-5-(N-(4-ethylphenyl)-N-isobutylsulfamoyl)phenyl)(methyl)-λ$^4$-sulfanylidene)-2,2,2-trifluoroacetamide (4.76 g; 76%) is obtained in the form of a white powder with a compliant $^1$H NMR.

MS: [M+H]=554

3. Synthesis of Intermediate 12.3

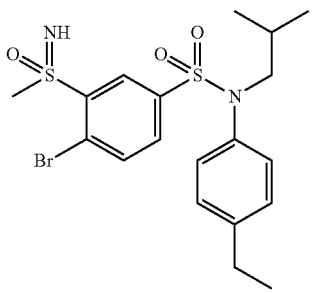 [SMILES: CCc1ccc(N(CC(C)C)S(=O)(=O)c2ccc(Br)c(S(C)(=N)=O)c2)cc1]

2-bromo-N-(4-ethylphenyl)-N-isobutyl-3-(S-ethyl sulfonimidoyl)benzenesulfonamide Potassium carbonate (2.79 g; 20.16 mmol) is added to (E)-N-((2-bromo-5-(N-(4-ethylphenyl)-N-isobutylsulfamoyl)phenyl)(methyl)-$\lambda^4$-sulfanylidene)-2,2,2-trifluoroacetamide (3.72 g; 6.72 mmol) dissolved in methanol (35 ml), and 3-chloroperoxybenzoic acid (2.26 g; 10.08 mmol) is then added slowly at a temperature of 0° C. The reaction medium is stirred for 16 hours at room temperature.

The reaction medium is hydrolyzed and then extracted with ethyl acetate. The organic phases are combined, washed with brine, dried ($Na_2SO_4$) and concentrated.

The crude product is chromatographed on silica gel (eluent: heptane/ethyl acetate, from 0 to 80% of ethyl acetate). The 4-bromo-N-(4-ethylphenyl)-N-isobutyl-3-(S-methylsulfonimidoyl)benzenesulfonamide (1.51 g; 47%) is obtained in the form of a white solid with a compliant $^1$H NMR.

MS: [M+H]=474

4. Synthesis of Compound 30 According to the Invention

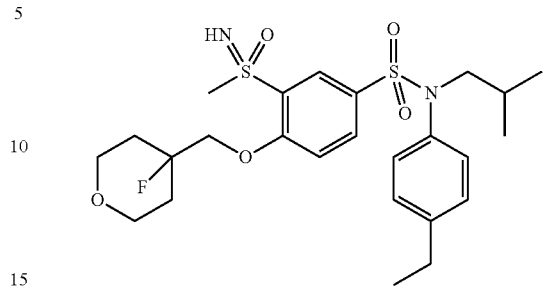

60% sodium hydride (9 mg; 0.22 mmol) is added slowly to (4-fluorotetrahydropyran-4-yl)methanol (28.33 mg; 0.21 mmol) dissolved in N,N-dimethylformamide (0.5 ml), followed by 4-bromo-N-(4-ethylphenyl)-N-isobutyl-3-(S-methylsulfonimidoyl)benzenesulfonamide (50 mg; 0.11 mmol).

The reaction medium is stirred for 2 hours at room temperature. The reaction medium is hydrolyzed without heating and then extracted with ethyl acetate. The organic phases are combined, washed with brine, dried ($Na_2SO_4$) and concentrated.

The crude product is purified by preparative HPLC (C18 column, eluent: acetonitrile in water/0.1% of formic acid). N-(4-Ethylphenyl)-4-((4-fluorotetrahydro-2H-pyran-4-yl)methoxy)-N-isobutyl-3-(S-methylsulfonimidoyl)benzenesulfonamide (46 mg; 82%) is obtained in the form of a white solid.

$^1$H NMR (DMSO-d6) δ: 0.86 (dd, J=6.7, 4.6 Hz, 6H), 1.19 (t, J=7.6 Hz, 3H), 1.36-1.51 (m, 1H), 1.76-2.05 (m, 4H), 2.61 (q, J=7.6 Hz, 2H), 3.19 (d, J=1.0 Hz, 3H), 3.22-3.32 (m, 2H), 3.63 (td, J=11.2, 3.0 Hz, 2H), 3.80 (dt, J=11.2, 2.8 Hz, 2H), 4.34-4.48 (m, 3H), 6.97-7.04 (m, 2H), 7.17-7.24 (m, 2H), 7.39 (d, J=8.8 Hz, 1H), 7.70 (dd, J=8.7, 2.4 Hz, 1H), 8.01 (d, J=2.4 Hz, 1H).

MS: [M+H]=527

With a procedure similar to that described for example 12, the following are obtained:

| Example 13 | 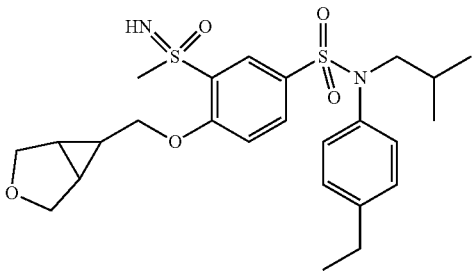<br>Compound 31 | 4-((3-oxabicyclo[3.1.0]hexan-6-yl)methoxy)-N-(4-ethylphenyl)-N-isobutyl-3-(S-methylsulfonimidoyl)benzenesulfonamide<br>$^1$H NMR (DMSO-d6) δ: 0.85 (dd, J = 6.7, 4.3 Hz, 6H), 1.12-1.23 (m, 4H), 1.43 (dt, J = 13.6, 6.9 Hz, 1H), 1.79-1.86 (m, 2H), 2.61 (q, J = 7.6 Hz, 2H), 3.23 (s, 3H), 3.25-3.36 (m, 2H), 3.61 (dt, J = 8.3, 1.4 Hz, 2H), 3.78 (d, J = 8.4 Hz, 2H), 4.21 (dd, J = 6.9, 1.9 Hz, 2H), 4.41 (d, J = 1.5 Hz, 1H), 6.96-7.03 (m, 2H), 7.17-7.24 (m, 2H), 7.34 (d, J = 8.8 Hz, 1H), 7.65 (dd, J = 8.7, 2.4 Hz, 1H), 8.00 (d, J = 2.5 Hz, 1H).<br>MS: [M + H] = 507 |
|---|---|---|
| Example 14 | 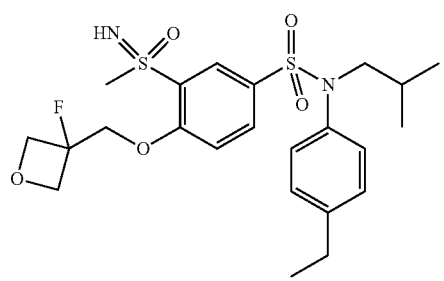<br>Compound 32 | N-(4-ethylphenyl)-4-((3-fluorooxetan-3-yl)methoxy)-N-isobutyl-3-(S-methylsulfonimidoyl)benzenesulfonamide<br>$^1$H NMR (DMSO-d6) δ: 0.86 (dd, J = 6.6, 4.3 Hz, 6H), 1.19 (t, J = 7.6 Hz, 3H), 1.38-1.50 (m, 1H), 2.61 (q, J = 7.6 Hz, 2H), 3.16 (d, J = 1.2 Hz, 3H), 3.22-3.41 (m, 2H), 4.46 (d, J = 1.5 Hz, 1H), 4.63-4.86 (m, 6H), 6.97-7.05 (m, 2H), 7.21 (d, J = 8.3 Hz, 2H), 7.74 (dd, J = 8.7, 2.4 Hz, 1H), 8.00 (d, J = 2.4 Hz, 1H).<br>MS: [M + H] = 499 |

| Example 15 | 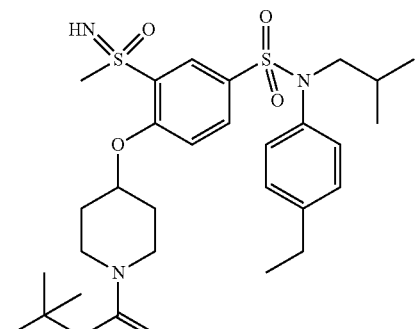
Compound 33 | tert-butyl 4-(4-(N-(4-ethylphenyl)-N-isobutylsulfamoyl)-2-(S-methylsulfonimidoyl)phenoxy)piperidine-1-carboxylate
¹H NMR (DMSO-d6) δ: 0.85 (dd, J = 6.6, 3.5 Hz, 6H), 1.19 (t, J = 7.6 Hz, 3H), 1.42 (s, 11H), 1.70-1.80 (m, 2H), 1.90 (t, J = 10.4 Hz, 2H), 2.61 (q, J = 7.5 Hz, 2H), 3.19 (s, 3H), 3.24-3.31 (m, 2H), 3.38-3.48 (m, 2H), 3.48-3.61 (m, 2H), 4.42 (d, J = 1.4 Hz, 1H), 4.97-5.05 (m, 1H), 6.98-7.05 (m, 2H), 7.17-7.25 (m, 2H), 7.45 (d, J = 9.0 Hz, 1H), 7.64 (dd, J = 8.7, 2.4 Hz, 1H), 8.01 (d, J = 2.3 Hz, 1H).
MS: [M + H] = 594 |
|---|---|---|
| Example 16 | 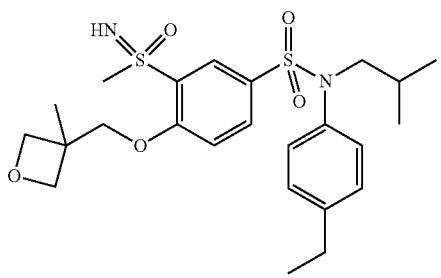
Compound 34 | N-(4-ethylphenyl)-N-isobutyl-4-((3-methyloxetan-3-yl)methoxy)-3-(S-methylsulfonimidoyl)benzenesulfonamide
¹H NMR (DMSO-d6) δ: 0.86 (dd, J = 6.6, 4.1 Hz, 6H), 1.19 (t, J = 7.6 Hz, 3H), 1.42 (s, 4H), 2.56-2.67 (m, 2H), 3.21 (d, J = 1.2 Hz, 3H), 3.24-3.32 (m, 2H), 4.30 (d, J = 3.3 Hz, 2H), 4.36 (d, J = 6.0 Hz, 2H), 4.42 (d, J = 1.4 Hz, 1H), 4.62 (dd, J = 5.9, 3.0 Hz, 2H), 6.98-7.05 (m, 2H), 7.18-7.25 (m, 2H), 7.43 (d, J = 8.8 Hz, 1H), 7.70 (dd, J = 8.7, 2.5 Hz, 1H), 8.02 (d, J = 2.4 Hz, 1H).
MS: [M + H] = 495 |
| Example 17 | 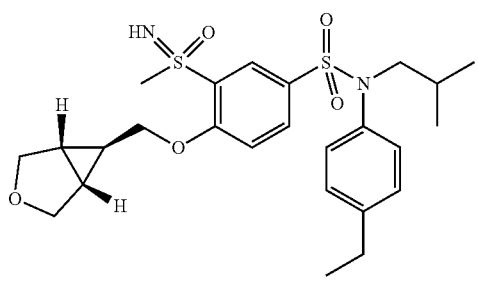
Compound 35 | 4-(((1R,5S,6R)-3-oxabicyclo[3.1.0]hexan-6-yl)methoxy)-N-(4-ethylphenyl)-N-isobutyl-3-(S-methylsulfonimidoyl)benzenesulfonamide
¹H NMR (DMSO-d6) δ: 0.85 (dd, J = 6.7, 4.3 Hz, 6H), 1.18 (t, J = 7.6 Hz, 4H), 1.35-1.51 (m, 1H), 1.79-1.86 (m, 2H), 2.61 (q, J = 7.6 Hz, 2H), 3.23 (d, J = 1.2 Hz, 3H), 3.25-3.31 (m, 2H), 3.61 (dt, J = 8.4, 1.3 Hz, 2H), 3.78 (d, J = 8.3 Hz, 2H), 4.21 (dd, J = 7.0, 1.9 Hz, 2H), 4.41 (d, J = 1.4 Hz, 1H), 6.96-7.03 (m, 2H), 7.17-7.24 (m, 2H), 7.34 (d, J = 8.8 Hz, 1H), 7.65 (dd, J = 8.7, 2.4 Hz, 1H), 8.00 (d, J = 2.5 Hz, 1H).
MS: [M + H] = 507 |
| Example 18 | 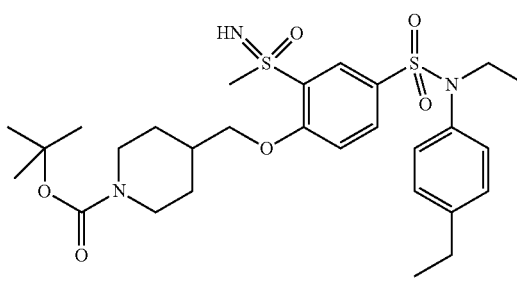
Compound 36 | tert-butyl 4-04-(N-(4-ethylphenyl)-N-isobutylsulfamoyl)-2-(S-methylsulfonimidoyl)phenoxy)methyl)piperidine-1-carboxylate
¹H NMR (DMSO-d6) δ: 0.85 (dd, J = 6.6, 4.4 Hz, 6H), 1.14-1.31 (m, 5H), 1.41 (s, 10H), 1.82 (s, 2H), 2.04 (s, 1H), 2.53-2.66 (m, 3H), 2.77 (s, 2H), 3.17 (d, J = 1.2 Hz, 3H), 3.21-3.31 (m, 2H), 3.99 (d, J = 12.8 Hz, 2H), 4.08-4.15 (m, 2H), 4.41 (d, J = 1.5 Hz, 1H), 6.97-7.04 (m, 2H), 7.17-7.24 (m, 2H), 7.37(d, J = 8.8 Hz, 1H), 7.67 (dd, J = 8.7, 2.5 Hz, 1H), 8.00 (d, J = 2.4 Hz, 1H).
MS: [M + H] = 608 |

-continued

| | | |
|---|---|---|
| Example 19 | 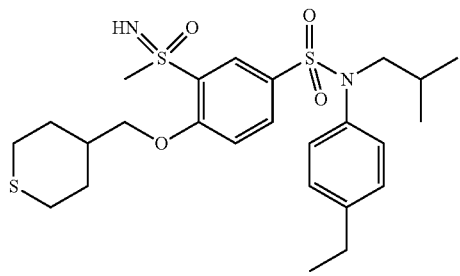

Compound 37 | N-(4-ethylphenyl)-N-isobutyl-3-(S-methylsulfonimidoyl)-4-(pyridin-4-ylmethoxy)benzenesulfonamide
$^1$H NMR (DMSO-d6) δ: 0.85 (dd, J = 6.6, 4.5 Hz, 6H), 1.18 (t, J = 7.6 Hz, 3H), 1.35-1.57 (m, 3H), 1.82-2.01 (m, 1H), 2.11-2.20 (m, 2H), 2.52-2.76 (m, 7H), 3.19 (d, J = 1.2 Hz, 3H), 3.32 (s, 8H), 4.05-4.12 (m, 2H), 4.40 (d, J = 1.5 Hz, 1H), 6.97-7.04 (m, 2H), 7.17-7.24 (m, 2H), 7.37 (d, J = 8.9 Hz, 1H), 7.67 (dd, J = 8.8, 2.5 Hz, 1H), 8.00 (d, J = 2.4 Hz, 1H).
MS: [M + H] = 525 |
| Example 20 | 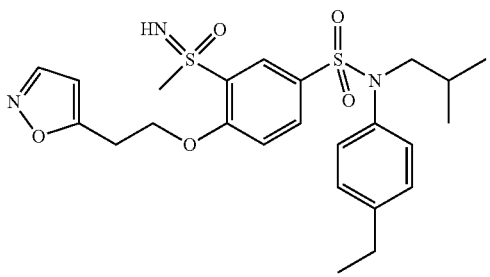

Compound 38 | N-(4-ethylphenyl)-N-isobutyl-4-(2-(isoxazol-5-yl)ethoxy)-3-(S-methylsulfonimidoyl)benzenesulfonamide
$^1$H NMR (DMSO-d6) δ: 0.85 (dd, J = 11.0, 6.7 Hz, 6H), 1.17 (t, J = 7.6 Hz, 3H), 1.43 (t, J = 7.2 Hz, 1H), 2.29-2.38 (m, 2H), 2.60 (d, J = 7.6 Hz, 2H), 3.22-3.39 (m, 4H), 3.54 (d, J = 2.5 Hz, 3H), 4.64 (s, 1H), 6.83 (s, 1H), 6.94-7.04 (m, 2H), 7.22 (d, J = 8.4 Hz, 4H), 7.64 (d, J = 2.3 Hz, 1H), 7.82 (dd, J = 8.9, 2.4 Hz, 1H)
MS: [M + H] = 506 |
| Example 21 | 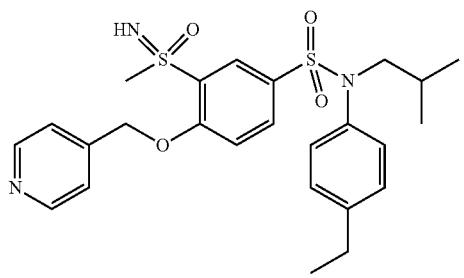

Compound 39 | N-(4-ethylphenyl)-N-isobutyl-3-(S-methylsulfonimidoyl)-4-(pyridin-4-ylmethoxy)benzenesulfonamide
$^1$H NMR (DMSO-d6) δ: 0.86 (dd, J = 6.7, 4.3 Hz, 7H), 1.19 (t, J = 7.6 Hz, 3H), 1.36-1.51 (m, 1H), 2.61 (q, J = 7.6 Hz, 2H), 3.15 (d, J = 1.2 Hz, 3H), 3.24-3.32 (m, 2H), 4.51 (d, J = 1.5 Hz, 1H), 5.47 (d, J = 2.5 Hz, 2H), 6.97-7.04 (m, 2H), 7.17-7.24 (m, 2H), 7.44-7.54 (m, 2H), 7.73 (dd, J = 8.7, 2.5 Hz, 1H), 8.00 (dt, J = 7.9, 2.0 Hz, 1H), 8.03 (d, J = 2.4 Hz, 1H), 8.59 (dd, J = 4.8, 1.6 Hz, 1H), 8.79 (d, J = 2.5 Hz, 1H).
MS: [M + H] = 502 |
| Example 22 | 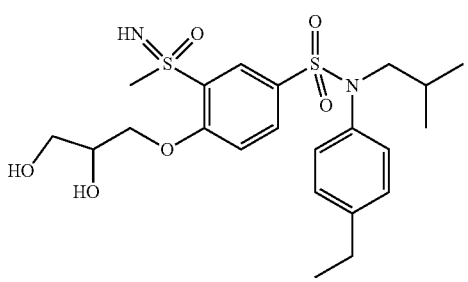

Compound 40 | 4-(2,3-dihydroxypropoxy)-N-(4-ethylphenyl)-N-isobutyl-3-(S-methylsulfonimidoyl)benzenesulfonamide
$^1$H NMR (DMSO-d6) δ: 0.85 (dd, J = 6.6, 3.5 Hz, 6H), 1.18 (t, J = 7.6 Hz, 3H), 1.37-1.49 (m, 1H), 2.61 (q, J = 7.6 Hz, 2H), 3.24 (t, J = 1.4 Hz, 3H), 3.25-3.31 (m, 2H), 3.53 (t, J = 5.8 Hz, 2H), 3.89 (dd, J = 10.2, 5.1 Hz, 1H), 4.11-4.34 (m, 2H), 4.41 (dd, J = 8.9, 1.4 Hz, 1H), 4.74 (dt, J = 7.7, 5.7 Hz, 1H), 5.08 (d, J = 4.9 Hz, 1H), 6.97-7.04 (m, 2H), 7.17-7.24 (m, 2H), 7.39 (dd, J = 8.9, 2.1 Hz, 1H), 7.64-7.73 (m, 1H), 7.95-8.00 (m, 1H).
MS: [M + H] = 485 |
| Example 23 | 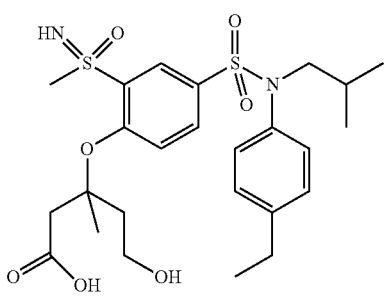

Compound 41 | 3-(4-(N-(4-ethylphenyl)-N-isobutylsulfamoyl)-2-(S-methylsulfonimidoyl)phenoxy)-5-hydroxy-3-methylpentanoic acid
$^1$H NMR (DMSO-d6) δ: 0.85 (t, J = 5.4 Hz, 7H), 1.17 (t, J = 7.6 Hz, 5H), 1.36-1.48 (m, 1H), 2.60 (q, J = 7.5 Hz, 2H), 3.14 (d, J = 4.9 Hz, 3H), 3.20-3.29 (m, 2H), 4.39-4.71 (m, 5H), 5.26 (s, 1H), 6.99 (d, J = 7.2 Hz, 2H), 7.20 (d, J = 8.0 Hz, 2H), 7.40 (dt, J = 8.5, 4.3 Hz, 1H), 7.65-7.76 (m, 1H), 7.99 (dd, J = 14.4, 2.4 Hz, 1H).
MS: [M + H] = 541 |

| | | |
|---|---|---|
| Example 24 | 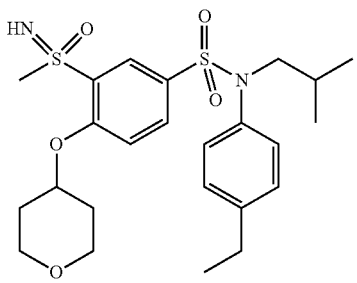<br>Compound 42 | N-(4-ethylphenyl)-N-isobutyl-3-(S-methylsulfonimidoyl)-4-((tetrahydro-2H-pyran-4-yl)oxy)benzenesulfonamide<br>$^1$H NMR (DMSO-d6) δ: 0.85 (dd, J = 6.6, 3.8 Hz, 6H), 1.19 (t, J = 7.6 Hz, 3H), 1.36-1.51 (m, 1H), 1.68-1.81 (m, 2H), 1.97-2.07 (m, 2H), 2.61 (q, J = 7.6 Hz, 2H), 3.21 (d, J = 1.2 Hz, 3H), 3.32 (m, 2H), 3.50-3.61 (m, 2H), 3.87-3.92 (m, 2H), 4.41 (d, J = 1.5 Hz, 1H), 5.00 (dt, J = 7.3, 3.6 Hz, 1H), 6.98-7.05 (m, 2H), 7.17-7.24 (m, 2H), 7.46 (d, J = 8.9 Hz, 1H), 7.63 (dd, J = 8.8, 2.4 Hz, 1H), 8.02 (d, J = 2.5 Hz, 1H)<br>MS: [M + H] = 495 |
| Example 25 | 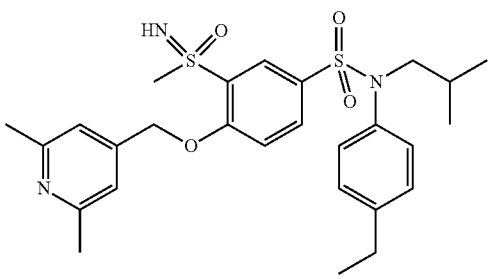<br>Compound 43 | 4-((2,6-dimethylpyridin-4-yl)methoxy)-N-(4-ethylphenyl)-N-isobutyl-3-(S-methylsulfonimidoyl)benzenesulfonamide<br>$^1$H NMR (DMSO-d6) δ: 0.85 (dd, J = 6.6, 4.0 Hz, 6H), 1.18 (t, J = 7.6 Hz, 3H), 1.36-1.49 (m, 1H), 2.44 (s, 6H), 2.50-2.66 (m, 3H), 3.21 (d, J = 1.1 Hz, 3H), 3.32 (m, 2H), 4.55 (d, J = 1.4 Hz, 1H), 5.40 (s, 2H), 6.95-7.04 (m, 2H), 7.16-7.24 (m, 4H), 7.40 (d, J = 8.8 Hz, 1H), 7.71 (dd, J = 8.7, 2.4 Hz, 1H), 8.04 (d, J = 2.4 Hz, 1H)<br>MS: [M + H] = 530 |
| Example 26 | 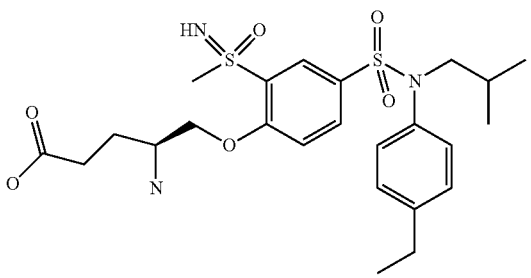<br>Compound 44 | ((4S)-4-amino-5-(4-(N-(4-ethylphenyl)-N-isobutylsulfamoyl)-2-(S-methylsulfonimidoyl)phenoxy)pentanoic acid<br>$^1$H NMR (DMSO-d6) δ: 0.84 (d, J = 6.4 Hz, 7H), 1.18 (t, J = 7.6 Hz, 3H), 1.42 (dt, J = 13.7, 6.8 Hz, 1H), 1.74 (dd, J = 14.3, 7.3 Hz, 1H), 1.88 (dt, J = 14.3, 6.9 Hz, 1H), 2.30-2.41 (m, 2H), 2.61 (q, J = 7.6 Hz, 2H), 3.01 (d, J = 5.9 Hz, 3H), 3.25 (d, J = 7.3 Hz, 3H), 3.50 (s, 2H), 3.68 (s, 1H), 4.67 (d, J = 23.1 Hz, 1H), 4.95 (d, J = 17.8 Hz, 1H), 7.01 (d, J = 8.1 Hz, 3H), 7.20 (d, J = 8.0 Hz, 2H), 7.47 (dd, J = 8.8, 2.9 Hz, 1H), 7.67-7.81 (m, 2H), 12.12 (s, 1H)<br>MS: [M + H] = 526 |
| Example 27 | 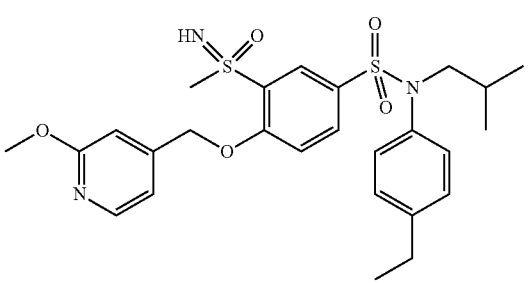<br>Compound 77 | N-(4-ethylphenyl)-N-isobutyl-4-((2-methoxypyridin-4-yl)methoxy)-3-(S-methylsulfonimidoyl)benzenesulfonamide<br>$^1$H NMR (DMSO-d6) δ: 0.89 (ddd, J = 10.8, 6.5, 3.9 Hz, 6H), 1.23 (t, J = 7.6 Hz, 3H), 1.42-1.54 (m, 1H), 2.66 (q, J = 7.7 Hz, 2H), 3.25 (s, 3H), 3.28-3.35 (m, 2H), 3.92 (s, 3H), 4.61 (s, 1H), 5.50 (s, 2H), 7.05 (d, J = 8.1 Hz, 3H), 7.25 (d, J = 8.0 Hz, 2H), 7.46 (d, J = 8.9 Hz, 1H), 7.57-7.73 (m, 2H), 7.76 (dd, J = 8.9, 2.4 Hz, 1H), 8.09 (d, J = 2.6 Hz, 1H), 8.26 (d, J = 5.3 Hz, 1H).<br>MS: [M + H] = 532 |
| Example 28 | 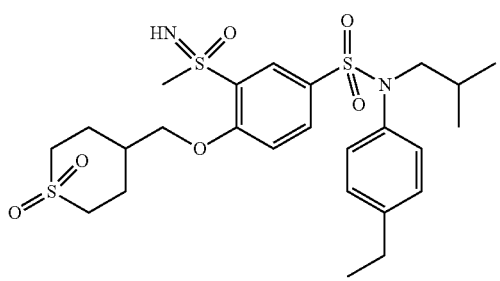<br>Compound 78 | N-(4-ethylphenyl)-N-isobutyl-4-((2-methoxypyridin-4-yl)methoxy)-3-(S-methylsulfonimidoyl)benzenesulfonamide<br>$^1$H NMR (DMSO-d6) δ: 0.85 (dd, J = 6.6, 4.7 Hz, 6H), 1.18 (t, J = 7.6 Hz, 3H), 1.36-1.50 (m, 1H), 1.88 (t, J = 12.8 Hz, 2H), 2.15-2.30 (m, 3H), 2.61 (q, J = 7.6 Hz, 2H), 3.07-3.18 (m, 2H), 3.19 (d, J = 1.2 Hz, 3H), 3.20-3.32 (m, 4H), 4.18 (dt, J = 6.0, 3.6 Hz, 2H), 4.44 (d, J = 1.5 Hz, 1H), 6.97-7.04 (m, 2H), 7.17-7.24 (m, 2H), 7.38 (d, J = 8.7 Hz, 1H), 7.68 (dd, J = 8.8, 2.4 Hz, 1H), 8.01 (d, J = 2.4 Hz, 1H).<br>MS: [M + H] = 557 |

| Example 29 CD13325 | 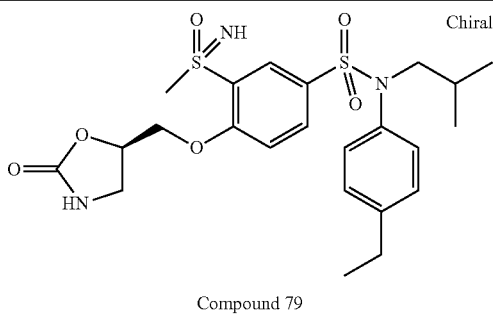

Compound 79 | N-(4-ethylphenyl)-N-isobutyl-3-(S-methylsulfonimidoyl)-4-(((R)-2-oxooxazolidin-5-yl)methoxy)benzenesulfonamide<br>$^1$H NMR (DMSO-d6) δ: 0.81-0.89 (m, 6H), 1.18 (t, J = 7.6 Hz, 3H), 1.35-1.50 (m, 1H), 2.61 (q, J = 7.6 Hz, 2H), 3.18 (dd, J = 4.2, 1.2 Hz, 3H), 3.22-3.32 (m, 2H), 3.59 (dt, J = 32.3, 8.2 Hz, 2H), 4.30-4.45 (m, 2H), 4.46-4.57 (m, 1H), 5.01 (dt, J = 4.8, 2.3 Hz, 1H), 6.96-7.04 (m, 2H), 7.17-7.24 (m, 2H), 7.42 (dd, J = 8.8, 2.2 Hz, 1H), 7.65-7.75 (m, 2H), 8.00 (dd, J = 10.9, 2.4 Hz, 1H).<br>MS: [M + H] = 510 |

Example 30: Synthesis of the Compound 4-((2,4-difluorobenzyl)oxy)-N-(4-ethylphenyl)-N-isobutyl-3-(S-methylsulfonimidoyl)benzenesulfonamide

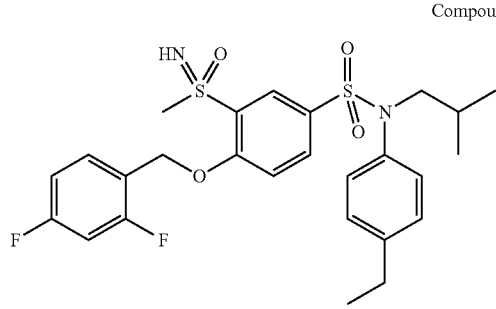

Compound 45

4-Bromo-N-(4-ethylphenyl)-N-isobutyl-3-(S-methylsulfonimidoyl)benzenesulfonamide (50.0 mg; 0.11 mmol) is added to a mixture comprising 2,4-difluorobenzyl alcohol (30.5 mg; 0.21 mmol) and cesium carbonate (103.2 mg; 0.32 mmol) dissolved in N,N-dimethylformamide (0.50 ml) after stirring for 20 minutes. The reaction medium is stirred for 20 hours at a temperature of 80° C., hydrolyzed without heating and then extracted with ethyl acetate. The organic phases are combined, washed with saturated sodium chloride solution, dried (sodium sulfate) and concentrated to dryness.

The crude product is purified by preparative HPLC (C18 column, eluent: acetonitrile in water/0.1% of formic acid). The 4-((2,4-difluorobenzyl)oxy)-N-(4-ethylphenyl)-N-isobutyl-3-(S-methylsulfonimidoyl)benzenesulfonamide (9.4 g; 16%) is obtained in the form of a white solid.

$^1$H NMR (DMSO-d6) δ: 0.86 (dd, J=6.8, 4.4 Hz, 6H), 1.19 (t, J=7.6 Hz, 3H), 1.33-1.53 (m, 1H), 2.62 (t, J=7.6 Hz, 2H), 3.12 (s, 3H), 4.47 (s, 1H), 5.42 (s, 2H), 7.01 (d, J=8.1 Hz, 2H), 7.21 (d, J=8.0 Hz, 3H), 7.38 (t, J=9.2 Hz, 1H), 7.55 (d, J=8.8 Hz, 1H), 7.72 (dd, J=8.7, 2.5 Hz, 1H), 7.80 (q, J=8.2 Hz, 1H), 8.03 (d, J=2.5 Hz, 1H).

MS: [M+H]=537

Example 31: Synthesis of the Compound 4-(4-cyanophenoxy)-N-(4-ethylphenyl)-N-isobutyl-3-(S-methylsulfonimidoyl)benzenesulfonamide

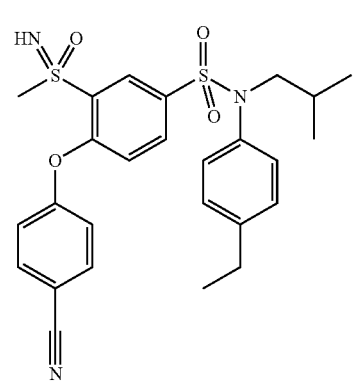

Compound 80

60% sodium hydride (6.3 mg; 0.16 mmol) is added to (1,1-dioxohexahydro-1λ$^6$-thiopyran-4-yl)methanol 4-cyanophenol (13.8 mg; 0.12 mmol) dissolved in N,N-dimethylformamide (1.0 ml). The reaction medium is stirred for 20 minutes, followed by addition of 4-bromo-N-(4-ethylphenyl)-N-isobutyl-3-(S-methylsulfonimidoyl)benzenesulfonamide (50.0 mg; 0.11 mmol).

The reaction medium is stirred for 1 hour at room temperature and then for 16 hours at a temperature of 80° C. The reaction medium is hydrolyzed by addition of cold water and then extracted with ethyl acetate. The organic phases are combined and then washed with brine, dried (Na$_2$SO$_4$) and concentrated.

The crude product is chromatographed on silica gel, eluting with heptane/ethyl acetate, from 0 to 100% of ethyl acetate. The 4-(4-cyanophenoxy)-N-(4-ethylphenyl)-N-isobutyl-3-(S-methylsulfonimidoyl)benzenesulfonamide (14.5 mg; 24%) is obtained in the form of a white solid.

$^1$H NMR (DMSO-d6) δ: 0.87 (dd, J=6.6, 3.9 Hz, 6H), 1.18 (t, J=7.6 Hz, 3H), 1.21-1.31 (m, 2H), 1.39-1.51 (m, 1H), 2.57-2.66 (m, 2H), 3.26 (s, 3H), 3.33-3.39 (m, 2H), 4.66 (d, J=1.5 Hz, 1H), 7.00-7.07 (m, 2H), 7.20-7.31 (m, 3H), 7.30-7.38 (m, 2H), 7.72 (dd, J=8.6, 2.4 Hz, 1H), 7.93-8.00 (m, 2H), 8.09 (d, J=2.4 Hz, 1H).

MS: [M+H]=512

Part III: Synthesis of the Sulfur-Based Sulfonamides Via Reaction Scheme 3
Reaction scheme 3:
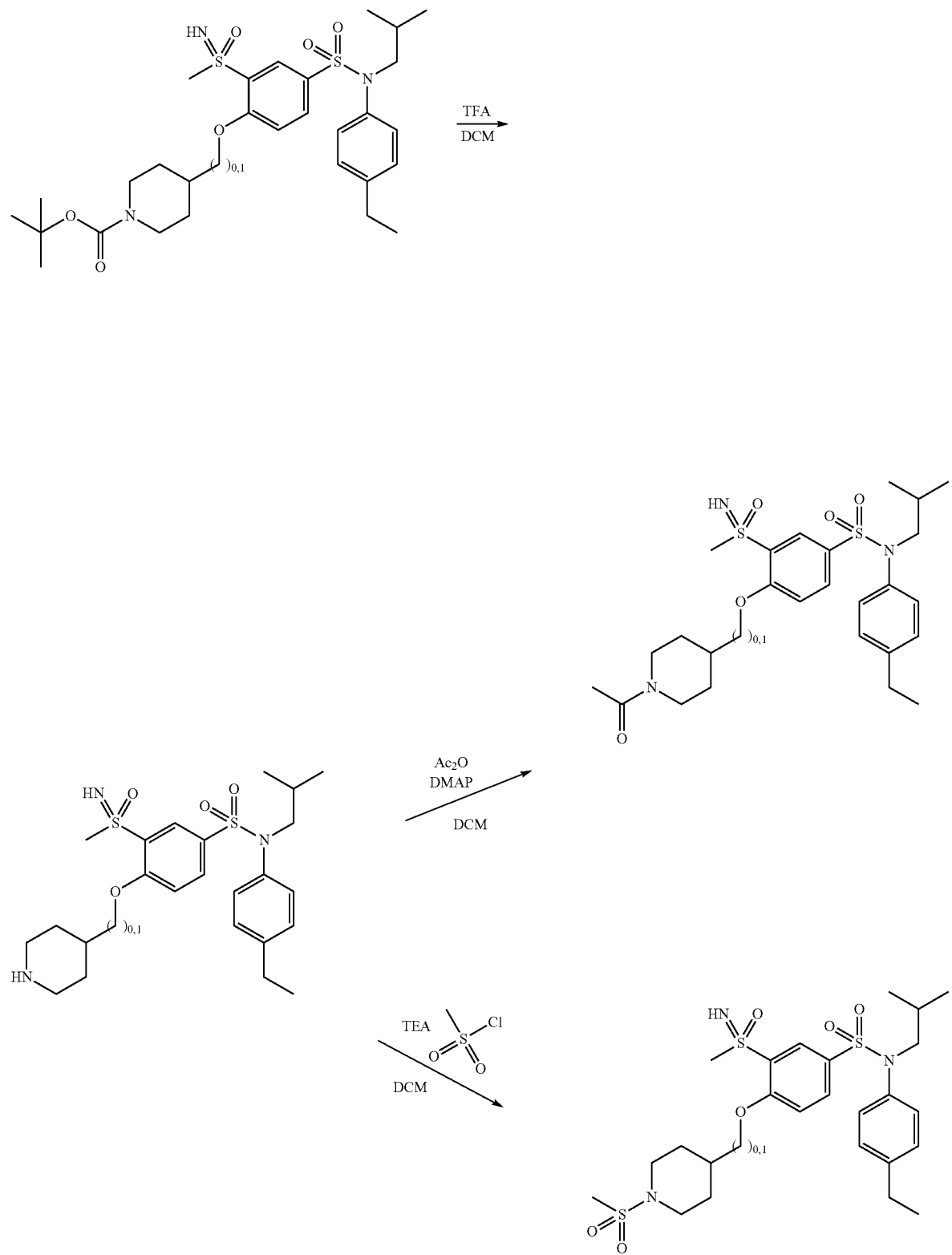

Example 32: Synthesis of N-(4-ethylphenyl)-N-isobutyl-3-(S-methylsulfonimidoyl)-4-(piperidin-4-ylmethoxy)benzenesulfonamide

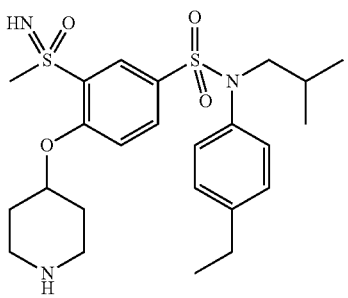

Compound 46

Trifluoroacetic acid (0.2 ml; 2.61 mmol) is added to tert-butyl 4-(4-(N-(4-ethylphenyl)-N-isobutylsulfamoyl)-2-(S-methylsulfonimidoyl)phenoxy)piperidine-1-carboxylate (40.0 mg; 0.07 mmol) dissolved in dichloromethane (1.6 ml). The reaction medium is stirred for 1 hour at room temperature, concentrated, diluted with dichloromethane, washed with saturated sodium hydrogen carbonate solution and then with saturated NaCl solution, and dried ($Na_2SO_4$). The solvents are evaporated off.

The crude product is purified by preparative HPLC (C18 column, eluent: acetonitrile in water/0.1% of formic acid). The N-(4-ethylphenyl)-N-isobutyl-3-(S-methylsulfonimidoyl)-4-(piperidin-4-yloxy)benzenesulfonamide (32.1 mg; 97%) is obtained in the form of a white powder.

Mixture of conformers: $^1$H NMR (DMSO-d6) δ: 0.86 (dd, J=6.6, 1.5 Hz, 6H), 1.20 (t, J=7.6 Hz, 3H), 1.46-1.61 (m, 1H), 1.77-1.96 (m, 2H), 1.96-2.15 (m, 2H), 2.57-2.68 (m, 2H), 2.77-2.96 (m, 2H), 3.20 (s, 3H), 3.28-3.38 (m, 2H), 3.98-4.21 (m, 1H), 4.75-5.03 (m, 1H), 6.98-7.06 (m, 2H), 7.16-7.23 (m, 2H), 7.41 (d, J=8.8 Hz, 1H), 7.64-7.72 (m, 1H), 8.05 (d, J=2.5 Hz, 1H).

MS: [M+H]=494

Example 33: Synthesis of 4-((1-acetylpiperidin-4-yl)oxy)-N-(4-ethylphenyl)-N-isobutyl-3-(S-methylsulfonimidoyl)benzenesulfonamide

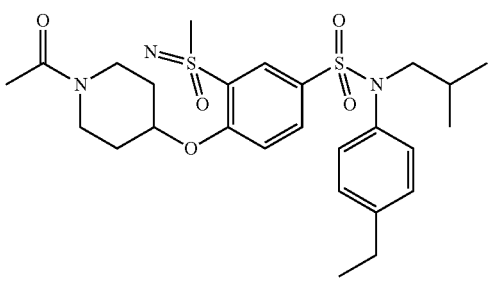

Compound 47

4-Dimethylaminopyridine (1.6 mg; 0.01 mmol) and acetic anhydride (11.2 µl; 0.12 mmol) are added to a solution of N-(4-ethylphenyl)-N-isobutyl-3-(S-methylsulfonimidoyl)-4-(piperidin-4-yloxy)benzenesulfonamide (65.0 mg; 0.13 mmol) in dichloromethane (2 ml) cooled to a temperature of −10° C.

The reaction medium is stirred for 2 hours at room temperature. The reaction medium is hydrolyzed, followed by addition of saturated sodium hydrogen carbonate solution, and then extracted with ethyl acetate. The organic phases are combined, washed with saturated sodium chloride solution, dried ($Na_2SO_4$) and concentrated to dryness.

The crude product is purified by preparative HPLC (C18 column, eluent: acetonitrile in water/0.1% of formic acid). The 4-((1-acetylpiperidin-4-yl)oxy)-N-(4-ethylphenyl)-N-isobutyl-3-(S-methylsulfonimidoyl)benzenesulfonamide (34.8 mg; 49%) is obtained in the form of a white solid.

$^1$H NMR (DMSO-d6) δ: 0.86 (dd, J=6.6, 2.3 Hz, 6H), 1.19 (t, 3H), 1.36-1.51 (m, 1H), 1.89-2.07 (m, 5H), 2.61 (q, J=7.6 Hz, 2H), 2.87 (s, 3H), 3.20 (d, J=1.2 Hz, 3H), 3.23-3.31 (m, 5H), 4.47 (d, J=1.5 Hz, 1H), 5.06 (t, J=4.1 Hz, 1H), 6.98-7.05 (m, 2H), 7.18-7.25 (m, 2H), 7.47 (d, J=9.0 Hz, 1H), 7.67 (dd, J=8.7, 2.4 Hz, 1H), 8.00 (d, J=2.4 Hz, 1H).

MS: [M+H]=536

Example 34: Synthesis of N-(4-ethylphenyl)-N-isobutyl-3-(S-methylsulfonimidoyl)-4-((1-(methylsulfonyl)piperidin-4-yl)oxy)benzenesulfonamide

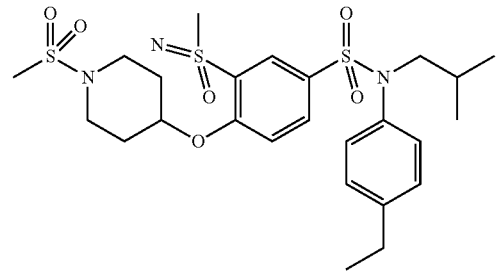

Compound 48

Triethylamine (18.3 µl; 0.13 mmol) and methanesulfonyl chloride (10.2 µl; 0.13 mmol) are added to a solution of N-(4-ethylphenyl)-N-isobutyl-3-(S-methylsulfonimidoyl)-4-(piperidin-4-ylmethoxy)benzenesulfonamide (65.0 mg; 0.13 mmol) in dichloromethane (1.3 ml).

The reaction medium is stirred for 2 hours at room temperature, hydrolyzed by addition of saturated sodium hydrogen carbonate solution, and extracted with ethyl acetate. The organic phases are combined, washed with saturated sodium chloride solution, dried over sodium sulfate and concentrated to dryness.

The crude product is purified by preparative HPLC (C18 column, eluent: acetonitrile in water/0.1% of formic acid). The N-(4-ethylphenyl)-N-isobutyl-3-(S-methylsulfonimidoyl)-4-((1-(methylsulfonyl)piperidin-4-yl)oxy)benzenesulfonamide (24.8 mg; 32%) is obtained in the form of a white solid.

$^1$H NMR (DMSO-d6) δ: 0.86 (dd, J=6.7, 3.4 Hz, 6H), 1.19 (t, J=7.6 Hz, 3H), 1.36-1.51 (m, 1H), 1.81-1.88 (m, 2H), 1.99 (d, J=9.4 Hz, 1H), 2.03 (s, 3H), 2.61 (q, J=7.6 Hz, 2H), 3.19 (d, J=1.2 Hz, 3H), 3.22-3.31 (m, 2H), 3.43-3.52 (m, 1H), 3.53-3.74 (m, 3H), 4.42 (dd, J=3.3, 1.5 Hz, 1H), 5.02-5.09 (m, 1H), 6.98-7.06 (m, 2H), 7.17-7.25 (m, 2H), 7.47 (d, J=8.9 Hz, 1H), 7.65 (dd, J=8.8, 2.4 Hz, 1H), 8.02 (d, J=2.4 Hz, 1H)).

MS: [M+H]=572

Example 35: Synthesis of N-(4-ethylphenyl)-N-isobutyl-3-(S-methylsulfonimidoyl)-4-(piperidin-4-ylmethoxy)benzenesulfonamide Compound 49

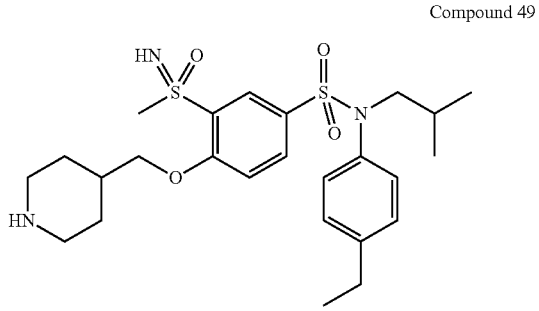 [SMILES: CCc1ccc(N(CC(C)C)S(=O)(=O)c2ccc(OCC3CCNCC3)c(S(C)(=N)=O)c2)cc1]

With a procedure similar to that described for example 31, N-(4-ethylphenyl)-N-isobutyl-3-(S-methylsulfonimidoyl)-4-(piperidin-4-ylmethoxy)benzenesulfonamide (68.2 mg; 100%) is obtained in the form of a white powder.

$^1$H NMR (DMSO-d6) δ: 0.77 (dd, J=6.6, 4.4 Hz, 6H), 1.11 (t, J=7.6 Hz, 3H), 1.14-1.24 (m, 2H), 1.24-1.43 (m, 1H), 1.70 (d, J=13.3 Hz, 2H), 1.82-1.89 (m, 1H), 2.45-2.51 (m, 2H), 2.51-2.58 (m, 2H), 2.93 (dt, J=12.1, 3.3 Hz, 2H), 3.11 (s, 3H), 3.18 (dd, J=13.0, 7.1 Hz, 3H), 3.99 (dd, J=6.3, 2.3 Hz, 2H), 4.32 (s, 1H), 6.93 (d, J=8.4 Hz, 2H), 7.13 (d, J=8.4 Hz, 2H), 7.30 (d, J=8.8 Hz, 1H), 7.58 (dd, J=8.8, 2.5 Hz, 1H), 7.92 (d, J=2.4 Hz, 1H).

MS: [M+H]=508

Example 36: Synthesis of 4-((1-acetylpiperidin-4-yl)methoxy)-N-(4-ethylphenyl)-N-isobutyl-3-(S-methylsulfonimidoyl)benzenesulfonamide Compound 50

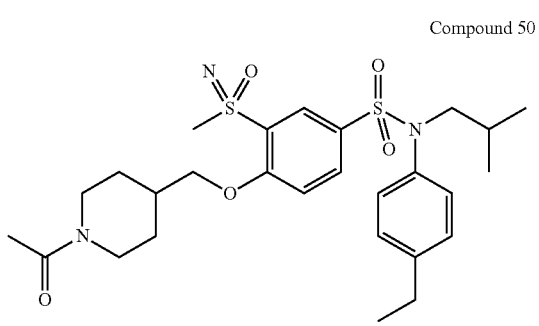 [SMILES: CCc1ccc(N(CC(C)C)S(=O)(=O)c2ccc(OCC3CCN(C(C)=O)CC3)c(S(C)(=N)=O)c2)cc1]

With a procedure similar to that described for example 32, 4-((1-acetylpiperidin-4-yl)methoxy)-N-(4-ethylphenyl)-N-isobutyl-3-(S-methylsulfonimidoyl)benzenesulfonamide (6.5 mg; 10%) is obtained in the form of a white solid.

$^1$H NMR (DMSO-d6) δ: 0.85 (dd, J=6.7, 4.2 Hz, 6H), 1.08-1.23 (m, 5H), 1.22-1.35 (m, 2H), 1.43 (dt, J=13.4, 6.8 Hz, 1H), 1.88 (d, J=26.7 Hz, 2H), 2.01 (s, 3H), 2.09-2.14 (m, 1H), 2.61 (q, J=7.6 Hz, 3H), 3.08 (t, J=12.8 Hz, 1H), 3.18 (s, 3H), 3.22-3.30 (m, 2H), 3.87 (d, J=13.6 Hz, 1H), 4.11 (q, J=4.4 Hz, 2H), 4.42 (d, J=11.5 Hz, 2H), 7.01 (d, J=7.9 Hz, 2H), 7.21 (d, J=8.2 Hz, 2H), 7.38 (d, J=8.8 Hz, 1H), 7.67 (dd, J=8.8, 2.4 Hz, 1H), 8.00 (d, J=2.4 Hz, 1H).

MS: [M+H]=550

Example 37: Synthesis of N-(4-ethylphenyl)-N-isobutyl-3-(S-methylsulfonimidoyl)-4-((1-(methylsulfonylpiperidin-4-yl)methoxy)benzenesulfonamide Compound 51

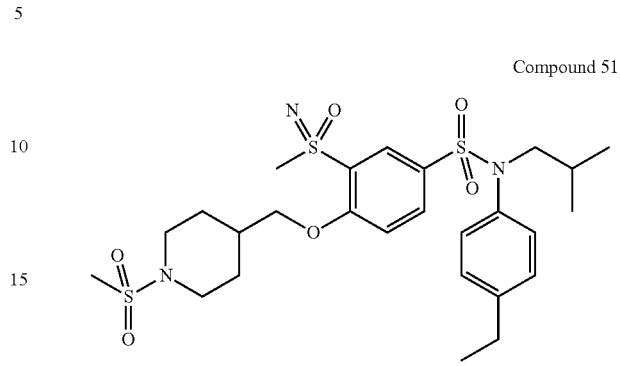

With a procedure similar to that described for example 33, N-(4-ethylphenyl)-N-isobutyl-3-(S-methylsulfonimidoyl)-4-((1-(methylsulfonylpiperidin-4-yl)methoxy)benzenesulfonamide (17.2 mg; 25%) is obtained in the form of a white solid.

$^1$H NMR (DMSO-d6) δ: 0.85 (dd, J=6.7, 4.3 Hz, 6H), 1.19 (t, J=7.6 Hz, 3H), 1.37-1.51 (m, 3H), 1.89-2.04 (m, 3H), 2.61 (q, J=7.7 Hz, 2H), 2.72-2.83 (m, 2H), 2.88 (s, 3H), 3.18 (s, 3H), 3.28 (d, J=7.8 Hz, 2H), 3.62 (d, J=11.5 Hz, 2H), 4.09-4.20 (m, 2H), 4.42 (s, 1H), 7.01 (d, J=8.0 Hz, 2H), 7.21 (d, J=8.1 Hz, 2H), 7.39 (d, J=8.8 Hz, 1H), 7.68 (dd, J=8.7, 2.5 Hz, 1H), 8.00 (d, J=2.5 Hz, 1H).

MS: [M+H]=586

Example 38: Synthesis of N-(4-ethylphenyl)-N-isobutyl-3-(S-methylsulfonimidoyl)-4-[(tetrahydropyran-4-ylmethyl)amino]benzenesulfonamide Compound 52

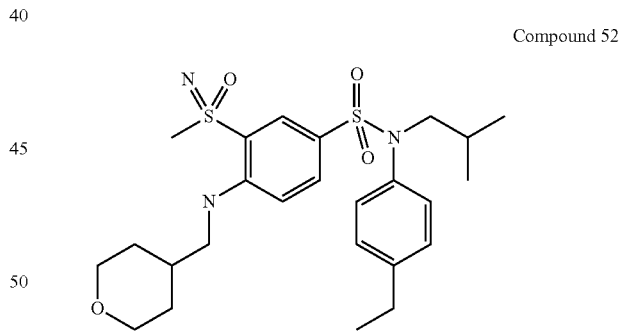

A mixture of 4-bromo-N-(4-ethylphenyl)-N-isobutyl-3-(S-methylsulfonimidoyl)benzenesulfonamide (15.0 mg; 0.03 mmol) and 4-aminomethyltetrahydropyran (7.5 µl; 0.06 mmol) is stirred overnight at room temperature.

The crude product is purified by preparative HPLC (C18 column, eluent: acetonitrile in water/0.1% of formic acid). The N-(4-ethylphenyl)-N-isobutyl-3-(S-methylsulfonimidoyl)-4-[(tetrahydropyran-4-ylmethyl)amino]benzenesulfonamide (9.0 mg; 56%) is obtained in the form of a white solid.

$^1$H NMR (DMSO-d6, 400 MHz): δ (ppm) 0.84 (dd, J=6.7, 2.6 Hz, 6H), 1.18 (t, J=7.7 Hz, 3H), 1.28 (dd, J=14.5, 10.3 Hz, 2H), 1.37-1.46 (m, 1H), 1.66 (d, J=13.3 Hz, 2H), 1.87 (s, 1H), 2.61 (q, J=7.4 Hz, 2H), 3.01 (s, 3H), 3.17 (q, J=6.8, 6.4 Hz, 2H), 3.24 (dd, J=7.4, 3.3 Hz, 2H), 3.89 (dd, J=11.6, 4.0 Hz, 2H), 4.74 (s, 1H), 6.95 (d, J=8.9 Hz, 1H), 7.00 (d, J=7.9 Hz, 2H), 7.20 (d, J=8.1 Hz, 2H), 7.50 (d, J=9.0 Hz, 1H), 7.70 (d, J=2.3 Hz, 1H), 7.84 (t, J=5.5 Hz, 1H).

MS: [M+H]=508

Example 39: Synthesis of N-(4-ethylphenyl)-N-isobutyl-4-(methyl((tetrahydro-2H-pyran-4-yl)methyl)amino)-3-(S-methylsulfonimidoyl)benzenesulfonamide

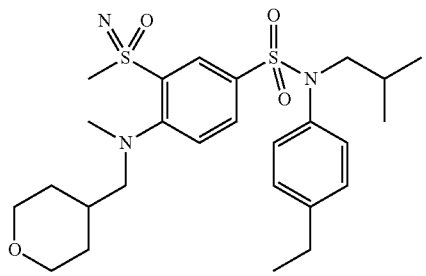

Compound 53

A solution of 4-bromo-N-(4-ethylphenyl)-N-isobutyl-3-(S-methylsulfonimidoyl)benzenesulfonamide (15.0 mg; 0.03 mmol) in N,N-dimethylformamide (0.20 ml) is stirred overnight at a temperature of 50° C.

The crude product is purified by preparative HPLC (C18 column, eluent: acetonitrile in water/0.1% of formic acid). The N-(4-ethylphenyl)-N-isobutyl-4-(methyl((tetrahydro-2H-pyran-4-yl)methyl)amino)-3-(S-methylsulfonimidoyl)benzenesulfonamide (9.0 mg; 49%) is obtained in the form of a colorless dry film.

$^1$H NMR (DMSO-d6) δ: 0.85 (dd, J=6.6, 3.2 Hz, 6H), 1.18 (t, J=7.6 Hz, 3H), 1.44 (dt, J=13.7, 6.8 Hz, 1H), 1.58 (d, J=13.4 Hz, 2H), 1.93 (s, 1H), 2.61 (q, J=7.6 Hz, 2H), 2.82 (s, 3H), 2.93-3.10 (m, 2H), 3.26 (d, J=1.3 Hz, 3H), 3.28-3.30 (m, 2H), 3.80-3.87 (m, 2H), 4.50 (d, J=1.5 Hz, 1H), 7.00 (d, J=8.4 Hz, 2H), 7.20 (d, J=8.3 Hz, 2H), 7.56 (d, J=8.6 Hz, 1H), 7.61 (dd, J=8.6, 2.2 Hz, 1H), 8.13 (d, J=2.3 Hz, 1H).

MS: [M+H]=522

Example 40: Synthesis of N-(4-ethylphenyl)-N-isobutyl-3-(S-methylsulfonimidoyl)-4-((oxetan-3-ylmethyl)amino)benzenesulfonamide

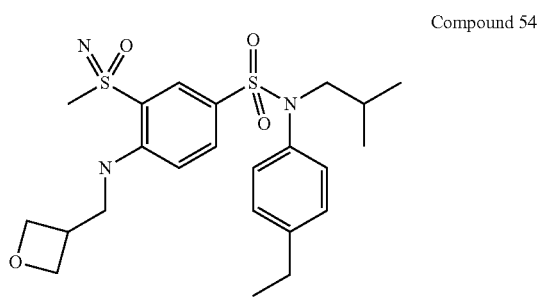 [SMILES: CCc1ccc(N(CC(C)C)S(=O)(=O)c2ccc(NCC3COC3)c(S(C)(=N)=O)c2)cc1]

Compound 54

3-Aminomethyloxetane hydrochloride (33 mg; 0.26 mmol) and triethylamine (51 μl; 0.37 mmol) are added to 4-bromo-N-(4-ethylphenyl)-N-isobutyl-3-(S-methylsulfonimidoyl)benzenesulfonamide (50.00 mg; 0.11 mmol) dissolved in N,N-dimethylformamide (250 μl). The reaction medium is stirred overnight at 50° C.

The crude product is purified directly by preparative HPLC (C18 column, eluent: acetonitrile in water/0.1% of formic acid). The N-(4-ethylphenyl)-N-isobutyl-3-(S-methylsulfonimidoyl)-4-((oxetan-3-ylmethyl)aminobenzenesulfonamide (14.0 mg; 26%) is obtained in the form of a white solid.

$^1$H NMR (DMSO-d6) δ: 0.84 (dd, J=6.7, 2.2 Hz, 6H), 1.18 (t, J=7.6 Hz, 3H), 1.35-1.50 (m, 1H), 2.61 (q, J=7.7 Hz, 2H), 3.00 (s, 3H), 3.25 (d, J=6.9 Hz, 2H), 3.58 (dt, J=14.5, 7.1 Hz, 2H), 4.35 (td, J=6.0, 2.8 Hz, 2H), 4.70 (td, J=6.4, 3.3 Hz, 3H), 6.99 (dd, J=8.5, 5.0 Hz, 3H), 7.20 (d, J=7.8 Hz, 2H), 7.51 (dd, J=8.8, 2.5 Hz, 1H), 7.71 (d, J=2.5 Hz, 1H), 7.82 (t, J=5.5 Hz, 1H).

MS: [M+H]=480

With a procedure similar to that described for example 40, the following are obtained:

| Example 41 | | |
|---|---|---|
| 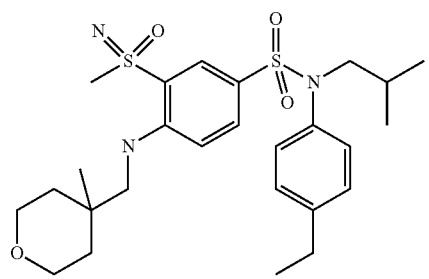<br>Compound 55 | | N-(4-ethylphenyl)-N-isobutyl-3-(S-methylsulfonimidoyl)-4-(((4-methyltetrahydro-2H-pyran-4-yl)methyl)amino)benzenesulfonamide<br>$^1$H NMR (DMSO-d6) δ: 0.84 (dd, J = 6.7, 3.3 Hz, 6H), 1.09 (s, 3H), 1.18 (t, J = 7.6 Hz, 3H), 1.31-1.38 (m, 2H), 1.38-1.47 (m, 1H), 1.54 (ddt, J = 14.2, 9.8, 5.0 Hz, 2H), 2.61 (q, J = 7.7 Hz, 2H), 3.01 (s, 3H), 3.07-3.21 (m, 2H), 3.24 (p, J = 5.6 Hz, 2H), 3.51-3.60 (m, 2H), 3.68 (dt, J = 11.8, 4.4 Hz, 2H), 4.84 (s, 1H), 7.00 (d, J = 8.1 Hz, 3H), 7.20 (d, J = 7.9 Hz, 2H), 7.49 (dd, J = 8.9, 2.4 Hz, 1H), 7.69 (d, J = 2.5 Hz, 1H), 7.98 (t, J = 5.1 Hz, 1H).<br>MS: [M + H] = 522 |

-continued

| | | |
|---|---|---|
| Example 42 | 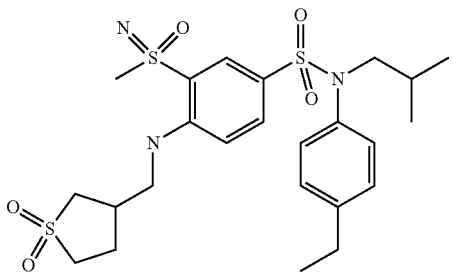

Compound 56 | 4-(((1,1-dioxidotetrahydrothiophen-3-yl)methyl)amino)-N-(4-ethylphenyl)-N-isobutyl-3-(S-methylsulfonimidoyl)benzenesulfonamide
$^1$H NMR (DMSO-d6) δ: 0.84 (dd, J = 6.6, 2.7 Hz, 6H), 1.18 (t, J = 7.6 Hz, 3H), 1.38-1.50 (m, 1H), 1.89 (d, J = 22.1 Hz, 1H), 2.61 (q, J = 7.6 Hz, 2H), 2.90 (t, J = 12.1 Hz, 1H), 3.03 (d, J = 1.5 Hz, 3H), 3.25 (dd, J = 7.5, 3.9 Hz, 2H), 3.44 (t, J = 6.3 Hz, 2H), 4.73 (d, J = 6.3 Hz, 1H), 7.01 (dd, J = 8.6, 5.9 Hz, 3H), 7.20 (d, J = 8.3 Hz, 2H), 7.49 (dd, J = 8.9, 2.4 Hz, 1H), 7.72 (d, J = 2.3 Hz, 1H), 7.85 (s, 1H).
MS: [M + H] = 542 |
| Example 43 | 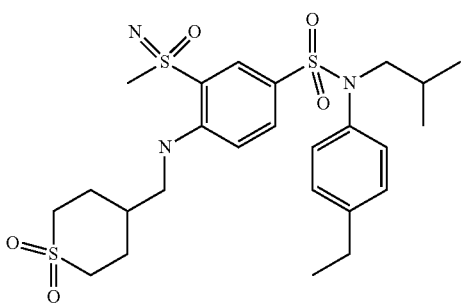

Compound 57 | 4-(((1,1-dioxidotetrahydro-2H-thiopyran-4-yl)methyl)amino)-N-(4-ethylphenyl)-N-isobutyl-3-(S-methylsulfonimidoyl)benzenesulfonamide
$^1$H NMR (DMSO-d6) δ: 0.84 (dd, J = 6.7, 2.2 Hz, 6H), 1.18 (t, J = 7.6 Hz, 3H), 1.42 (dt, J = 13.5, 6.8 Hz, 1H), 1.71 (q, J = 12.2 Hz, 2H), 1.91-1.98 (m, 1H), 2.06-2.14 (m, 2H), 2.61 (q, J = 7.6 Hz, 2H), 3.02 (s, 3H), 3.10 (dd, J = 28.9, 13.4 Hz, 2H), 3.23-3.28 (m, 4H), 4.74 (d, J = 1.1 Hz, 1H), 6.97-7.02 (m, 3H), 7.20 (d, J = 8.3 Hz, 2H), 7.50 (dd, J = 8.9, 2.4 Hz, 1H), 7.71 (d, J = 2.3 Hz, 1H), 7.84 (t, J = 5.8 Hz, 1H).
MS: [M + H] = 556 |
| Example 44 | 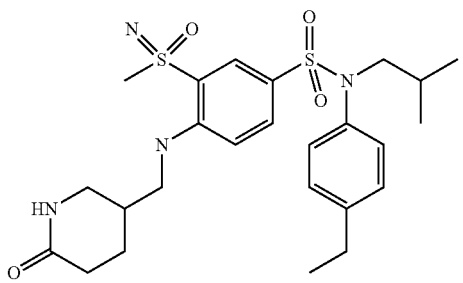

Compound 58 | N-(4-ethylphenyl)-N-isobutyl-3-(S-methylsulfonimidoyl)-4-(((6-oxopiperidin-3-yl)methyl)amino)benzenesulfonamide
$^1$H NMR (DMSO-d6) δ: 0.84 (dd, J = 6.6, 2.5 Hz, 6H), 1.18 (t, J = 7.6 Hz, 3H), 1.42 (dt, J = 13.6, 6.8 Hz, 1H), 1.47-1.59 (m, 1H), 1.83-1.93 (m, 1H), 2.02-2.11 (m, 1H), 2.16-2.25 (m, 2H), 2.60 (q, J = 7.7 Hz, 2H), 2.90-2.98 (m, 1H), 3.02 (s, 3H), 3.23-3.29 (m, 3H), 4.75 (s, 1H), 6.97-7.04 (m, 3H), 7.17-7.23 (m, 2H), 7.44-7.53 (m, 2H), 7.71 (dd, J = 2.3, 1.1 Hz, 1H), 7.83 (s, 1H).
MS: [M + H] = 521 |
| Example 45 | 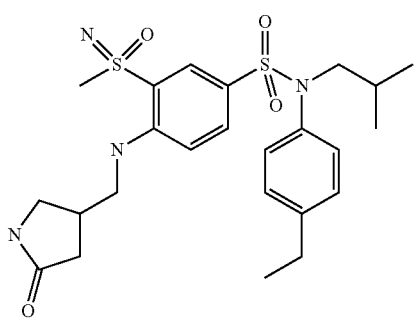

Compound 59 | N-(4-ethylphenyl)-N-isobutyl-3-(S-methylsulfonimidoyl)-4-(((5-oxopyrrolidin-3-yl)methyl)amino)benzenesulfonamide
$^1$H NMR (DMSO-d6) δ: 0.84 (dd, J = 6.6, 2.7 Hz, 6H), 1.18 (t, J = 7.6 Hz, 3H), 1.42 (dt, J = 13.5, 6.8 Hz, 1H), 2.00 (ddd, J = 16.6, 6.8, 3.6 Hz, 1H), 2.29 (d, J = 8.8 Hz, 1H), 2.60 (q, J = 7.7 Hz, 2H), 2.68-2.78 (m, 1H), 3.02 (s, 3H), 3.24 (dd, J = 7.3, 3.6 Hz, 2H), 3.33-3.44 (m, 2H), 4.74 (s, 1H), 6.97 (s, 1H), 7.00 (d, J = 8.1 Hz, 2H), 7.16-7.23 (m, 2H), 7.50 (dd, J = 8.9, 2.4 Hz, 1H), 7.59 (s, 1H), 7.71 (d, J = 2.3 Hz, 1H), 7.83 (d, J = 5.0 Hz, 1H).
MS: [M + H] = 507 |
| Example 46 | 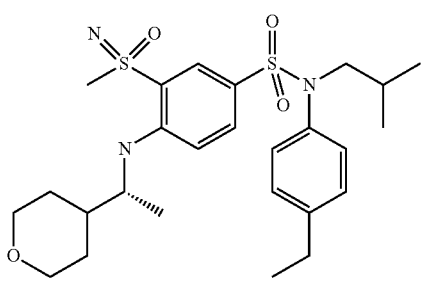

Compound 60 | N-(4-ethylphenyl)-N-isobutyl-3-(S-methylsulfonimidoyl)-4-(((R)-1-(tetrahydro-2H-pyran-4-yl)ethyl)amino)benzenesulfonamide
$^1$H NMR (DMSO-d6) δ: 0.84 (dd, J = 6.7, 3.0 Hz, 6H), 1.10-1.23 (m, 6H), 1.26-1.40 (m, 1H), 1.42 (p, J = 7.0 Hz, 2H), 1.57 (d, J = 13.1 Hz, 2H), 1.62-1.79 (m, 1H), 2.61 (q, J = 7.6 Hz, 2H), 2.99 (dd, J = 4.0, 1.0 Hz, 3H), 3.19-3.30 (m, 4H), 3.56-3.69 (m, 1H), 3.84-3.95 (m, 2H), 4.78 (d, J = 4.6 Hz, 1H), 6.94-7.02 (m, 1H), 7.01 (d, J = 8.4 Hz, 2H), 7.16-7.25 (m, 2H), 7.43-7.53 (m, 1H), 7.70 (t, J = 2.0 Hz, 1H), 7.80-7.90 (m, 1H).
MS: [M + H] = 522 |

| Example 47 | 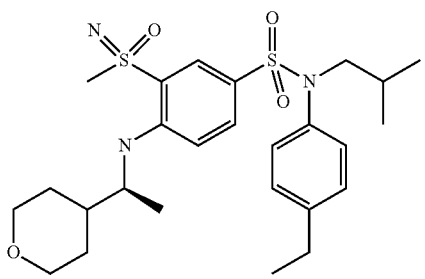

Compound 81 | N-(4-ethylphenyl)-N-isobutyl-3-(S-methylsulfonimidoyl)-4-(((S)-1-(tetrahydro-2H-pyran-4-yl)ethyl)amino)benzenesulfonamide
$^1$H NMR (DMSO-d6) δ: 0.84 (dd, J = 6.7, 3.0 Hz, 6H), 1.10-1.23 (m, 6H), 1.24-1.48 (m, 2H), 1.57 (d, J = 13.0 Hz, 1H), 1.62-1.77 (m, 3H), 2.61 (q, J = 7.6 Hz, 2H), 2.99 (dd, J = 4.0, 1.0 Hz, 3H), 3.21-3.30 (m, 4H), 3.60 (d, J = 20.4 Hz, 1H), 3.84-3.97 (m, 2H), 4.75-4.82 (m, 1H), 6.94-7.01 (m, 1H), 7.01 (d, J = 8.4 Hz, 2H), 7.16-7.24 (m, 2H), 7.43-7.52 (m, 1H), 7.67-7.73 (m, 1H), 7.80-7.88 (m, 1H).
MS: [M + H] = 522 |
| Example 48 | 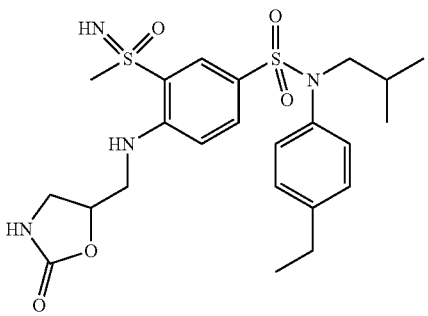

Compound 82 | N-(4-ethylphenyl)-N-isobutyl-3-(S-methylsulfonimidoyl)-4-(((2-oxooxazolidin-5-yl)methyl)amino)benzenesulfonamide
$^1$H NMR (DMSO-d6) δ: 0.81-0.87 (m, 6H), 1.18 (t, J = 7.6 Hz, 3H), 1.42 (p, J = 6.6 Hz, 1H), 2.60 (q, J = 7.6 Hz, 2H), 3.02 (t, J = 1.1 Hz, 3H), 3.22-3.28 (m, 3H), 3.60 (ddt, J = 11.1, 6.9, 3.9 Hz, 2H), 4.55 (s, 1H), 4.73 (d, J = 11.6 Hz, 1H), 4.82 (s, 1H), 6.94-7.04 (m, 2H), 7.06 (d, J = 8.9 Hz, 1H), 7.20 (d, J = 8.2 Hz, 2H), 7.51 (dt, J = 8.9, 2.1 Hz, 1H), 7.60 (s, 1H), 7.72 (dd, J = 3.4, 2.3 Hz, 1H), 7.86-8.01 (m, 1H).
MS: [M + H] = 509 |
| Example 49 | 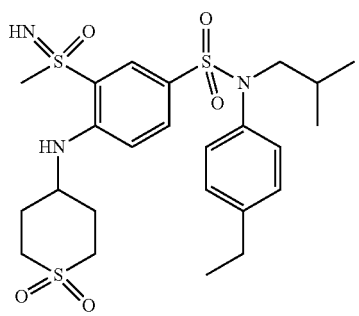

Compound 83 | 4-((1,1-dioxidotetrahydro-2H-thiopyran-4-yl)amino)-N-(4-ethylphenyl)-N-isobutyl-3-(S-methylsulfonimidoyl)benzenesulfonamide
$^1$H NMR (Chloroform-d) δ: 0.90 (dd, J = 9.1, 6.6 Hz, 6H), 1.25 (d, J = 8.2 Hz, 4H), 2.31 (s, 2H), 2.44 (s, 2H), 2.58-2.66 (m, 2H), 3.04 (s, 3H), 3.07-3.23 (m, 4H), 3.24-3.37 (m, 2H), 3.75 (s, 1H), 6.67 (d, J = 8.9 Hz, 1H), 7.00 (d, J = 8.3 Hz, 2H), 7.14 (d, J = 8.0 Hz, 2H), 7.58 (dd, J = 8.8, 2.2 Hz, 1H), 8.03 (d, J = 2.2 Hz, 1H).
MS: [M + H] = 542 |
| Example 50 | 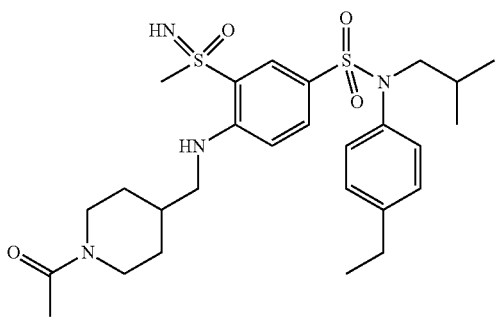

Compound 84 | 4-(((1-acetylpiperidin-4-yl)methyl)amino)-N-(4-ethylphenyl)-N-isobutyl-3-(S-methylsulfonimidoyl)benzenesulfonamide
$^1$H NMR (Chloroform-d) δ: 0.92 (dd, J = 8.9, 6.7 Hz, 6H), 1.22-1.28 (m, 4H), 1.59 (hept, J = 6.8 Hz, 1H), 1.90 (dddd, J = 26.2, 18.2, 8.2, 4.9 Hz, 4H), 2.12 (s, 3H), 2.65 (q, J = 7.8 Hz, 2H), 3.04 (s, 3H), 3.09-3.17 (m, 4H), 3.24 (dd, J = 12.8, 6.9 Hz, 1H), 3.34 (dd, J = 12.7, 7.7 Hz, 1H), 3.89 (d, J = 13.2, 3.5 Hz, 1H), 4.66-4.76 (m, 1H), 6.68 (d, J = 9.0 Hz, 1H), 7.01 (d, J = 8.0 Hz, 2H), 7.15 (d, J = 8.0 Hz, 2H), 7.55 (dd, J = 8.8, 2.0 Hz, 1H), 7.65 (q, J = 4.4, 3.9 Hz, 1H), 7.99 (d, J = 2.2 Hz, 1H).
MS: [M + H] = 549 |

| | | |
|---|---|---|
| Example 51 | 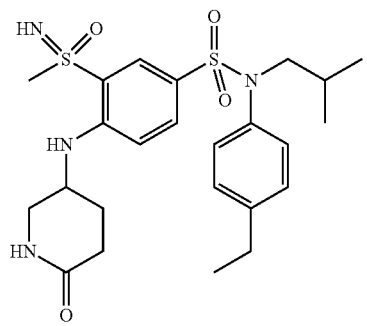<br>Compound 85 | N-(4-ethylphenyl)-N-isobutyl-3-(S-methylsulfonimidoyl)-4-((6-oxopiperidin-3-yl)amino)benzenesulfonamide<br>$^1$H NMR (Chloroform-d) δ: 0.90 (dd, J = 9.2, 6.6 Hz, 6H), 1.19-1.27 (m, 5H), 1.58 (hept, J = 7.0 Hz, 1H), 2.55 (s, 2H), 2.64 (d, J = 7.9 Hz, 2H), 3.03 (s, 3H), 3.29 (ddd, J = 39.3, 12.4, 6.9 Hz, 3H), 3.67 (s, 1H), 3.87-3.99 (m, 1H), 6.02 (s, 1H), 6.74 (d, J = 8.4 Hz, 1H), 7.00 (d, J = 7.6 Hz, 2H), 7.14 (d, J = 7.6 Hz, 2H), 7.56 (d, J = 7.6 Hz, 1H), 7.92 (s, 1H), 8.02 (d, J = 5.8 Hz, 1H).<br>MS: [M + H] = 507 |
| Example 52 | 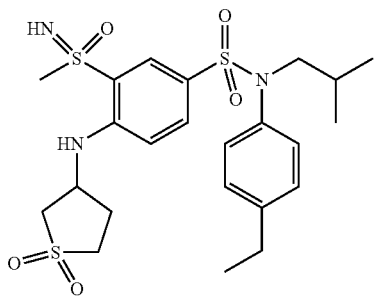<br>Compound 86 | 4-((1,1-dioxidotetrahydrothiophen-3-yl)amino)-N-(4-ethylphenyl)-N-isobutyl-3-(S-methylsulfonimidoyl)benzenesulfonamide<br>$^1$H NMR (DMSO-d6) δ: 0.84 (ddd, J = 6.6, 2.3, 1.0 Hz, 6H), 1.18 (t, J = 7.6 Hz, 3H), 1.42 (dt, J = 13.6, 6.7 Hz, 1H), 2.12-2.24 (m, 1H), 2.61 (q, J = 7.5 Hz, 2H), 3.04 (d, J = 2.6 Hz, 3H), 3.07-3.21 (m, 1H), 3.23-3.27 (m, 2H), 3.65 (ddd, J = 20.2, 13.3, 7.0 Hz, 1H), 4.44-4.56 (m, 1H), 4.74 (s, 1H), 4.80 (s, 1H), 7.00 (d, J = 8.3 Hz, 2H), 7.20 (d, J = 8.4 Hz, 2H), 7.54 (dt, J = 8.3, 1.4 Hz, 1H), 7.73 (dd, J = 4.0, 2.3 Hz, 1H), 7.98 (d, J = 7.1 Hz, 1H), 8.12 (d, J = 6.6 Hz, 1H).<br>MS: [M + H] = 528 |
| Example 53 | 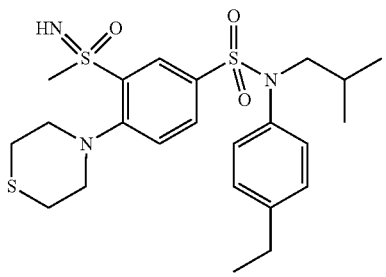<br>Compound 87 | N-(4-ethylphenyl)-N-isobutyl-3-(S-methylsulfonimidoyl)-4-thiomorpholinobenzenesulfonamide<br>$^1$H NMR (DMSO-d6) δ: 0.84 (ddd, J = 6.6, 2.3, 1.0 Hz, 6H), 1.18 (t, J = 7.6 Hz, 3H), 1.42 (dt, J = 13.6, 6.7 Hz, 1H), 2.12-2.24 (m, 1H), 2.61 (q, J = 7.5 Hz, 2H), 3.04 (d, J = 2.6 Hz, 3H), 3.07-3.21 (m, 1H), 3.23-3.27 (m, 2H), 3.65 (ddd, J = 20.2, 13.3, 7.0 Hz, 1H), 4.44-4.56 (m, 1H), 4.74 (s, 1H), 4.80 (s, 1H), 7.00 (d, J = 8.3 Hz, 2H), 7.20 (d, J = 8.4 Hz, 2H), 7.54 (dt, J = 8.3, 1.4 Hz, 1H), 7.73 (dd, J = 4.0, 2.3 Hz, 1H), 7.98 (d, J = 7.1 Hz, 1H), 8.12 (d, J = 6.6 Hz, 1H).<br>MS: [M + H] = 528 |
| Example 54 | 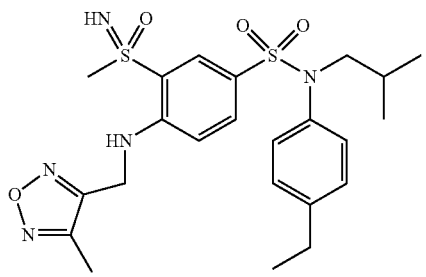<br>Compound 88 | N-(4-ethylphenyl)-N-isobutyl-4-(((4-methyl-1,2,5-oxadiazol-3-yl)methyl)amino)-3-(S-methylsulfonimidoyl)benzenesulfonamide<br>$^1$H NMR (DMSO-d6) δ: 0.85 (dd, J = 6.6, 3.5 Hz, 6H), 1.13-1.23 (m, 3H), 1.43 (dt, J = 13.6, 6.8 Hz, 1H), 2.61 (q, J = 7.6 Hz, 2H), 2.80 (dt, J = 6.8, 3.6 Hz, 4H), 3.25 (q, J = 5.9, 5.3 Hz, 4H), 3.31 (s, 3H), 4.53-4.57 (m, 1H), 6.97-7.05 (m, 2H), 7.17-7.26 (m, 2H), 7.63 (d, J = 8.4 Hz, 1H), 7.71 (dd, J = 8.4, 2.3 Hz, 1H), 8.12 (d, J = 2.3 Hz, 1H).<br>MS: [M + H] = 496 |

Example 55: Synthesis of N-(4-ethylphenyl)-4-(((3-hydroxycyclobutyl)methyl)amino)-N-isobutyl-3-(S-methylsulfonimidoyl)benzenesulfonamide

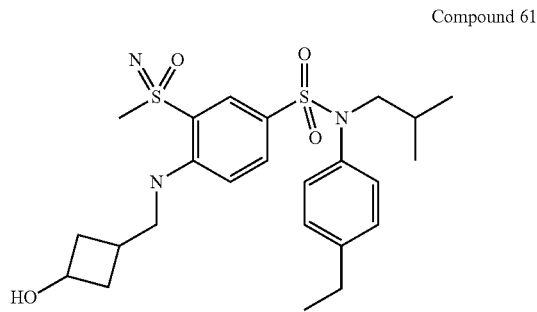 [SMILES: CCc1ccc(N(CC(C)C)S(=O)(=O)c2ccc(NCC3CC(O)C3)c(S(C)(=N)=O)c2)cc1]

Compound 61

3-Aminomethylcyclobutanol hydrochloride (36.33 mg; 0.26 mmol) and cesium carbonate (120.43 mg; 0.37 mmol) are added to 4-bromo-N-(4-ethylphenyl)-N-isobutyl-3-(S-methylsulfonimidoyl)benzenesulfonamide (50.00 mg; 0.11 mmol) dissolved in N,N-dimethylformamide (150 µl).

The reaction medium is stirred over the weekend at a temperature of 50° C.

The crude product is purified directly by preparative HPLC (C18 column, eluent: acetonitrile in water/0.1% of formic acid). The N-(4-ethylphenyl)-4-(((3-hydroxycyclobutyl)methyl)amino)-N-isobutyl-3-(S-methylsulfonimidoyl)benzenesulfonamide (20.0 mg; 38%) is obtained in the form of a white solid.

$^1$H NMR (DMSO-d6) δ: 0.84 (dd, J=6.7, 2.4 Hz, 6H), 1.18 (t, J=7.6 Hz, 3H), 1.42 (dt, J=13.5, 6.7 Hz, 1H), 1.56 (q, J=8.7 Hz, 1H), 1.94-2.07 (m, 2H), 2.27-2.36 (m, 2H), 2.60 (q, J=7.6 Hz, 2H), 2.99 (s, 3H), 3.24 (dd, J=7.3, 3.5 Hz, 2H), 3.98 (dt, J=14.2, 7.4 Hz, 1H), 4.70 (d, J=1.3 Hz, 1H), 5.03 (t, J=3.1 Hz, 1H), 6.91 (t, J=8.6 Hz, 1H), 6.99 (dd, J=8.4, 1.6 Hz, 2H), 7.17-7.23 (m, 2H), 7.50 (dt, J=8.8, 2.9 Hz, 1H), 7.69 (d, J=2.3 Hz, 1H).

MS: [M+H]=494

With a procedure similar to that described for example 55, the following are obtained:

| Example 56 | 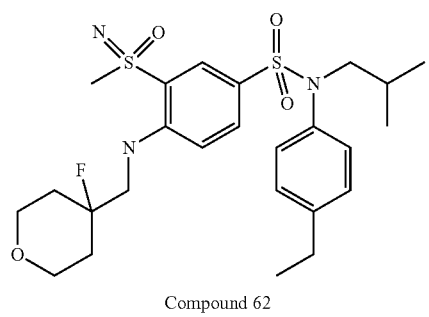 [SMILES: CCc1ccc(N(CC(C)C)S(=O)(=O)c2ccc(NCC3(F)CCOCC3)c(S(C)(=N)=O)c2)cc1]<br>Compound 62 | N-(4-ethylphenyl)-4-(((4-fluorotetrahydro-2H-pyran-4-yl)methyl)amino)-N-isobutyl-3-(S-methylsulfonimidoyl)benzenesulfonamide<br>$^1$H NMR (DMSO-d6) δ: 0.84 (dd, J = 6.7, 2.4 Hz, 6H), 1.18 (t, J = 7.6 Hz, 3H), 1.42 (dt, J = 13.6, 6.8 Hz, 1H), 1.81 (tq, J = 19.3, 9.1 Hz, 4H), 2.09 (s, 1H), 2.60 (q, J = 7.6 Hz, 2H), 3.02 (d, J = 0.9 Hz, 3H), 3.25 (dd, J = 7.3, 3.1 Hz, 2H), 3.51-3.63 (m, 4H), 3.74-3.82 (m, 2H), 4.76-4.83 (m, 1H), 7.00 (d, J = 8.3 Hz, 2H), 7.06 (d, J = 8.9 Hz, 1H), 7.17-7.22 (m, 2H), 7.50 (dd, J = 8.9, 2.3 Hz, 1H), 7.72 (d, J = 2.3 Hz, 1H), 8.01 (t, J = 5.8 Hz, 1H)<br>MS: [M + H] = 526 |
|---|---|---|
| Example 57 | 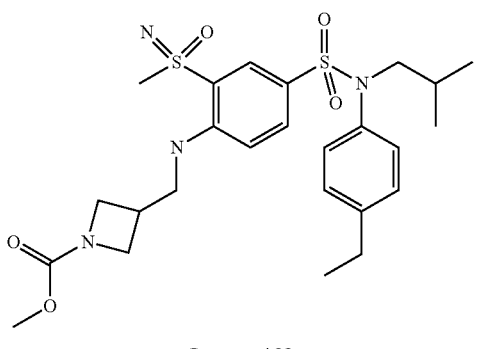<br>Compound 89 | methyl 3-(((4-(N-(4-ethylphenyl)-N-isobutylsulfamoyl)-2-(S-methylsulfonimidoyl)phenyl)amino)methyl)azetidine-1-carboxylate<br>$^1$H NMR (DMSO-d6) δ: 0.84 (dd, J = 6.7, 2.3 Hz, 6H), 1.11-1.23 (m, 3H), 1.42 (dt, J = 13.6, 6.7 Hz, 1H), 2.55-2.66 (m, 2H), 2.99 (s, 3H), 3.25 (ddd, J = 17.8, 9.7, 4.2 Hz, 4H), 3.51 (q, J = 6.5 Hz, 1H), 3.56 (s, 3H), 3.67 (dt, J = 12.1, 6.8 Hz, 2H), 4.00 (p, J = 8.0 Hz, 2H), 4.69 (s, 1H), 6.95-7.05 (m, 3H), 7.16-7.24 (m, 2H), 7.50 (dd, J = 8.9, 2.3 Hz, 1H), 7.71 (d, J = 2.4 Hz, 1H), 7.81 (t, J = 5.5 Hz, 1H).<br>MS: [M + H] = 537 |
| Example 58 | 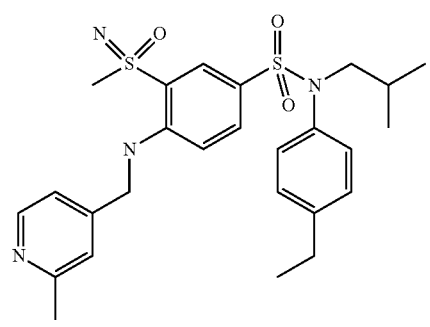<br>Compound 90 | N-(4-ethylphenyl)-N-isobutyl-4-(((2-methylpyridin-4-yl)methyl)amino)-3-(S-methylsulfonimidoyl)benzenesulfonamide<br>$^1$H NMR (DMSO-d6) δ: 0.83 (dd, J = 6.6, 2.0 Hz, 6H), 1.17 (t, J = 7.6 Hz, 3H), 1.41 (dt, J = 13.6, 6.9 Hz, 1H), 2.45 (s, 3H), 2.59 (q, J = 7.7 Hz, 2H), 3.10 (d, J = 1.0 Hz, 3H), 3.24 (dd, J = 7.4, 2.7 Hz, 2H), 4.58 (d, J = 6.1 Hz, 2H), 4.79 (s, 1H), 6.74 (d, J = 8.9 Hz, 1H), 6.95-7.00 (m, 2H), 7.13-7.23 (m, 4H), 7.45 (dd, J = 8.8, 2.3 Hz, 1H), 7.76 (d, J = 2.3 Hz, 1H), 8.19 (t, J = 6.0 Hz, 1H), 8.40 (d, J = 5.3 Hz, 1H).<br>MS: [M + H] = 515 |

| | | |
|---|---|---|
| Example 59 | 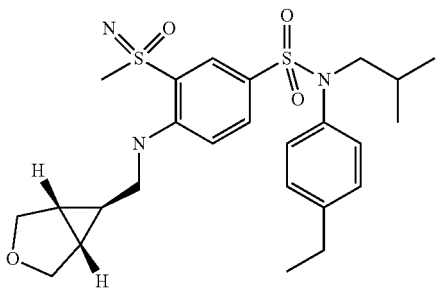<br>Compound 91 | 4-((((1R,5S,6S)-3-oxabicyclo[3.1.0]hexan-6-yl)methyl)amino)-N-(4-ethylphenyl)-N-isobutyl-3-(S-methylsulfonimidoyl)benzenesulfonamide<br>$^1$H NMR (DMSO-d6) δ: 0.84 (dd, J = 6.7, 2.1 Hz, 6H), 1.00 (dt, J = 7.0, 3.6 Hz, 1H), 1.18 (t, J = 7.6 Hz, 3H), 1.42 (dt, J = 13.6, 6.8 Hz, 1H), 1.69 (hept, J = 3.5 Hz, 2H), 2.56-2.66 (m, 2H), 3.02 (d, J = 0.9 Hz, 3H), 3.25 (dd, J = 7.4, 2.5 Hz, 2H), 3.58 (dd, J = 8.2, 2.5 Hz, 2H), 3.74 (dd, J = 8.3, 1.7 Hz, 2H), 4.71 (d, J = 1.3 Hz, 1H), 6.91 (d, J = 9.0 Hz, 1H), 6.95-7.01 (m, 2H), 7.15-7.25 (m, 2H), 7.50 (dd, J = 8.8, 2.3 Hz, 1H), 7.70 (d, J = 2.3 Hz, 1H), 7.77 (t, J = 5.1 Hz, 1H).<br>MS: [M + H] = 506 |
| Example 60 | 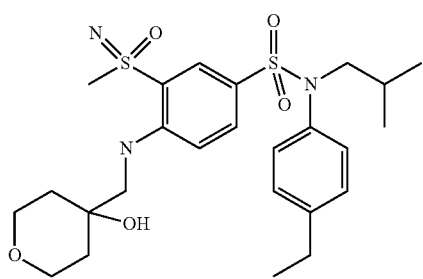<br>Compound 92 | N-(4-ethylphenyl)-4-(((4-hydroxytetrahydro-2H-pyran-4-yl)methyl)amino)-N-isobutyl-3-(S-methylsulfonimidoyl)benzenesulfonamide<br>$^1$H NMR (DMSO-d6) δ: 0.84 (dd, J = 6.7, 1.9 Hz, 6H), 1.18 (t, J = 7.6 Hz, 3H), 1.42 (dt, J = 13.6, 6.8 Hz, 1H), 1.51 (d, J = 13.3 Hz, 2H), 1.62 (dt, J = 15.5, 8.6 Hz, 2H), 2.61 (q, J = 7.6 Hz, 2H), 3.02 (d, J = 0.8 Hz, 3H), 3.20-3.30 (m, 2H), 3.59-3.70 (m, 2H), 4.69 (d, J = 1.1 Hz, 1H), 4.80 (s, 1H), 6.93-7.03 (m, 3H), 7.16-7.23 (m, 2H), 7.48 (dd, J = 8.9, 2.4 Hz, 1H), 7.72 (d, J = 2.3 Hz, 1H), 7.88 (t, J = 5.1 Hz, 1H).<br>MS: [M + H] = 524 |
| Example 61 | 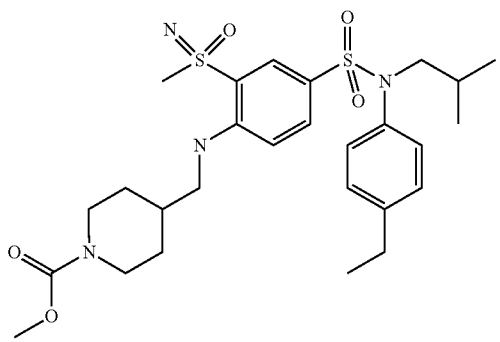<br>Compound 93 | methyl 4-(((4-(N-(4-ethylphenyl)-N-isobutylsulfamoyl)-2-(S-methylsulfonimidoyl)phenyl)amino)methyl)piperidine-1-carboxylate<br>$^1$H NMR (DMSO-d6) δ: 0.84 (dd, J = 6.7, 2.5 Hz, 6H), 1.18 (t, J = 7.6 Hz, 3H), 1.41 (dq, J = 13.8, 6.9 Hz, 1H), 1.73 (d, J = 13.3 Hz, 4H), 1.76-1.88 (m, 1H), 2.60 (q, J = 7.6 Hz, 2H), 3.01 (d, J = 1.0 Hz, 3H), 3.13-3.20 (m, 2H), 3.24 (dd, J = 7.2, 3.3 Hz, 2H), 3.59 (s, 3H), 3.93-4.10 (m, 4H), 4.74 (d, J = 1.3 Hz, 1H), 6.95 (d, J = 8.9 Hz, 1H), 6.97-7.02 (m, 2H), 7.17-7.23 (m, 2H), 7.50 (dd, J = 8.9, 2.4 Hz, 1H), 7.70 (d, J = 2.3 Hz, 1H), 7.83 (t, J = 5.4 Hz, 1H).<br>MS: [M + H] = 565 |
| Example 62 | 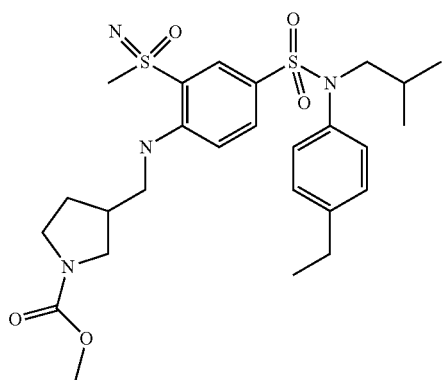<br>Compound 94 | methyl 3-(((4-(N-(4-ethylphenyl)-N-isobutylsulfamoyl)-2-(S-methylsulfonimidoyl)phenyl)amino)methyl)pyrrolidine-1-carboxylate<br>$^1$H NMR (DMSO-d6) δ: 0.84 (dd, J = 6.6, 2.5 Hz, 6H), 1.18 (t, J = 7.6 Hz, 3H), 1.41 (dt, J = 13.5, 6.8 Hz, 1H), 1.58-1.76 (m, 1H), 1.93-2.08 (m, 2H), 2.60 (q, J = 7.6 Hz, 2H), 3.02 (s, 3H), 3.07 (td, J = 8.5, 7.9, 3.9 Hz, 1H), 3.24 (dd, J = 7.3, 3.2 Hz, 4H), 3.43 (td, J = 9.6, 8.2, 4.3 Hz, 1H), 3.50 (ddd, J = 10.2, 7.3, 2.3 Hz, 1H), 3.58 (s, 3H), 4.75 (s, 1H), 6.96-7.03 (m, 3H), 7.17-7.23 (m, 2H), 7.50 (ddd, J = 8.9, 2.3, 1.2 Hz, 1H), 7.70 (d, J = 2.2 Hz, 1H), 7.83 (s, 1H).<br>MS: [M + H] = 551 |

-continued

Example 63

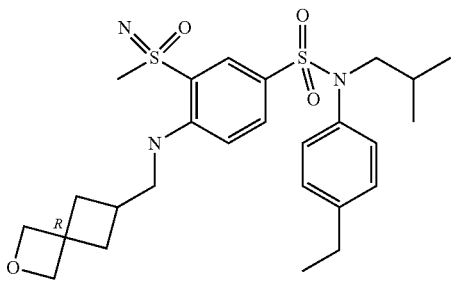

Compound 95

4-(((2-oxaspiro[3.3]heptan-6-yl)methyl)amino)-N-(4-ethylphenyl)-N-isobutyl-3-(S-methylsulfonimidoyl)benzenesulfonamide
$^1$H NMR (DMSO-d6) δ: 0.84 (dd, J = 6.6, 2.4 Hz, 6H), 1.18 (t, J = 7.6 Hz, 3H), 1.40 (dq, J = 13.7, 6.9 Hz, 1H), 1.96 (ddd, J = 10.0, 5.7, 2.0 Hz, 2H), 2.28-2.46 (m, 3H), 2.60 (q, J = 7.6 Hz, 2H), 2.99 (d, J = 0.9 Hz, 3H), 3.22 (dtd, J = 14.0, 7.6, 7.0, 5.1 Hz, 4H), 4.49 (s, 2H), 4.59 (s, 2H), 4.71 (d, J = 1.1 Hz, 1H), 6.89 (d, J = 9.0Hz, 1H), 6.97-7.02 (m, 2H), 7.17-7.21 (m, 2H), 7.49 (dd, J = 8.9, 2.3 Hz, 1H), 7.69 (d, J = 2.3 Hz, 1H).
MS: [M + H] = 520

Example 64

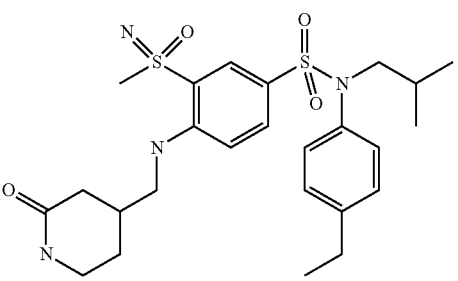

Compound 96

4-N-(4-ethylphenyl)-N-isobutyl-3-(S-methylsulfonimidoyl)-4-(((2-oxopiperidin-4-yl)methyl)amino)benzenesulfonamide
$^1$H NMR (DMSO-d6) δ: 0.84 (dd, J = 6.6, 2.7 Hz, 6H), 1.18 (t, J = 7.6 Hz, 3H), 1.42 (dq, J = 13.9, 7.0 Hz, 2H), 1.86 (d, J = 13.6 Hz, 1H), 1.96 (ddd, J = 16.8, 10.8, 3.4 Hz, 1H), 2.10-2.32 (m, 2H), 2.60 (q, J = 7.6 Hz, 2H), 3.02 (s, 3H), 3.13 (td, J = 12.4, 11.2, 6.5 Hz, 2H), 3.14-3.30 (m, 4H), 4.77 (s, 1H), 6.96-7.03 (m, 2H), 7.16-7.24 (m, 2H), 7.47-7.55 (m, 1H), 7.54-7.66 (m, 1H), 7.70 (dd, J = 2.4, 1.4 Hz, 1H), 7.86 (d, J = 5.9 Hz, 1H).
MS: [M + H] = 521

Example 65

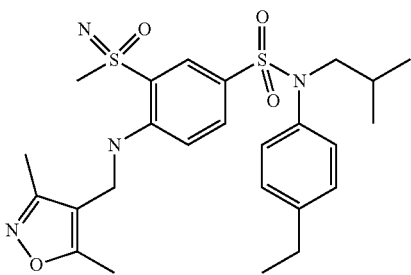

Compound 97

4-(((3,5-dimethylisoxazol-4-yl)methyl)amino)-N-(4-ethylphenyl)-N-isobutyl-3-(S-methylsulfonimidoyl)benzenesulfonamide
$^1$H NMR (DMSO-d6) δ: 0.84 (dd, J = 6.7, 2.2 Hz, 6H), 1.18 (t, J = 7.6 Hz, 3H), 1.41 (dq, J = 13.7, 6.9 Hz, 1H), 2.23 (s, 3H), 2.42 (s, 3H), 2.61 (q, J = 7.6 Hz, 2H), 3.00 (s, 3H), 3.26 (dd, J = 7.3, 2.9 Hz, 2H), 4.28 (t, J = 5.3 Hz, 2H), 4.75 (s, 1H), 6.95 (d, J = 8.8 Hz, 1H), 6.99 (d, J = 8.2 Hz, 2H), 7.20 (d, J = 8.1 Hz, 2H), 7.59 (dd, J = 8.7, 2.4 Hz, 1H), 7.72 (d, J = 2.3 Hz, 1H), 7.80 (t, J = 5.1 Hz, 1H).
MS: [M + H] = 519

Example 66

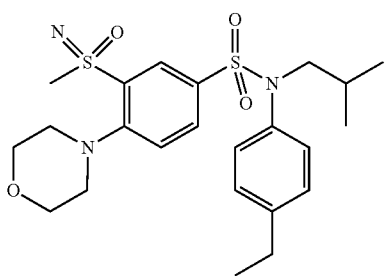

Compound 123

N-(4-ethylphenyl)-4-(((4-hydroxycyclohexyl)methyl)amino)-N-isobutyl-3-(S-methylsulfonimidoyl)benzenesulfonamide
$^1$H NMR (DMSO-d6) δ: 0.84 (dd, J = 6.7, 2.8 Hz, 6H), 1.01-1.10 (m, 2H), 1.18 (t, J = 7.6 Hz, 3H), 1.42 (dt, J = 13.7, 6.8 Hz, 1H), 1.53 (td, J = 18.2, 15.7, 6.5 Hz, 2H), 1.73-1.90 (m, 4H), 2.60 (q, J = 7.5 Hz, 2H), 3.00 (s, 3H), 3.08 (d, J = 6.8 Hz, 2H), 3.24 (dd, J = 7.5, 3.6 Hz, 2H), 4.53 (d, J = 4.5 Hz, 1H), 4.74 (s, 1H), 6.91 (d, J = 9.0 Hz, 1H), 7.00 (d, J = 8.1 Hz, 2H), 7.20 (d, J = 8.1 Hz, 2H), 7.49 (dd, J = 8.8, 2.5 Hz, 1H), 7.69 (d, J = 2.2 Hz, 1H), 7.81 (t, J = 5.4 Hz, 1H).
MS: [M + H] = 522

Example 67

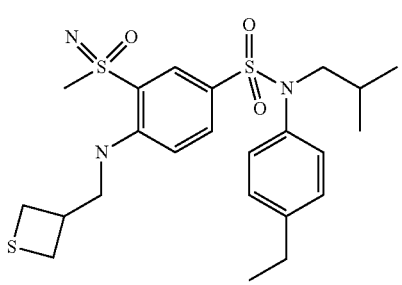

Compound 99

N-(4-ethylphenyl)-N-isobutyl-3-(S-methylsulfonimidoyl)-4-((thietan-3-ylmethyl)amino)benzenesulfonamide
$^1$H NMR (Chloroform-d) δ: 0.93 (dd, J = 9.2, 6.8 Hz, 6H), 1.26 (t, J = 7.6 Hz, 3H), 1.62 (dq, J = 13.6, 7.0 Hz, 1H), 2.67 (q, J = 7.6 Hz, 2H), 3.04 (dd, J = 9.4, 6.0 Hz, 2H), 3.11 (s, 3H), 3.26 (dd, J = 12.9, 7.0 Hz, 1H), 3.32-3.44 (m, 2H), 3.49 (d, J = 7.0 Hz, 2H), 3.57 (h, J = 6.8, 6.4 Hz, 1H), 6.74 (d, J = 9.0 Hz, 1H), 7.02 (d, J = 8.1 Hz, 2H), 7.17 (d, J = 7.9 Hz, 2H), 7.58 (dd, J = 8.8, 2.3 Hz, 1H), 8.03 (d, J = 2.2 Hz, 1H).
MS: [M + H] = 496

| Example 68 | 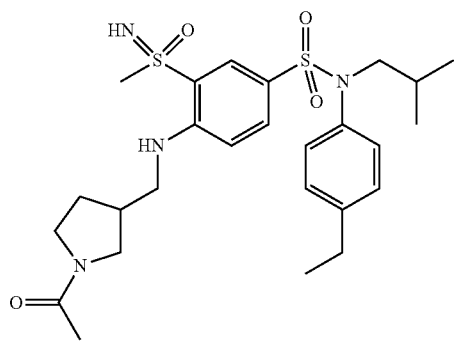

Compound 100 | 4-(((1-acetylpyrrolidin-3-yl)methyl)amino)-N-(4-ethylphenyl)-N-isobutyl-3-(S-methylsulfonimidoyl)benzenesulfonamide
¹H 1H NMR (Chloroform-d) δ: 0.89 (dd, J = 8.8, 6.6 Hz, 6H), 1.23 (t, J = 7.9 Hz, 3H), 1.57 (hept, J = 6.8 Hz, 1H), 1.65-1.90 (m, 1H), 2.06 (d, J = 2.9 Hz, 3H), 2.21-2.24 (m, 2H), 2.63 (q, J = 7.7 Hz, 2H), 3.03 (d, J = 4.6 Hz, 3H), 3.27 (dtd, J = 20.1, 12.9, 7.5 Hz, 5H), 3.47 (dt, J = 19.3, 9.3 Hz, 1H), 3.55-3.83 (m, 2H), 6.60-6.72 (m, 1H), 6.98 (d, J = 7.8 Hz, 2H), 7.13 (d, J = 7.8 Hz, 2H), 7.54 (d, J = 8.3 Hz, 1H), 7.69 (s, 1H), 7.98 (dd, J = 4.5, 2.1 Hz, 1H).
MS: [M + H] = 535 |
| Example 71 | 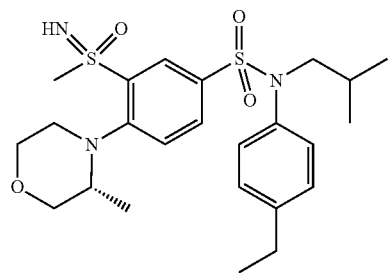 [SMILES: CCc1ccc(N(CC(C)C)S(=O)(=O)c2ccc(N3CCOC[C@H]3C)c(S(C)(=N)=O)c2)cc1] | N-(4-ethylphenyl)-N-isobutyl-4-((R)-3-methylmorpholino)-3-(S-methylsulfonimidoyl)benzenesulfonamide
¹H NMR (DMSO-d6) δ: 0.77 (dd, J = 6.3, 2.6 Hz, 3H), 0.82-0.88 (m, 6H), 1.18 (t, J = 7.6 Hz, 3H), 1.44 (dt, J = 13.7, 6.8 Hz, 1H), 2.61 (ddt, J = 8.7, 6.3, 3.4 Hz, 2H), 3.40 (dd, J = 17.2, 1.2 Hz, 3H), 3.44-3.50 (m, 1H), 3.68 (ddd, J = 11.1, 8.0, 3.0 Hz, 1H), 3.78 (ddt, J = 7.9, 5.2, 2.8 Hz, 1H), 3.87 (dd, J = 10.9, 2.4 Hz, 1H), 4.47 (d, J = 1.5 Hz, 1H), 4.62 (d, J = 1.5 Hz, 1H), 6.92-7.05 (m, 2H), 7.19 (dd, J = 8.4, 2.2 Hz, 2H), 7.68 (d, J = 1.3 Hz, 1H), 7.70-7.72 (m, 1H), 8.09 (d, J = 1.9 Hz, 1H), 8.25 (t, J = 1.3 Hz, 1H).
MS: [M + H] = 494 |
| Example 73 | 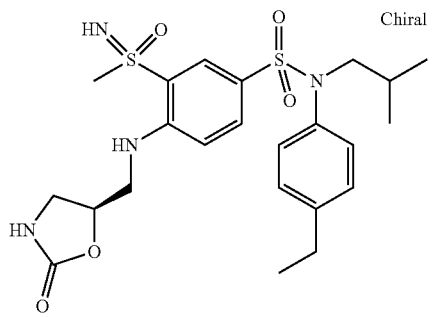 [SMILES: CCc1ccc(N(CC(C)C)S(=O)(=O)c2ccc(NC[C@@H]3CNC(=O)O3)c(S(C)(=N)=O)c2)cc1] Chiral | N-(4-ethylphenyl)-N-isobutyl-3-(S-methylsulfonimidoyl)-4-((((R)-2-oxooxazolidin-5-yl)methyl)amino)benzenesulfonamide
¹H NMR (Chloroform-d) δ: 0.90 (dd, J = 9.3, 6.7 Hz, 6H), 1.23 (t, J = 7.6 Hz, 3H), 1.59 (dq, J = 13.8, 6.8 Hz, 1H), 2.64 (q, J = 7.6 Hz, 2H), 3.06 (d, J = 2.6 Hz, 3H), 3.24 (ddd, J = 12.8, 7.0, 2.1 Hz, 1H), 3.34 (ddd, J = 12.9, 7.8, 3.3 Hz, 1H), 3.44 (ddd, J = 8.6, 5.9, 2.4 Hz, 1H), 3.53-3.68 (m, 1H), 3.82 (t, J = 8.7 Hz, 1H), 4.93 (qd, J = 6.0, 3.9 Hz, 1H), 5.07 (s, 1H), 6.75 (dd, J = 8.8, 3.0 Hz, 1H), 6.94-7.03 (m, 2H), 7.13-7.19 (m, 2H), 7.57 (dt, J = 8.8, 2.4 Hz, 1H), 8.01 (dd, J = 5.5, 2.2 Hz, 1H).
MS: [M + H] = 509 |
| Example 74 | 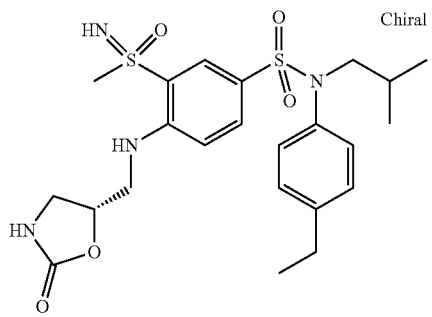 Chiral Compound 106 | N-(4-ethylphenyl)-N-isobutyl-3-(S-methylsulfonimidoyl)-4-((((S)-2-oxooxazolidin-5-yl)methyl)amino)benzenesulfonamide
¹H NMR (DMSO-d6) δ: 0.84 (dd, J = 6.6, 1.9 Hz, 6H), 1.18 (t, J = 7.6 Hz, 3H), 1.42 (dd, J = 13.7, 7.0 Hz, 1H), 1.52 (td, J = 17.8, 15.2, 7.1 Hz, 1H), 1.94-2.09 (m, 2H), 2.60 (q, J = 7.6 Hz, 2H), 3.01 (s, 3H), 3.24 (d, J = 7.4 Hz, 2H), 3.37-3.46 (m, 2H), 3.78 (d, J = 11.5 Hz, 2H), 4.69 (s, 1H), 6.99 (d, J = 8.2 Hz, 3H), 7.20 (d, J = 8.4 Hz, 2H), 7.47 (dd, J = 8.9, 2.4 Hz, 1H), 7.70 (d, J = 2.3 Hz, 1H), 7.85 (s, 1H).
MS: [M + H] = 509 |

Example 75

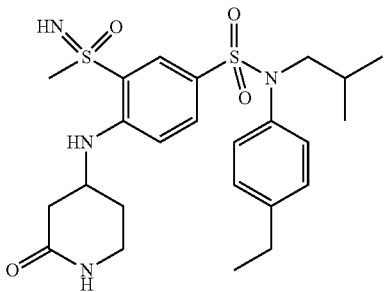

Compound 107

N-(4-ethylphenyl)-N-isobutyl-3-(S-methylsulfonimidoyl)-4-((2-oxopiperidin-4-yl)amino)benzenesulfonamide
$^1$H NMR (Chloroform-d) δ: 0.90 (d, J = 7.3 Hz, 6H), 1.17-1.27 (m, 3H), 1.45-1.68 (m, 2H), 2.57-2.68 (m, 2H), 3.01-3.4 (m, 2H), 3.19-3.40 (m, 2H), 3.48-3.52 (m, 1H), 3.99 (s, 1H), 6.03 (d, J = 40.9 Hz, 1H), 6.72 (s, 1H), 7.00 (d, J = 7.3 Hz, 2H), 7.15 (d, J = 7.3 Hz, 2H), 7.57 (s, 1H), 8.00 (s, 1H).
MS: [M + H] = 508

Example 77

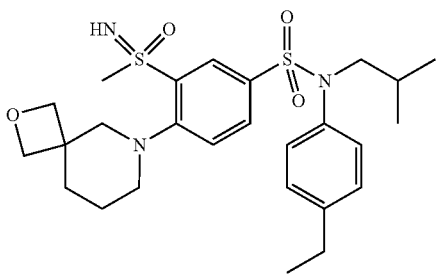

Compound 109

N-(4-ethylphenyl)-N-isobutyl-3-(S-methylsulfonimidoyl)-4-(2-oxa-6-azaspiro[3.5]nonan-6-yl)benzenesulfonamide
$^1$H NMR (DMSO-d6) δ: 0.86 (dd, J = 6.7, 4.1 Hz, 6H), 1.19 (t, J = 7.6 Hz, 3H), 1.44 (dt, J = 13.6, 6.8 Hz, 1H), 1.63 (q, J = 5.6 Hz, 2H), 1.83 (s, 2H), 2.61 (q, J = 7.6 Hz, 2H), 2.92 (d, J = 17.9 Hz, 2H), 3.17 (s, 2H), 3.27 (d, J = 1.2 Hz, 3H), 3.33 (s, 2H), 4.29 (d, J = 5.6 Hz, 2H), 4.42-4.62 (m, 3H), 6.97-7.05 (m, 2H), 7.18-7.25 (m, 2H), 7.64-7.75 (m, 2H), 8.15 (d, J = 2.0 Hz, 1H).
MS: [M + H] = 520

Example 78

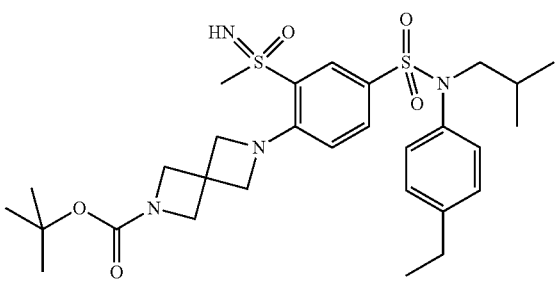

Compound 110 tert-butyl 6-(4-(N-(4-ethylphenyl)-N-isobutylsulfamoyl)-2-(S-methylsulfonimidoyl)phenyl)-2,6-diazaspiro[3.3]heptane-2-carboxylate
$^1$H NMR (DMSO-d6) δ: 0.83 (dd, J = 6.6, 3.4 Hz, 6H), 1.18 (t, J = 7.6 Hz, 3H), 1.39 (s, 9H), 2.60 (q, J = 7.6 Hz, 2H), 3.12 (d, J = 1.5 Hz, 3H), 3.23 (dd, J = 7.3, 5.1 Hz, 2H), 4.05 (s, 4H), 4.20 (d, J = 1.7 Hz, 1H), 4.43 (s, 4H), 6.59 (d, J = 8.9 Hz, 1H), 6.94-7.01 (m, 2H), 7.15-7.23 (m, 2H), 7.42 (dd, J = 8.8, 2.4 Hz, 1H), 7.94 (d, J = 2.3 Hz, 1H).
MS: [M + H] = 591

Example 79

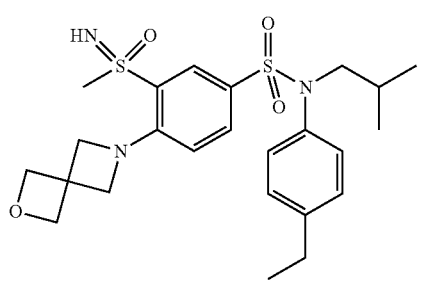

Compound 111

N-(4-ethylphenyl)-N-isobutyl-3-(S-methylsulfonimidoyl)-4-(2-oxa-6-azaspiro[3.3]heptan-6-yl)benzenesulfonamide
$^1$H NMR (DMSO-d6) δ: 0.83 (dd, J = 6.4, 3.3 Hz, 6H), 1.18 (t, J = 7.6 Hz, 3H), 1.33-1.47 (m, 1H), 2.60 (q, J = 7.6 Hz, 2H), 3.12 (s, 3H), 3.24 (h, J = 6.7, 5.8 Hz, 3H), 4.20 (s, 1H), 4.48 (s, 4H), 4.73 (s, 4H), 6.61 (d, J = 8.8 Hz, 1H), 6.98 (d, J = 7.9 Hz, 2H), 7.19 (d, J = 8.2 Hz, 2H), 7.42 (dd, J = 8.8, 2.3 Hz, 1H), 7.93 (d, J = 2.4 Hz, 1H).
MS: [M + H] = 493

Example 80

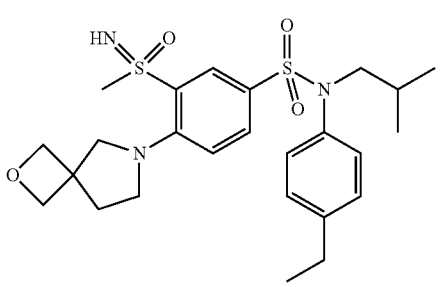

Compound 112

N-(4-ethylphenyl)-N-isobutyl-3-(S-methylsulfonimidoyl)-4-(2-oxa-6-azaspiro[3.4]octan-6-yl)benzenesulfonamide
$^1$H 1H NMR (DMSO-d6) δ: 0.90 (dd, J = 6.8, 3.4 Hz, 6H), 1.23 (t, J = 7.6 Hz, 3H), 1.41-1.55 (m, 1H), 2.00 (d, J = 5.7 Hz, 4H), 2.66 (q, J = 7.6 Hz, 2H), 2.89-3.09 (m, 4H), 3.36 (s, 3H), 4.43 (s, 4H), 4.57 (s, 1H), 7.04 (d, J = 8.0 Hz, 2H), 7.25 (d, J = 8.1 Hz, 2H), 7.62 (d, J = 8.4 Hz, 1H), 7.72 (dd, J = 8.3, 2.3 Hz, 1H), 8.18 (d, J = 2.3 Hz, 1H).
MS: [M + H] = 407

| | | |
|---|---|---|
| Example 81 | 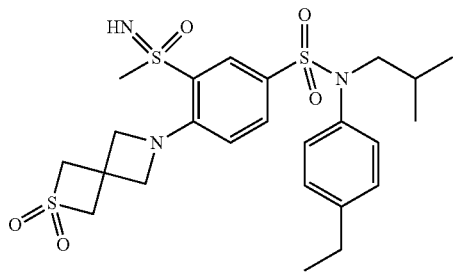<br>Compound 113 | 4-(2,2-dioxido-2-thia-6-azaspiro[3.3]heptan-6-371)-N-(4-ethylphenyl)-N-isobutyl-3-(S-methylsulfonimidoyl)benzenesulfonamide<br>$^1$H NMR (DMSO-d6) δ: 0.84 (dd, J = 6.8, 3.4 Hz, 6H), 1.18 (t, J = 7.6 Hz, 3H), 1.34-1.49 (m, 1H), 2.60 (q, J = 7.6 Hz, 2H), 3.13 (s, 3H), 3.25 (dd, J = 7.4, 5.1 Hz, 2H), 4.28 (s, 1H), 4.52 (d, J = 4.5 Hz, 8H), 6.66 (d, J = 8.9 Hz, 1H), 6.98 (d, J = 8.1 Hz, 2H), 7.19 (d, J = 8.0 Hz, 2H), 7.45 (dd, J = 8.8, 2.3 Hz, 1H), 7.96 (d, J = 2.3 Hz, 1H).<br>MS: [M + H] = 540 |
| Example 82 | 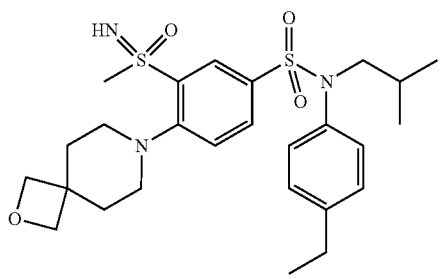<br>Compound 114 | N-(4-ethylphenyl)-N-isobutyl-3-(S-methylsulfonimidoyl)-4-(2-oxa-7-azaspiro[3.5]nonan-7-yl)benzenesulfonamide<br>$^1$H NMR (DMSO-d6) δ: 0.84 (d, J = 6.7 Hz, 6H), 1.18 (t, J = 7.6 Hz, 3H), 1.35-1.50 (m, 1H), 2.16-2.30 (m, 2H), 2.61 (q, J = 7.5 Hz, 2H), 3.21 (s, 3H), 3.28 (d, J = 7.3 Hz, 2H), 3.42-3.62 (m, 2H), 3.68-3.83 (m, 2H), 4.21 (s, 1H), 4.54 (dd, J = 6.0, 3.6 Hz, 2H), 4.60 (dd, J = 14.2, 5.9 Hz, 2H), 7.01 (d, J = 7.9 Hz, 2H), 7.19 (dd, J = 8.5, 4.5 Hz, 3H), 7.49 (dd, J = 8.8, 2.4 Hz, 1H), 8.05 (d, J = 2.4 Hz, 1H).<br>MS: [M + H] = 520 |
| Example 83 | 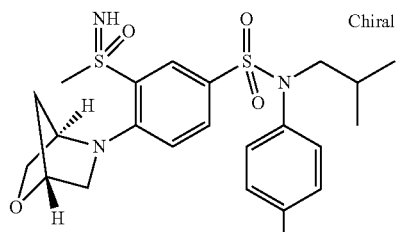 Chiral<br>Compound 115 | 4-((1R,4R)-2-oxa-5-azabicyclo[2.2.1]heptan-5-yl)-N-(4-ethylphenyl)-N-isobutyl-3-(S-methylsulfonimidoyl)benzenesulfonamide<br>$^1$H 1H NMR (DMSO-d6) δ: 0.84 (dd, J = 6.7, 1.5 Hz, 6H), 1.18 (t, J = 7.6 Hz, 3H), 1.36-1.48 (m, 1H), 1.82-1.97 (m, 2H), 2.53-2.66 (m, 3H), 3.18 (dd, J = 7.4, 1.3 Hz, 3H), 3.28 (d, J = 7.3, 1.7 Hz, 2H), 3.35-3.48 (m, 1H), 3.77 (td, J = 7.6, 1.7 Hz, 1H), 3.81-3.97 (m, 2H), 4.11 (d, J = 1.7 Hz, 0.5H), 4.46 (d, J = 1.5 Hz, 0.5H), 4.60-4.84 (m, 2H), 6.97-7.05 (m, 2H), 7.14-7.27 (m, 3H), 7.44 (ddd, J = 8.4, 5.7, 2.4 Hz, 1H), 8.07 (dd, J = 14.5, 2.4 Hz, 1H).<br>MS: [M + H] = 493 |
| Example 85 | 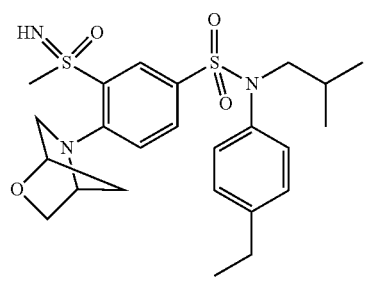<br>Compound 117 | 4-((1R,4R)-2-oxa-5-azabicyclo[2.2.1]heptan-5-yl)-N-(4-ethylphenyl)-N-isobutyl-3-(S-methylsulfonimidoyl)benzenesulfonamide<br>$^1$H NMR (DMSO-d6) δ: 0.83 (dt, J = 5.7, 2.8 Hz, 6H), 1.16 (td, J = 7.6, 2.7 Hz, 3H), 1.20-1.31 (m, 1H), 1.34-1.49 (m, 1H), 1.87-1.99 (m, 2H), 2.59 (q, J = 7.6 Hz, 2H), 3.17-3.26 (m, 4H), 3.34 (s, 3H), 3.67-3.88 (m, 3H), 4.49 (s, 1H), 6.95-7.01 (m, 2H), 7.15-7.22 (m, 2H), 7.58-7.68 (m, 2H), 8.10 (d, J = 2.2 Hz, 1H).<br>MS: [M + H] = 493 |
| Example 86 | 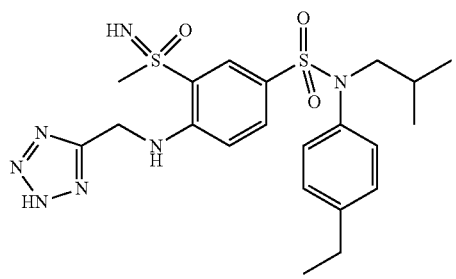<br>Compound 118 | 4-(((2H-tetrazol-5-yl)methyl)amino)-N-(4-ethylphenyl)-N-isobutyl-3-(S-methylsulfonimidoyl)benzenesulfonamide<br>$^1$H NMR (DMSO-d6) δ: 0.84 (dd, J = 6.7, 1.4 Hz, 7H), 1.18 (t, J = 7.6 Hz, 3H), 1.34-1.47 (m, 1H), 2.60 (q, J = 7.6 Hz, 2H), 3.08 (s, 3H), 3.25 (d, J = 7.4 Hz, 4H), 4.86 (d, J = 5.7 Hz, 2H), 6.92-7.03 (m, 3H), 7.15-7.23 (m, 2H), 7.53 (dd, J = 8.8, 2.3 Hz, 1H), 7.74 (d, J = 2.3 Hz, 1H), 8.20 (t, J = 5.7 Hz, 1H).<br>MS: [M + H] = 494 |

Example 89: Synthesis of N-(4-ethylphenyl)-N-isobutyl-3-(S-methylsulfonimidoyl)-4-(2,6-diazaspiro[3.3]heptan-2-yl)benzenesulfonamide Compound 121

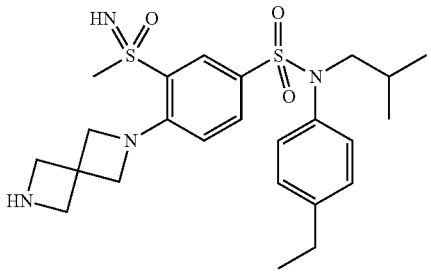

Trifluoroacetic acid (0.28 ml; 3.59 mmol) is added to tert-butyl 6-(4-(N-(4-ethylphenyl)-N-isobutylsulfamoyl)-2-(S-methylsulfonimidoyl)phenyl)-2,6-diazaspiro[3.3]heptane-2-carboxylate (55.0 mg; 0.09 mmol) dissolved in dichloromethane (2.75 ml). The reaction medium is stirred for 4 hours at room temperature, concentrated under vacuum, diluted with ethyl acetate, washed with saturated sodium hydrogen carbonate solution and then with saturated sodium chloride solution, dried (Na$_2$SO$_4$) and concentrated. The residue is taken up in ether and suction-filtered.

The N-(4-ethylphenyl)-N-isobutyl-3-(S-methylsulfonimidoyl)-4-(2,6-diazaspiro[3.3]heptan-2-yl)benzenesulfonamide (44.9 mg; 880%) is obtained in the form of a white solid.

$^1$H NMR (DMSO-d6) δ: 0.83 (dd, J=6.6, 3.3 Hz, 6H), 1.18 (t, J=7.6 Hz, 3H), 1.25 (s, 1H), 1.34-1.47 (m, 1H), 2.60 (q, J=7.6 Hz, 2H), 3.12 (d, J=1.8 Hz, 3H), 3.23 (dd, J=7.2, 4.7 Hz, 2H), 3.79 (s, 2H), 4.21 (d, J=7.3 Hz, 1H), 4.37 (s, 1H), 4.40 (s, 2H), 6.61 (dd, J=9.1, 3.7 Hz, 1H), 6.94-7.01 (m, 2H), 7.15-7.23 (m, 2H), 7.41 (dd, J=8.8, 2.3 Hz, 1H), 7.93 (dd, J=4.7, 2.3 Hz, 1H).

MS: [M+H]=492

Example 90: Synthesis of 4-(6-acetyl-2,6-diazaspiro[3.3]heptan-2-yl)-N-(4-ethylphenyl)-N-isobutyl-3-(S-methylsulfonimidoyl)benzenesulfonamide Compound 122

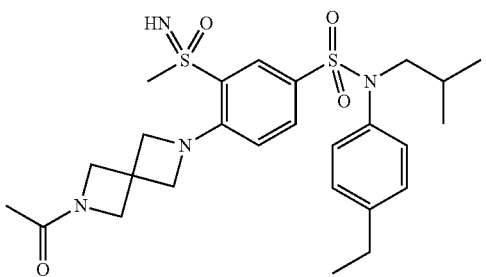

4-Dimethylaminopyridine (0.72 mg; 0.01 mmol) and acetic anhydride (5.6 µl; 0.06 mmol) are added to a solution of 4-oxo-1-piperidin-4-yl-1,2,3,4-tetrahydroquinoline-6-sulfonic acid (4-ethylphenyl)isobutylamide (29.0 mg; 0.06 mmol) in dichloromethane (1.45 ml) cooled to −10° C. The reaction medium is stirred for 30 minutes at room temperature. The reaction medium is hydrolyzed with saturated sodium hydrogen carbonate solution and then extracted with ethyl acetate. The organic phases are combined, washed with brine, dried (Na$_2$SO$_4$) and concentrated.

The crude product is purified by preparative HPLC (C18 column, eluent: acetonitrile in water/0.1% of formic acid). The 4-(6-acetyl-2,6-diazaspiro[3.3]heptan-2-yl)-N-(4-ethylphenyl)-N-isobutyl-3-(S-methylsulfonimidoyl)benzenesulfonamide (23.10 mg; 73%) is obtained in the form of a white solid.

$^1$H NMR (DMSO-d6) δ: 0.84 (dd, J=6.8, 3.4 Hz, 6H), 1.18 (t, J=7.6 Hz, 3H), 1.34-1.47 (m, 1H), 1.76 (s, 3H), 2.60 (q, J=7.6 Hz, 2H), 3.12 (s, 3H), 3.16-3.28 (m, 2H), 4.03 (s, 2H), 4.21 (s, 1H), 4.31 (s, 2H), 4.45 (s, 4H), 6.61 (d, J=8.9 Hz, 1H), 6.98 (d, J=8.0 Hz, 2H), 7.19 (d, J=8.0 Hz, 2H), 7.43 (dd, J=8.8, 2.3 Hz, 1H), 7.94 (d, J=2.3 Hz, 1H).

MS: [M+H]=533

Example 91: Synthesis of 4-(4-acetylpiperazin-1-yl)-N-(4-ethylphenyl)-N-isobutyl-3-(S-methylsulfonimidoyl)benzenesulfonamide Compound 63

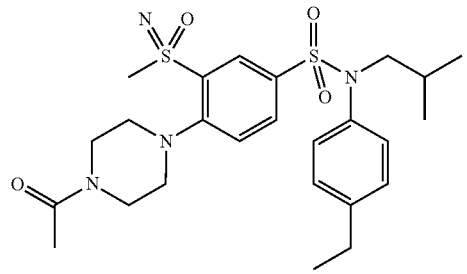

A mixture of 4-bromo-N-(4-ethylphenyl)-N-isobutyl-3-(S-methylsulfonimidoyl)benzenesulfonamide (50.0 mg; 0.11 mmol) and 1-piperazin-1-ylethanone (67.68 mg; 0.53 mmol) is stirred over the weekend at 50° C.

The crude product is purified directly by preparative HPLC (C18 column, eluent: acetonitrile in water/0.1% of formic acid). The 4-(4-acetylpiperazin-1-yl)-N-(4-ethylphenyl)-N-isobutyl-3-(S-methylsulfonimidoyl)benzenesulfonamide (20.0 mg; 36%) is obtained in the form of a white solid.

$^1$H NMR (DMSO-d6) δ: 0.85 (dd, J=6.7, 3.5 Hz, 6H), 1.18 (t, J=7.6 Hz, 3H), 1.44 (dt, J=13.7, 6.9 Hz, 1H), 2.61 (q, J=7.6 Hz, 2H), 3.04 (dq, J=23.9, 5.3 Hz, 4H), 3.34 (d, J=1.2 Hz, 3H), 3.61 (d, J=5.4 Hz, 4H), 4.57 (d, J=1.4 Hz, 1H), 6.97-7.05 (m, 2H), 7.17-7.25 (m, 2H), 7.62 (d, J=8.4 Hz, 1H), 7.71 (dd, J=8.4, 2.3 Hz, 1H), 8.14 (d, J=2.3 Hz, 1H).

MS: [M+H]=521

Example 92: Synthesis of N-(4-ethylphenyl)-N-isobutyl-3-(S-methylsulfonimidoyl)-4-((pyridin-4-ylmethyl)amino)benzenesulfonamide

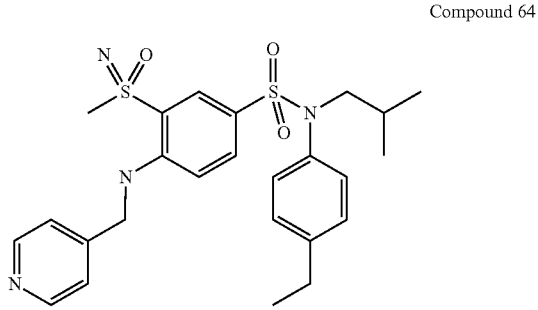 [SMILES: CCc1ccc(N(CC(C)C)S(=O)(=O)c2ccc(NCc3ccncc3)c(S(C)(=N)=O)c2)cc1]

Compound 64

A mixture of 4-bromo-N-(4-ethylphenyl)-N-isobutyl-3-(S-methylsulfonimidoyl)benzenesulfonamide (50.0 mg; 0.11 mmol) and 4-picolylamine (53.62 µl; 0.53 mmol) is stirred over the weekend at 50° C.

The crude product is purified directly by preparative HPLC (C18 column, eluent: acetonitrile in water/0.1% of formic acid). The N-(4-ethylphenyl)-N-isobutyl-3-(S-methylsulfonimidoyl)-4-((pyridin-4-ylmethyl)amino)benzenesulfonamide (26.0 mg; 49%) is obtained in the form of a white solid.

$^1$H NMR (DMSO-d6) δ: 0.83 (d, J=6.7 Hz, 6H), 1.17 (t, J=7.6 Hz, 3H), 1.41 (hept, J=6.7 Hz, 1H), 2.59 (q, J=7.5 Hz, 2H), 3.11 (s, 3H), 3.23 (dd, J=7.3, 2.5 Hz, 2H), 4.64 (d, J=5.9 Hz, 2H), 4.79 (s, 1H), 6.75 (d, J=8.8 Hz, 1H), 6.97 (d, J=7.9 Hz, 2H), 7.18 (d, J=8.0 Hz, 2H), 7.36 (d, J=5.1 Hz, 2H), 7.44 (dd, J=9.1, 2.4 Hz, 1H), 7.76 (d, J=2.4 Hz, 1H), 8.21 (t, J=6.0 Hz, 1H), 8.54 (d, J=5.2 Hz, 2H).

MS: [M+H]=501

With a procedure similar to that described for example 92, the following are obtained:

Example 94

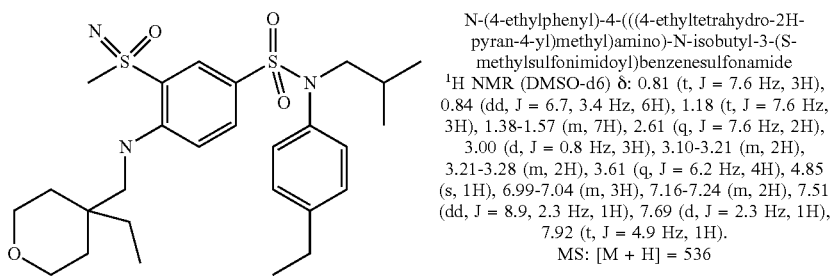

Compound 124

N-(4-ethylphenyl)-4-(((4-ethyltetrahydro-2H-pyran-4-yl)methyl)amino)-N-isobutyl-3-(S-methylsulfonimidoyl)benzenesulfonamide
$^1$H NMR (DMSO-d6) δ: 0.81 (t, J = 7.6 Hz, 3H), 0.84 (dd, J = 6.7, 3.4 Hz, 6H), 1.18 (t, J = 7.6 Hz, 3H), 1.38-1.57 (m, 7H), 2.61 (q, J = 7.6 Hz, 2H), 3.00 (d, J = 0.8 Hz, 3H), 3.10-3.21 (m, 2H), 3.21-3.28 (m, 2H), 3.61 (q, J = 6.2 Hz, 4H), 4.85 (s, 1H), 6.99-7.04 (m, 3H), 7.16-7.24 (m, 2H), 7.51 (dd, J = 8.9, 2.3 Hz, 1H), 7.69 (d, J = 2.3 Hz, 1H), 7.92 (t, J = 4.9 Hz, 1H).
MS: [M + H] = 536

Example 95

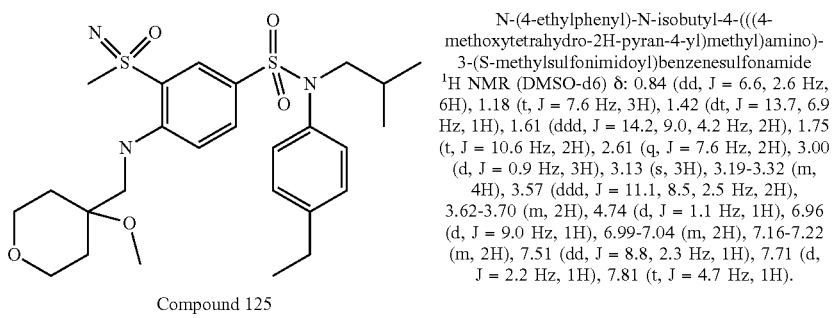

Compound 125

N-(4-ethylphenyl)-N-isobutyl-4-(((4-methoxytetrahydro-2H-pyran-4-yl)methyl)amino)-3-(S-methylsulfonimidoyl)benzenesulfonamide
$^1$H NMR (DMSO-d6) δ: 0.84 (dd, J = 6.6, 2.6 Hz, 6H), 1.18 (t, J = 7.6 Hz, 3H), 1.42 (dt, J = 13.7, 6.9 Hz, 1H), 1.61 (ddd, J = 14.2, 9.0, 4.2 Hz, 2H), 1.75 (t, J = 10.6 Hz, 2H), 2.61 (q, J = 7.6 Hz, 2H), 3.00 (d, J = 0.9 Hz, 3H), 3.13 (s, 3H), 3.19-3.32 (m, 4H), 3.57 (ddd, J = 11.1, 8.5, 2.5 Hz, 2H), 3.62-3.70 (m, 2H), 4.74 (d, J = 1.1 Hz, 1H), 6.96 (d, J = 9.0 Hz, 1H), 6.99-7.04 (m, 2H), 7.16-7.22 (m, 2H), 7.51 (dd, J = 8.8, 2.3 Hz, 1H), 7.71 (d, J = 2.2 Hz, 1H), 7.81 (t, J = 4.7 Hz, 1H).

Example 96

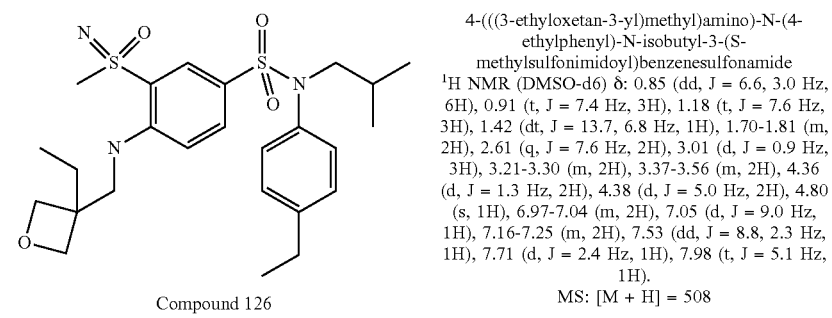

Compound 126

4-(((3-ethyloxetan-3-yl)methyl)amino)-N-(4-ethylphenyl)-N-isobutyl-3-(S-methylsulfonimidoyl)benzenesulfonamide
$^1$H NMR (DMSO-d6) δ: 0.85 (dd, J = 6.6, 3.0 Hz, 6H), 0.91 (t, J = 7.4 Hz, 3H), 1.18 (t, J = 7.6 Hz, 3H), 1.42 (dt, J = 13.7, 6.8 Hz, 1H), 1.70-1.81 (m, 2H), 2.61 (q, J = 7.6 Hz, 2H), 3.01 (d, J = 0.9 Hz, 3H), 3.21-3.30 (m, 2H), 3.37-3.56 (m, 2H), 4.36 (d, J = 1.3 Hz, 2H), 4.38 (d, J = 5.0 Hz, 2H), 4.80 (s, 1H), 6.97-7.04 (m, 2H), 7.05 (d, J = 9.0 Hz, 1H), 7.16-7.25 (m, 2H), 7.53 (dd, J = 8.8, 2.3 Hz, 1H), 7.71 (d, J = 2.4 Hz, 1H), 7.98 (t, J = 5.1 Hz, 1H).
MS: [M + H] = 508

| | | |
|---|---|---|
| Example 97 <br> 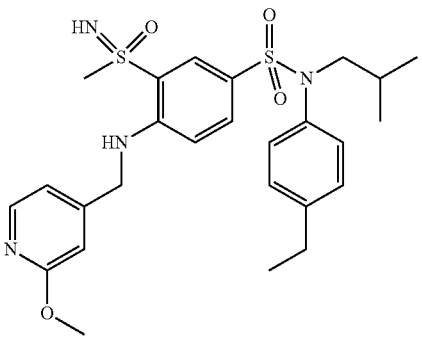 <br> Compound 127 | | N-(4-ethylphenyl)-N-isobutyl-4-(((2-methoxypyridin-4-yl)methyl)amino)-3-(S-methylsulfonimidoyl)benzenesulfonamide <br> $^1$H NMR (DMSO-d6) δ: 0.83 (dd, J = 6.6, 1.9 Hz, 6H), 1.17 (t, J = 7.6 Hz, 3H), 1.42 (dq, J = 13.6, 6.7 Hz, 1H), 2.54-2.64 (m, 2H), 3.09 (d, J = 0.9 Hz, 3H), 3.24 (dd, J = 7.3, 2.6 Hz, 2H), 3.84 (s, 3H), 4.58 (d, J = 6.0 Hz, 2H), 4.79 (s, 1H), 6.73-6.77 (m, 2H), 6.95-6.99 (m, 3H), 7.15-7.20 (m, 2H), 7.44 (dd, J = 8.8, 2.4 Hz, 1H), 7.76 (d, J = 2.3 Hz, 1H), 8.13 (dd, J = 5.3, 0.7 Hz, 1H), 8.17 (t, J = 6.1 Hz, 1H). <br> MS: [M + H] = 531 |
| Example 98 <br> 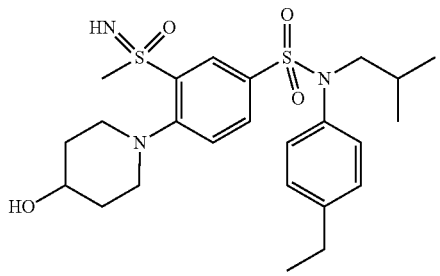 <br> Compound 128 | | N-(4-ethylphenyl)-4-(4-hydroxypiperidin-1-yl)-N-isobutyl-3-(S-methylsulfonimidoyl)benzenesulfonamide <br> $^1$H NMR (DMSO-d6) δ: 0.85 (dd, J = 6.7, 3.3 Hz, 6H), 1.18 (t, J = 7.6 Hz, 3H), 1.43 (dt, J = 13.4, 6.6 Hz, 1H), 1.60 (t, J = 9.5 Hz, 2H), 1.82-1.91 (m, 2H), 2.61 (q, J = 7.6 Hz, 2H), 2.84 (q, J = 9.2 Hz, 2H), 3.18-3.30 (m, 4H), 3.66 (s, 1H), 4.52 (d, J = 1.5 Hz, 1H), 4.71 (d, J = 4.3 Hz, 1H), 6.95-7.04 (m, 2H), 7.17-7.24 (m, 2H), 7.59 (d, J = 8.4 Hz, 1H), 7.67 (dd, J = 8.4, 2.3 Hz, 1H), 8.12 (d, J = 2.3 Hz, 1H). <br> MS: [M + H] = 494 |
| Example 99 <br> 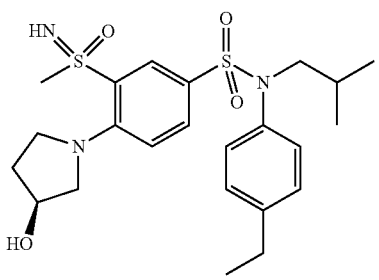 <br> Compound 129 | | N-(4-ethylphenyl)-4-((S)-3-hydroxypyrrolidin-1-yl)-N-isobutyl-3-(S-methylsulfonimidoyl)benzenesulfonamide <br> $^1$H NMR (DMSO-d6) δ: 0.84 (dd, J = 6.6, 1.5 Hz, 6H), 1.18 (t, J = 7.6 Hz, 3H), 1.42 (dt, J = 13.6, 6.8 Hz, 1H), 1.86 (d, J = 9.6 Hz, 1H), 2.01 (ddd, J = 14.4, 10.7, 4.8 Hz, 1H), 2.60 (q, J = 7.6 Hz, 2H), 3.21 (dd, J = 12.9, 1.3 Hz, 3H), 3.27-3.29 (m, 2H), 3.67 (q, J = 8.2 Hz, 1H), 3.73-3.85 (m, 1H), 3.91 (dd, J = 10.8, 4.5 Hz, 1H), 4.01 (d, J = 1.8 Hz, 1H), 4.28 (d, J = 1.5 Hz, 1H), 4.39 (s, 1H), 5.01 (dd, J = 19.6, 3.4 Hz, 1H), 7.01 (d, J = 8.4 Hz, 1H), 7.12 (dd, J = 12.6, 8.9 Hz, 1H), 7.20 (d, J = 8.4 Hz, 2H), 7.43 (dd, J = 8.9, 2.4 Hz, 1H), 8.05 (d, J = 2.4 Hz, 1H). <br> MS: [M + H] = 480 |
| Example 100 <br> 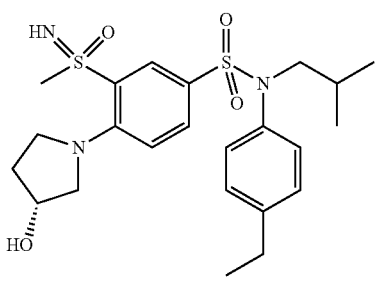 <br> Compound 130 | | N-(4-ethylphenyl)-4-((R)-3-hydroxypyrrolidin-1-yl)-N-isobutyl-3-(S-methylsulfonimidoyl)benzenesulfonamide <br> $^1$H NMR (DMSO-d6) δ: 0.84 (dd, J = 6.6, 1.5 Hz, 6H), 1.18 (t, J = 7.6 Hz, 3H), 1.42 (dt, J = 13.6, 6.8 Hz, 1H), 1.86 (d, J = 9.6 Hz, 1H), 2.01 (ddd, J = 14.4, 10.7, 4.8 Hz, 1H), 2.60 (q, J = 7.6 Hz, 2H), 3.21 (dd, J = 12.9, 1.3 Hz, 3H), 3.27-3.29 (m, 2H), 3.67 (q, J = 8.2 Hz, 1H), 3.73-3.85 (m, 1H), 3.91 (dd, J = 10.8, 4.5 Hz, 1H), 4.01 (d, J = 1.8 Hz, 1H), 4.28 (d, J = 1.5 Hz, 1H), 4.39 (s, 1H), 5.01 (dd, J = 19.6, 3.4 Hz, 1H), 7.01 (d, J = 8.4 Hz, 1H), 7.12 (dd, J = 12.6, 8.9 Hz, 1H), 7.20 (d, J = 8.4 Hz, 2H), 7.43 (dd, J = 8.9, 2.4 Hz, 1H), 8.05 (d, J = 2.4 Hz, 1H). <br> MS: [M + H] = 480 |

| Example 101 | 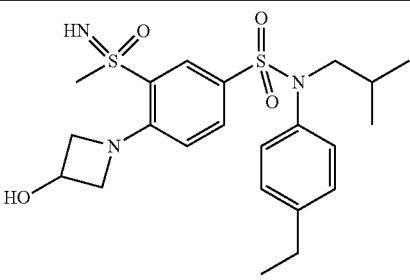

Compound 131 | N-(4-ethylphenyl)-4-(3-hydroxyazetidin-1-yl)-N-isobutyl-3-(S-methylsulfonimidoyl)benzenesulfonamide
¹H NMR (DMSO-d6) δ: 0.84 (dd, J = 6.6, 3.1 Hz, 6H), 1.18 (t, J = 7.6 Hz, 3H), 1.41 (dt, J = 14.1, 7.0 Hz, 1H), 2.60 (q, J = 7.7 Hz, 2H), 3.11 (d, J = 1.3 Hz, 3H), 3.24 (dd, J = 7.3, 4.5 Hz, 2H), 4.02 (dd, J = 10.5, 5.7 Hz, 2H), 4.20 (d, J = 1.5 Hz, 1H), 4.50 (s, 2H), 5.71 (s, 1H), 6.63 (d, J = 8.9 Hz, 1H), 6.99 (d, J = 8.4 Hz, 2H), 7.16-7.25 (m, 2H), 7.40 (dd, J = 8.8, 2.3 Hz, 1H), 7.94 (d, J = 2.4 Hz, 1H).
MS: [M + H] = 466 |
| Example 102 | 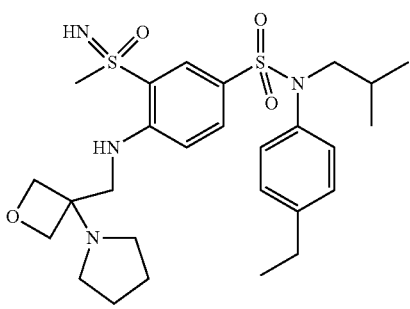

Compound 132 | N-(4-ethylphenyl)-N-isobutyl-3-(S-methylsulfonimidoyl)-4-(((3-(pyrrolidin-1-yl)oxetan-3-yl)methyl)amino)benzenesulfonamide
¹H NMR (DMSO-d6) δ: 0.84 (dd, J = 6.6, 2.0 Hz, 6H), 1.18 (t, J = 7.6 Hz, 3H), 1.42 (p, J = 6.9 Hz, 1H), 1.76 (d, J = 6.2 Hz, 4H), 2.61 (q, J = 7.6 Hz, 2H), 2.73 (q, J = 5.9 Hz, 4H), 2.96 (d, J = 0.9 Hz, 3H), 3.25 (dd, J = 7.4, 1.6 Hz, 2H), 3.55-3.72 (m, 2H), 4.29 (dd, J = 8.5, 6.6 Hz, 2H), 4.59 (s, 1H), 4.78 (d, J = 6.7 Hz, 2H), 6.97-7.02 (m, 3H), 7.17-7.23 (m, 2H), 7.53 (dd, J = 8.8, 2.4 Hz, 1H), 7.72 (d, J = 2.3 Hz, 1H), 7.85 (t, J = 4.2 Hz, 1H).
MS: [M + H] = 549 |

Example 103: Synthesis of N-(4-ethylphenyl)-N-isobutyl-3-(S-methylsulfonimidoyl)-4-((pyrimidin-4-ylmethyl)amino)benzenesulfonamide Compound 133

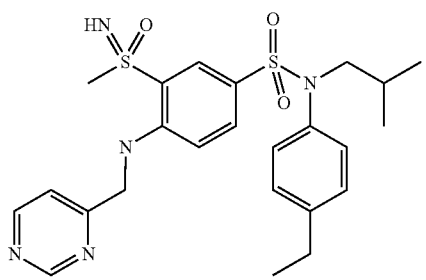

4-Bromo-N-(4-ethylphenyl)-N-isobutyl-3-(S-methylsulfonimidoyl)benzenesulfonamide (50.0 mg; 0.11 mmol) and 4-(aminomethyl)pyrimidine (34.6 mg; 0.32 mmol) are introduced into a microwave tube. The reaction medium is stirred for 30 minutes at 100° C. under microwave irradiation.

The crude product is purified by preparative HPLC (C18 column, eluent: acetonitrile in water/0.1% of formic acid). The N-(4-ethylphenyl)-N-isobutyl-3-(S-methylsulfonimidoyl)-4-((pyrimidin-4-ylmethyl)amino)benzenesulfonamide (15.0 mg; 28%) is obtained in the form of a beige-colored solid.

¹H NMR (DMSO-d6) δ: 0.83 (dd, J=6.6, 1.5 Hz, 6H), 1.17 (t, J=7.6 Hz, 3H), 1.41 (dt, J=13.7, 6.8 Hz, 1H), 2.60 (q, J=7.6 Hz, 2H), 3.11 (d, J=1.0 Hz, 3H), 3.24 (dd, J=7.4, 1.4 Hz, 2H), 4.72 (dd, J=5.7, 1.9 Hz, 2H), 4.75-4.79 (m, 1H), 6.81 (d, J=8.9 Hz, 1H), 6.93-7.01 (m, 2H), 7.15-7.23 (m, 2H), 7.47 (dd, J=8.8, 2.3 Hz, 1H), 7.50 (dd, J=5.2, 1.4 Hz, 1H), 7.77 (d, J=2.3 Hz, 1H), 8.35 (t, J=5.9 Hz, 1H), 8.77 (d, J=5.2 Hz, 1H), 9.17 (d, J=1.4 Hz, 1H).

MS: [M+H]=502

Example 107: Synthesis of N-(4-ethylphenyl)-N-isobutyl-3-(S-methylsulfonimidoyl)-4-(1,4-oxazepan-4-yl)benzenesulfonamide 4-Bromo-N-(4-ethylphenyl)-N-isobutyl-3-(S-methylsulfonimidoyl)benzenesulfonamide (50.0 mg; 0.11 mmol) is added to 1,4-oxazepane (16.0 mg; 0.16 mmol) and N,N-diisopropylethylamine (0.11 ml; 0.63 mmol) dissolved in dimethyl sulfoxide (2 ml).

The reaction medium is heated at a temperature of 150° C. for 20 minutes with microwave irradiation. The reaction medium is hydrolyzed with 1N hydrochloric acid solution and diluted, and then extracted with ethyl acetate. The organic phases are combined, washed with brine, dried (Na₂SO₄) and concentrated under vacuum.

The crude product is purified directly by preparative HPLC (C18 column, eluent: acetonitrile in water/0.1% of formic acid). The N-(4-ethylphenyl)-N-isobutyl-3-(S-methylsulfonimidoyl)-4-(1,4-oxazepan-4-yl)benzenesulfonamide (23.8 mg; 46%) is obtained in the form of a white solid.

¹H NMR (Methanol-d4) δ: 0.93 (d, J=6.7 Hz, 6H), 1.25 (t, J=7.6 Hz, 3H), 1.49-1.64 (m, 1H), 2.09 (p, J=6.0 Hz, 2H), 2.67 (q, J=7.6 Hz, 2H), 3.39 (d, J=7.3 Hz, 2H), 3.48 (s, 3H), 3.90 (dd, J=6.2, 3.5 Hz, 2H), 3.95 (t, J=6.1 Hz, 2H), 6.98-7.05 (m, 2H), 7.17-7.24 (m, 2H), 7.66 (d, J=8.4 Hz, 1H), 7.74 (dd, J=8.4, 2.3 Hz, 1H), 8.23 (d, J=2.2 Hz, 1H).

MS: [M+H]=494

Example 107

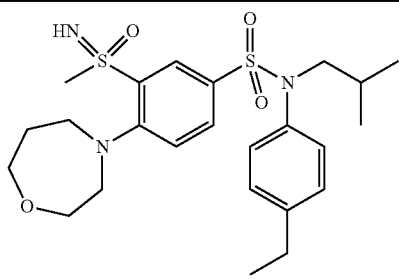

Compound 137

N-(4-ethylphenyl)-N-isobutyl-3-(S-methylsulfonimidoyl)-4-(1,4-oxazepan-4-yl)benzenesulfonamide $^1$H NMR (Methanol-d4) δ: 0.93 (d, J = 6.7 Hz, 6H), 1.25 (t, J = 7.6 Hz, 3H), 1.49-1.64 (m, 1H), 2.09 (p, J = 6.0 Hz, 2H), 2.67 (q, J = 7.6 Hz, 2H), 3.39 (d, J = 7.3 Hz, 2H), 3.48 (s, 3H), 3.90 (dd, J = 6.2, 3.5 Hz, 2H), 3.95 (t, J = 6.1 Hz, 2H), 6.98-7.05 (m, 2H), 7.17-7.24 (m, 2H), 7.66 (d, J = 8.4 Hz, 1H), 7.74 (dd, J = 8.4, 2.3 Hz, 1H), 8.23 (d, J = 2.2 Hz, 1H).

MS: [M + H] = 494

Example 110: Synthesis of N-(4-ethylphenyl)-N-isobutyl-3-(S-methylsulfonimidoyl)-4-(piperazin-1-yl)benzenesulfonamide

Example 111: Synthesis of N-(4-ethylphenyl)-4-(((3-hydroxycyclobutyl)methyl)amino)-N-isobutyl-3-(S-methylsulfonimidoyl)benzenesulfonamide

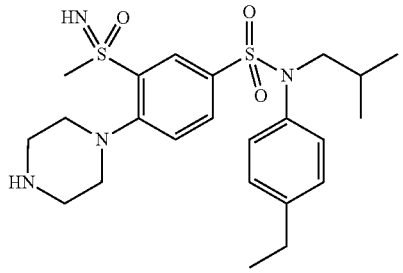

Compound 140

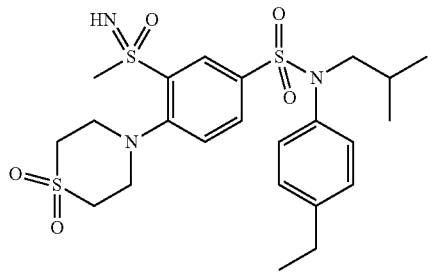

Compound 141

Piperazine (18.2 mg; 0.21 mmol) is added to a solution of 4-bromo-N-(4-ethylphenyl)-N-isobutyl-3-(S-methylsulfonimidoyl)benzenesulfonamide (50.00 mg; 0.11 mmol) in N,N-dimethylformamide (0.20 μl). The reaction medium is stirred overnight at 60° C. The crude product is purified by preparative HPLC (C18 column, eluent: acetonitrile in water/0.2% of ammonium carbonate). The N-(4-ethylphenyl)-N-isobutyl-3-(S-methylsulfonimidoyl)-4-(piperazin-1-yl)benzenesulfonamide (30.0 mg; 53%) is obtained in the form of a white solid.

$^1$H NMR (DMSO-d6) δ: 0.85 (dd, J=6.6, 3.5 Hz, 6H), 1.18 (t, J=7.6 Hz, 3H), 1.43 (dt, J=13.8, 6.9 Hz, 1H), 2.61 (q, J=7.6 Hz, 2H), 2.87 (t, J=4.7 Hz, 4H), 2.99 (d, J=5.0 Hz, 4H), 3.35 (s, 3H), 4.53 (s, 1H), 6.97-7.04 (m, 2H), 7.21 (d, J=8.4 Hz, 2H), 7.59 (d, J=8.5 Hz, 1H), 7.69 (dd, J=8.4, 2.3 Hz, 1H), 8.14 (d, J=2.3 Hz, 1H).

MS: [M+H] 479

3-Chloroperbenzoic acid (24.4 mg; 0.11 mmol) is added at 0° C. to N-(4-ethylphenyl)-N-isobutyl-3-(S-methylsulfonimidoyl)-4-thiomorpholinobenzenesulfonamide (27.0 mg; 0.05 mmol) dissolved in dichloromethane (250 μl). The reaction medium is stirred for 5 hours at room temperature, hydrolyzed with 1N sodium hydroxide solution and extracted with dichloromethane. The organic phases are combined, washed with water, dried (MgSO$_4$) and concentrated under vacuum.

The crude product is purified by preparative HPLC (C18 column, eluent: acetonitrile in water/0.1% of formic acid). The 4-(1,1-dioxidothiomorpholino)-N-(4-ethylphenyl)-N-isobutyl-3-(S-methylsulfonimidoyl)benzenesulfonamide (8.0 mg; 28%) is obtained in the form of an off-white solid.

$^1$H NMR (DMSO-d6) δ: 0.86 (d, J=6.6 Hz, 6H), 1.18 (t, J=7.6 Hz, 3H), 1.43 (dt, J=13.5, 6.8 Hz, 1H), 2.61 (q, J=7.6 Hz, 2H), 3.31 (d, J=7.8 Hz, 2H), 3.35-3.40 (m, 7H), 3.49 (dd, J=6.8, 3.4 Hz, 4H), 6.94-7.05 (m, 2H), 7.17-7.25 (m, 2H), 7.83-7.91 (m, 3H).

MS: [M+H] 529

Part III: Synthesis of Sulfur-Based Sulfonamides Via Reaction Scheme 3

Reaction scheme 3

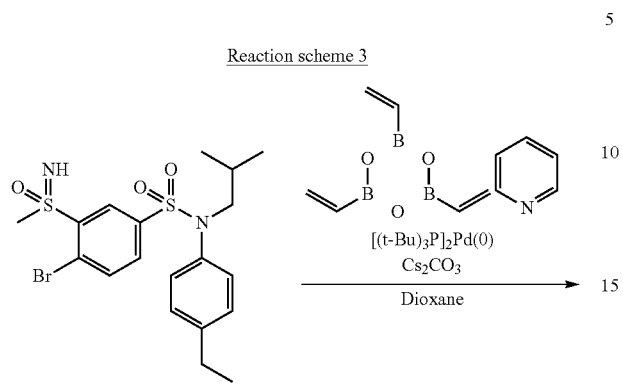

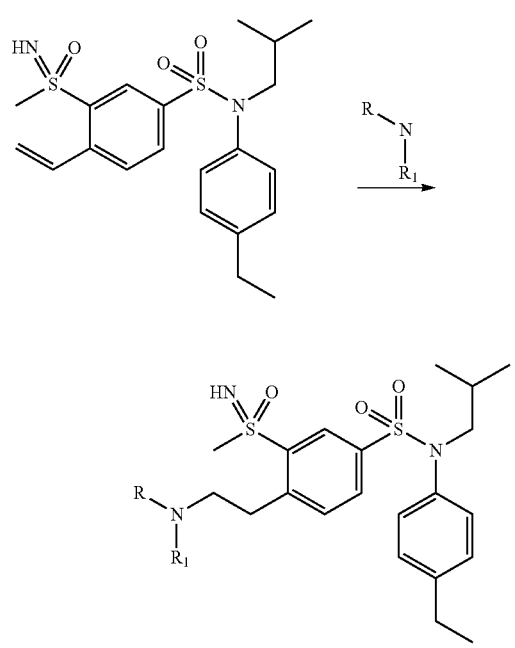

Example 112: Synthesis of N-(4-ethylphenyl)-N-isobutyl-3-(S-methylsulfonimidoyl)-4-(2-morpholinoethyl)benzenesulfonamide Compound 65

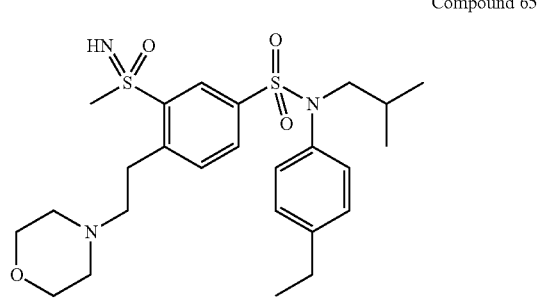

1. Synthesis of Intermediate 112.1

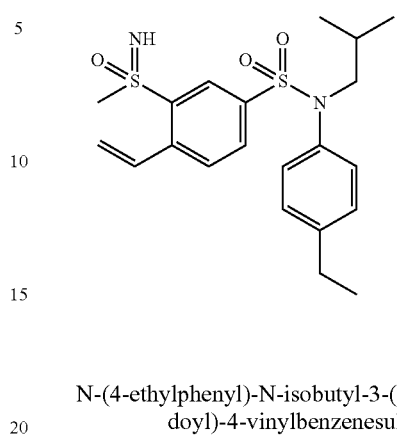

N-(4-ethylphenyl)-N-isobutyl-3-(S-methylsulfonimidoyl)-4-vinylbenzenesulfonamide Cesium carbonate (206.45 mg; 0.63 mmol), tert-butyl N-(2-oxiranylmethyl)carbamate (101.66 mg; 0.42 mmol) and water (0.40 ml) are added to a solution of 4-bromo-N-(4-ethylphenyl)-N-isobutyl-3-(S-methylsulfonimidoyl)benzenesulfonamide (100.0 mg; 0.21 mmol) in 1,4-dioxane (1.2 ml). The reaction medium is degassed under argon for 10 minutes, followed by addition of bis(tri-tert-butylphosphine)palladium(0) (10.79 mg; 0.02 mmol; 0.10 eq.). The reaction medium is stirred for 2 hours at 90° C., filtered through Celite and rinsed with ethyl acetate. The organic phase is washed with saturated sodium hydrogen carbonate solution and then with water, dried (MgSO$_4$), filtered and concentrated to dryness. The crude product is purified by chromatography on silica gel (eluent: heptane/ethyl acetate, from 0 to 100% of ethyl acetate). The N-(4-ethylphenyl)-N-isobutyl-3-(S-methylsulfonimidoyl)-4-vinylbenzenesulfonamide (70.0 mg; 79%) is obtained in the form of a colorless oil with a compliant $^1$H NMR.

MS: [M+H]=422

2. Synthesis of the Compound N-(4-ethylphenyl)-N-isobutyl-3-(S-methylsulfonimidoyl)-4-(2-morpholinoethyl)benzenesulfonamide A mixture of N-(4-ethylphenyl)-N-isobutyl-3-(S-methylsulfonimidoyl)-4-vinylbenzenesulfonamide (70.0 mg; 0.17 mmol; 1.00 eq.) and morpholine (1.0 ml; 11.59 mmol) is stirred for 30 minutes at room temperature.

The crude product is purified by preparative HPLC (C18 column, eluent: acetonitrile in water/0.1% of formic acid). The N-(4-ethylphenyl)-N-isobutyl-3-(S-methylsulfonimidoyl)-4-(2-morpholinoethyl)benzenesulfonamide (25.00 mg; 29.59%) is obtained in the form of an ocher-colored powder.

$^1$H NMR (DMSO-d6) δ: 1.10 (d, J=6.5 Hz, 6H), 1.43 (t, J=7.6 Hz, 3H), 1.69 (dt, J=13.4, 6.8 Hz, 1H), 2.71 (d, J=5.4 Hz, 2H), 2.83-2.90 (m, 2H), 3.36 (s, 8H), 3.84 (t, J=4.5 Hz, 3H), 4.79 (s, 1H), 7.24 (d, J=8.0 Hz, 2H), 7.45 (d, J=8.0 Hz, 2H), 7.95 (s, 2H), 8.32 (s, 1H).

MS: [M+H]=508

Part IV: Synthesis of Sulfur-Based Sulfonamides
Via Reaction Scheme 4
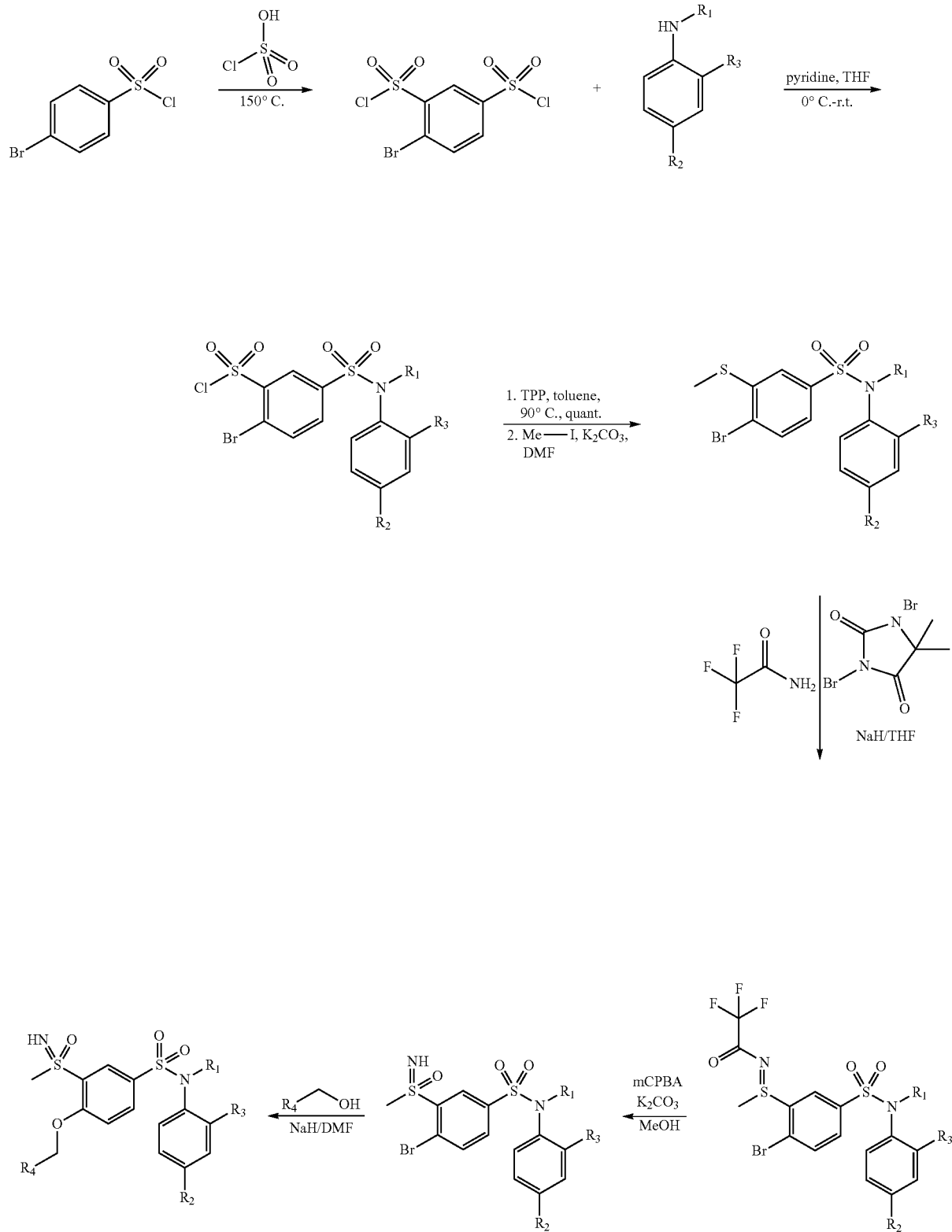

147

Example 113: Synthesis of N-(2,4-dimethylphenyl)-N-isobutyl-3-(S-methylsulfonimidoyl)-4-((tetrahydro-2H-pyran-4-yl)methoxy)benzenesulfonamide Compound 142

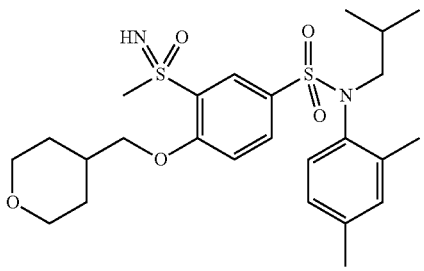

1. Synthesis of Intermediate 113.1

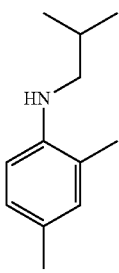

(2,4-dimethylphenyl)isobutylamine

A solution of 2,4-dimethylaniline (30 ml; 0.24 mol) and of isobutyraldehyde (20 ml; 0.22 mol) in tetrahydrofuran (320 ml) is stirred for 30 minutes at room temperature, and sodium triacetoxyborohydride (70 g; 0.33 mol) is then added portionwise. The reaction medium is stirred for 3 hours at room temperature, hydrolyzed and extracted with ethyl acetate. The organic phases are combined, washed with saturated sodium chloride solution and dried (MgSO$_4$).

The solvents are evaporated off. The crude product is chromatographed on silica gel (eluent: heptane/ethyl acetate, from 0 to 10% of ethyl acetate).

The (2,4-dimethylphenyl)isobutylamine (29.9 g; 77%) is obtained in the form of a yellow oil with a compliant NMR.

MS: [M+H]=177

2. Synthesis of Intermediate 113.2

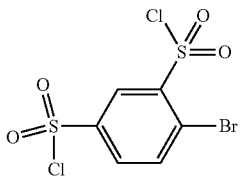

148

4-bromobenzene-1,3-disulfonyl dichloride

A mixture of 4-bromobenzenesulfonyl chloride (50 g; 0.20 mol) and of chlorosulfonic acid (260 ml; 3.91 mol) is stirred for 6 hours at 150° C. The reaction medium is poured slowly and cautiously onto a mixture of water and ice and is extracted with dichloromethane. The organic phases are combined, dried (MgSO$_4$), filtered and concentrated. The 4-bromobenzene-1,3-disulfonyl dichloride (54 g; 78%) is obtained in the form of a grayish powder with a compliant NMR.

MS: [M+H]=177

3. Synthesis of Intermediate 113.3

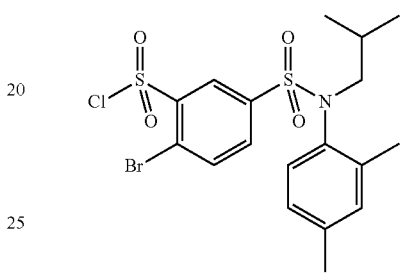

2-bromo-5-[(2,4-dimethylphenyl)isobutylsulfamoyl]benzenesulfonyl chloride

4-Bromobenzene-1,3-disulfonyl dichloride (1.0 g; 2.82 mmol) dissolved in tetrahydrofuran (5 ml) is added to (2,4-dimethylphenyl)isobutylamine (0.50 g; 2.82 mmol) and pyridine (1.4 ml; 17.0 mmol) dissolved in tetrahydrofuran (20 ml). The reaction medium is stirred for 16 hours at room temperature. The reaction medium is hydrolyzed and then extracted with ethyl acetate. The organic phases are combined, washed with aqueous 1M hydrochloric acid solution and then with saturated NaCl solution, dried (Na$_2$SO$_4$) and concentrated.

The 2-bromo-5-[(2,4-dimethylphenyl)isobutylsulfamoyl] benzenesulfonyl chloride (1.23 g; 88%) is obtained in the form of a yellow oil with a compliant NMR.

4. Synthesis of Intermediate 113.4

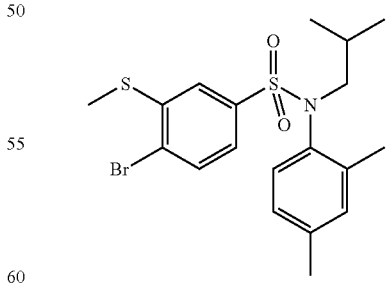

4-bromo-N-(4-ethylphenyl)-N-isobutyl-3-methylsulfanylbenzenesulfonamide

2-Bromo-5-[(2,4-dimethylphenyl)isobutylsulfamoyl]benzenesulfonyl chloride (1.67 g; 3.37 mmol) dissolved in toluene (8 ml) is added slowly to triphenylphosphine (2.66 g; 10.12 mmol) suspended in toluene (17 ml). The reaction medium is stirred for 4 hours at 90° C. The reaction medium is concentrated under vacuum and dissolved in N,N-dimethylformamide (14.5 ml) without purification, and potassium carbonate (0.51 g; 3.72 mmol) and iodomethane (0.32 ml; 5.08 mmol) are then added. The reaction medium is stirred for 20 minutes at room temperature, hydrolyzed and extracted with ethyl acetate. The organic phases are combined, washed with saturated sodium chloride solution and dried (Na$_2$SO$_4$).

The solvents are evaporated off. The crude product is chromatographed on silica gel (eluent: heptane/ethyl acetate, from 0 to 10% of ethyl acetate).

The 4-bromo-N-(4-ethylphenyl)-N-isobutyl-3-methylsulfanylbenzenesulfonamide (775.30 mg; 52%) is obtained in the form of a white solid with a compliant NMR.

MS: [M−H]=441

5. Synthesis of Intermediate 113.5

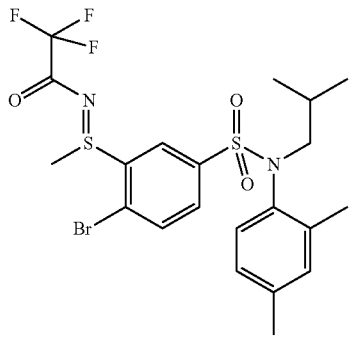 [SMILES: Cc1ccc(N(CC(C)C)S(=O)(=O)c2ccc(Br)c(/S(C)=N/C(=O)C(F)(F)F)c2)c(C)c1]

(E)-N-((2-bromo-5-(N-(2,4-dimethylphenyl)-N-isobutylsulfamoyl)phenyl)(methyl)-λ$^4$-sulfanylidene)-2,2,2-trifluoroacetamide 4-Bromo-N-(2,4-dimethylphenyl)-N-isobutyl-3-methylsulfanylbenzenesulfonamide (755.0 mg; 1.71 mmol) and 2,2,2-trifluoroacetamide (289.34 mg; 2.56 mmol) dissolved in tetrahydrofuran (1.51 ml) are added slowly to 60% sodium hydride (61.43 mg; 1.54 mmol) suspended in tetrahydrofuran (3.78 ml) at 0-5° C. 1,3-Dibromo-5,5-dimethylhydantoin (732 mg; 2.56 mmol) dissolved in tetrahydrofuran (1.5 ml) is then added.

The medium is stirred for 1 hour at room temperature, hydrolyzed by addition of saturated sodium hydrogen carbonate solution, and extracted with ethyl acetate. The organic phases are combined and then washed with 25% sodium sulfite solution and then twice with saturated sodium chloride solution and dried (Na$_2$SO$_4$). The solvents are evaporated off.

The crude product is chromatographed on silica gel (eluent: heptane/ethyl acetate, from 0 to 50% of ethyl acetate). The (E)-N-((2-bromo-5-(N-(2,4-dimethylphenyl)-N-isobutylsulfamoyl)phenyl)(methyl)-4-sulfanylidene)-2,2,2-trifluoroacetamide (233.0 mg; 25%) is obtained in the form of a white powder with a compliant 1H NMR.

MS: [M−H]=552

6. Synthesis of Intermediate 113.6

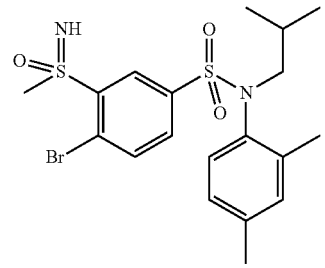 [SMILES: Cc1ccc(N(CC(C)C)S(=O)(=O)c2ccc(Br)c(S(C)(=N)=O)c2)c(C)c1]

4-bromo-N-(2,4-dimethylphenyl)-N-isobutyl-3-(S-methylsulfonimidoyl)benzenesulfonamide Potassium carbonate (172.30 mg; 1.25 mmol) is added to (E)-N-((2-bromo-5-(N-(4-ethylphenyl)-N-isobutylsulfamoyl)phenyl)(methyl)-4-sulfanylidene)-2,2,2-trifluoroacetamide (230.0 mg; 0.42 mmol) dissolved in methanol (2.3 ml), and 3-chloroperoxybenzoic acid (139.7 mg; 0.62 mmol) is then added slowly at 0° C. The reaction medium is stirred for 3 days at room temperature. The reaction medium is hydrolyzed and then extracted with ethyl acetate. The organic phases are combined, washed with saturated sodium chloride solution and dried (Na$_2$SO$_4$). The solvents are evaporated off.

The crude product is chromatographed on silica gel (eluent: heptane/ethyl acetate, from 0 to 80% of ethyl acetate). The 4-bromo-N-(2,4-dimethylphenyl)-N-isobutyl-3-(S-methylsulfonimidoyl)benzenesulfonamide (70.8 mg; 36%) is obtained in the form of a white solid with a compliant NMR.

MS: [M+H]=475

7. Synthesis of N-(2,4-dimethylphenyl)-N-isobutyl-3-(S-methylsulfonimidoyl)-4-((tetrahydro-2H-pyran-4-yl)methoxy)benzenesulfonamide

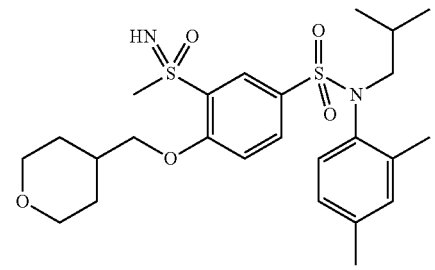 [SMILES: Cc1ccc(N(CC(C)C)S(=O)(=O)c2ccc(OCC3CCOCC3)c(S(C)(=N)=O)c2)c(C)c1]

60% sodium hydride (8.74 mg; 0.22 mmol) is added slowly at a temperature of 0° C. to (tetrahydropyran-4-yl)methanol (18.62 mg; 0.16 mmol) dissolved in N,N-dimethylformamide (1.38 ml), followed by 4-bromo-N-(2,4-dimethylphenyl)-N-isobutyl-3-(S-methylsulfonimidoyl)benzenesulfonamide (69.0 mg; 0.15 mmol). The reaction medium is stirred for 2 hours at room temperature and then for 1 hour at 80° C. The reaction medium is hydrolyzed without heating and then extracted with ethyl acetate. The organic phases are combined, washed with saturated sodium chloride solution and dried (Na$_2$SO$_4$). The solvents are evaporated off.

The crude product is purified by preparative HPLC (C18 column, eluent: acetonitrile in water/0.1% of formic acid). The N-(2,4-dimethylphenyl)-N-isobutyl-3-(S-methylsulfonimidoyl)-4-((tetrahydro-2H-pyran-4-yl)methoxy)benzenesulfonamide (44.81 mg; 59.54%) is obtained in the form of a white solid.

$^1$H NMR (DMSO-d6) δ: 0.76 (dd, J=6.8, 3.2 Hz, 3H), 0.82-0.91 (m, 1H), 0.95 (t, J=6.7 Hz, 3H), 1.25 (q, J=3.6, 2.6 Hz, 1H), 1.40 (p, J=4.2 Hz, 2H), 1.43 (s, 1H), 1.75 (d, J=7.5 Hz, 1H), 2.23-2.32 (m, 6H), 3.06 (ddd, J=21.2, 13.1, 4.6 Hz, 1H), 3.20 (dd, J=2.7, 1.2 Hz, 3H), 3.35-3.44 (m, 2H), 3.87-3.95 (m, 2H), 4.12 (dd, J=6.3, 3.6 Hz, 2H), 4.45 (dd, J=50.6, 1.5 Hz, 1H), 6.58 (dd, J=16.3, 8.1 Hz, 1H), 6.94 (dd, J=8.1, 2.0 Hz, 1H), 7.13 (s, 1H), 7.41 (d, J=8.9 Hz, 1H), 7.74 (td, J=8.6, 2.5 Hz, 1H), 8.05 (dd, J=4.9, 2.4 Hz, 1H)

MS: [M+H]=509

Part V: Synthesis of Sulfur-Based Sulfonamides Via Reaction Scheme 5

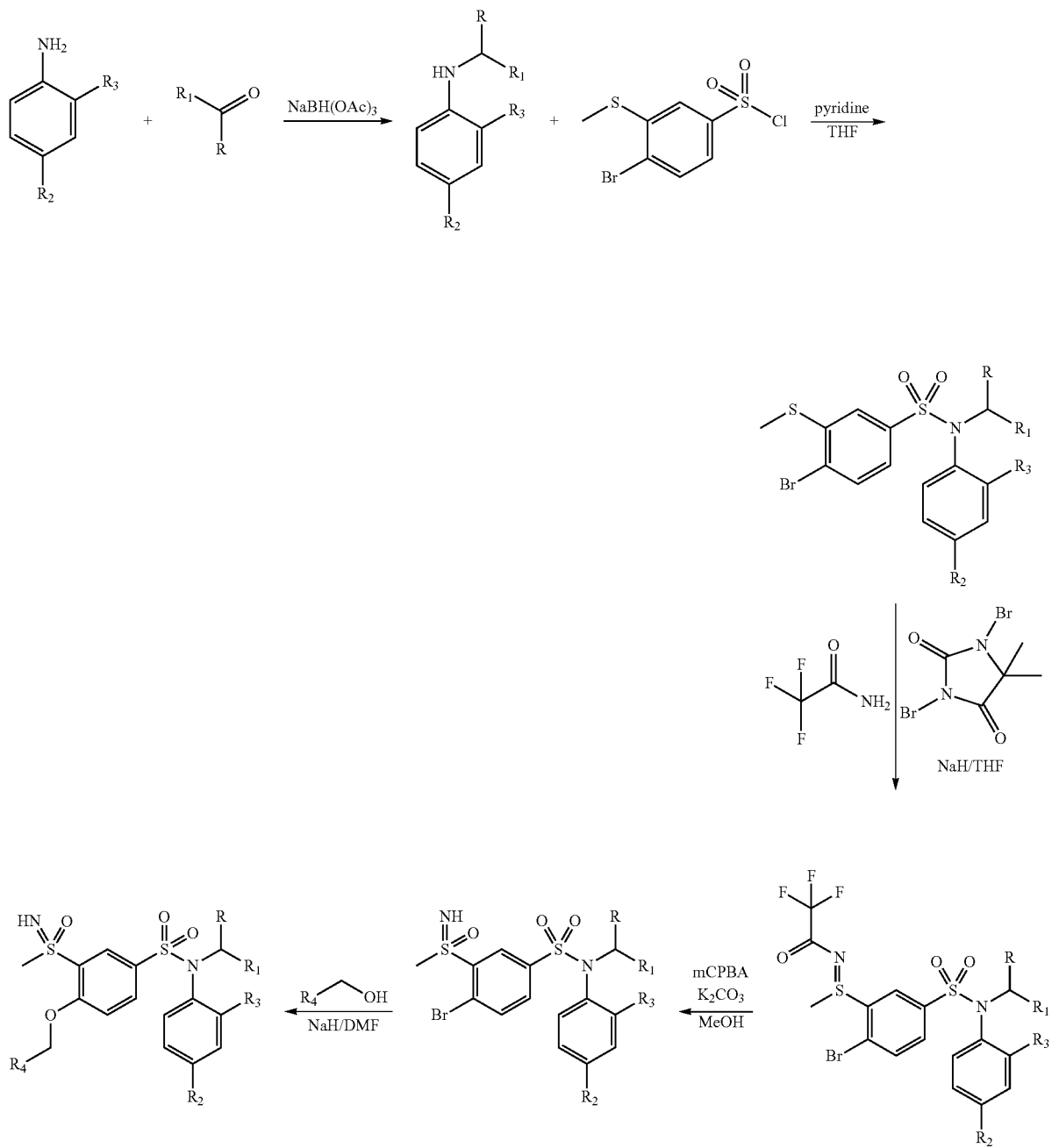

Reaction scheme 5

Example 114: Synthesis of N-isopropyl-N-(4-methoxy-2-methylphenyl)-3-(S-methylsulfonimidoyl)-4-((tetrahydro-2H-pyran-4-yl)methoxy)benzenesulfonamide

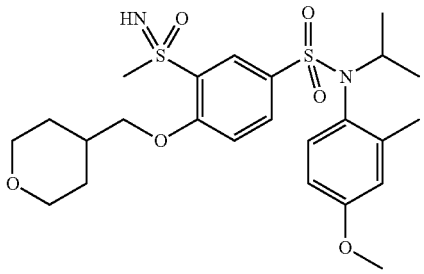 [SMILES: COc1ccc(N(C(C)C)S(=O)(=O)c2ccc(OCC3CCOCC3)c(S(C)(=N)=O)c2)c(C)c1]

1. Synthesis of Intermediate 114.1

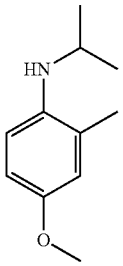

Isopropyl(4-methoxy-2-methylphenyl)amine

Sodium triacetoxyborohydride (4.63 g; 21.9 mmol) is added to a solution of 4-methoxy-2-methylaniline (2.0 g; 14.6 mmol) in acetone (20 ml). The reaction medium is heated for 10 minutes at a temperature of 70° C. under microwave irradiation. The reaction medium is poured onto ice and extracted with dichloromethane. The organic phases are combined, washed with saturated sodium chloride solution, dried (MgSO$_4$), filtered and concentrated. The crude product is chromatographed on silica gel (eluent: heptane/ethyl acetate, from 0 to 15% of ethyl acetate). The isopropyl (4-methoxy-2-methylphenyl)amine (1.43 g; 55%) is obtained in the form of a yellow oil with a compliant NMR.
MS: [M+H]=180

2. Synthesis of Intermediate 114.2

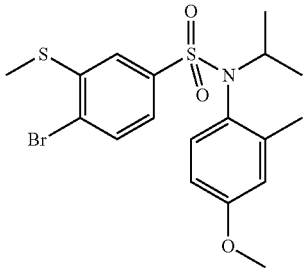 [SMILES: COc1ccc(N(C(C)C)S(=O)(=O)c2ccc(Br)c(SC)c2)c(C)c1]

4-bromo-N-isopropyl-N-(4-methoxy-2-methylphenyl)-3-methylsulfanylbenzenesulfonamide 4-Bromo-3-(methylthio)benzene-1-sulfonyl chloride (500 mg; 1.57 mmol) is added to isopropyl(4-methoxy-2-methylphenyl)amine (290 mg; 1.62 mmol) and pyridine (2.4 ml). The reaction medium is heated for 20 minutes at a temperature of 100° C. under microwave irradiation, hydrolyzed and extracted with ethyl acetate. The organic phases are combined, washed with 1N hydrochloric acid solution and then with saturated sodium chloride solution and dried (MgSO$_4$). The solvents are evaporated off.

The crude product is chromatographed on silica gel (eluent: heptane/ethyl acetate, from 0 to 40% of ethyl acetate). The 4-bromo-N-isopropyl-N-(4-methoxy-2-methylphenyl)-3-methylsulfanylbenzenesulfonamide (570 mg; 81%) is obtained in the form of a yellow oil with a compliant NMR.
MS: [M+H]=444

3. Synthesis of Intermediate 114.3

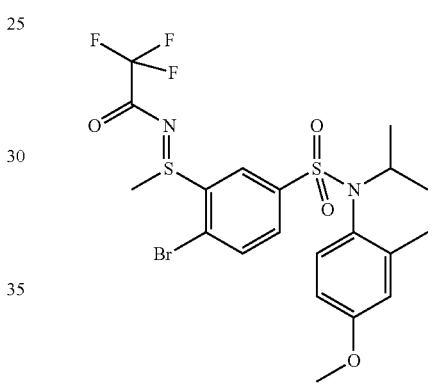

(E)-N-((2-bromo-5-(N-isopropyl-N-(4-methoxy-2-methylphenyl)sulfamoyl)phenyl)(methyl)-λ$^4$-sulfanylidene)-2,2,2-trifluoroacetamide 4-Bromo-N-isopropyl-N-(4-methoxy-2-methylphenyl)-3-methylsulfanylbenzenesulfonamide (565 mg; 1.27 mmol) and 2,2,2-trifluoroacetamide (215.6 mg; 1.91 mmol) dissolved in tetrahydrofuran (1.1 ml) are added slowly to 60% sodium hydride (45.8 mg; 1.14 mmol) suspended in tetrahydrofuran (2.8 ml) at 0-5° C., followed by addition of the solution of 1,3-dibromo-5,5-dimethylhydantoin (545.3 mg; 1.91 mmol) in tetrahydrofuran (1.13 ml). The medium is stirred for 2 hours at room temperature, hydrolyzed by addition of 10% citric acid solution and then extracted with ethyl acetate. The organic phases are combined, then washed with 25% sodium sulfite solution and then twice with saturated sodium chloride solution and dried (Na$_2$SO$_4$). The solvents are evaporated off.

The crude product is chromatographed on silica gel (eluent: heptane/ethyl acetate, from 0 to 60% of ethyl acetate). The (E)-N-((2-bromo-5-(N-isopropyl-N-(4-methoxy-2-methylphenyl)sulfamoyl)phenyl)(methyl)-λ$^4$-sulfanylidene)-2,2,2-trifluoroacetamide (706 mg; 100%) is obtained in the form of a colorless oil with a compliant NMR.
MS: [M−H]=557

4. Synthesis of Intermediate 114.4

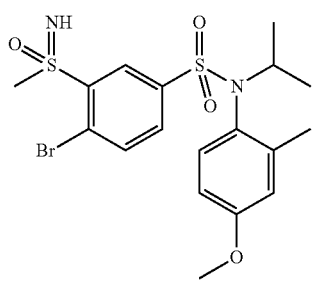 [SMILES: COc1ccc(N(C(C)C)S(=O)(=O)c2ccc(Br)c(S(C)(=N)=O)c2)c(C)c1]

4-bromo-N-isopropyl-N-(4-methoxy-2-methylphenyl)-3-(S-methylsulfonimidoyl)benzenesulfonamide Potassium carbonate (549 mg; 3.97 mmol) is added to (E)-N-((2-bromo-5-(N-isopropyl-N-(4-methoxy-2-methylphenyl)sulfamoyl)phenyl)(methyl)-$\lambda^4$-sulfanylidene)-2,2,2-trifluoroacetamide (735 mg; 1.32 mmol) dissolved in methanol (7.4 ml), and 3-chloroperoxybenzoic acid (445 mg; 1.98 mmol) is then added slowly at 0° C. The reaction medium is stirred for 2 hours at room temperature, hydrolyzed and then extracted with ethyl acetate. The organic phases are combined, washed with saturated sodium chloride solution and dried (MgSO$_4$). The solvents are evaporated off.

The crude product is chromatographed on silica gel (heptane/ethyl acetate, from 40 to 80% of ethyl acetate). The 4-bromo-N-isopropyl-N-(4-methoxy-2-methylphenyl)-3-(S-methylsulfonimidoyl)benzenesulfonamide (211.6 mg; 34%) is obtained in the form of a white solid with a compliant NMR.

MS: [M+H]=477

5. Synthesis of N-isopropyl-N-(4-methoxy-2-methylphenyl)-3-(S-methylsulfonimidoyl)-4-((tetrahydro-2H-pyran-4-yl)methoxy)benzenesulfonamide 60% sodium hydride (12.6 mg; 0.32 mmol) is added slowly at 0° C. to (tetrahydropyran-4-yl)methanol (26.8 mg; 0.23 mmol) dissolved in N,N-dimethylformamide (2 ml), followed by 4-bromo-N-isopropyl-N-(4-methoxy-2-methylphenyl)-3-(S-methylsulfonimidoyl)benzenesulfonamide (100 mg; 0.21 mmol). The reaction medium is stirred for 1 hour at room temperature and for 90 minutes at a temperature of 60° C., and then hydrolyzed and extracted with ethyl acetate. The organic phases are combined and then washed with saturated sodium chloride solution and dried (Na$_2$SO$_4$). The solvents are evaporated off.

The product is chromatographed on silica gel (eluent: dichloromethane/methanol from 0 to 10% of methanol).

The N-isopropyl-N-(4-methoxy-2-methylphenyl)-3-(S-methylsulfonimidoyl)-4-((tetrahydro-2H-pyran-4-yl)methoxy)benzenesulfonamide (76.2 mg; 71%) is obtained in the form of a white solid.

$^1$H NMR (DMSO-d6) δ: 0.79-0.93 (m, 4H), 0.98 (dd, J=6.8, 2.1 Hz, 3H), 1.26 (dd, J=10.8, 4.6 Hz, 2H), 1.41 (tdd, J=12.3, 7.6, 4.4 Hz, 2H), 1.75 (t, J=11.7 Hz, 2H), 2.10 (d, J=8.7 Hz, 1H), 2.25 (d, J=8.3 Hz, 3H), 3.19 (d, J=1.2 Hz, 3H), 3.33-3.43 (m, 2H), 3.82-3.99 (m, 2H), 4.02-4.19 (m, 2H), 4.34-4.55 (m, 2H), 6.57-6.76 (m, 2H), 6.92 (t, J=2.2 Hz, 1H), 7.41 (dd, J=8.8, 2.9 Hz, 1H), 7.84 (dd, J=8.7, 2.4 Hz, 1H), 8.14 (t, J=2.7 Hz, 1H)

MS: [M+H]=511

Part VI: Synthesis of Sulfur-Based Sulfonamides Via Reaction Scheme 6

Reaction scheme 6

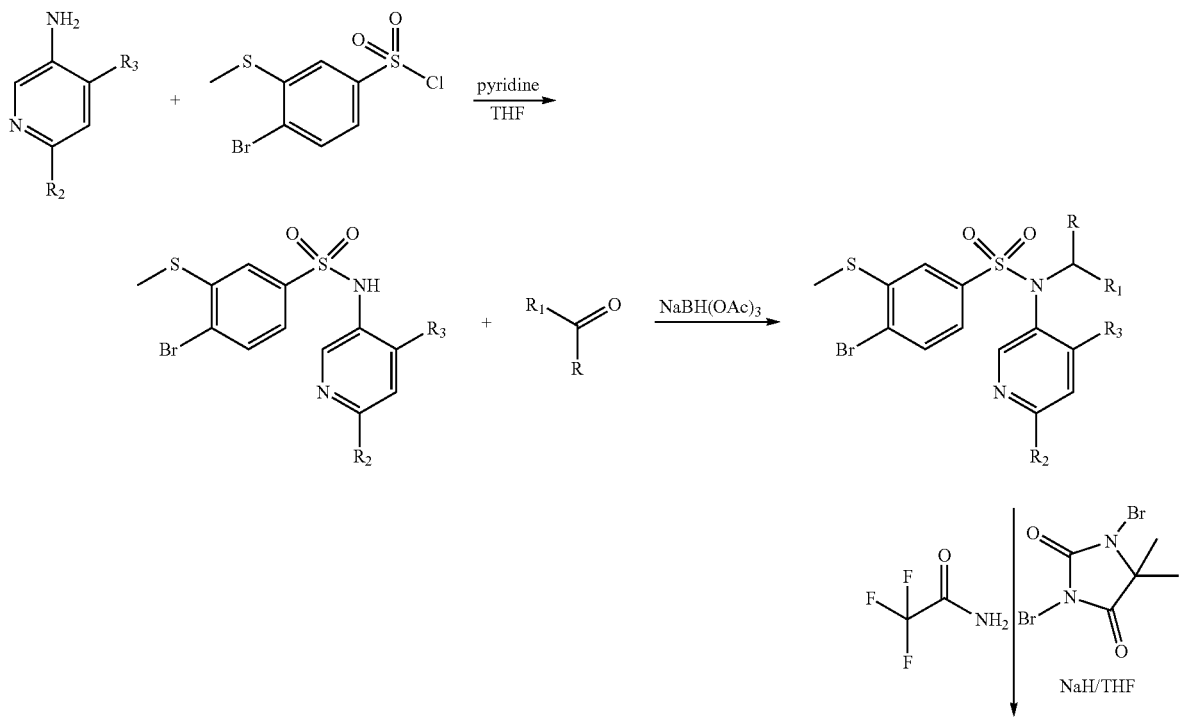

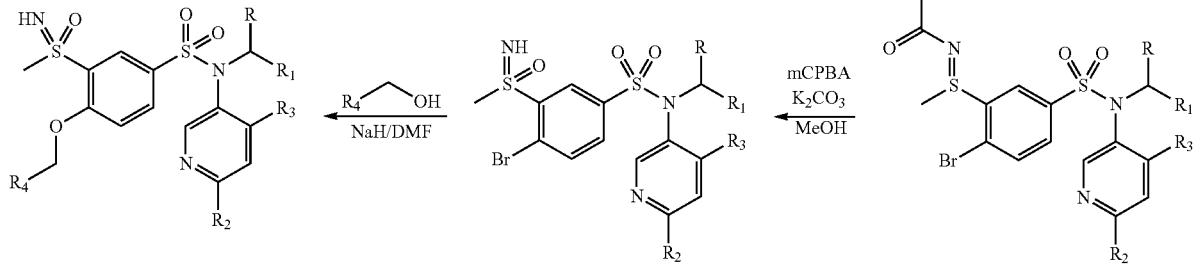

Example 116: Synthesis of N-(4-ethylphenyl)-N-isobutyl-4-(tetrahydropyran-4-ylmethylsulfanyl) benzenesulfonamide Compound 68

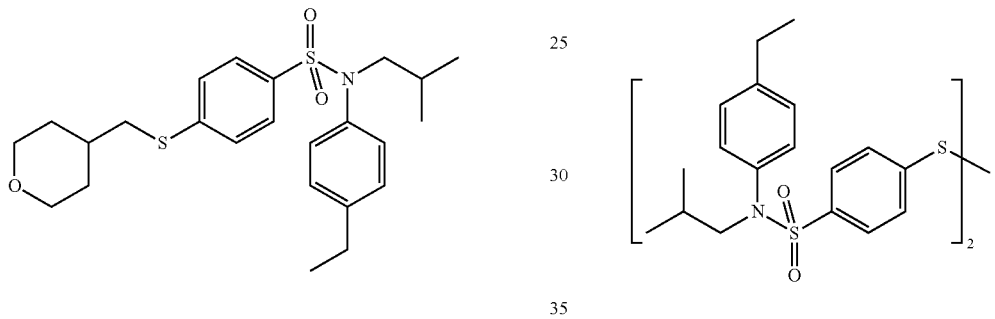

1. Synthesis of Intermediate 116.1

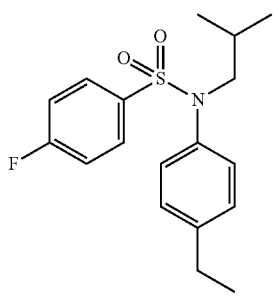 [SMILES: CCc1ccc(N(CC(C)C)S(=O)(=O)c2ccc(F)cc2)cc1]

N-(4-ethylphenyl)-4-fluoro-N-isobutylbenzenesulfonamide

4-Fluorobenzenesulfonyl chloride (2.78 g; 14.27 mmol) is added to the (4-ethylphenyl)isobutylamine (2.3 g; 12.28 mmol) and diisopropylamine (5.5 ml; 67.69 mmol) dissolved in tetrahydrofuran (25 ml). The reaction medium is stirred for 16 hours at room temperature, hydrolyzed and extracted with ethyl acetate. The organic phases are combined, washed with saturated ammonium chloride solution and then with brine, dried (Na$_2$SO$_4$) and concentrated.

The crude product is chromatographed on silica gel (eluent: heptane/ethyl acetate, from 0 to 10% of ethyl acetate). The N-(4-ethylphenyl)-4-fluoro-N-isobutylbenzenesulfonamide (2.09 g; 48%) is obtained in the form of an orange-yellow solid with a compliant $^1$H NMR.

MS: [M+H]=336

2. Synthesis of Intermediate 116.2

Bis[4-[(4-ethylphenyl)isobutylsulfamoyl]thiobenzene] disulfide

A mixture of N-(4-ethylphenyl)-4-fluoro-N-isobutylbenzenesulfonamide (1.0 g; 2.98 mmol) and sodium hydrogen sulfide (2.1 g; 37.26 mmol) in 1-methyl-2-pyrrolidinone (4 ml) is stirred for 2 hours at 80° C. and then for 16 hours at room temperature. The reaction medium is diluted with ethyl acetate and acidified by addition of concentrated HCl and then extracted. The organic phases are combined, washed with water, dried (MgSO$_4$), filtered and concentrated to dryness. The bis[4-[(4-ethylphenyl)isobutylsulfamoyl]thiobenzene] disulfide (1.04 g; 50%) obtained is used directly in the next reaction.

MS: [M+H]=698

3. Synthesis of N-(4-ethylphenyl)-N-isobutyl-4-(tetrahydropyran-4-ylmethylsulfanyl)benzenesulfonamide Potassium carbonate (0.41 g; 2.96 mmol) is added to a solution of bis[4-[(4-ethylphenyl)isobutylsulfamoyl]thiobenzene] disulfide (1.03 g; 1.48 mmol) in N,N-dimethylformamide (15 ml). The reaction medium is stirred for 5 minutes, followed by addition of 4-(bromomethyl)tetrahydropyran (0.53 g; 2.96 mmol) and then sodium formaldehyde sulfoxylate (0.60 g; 4.44 mmol) and water (20 μl; 1.10 mmol). The reaction medium is stirred for 1 hour at room temperature, hydrolyzed and extracted with ethyl acetate. The organic phases are combined, washed with brine, dried (MgSO$_4$), filtered and concentrated. The crude product is chromatographed on silica gel, eluting with heptane/ethyl acetate, from 5 to 30% of ethyl acetate. The N-(4-ethylphenyl)-N-isobutyl-4-(tetrahydropyran-4-ylmethylsulfanyl)benzenesulfonamide (1.10 g; 83%) is obtained in the form of a solid.

¹H NMR (400 MHz, DMSO-d6) δ 7.55-7.34 (m, 4H), 7.23-7.15 (m, 2H), 7.02-6.93 (m, 2H), 3.90-3.81 (m, 2H), 3.30-3.21 (m, 3H), 3.02 (d, J=6.6 Hz, 2H), 2.60 (q, J=7.6 Hz, 2H), 1.79-1.68 (m, 2H), 1.48-1.36 (m, 1H), 1.36-1.22 (m, 1H), 1.18 (t, J=7.6 Hz, 3H), 0.84 (d, J=6.7 Hz, 6H).

MS: [M+H]=448

Example 117: Synthesis of N-(4-ethylphenyl)-N-isobutyl-4-(tetrahydropyran-4-ylmethylsulfinyl)benzenesulfonamide

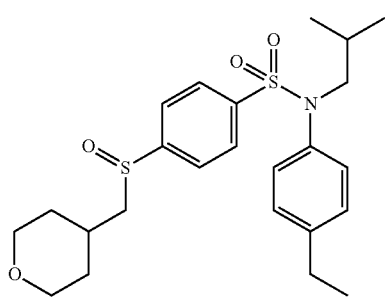

Compound 29

3-Chloroperbenzoic acid (414 mg; 1.85 mmol) is added portionwise to a solution of N-(4-ethylphenyl)-N-isobutyl-4-(tetrahydropyran-4-ylmethylsulfanyl)benzenesulfonamide (787 mg; 1.76 mmol) in dichloromethane (20 ml) at 0° C.

The medium is stirred for 3 hours 30 minutes. At 0° C., 13 ml of 1N sodium hydroxide solution are added dropwise, followed by addition of 13 ml of water. The reaction medium is extracted with dichloromethane. The organic phases are washed with aqueous sodium thiosulfate solution, dried over magnesium sulfate, filtered and concentrated. The oil obtained is precipitated from dichloromethane and heptane. The solid is filtered off, rinsed with heptane and dried. The N-(4-ethylphenyl)-N-isobutyl-4-(tetrahydropyran-4-ylmethylsulfinyl)benzenesulfonamide (755 mg; 88%) is obtained in the form of a white solid.

1H NMR (400 MHz, DMSO-d6) δ0.86 (d, J=6.6 Hz, 7H), 1.18 (t, J=7.6 Hz, 3H), 1.51-1.24 (m, 3H), 1.55 (d, J=13.3 Hz, 1H), 1.83 (d, J=13.0 Hz, 1H), 2.16-1.98 (m, 1H), 2.60 (q, J=7.6 Hz, 2H), 2.81 (dd, J=13.1, 5.0 Hz, 1H), 2.93 (dd, J=13.2, 8.6 Hz, 1H), 3.38-3.28 (m, 4H), 3.95-3.70 (m, 2H), 7.08-6.85 (m, 2H), 7.27-7.14 (m, 2H), 7.80-7.66 (m, 2H), 7.95-7.81 (m, 2H),

MS: [M+H]=464

The compound N-(4-ethylphenyl)-N-isobutyl-4-(tetrahydropyran-4-ylmethylsulfinyl)benzenesulfonamide (450 mg; 1.11 mmol) is chromatographed by chiral SFC to separate the two enantiomers (compound 13 and compound 14) below:

[Supercritical conditions: 100 bar, 70° C.; Chiralpak IC 250×4.6 mm 5 column, eluent: CO₂/ethanol: 30 g of ethanol]

Example 118: N-(4-ethylphenyl)-N-isobutyl-4-(tetrahydropyran-4-ylmethanesulfinyl)benzenesulfoximine (Compound 13)—Enantiomer A of Compound 29

(150 mg; 22%) in the form of a white crystalline solid

¹H NMR (400 MHz, DMSO-d6) δ 7.91-7.84 (m, 2H), 7.76-7.69 (m, 2H), 7.20 (d, J=8.4 Hz, 2H), 6.98 (d, J=8.3 Hz, 2H), 3.84 (dd, J=22.1, 12.3 Hz, 2H), 3.45-3.17 (m, 4H), 2.93 (dd, J=13.2, 8.6 Hz, 1H), 2.81 (dd, J=13.1, 5.0 Hz, 1H), 2.66-2.48 (m, 2H), 2.08 (dddd, J=19.9, 12.3, 8.7, 4.1 Hz, 1H), 1.89-1.79 (m, 1H), 1.60-1.25 (m, 4H), 1.18 (t, J=7.6 Hz, 3H), 0.86 (d, J=6.7 Hz, 6H).

Retention time (chiral SFC) of 6.92 minutes

Example 119: N-(4-ethylphenyl)-N-isobutyl-4-(tetrahydropyran-4-ylmethanesulfinyl)benzenesulfonamide (Compound 14)—Enantiomer B of Compound 29

(120 mg; 18%) in the form of a white solid

¹H NMR (400 MHz, DMSO-d6) δ 7.92-7.80 (m, 2H), 7.80-7.64 (m, 2H), 7.28-7.11 (m, 2H), 7.04-6.92 (m, 2H), 3.85 (ddd, J=21.3, 10.9, 4.2 Hz, 2H), 3.47-3.18 (m, 4H), 2.93 (dd, J=13.2, 8.6 Hz, 1H), 2.81 (dd, J=13.1, 5.0 Hz, 1H), 2.61 (q, J=7.6 Hz, 2H), 2.08 (dtt, J=19.8, 8.2, 4.1 Hz, 1H), 1.94-1.72 (m, 1H), 1.64-1.24 (m, 4H), 1.18 (t, J=7.6 Hz, 3H), 0.86 (d, J=6.7 Hz, 6H).

Retention time (chiral SFC) of 9.31 minutes

Example 120: Synthesis of N-(4-ethylphenyl)-N-isobutyl-4-(tetrahydropyran-4-ylmethanesulfoximinyl)benzenesulfonamide

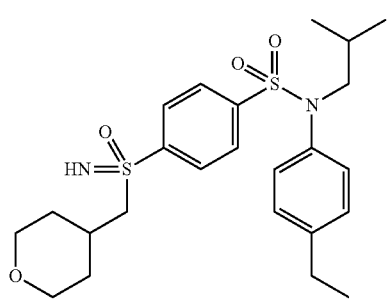

Compound 28

2,2,2-Trifluoroacetamide (121 mg; 1.07 mmol), magnesium oxide (87 mg; 2.15 mmol), rhodium(II) acetate dimer (28 mg; 0.06 mmol) and iodobenzene diacetate (263 mg; 0.82 mmol) are added to a solution, degassed beforehand with argon, of N-(4-ethylphenyl)-N-isobutyl-4-(tetrahydropyran-4-ylmethanesulfinyl)benzenesulfonamide (199 mg; 0.43 mmol) in dichloromethane (7 ml). The reaction medium is stirred at room temperature for 20 hours, filtered through Celite and concentrated. The residue obtained is diluted in methanol (7 ml), and potassium carbonate (297 mg; 2.15 mmol) is added.

The medium is stirred for 30 minutes at room temperature, hydrolyzed and extracted with ethyl acetate. The organic phases are combined, washed with brine, dried (Na₂SO₄) and concentrated.

The crude product is chromatographed on silica gel (eluent: 10/90 heptane/ethyl acetate). The N-(4-ethylphenyl)-N-isobutyl-4-(tetrahydropyran-4-ylmethanesulfoximinyl)benzenesulfonamide (87 mg; 41%) is obtained in the form of a cream-colored solid.

$^1$H NMR (400 MHz, DMSO-d6) δ 0.86 (dd, J=6.8, 1.9 Hz, 6H), 1.35-1.06 (m, 5H), 1.44 (dt, J=13.5, 6.9 Hz, 1H), 1.77-1.50 (m, 2H), 2.06 (t, J=9.2 Hz, 1H), 2.61 (d, J=7.6 Hz, 2H), 3.29-3.16 (m, 3H), 3.37 (d, J=7.2 Hz, 2H), 3.76 (dt, J=11.7, 3.1 Hz, 2H), 4.55 (s, 1H), 7.07-6.84 (m, 2H), 7.19 (dd, J=8.6, 2.0 Hz, 2H), 7.89-7.62 (m, 2H), 8.09 (dd, J=8.4, 2.0 Hz, 2H).

MS: [M+H]=479

Part VII: Synthesis of Sulfur-Based Sulfonamides Via Reaction Scheme 7

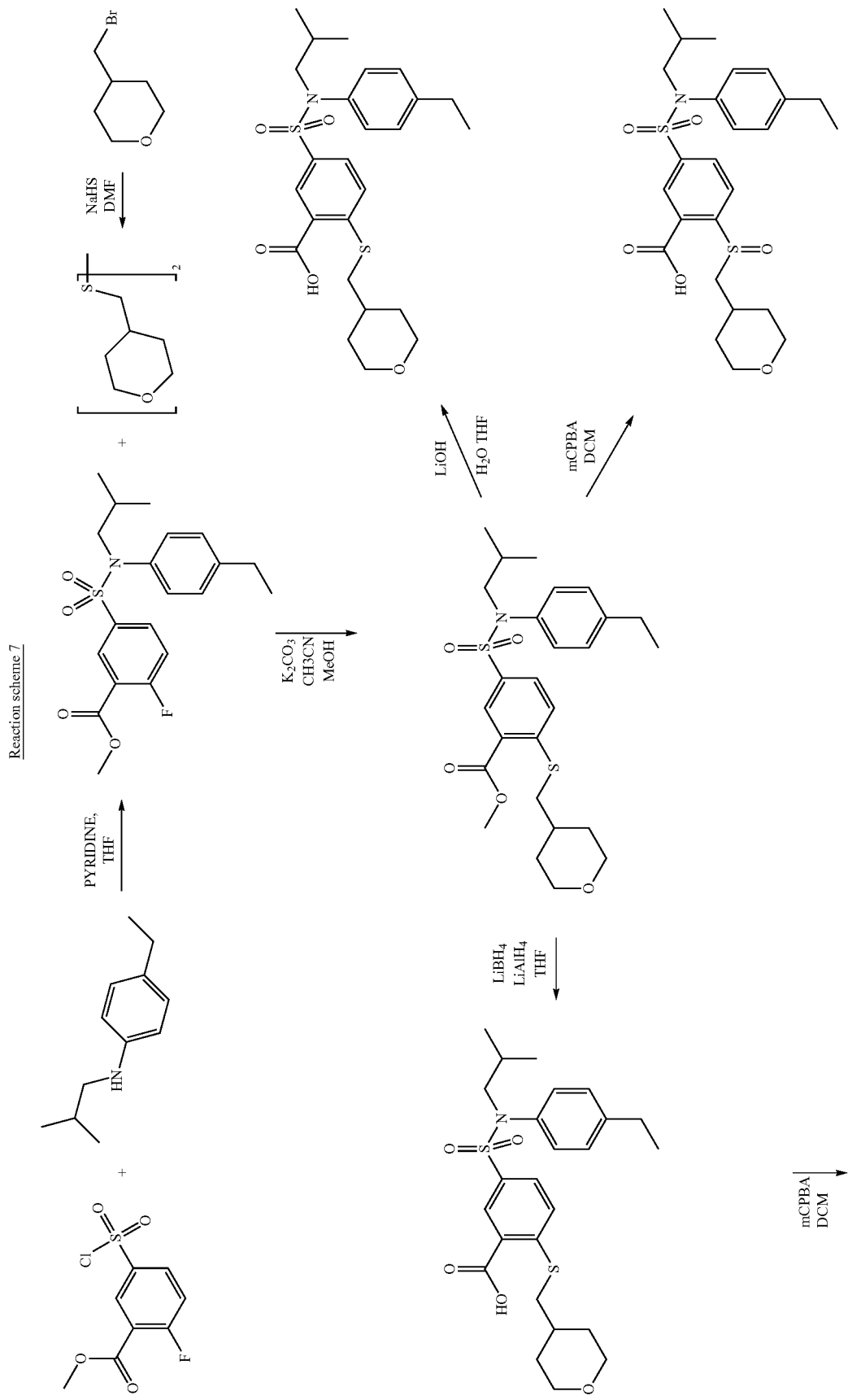

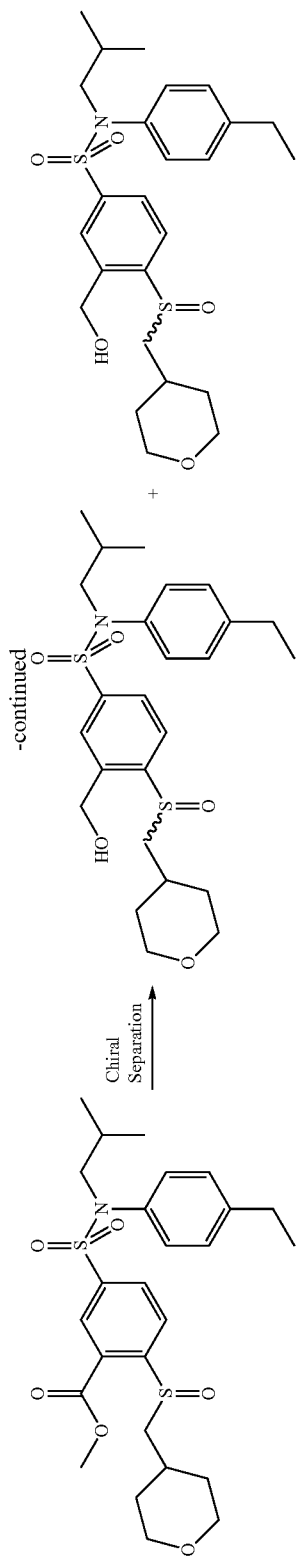

Example 121: Synthesis of methyl 5-[(4-ethylphenyl)isobutylsulfamoyl]-2-(tetrahydropyran-4-ylmethylsulfanyl)benzoate Compound 17

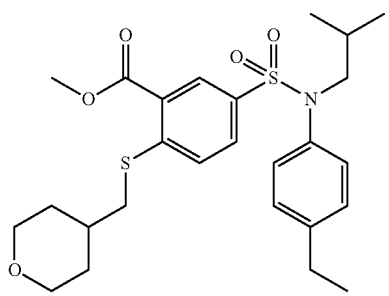

1. Synthesis of Intermediate 121.1

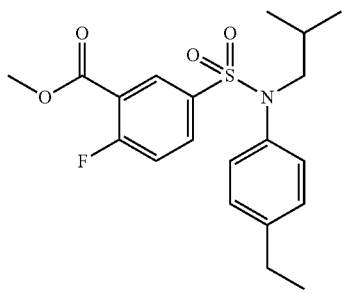 [SMILES: CCc1ccc(N(CC(C)C)S(=O)(=O)c2ccc(F)c(C(=O)OC)c2)cc1]

methyl 5-[(4-ethylphenyl)isobutylsulfamoyl]-2-fluorobenzoate

Methyl 5-chlorosulfonyl-2-fluorobenzoate (720 mg; 2.85 mmol) is added to (4-ethylphenyl)isobutylamine (0.95 g; 4.27 mmol) and pyridine (1.38 ml; 0.02 mol; 6.00 eq.) dissolved in tetrahydrofuran (16 ml). The reaction medium is stirred at room temperature for 16 hours, hydrolyzed and extracted with ethyl acetate. The organic phases are combined, washed with brine, dried (Na$_2$SO$_4$) and concentrated.

The crude product is chromatographed on silica gel (eluent: heptane/ethyl acetate, from 5 to 20% of ethyl acetate). The methyl 5-[(4-ethylphenyl)isobutylsulfamoyl]-2-fluorobenzoate (800 mg; 71%) is obtained in the form of a beige-colored solid with a compliant $^1$H NMR.

MS: [M+H]=394

2. Synthesis of Intermediate 121.2

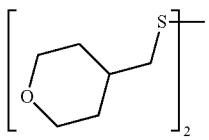

Bis[(tetrahydropyran-4-yl)methane bisulfide

A mixture of 4-(bromomethyl)tetrahydropyran (1.0 g; 5.58 mmol) and sodium hydrogen sulfide (0.44 g; 7.82 mmol) in dimethylformamide (4 ml) is stirred at room temperature for 2 hours. The reaction medium is diluted with ether and acidified by addition of concentrated HCl and then extracted. The organic phases are combined, washed with water, dried over magnesium sulfate, filtered and concentrated to dryness. The bis[(tetrahydropyran-4-yl)methane bisulfide (565.00 mg; 77%) obtained in the form of a clear oil is used directly in the next reaction.

MS: [M+H]=263

3. Synthesis of methyl 5-[(4-ethylphenyl)isobutylsulfamoyl]-2-(tetrahydropyran-4-ylmethylsulfanyl)benzoate

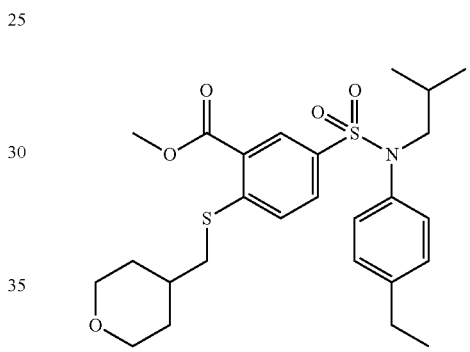

Potassium carbonate (81 mg; 0.59 mmol) is added to methyl 5-[(4-ethylphenyl)isobutylsulfamoyl]-2-fluorobenzoate (200 mg; 0.51 mmol) and bis(tetrahydropyran-4-yl)methane bisulfide (133.39 mg; 0.51 mmol; 1.00 eq.) in acetonitrile (2 ml). The reaction medium is stirred at room temperature for 16 hours, hydrolyzed and extracted with ethyl acetate. The organic phases are combined, washed with brine, dried and concentrated.

The crude product is chromatographed on silica gel, eluting with heptane/ethyl acetate: 5 to 20% of ethyl acetate. The methyl 5-[(4-ethylphenyl)isobutylsulfamoyl]-2-(tetrahydropyran-4-ylmethylsulfanyl)benzoate (214 mg; 83%) is obtained in the form of a white solid.

1H NMR (400 MHz, DMSO-d6) δ 0.85 (d, J=6.6 Hz, 7H), 1.18 (t, J=7.6 Hz, 3H), 1.37 (dtd, J=36.3, 12.9, 12.1, 7.3 Hz, 3H), 1.91-1.70 (m, 4H), 2.61 (q, J=7.6 Hz, 2H), 2.98 (d, J=6.7 Hz, 2H), 3.35-3.24 (m, 4H), 3.91-3.80 (m, 5H), 7.05-6.98 (m, 2H), 7.23-7.17 (m, 2H), 7.66-7.59 (m, 2H), 7.89 (d, J=1.9 Hz, 1H).

MS: [M+H]=506

Example 122: Synthesis of methyl 5-[(4-ethylphenyl)isobutylsulfamoyl]-2-(tetrahydropyran-4-ylmethanesulfinyl)benzoate

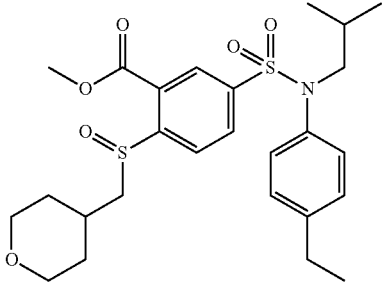

Compound 16

3-Chloroperbenzoic acid (70 mg; 0.31 mmol) is added to a solution of methyl 5-[(4-ethylphenyl)isobutylsulfamoyl]-2-(tetrahydropyran-4-ylmethylsulfanyl)benzoate (150 mg; 0.30 mmol) in dichloromethane (5 ml) at a temperature of 0° C. The reaction medium is stirred for 2 hours. At 0° C., 1N sodium hydroxide is added dropwise, followed by addition of water, and the reaction medium is then extracted with dichloromethane.

The organic phases are washed with aqueous sodium thiosulfate solution, dried over magnesium sulfate, filtered and evaporated.

The crude product is chromatographed on silica gel (eluent: heptane/ethyl acetate, from 10 to 30% of ethyl). The methyl 5-[(4-ethylphenyl)isobutylsulfamoyl]-2-(tetrahydropyran-4-ylmethanesulfinyl)benzoate (140 mg; 90%) is obtained in the form of a white solid.

1H NMR (400 MHz, DMSO-d6) δ 0.86 (dd, J=6.7, 4.0 Hz, 6H), 1.19 (t, J=7.6 Hz, 3H), 1.67-1.23 (m, 3H), 1.97 (dd, J=16.3, 5.1 Hz, 1H), 2.66-2.55 (m, 3H), 2.22 (s, 1H), 3.09 (dd, J=12.8, 9.7 Hz, 1H), 3.44-3.31 (m, 4H), 3.89 (s, 5H), 7.07-6.97 (m, 2H), 7.22 (d, J=8.3 Hz, 2H), 8.02 (d, J=1.9 Hz, 1H), 8.08 (dd, J=8.3, 2.0 Hz, 1H), 8.30 (d, J=8.3 Hz, 1H).

MS: [M+H]=522

Example 123: Synthesis of 5-[(4-ethylphenyl)isobutylsulfamoyl]-2-(tetrahydropyran-4-ylmethylsulfanyl)benzoic Acid

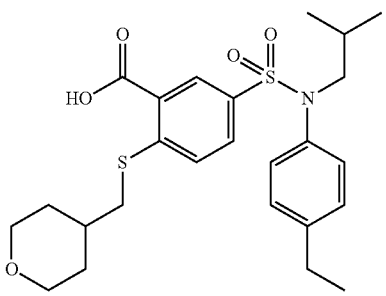 [SMILES: CCc1ccc(N(CC(C)C)S(=O)(=O)c2ccc(SCC3CCOCC3)c(C(=O)OC)c2)cc1]

Compound 23

A mixture of methyl 5-[(4-ethylphenyl)isobutylsulfamoyl]-2-(tetrahydropyran-4-ylmethanesulfanyl)tetrahydropyran-4-ylbenzoate (277 mg; 0.47 mmol) and lithium hydroxide (0.70 ml; 1.00 M; 0.70 mmol) in tetrahydrofuran (6.93 ml) is stirred at a temperature of 60° C. for 24 hours. The reaction medium is hydrolyzed with 1N sodium hydroxide and extracted with ethyl acetate. The organic phases are combined and washed with 1N sodium hydroxide.

The aqueous phases are combined, acidified with HCl and extracted with ethyl acetate. The organic phases are combined, washed with brine, dried over magnesium sulfate, filtered and concentrated.

The crude product is chromatographed on silica gel, eluting with heptane/ethyl acetate+1% AcOH, 10 to 50% of ethyl acetate. The 5-[(4-ethylphenyl)isobutylsulfamoyl]-2-(tetrahydropyran-4-ylmethylsulfanyl)benzoic acid (87.00 mg; 36%) is obtained in the form of a solid after crystallization from a mixture of methanol and dichloromethane.

1H NMR (400 MHz, DMSO-d6) δ 0.85 (d, J=6.6 Hz, 6H), 1.18 (t, J=7.6 Hz, 3H), 1.50-1.24 (m, 3H), 1.89-1.67 (m, 3H), 2.66-2.55 (m, 2H), 2.94 (d, J=6.6 Hz, 2H), 3.30 (d, J=7.1 Hz, 3H), 4.03-3.71 (m, 2H), 7.04-6.97 (m, 2H), 7.25-7.16 (m, 2H), 7.59 (s, 2H), 8.10-7.74 (m, 1H), 13.46 (s, 1H).

MS: [M+H]=492

Example 124: Synthesis of N-(4-ethylphenyl)-3-hydroxymethyl-N-isobutyl-4-(tetrahydropyran-4-ylmethylsulfanyl)benzenesulfonamide

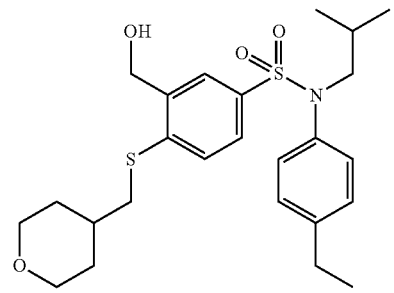

Compound 21

Lithium borohydride (9 mg; 0.40 mmol) is added to methyl 5-[(4-ethylphenyl)isobutylsulfamoyl]-2-(tetrahydropyran-4-ylmethylsulfanyl)benzoate (113 mg; 0.22 mmol) in tetrahydrofuran (3 ml). The reaction medium is stirred at room temperature for 16 hours, hydrolyzed with 5% citric acid for 1 hour and extracted with ethyl acetate. The organic phases are combined, washed with brine, dried over magnesium sulfate, filtered and evaporated.

The crude product is chromatographed on silica gel (eluent: 80/20 heptane/ethyl acetate). The N-(4-ethylphenyl)-3-hydroxymethyl-N-isobutyl-4-(tetrahydropyran-4-ylmethylsulfanyl)benzenesulfonamide (106 mg; 96%) is obtained in the form of a white solid.

¹H NMR (Chloroform-d) δ: 0.84 (d, J=6.7 Hz, 6H), 1.16 (t, J=7.6 Hz, 3H), 1.35 (qd, J=13.1, 12.4, 3.6 Hz, 2H), 1.50 (hept, J=6.7 Hz, 1H), 1.73 (d, J=12.3 Hz, 1H), 2.51-2.62 (m, 2H), 2.64 (d, J=1.7 Hz, 2H), 2.87 (d, J=6.5 Hz, 2H), 3.22 (d, J=7.4 Hz, 2H), 3.31 (td, J=11.8, 1.9 Hz, 2H), 3.92 (ddd, J=12.5, 4.6, 1.5 Hz, 2H), 4.65 (s, 2H), 6.87-6.94 (m, 2H), 7.06 (d, J=8.3 Hz, 2H), 7.19 (d, J=8.2 Hz, 1H), 7.33 (dd, J=8.3, 2.2 Hz, 1H), 7.56 (d, J=2.1 Hz, 1H)

MS: [M+H]=478

Example 125: Synthesis of N-(4-ethylphenyl)-3-hydroxymethyl-N-isobutyl-4-(tetrahydropyran-4-ylmethanesulfinyl)benzenesulfonamide

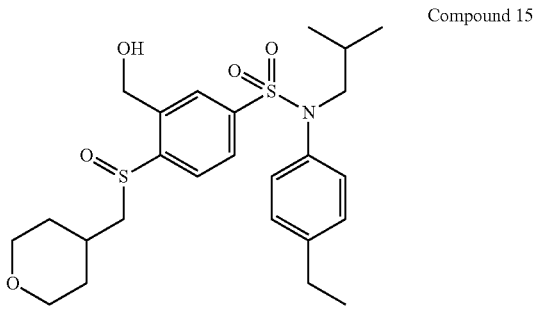 [SMILES: CCc1ccc(N(CC(C)C)S(=O)(=O)c2ccc(S(=O)CC3CCOCC3)c(CO)c2)cc1]

Compound 15

3-Chloroperoxybenzoic acid (302.47 mg; 1.35 mmol) is added to a solution of N-(4-ethylphenyl)-3-hydroxymethyl-N-isobutyl-4-(tetrahydropyran-4-ylmethylsulfanyl)benzenesulfonamide (614.00 mg; 1.29 mmol) in dichloromethane (20.00 ml). The medium is stirred at room temperature for 4 hours. At a temperature of 0° C., the reaction medium is added to water and extracted with ethyl acetate. The organic phases are washed with brine, dried over magnesium sulfate, filtered and evaporated.

The crude product is chromatographed on silica gel, eluting with heptane/ethyl acetate, from 50 to 100% of ethyl acetate). The N-(4-ethylphenyl)-3-hydroxymethyl-N-isobutyl-4-(tetrahydropyran-4-ylmethanesulfinyl)benzenesulfonamide (455 mg; 71%) is obtained in the form of a white solid.

$^1$H NMR (DMSO-$d_6$) δ 0.84 (d, J=6.7 Hz, 6H), 1.16 (t, J=7.6 Hz, 3H), 1.19-1.50 (m, 3H), 1.47-1.63 (m, 1H), 1.86 (ddd, J=13.1, 3.9, 2.1 Hz, 1H), 2.12 (dq, J=15.5, 5.7, 4.0 Hz, 2H), 2.55-2.69 (m, 3H), 2.94 (dd, J=13.2, 9.4 Hz, 1H), 3.33 (d, J=3.1 Hz, 3H), 3.74-3.95 (m, 2H), 4.60 (dd, J=5.3, 3.3 Hz, 2H), 5.65 (dd, J=5.9, 4.8 Hz, 1H), 6.86-7.07 (m, 2H), 7.10-7.30 (m, 2H), 7.57-7.76 (m, 2H), 8.01 (d, J=8.1 Hz, 1H).

MS: [M+H]=494

Compound 15 (377 mg; 0.76 mmol) is chromatographed by chiral SFC to separate the two enantiomers below

[Supercritical conditions: 100 bar, 70° C.; Chiralpak IC 250×4.6 mm 5µ column, eluent: CO$_2$/methanol: 45% of methanol]

Example 126: N-(4-ethylphenyl)-3-hydroxymethyl-N-isobutyl-4-(tetrahydropyran-4-ylmethanesulfinyl)benzenesulfonamide (Compound 11)—Enantiomer A of Compound 15

(146 mg; 39%) in the form of a white solid $^1$H NMR (400 MHz, DMSO-d6) δ 8.01 (d, J=8.1 Hz, 1H), 7.76-7.57 (m, 2H), 7.30-7.10 (m, 2H), 7.07-6.86 (m, 2H), 5.65 (dd, J=5.9, 4.8 Hz, 1H), 4.60 (dd, J=5.3, 3.3 Hz, 2H), 3.95-3.74 (m, 1H), 3.33 (d, J=3.1 Hz, 2H), 2.94 (dd, J=13.2, 9.4 Hz, 1H), 2.69-2.55 (m, 2H), 2.12 (dq, J=15.5, 5.7, 4.0 Hz, 1H), 1.86 (ddd, J=13.1, 3.9, 2.1 Hz, 1H), 1.63-1.47 (m, 1H), 1.50-1.19 (m, 2H), 1.16 (t, J=7.6 Hz, 3H), 0.84 (d, J=6.7 Hz, 6H).

Retention time (chiral SFC) of 2.49 minutes

Example 127: N-(4-ethylphenyl)-3-hydroxymethyl-N-isobutyl-4-(tetrahydropyran-4-ylmethanesulfinyl)benzenesulfonamide (Compound 12)—Enantiomer B of Compound 15 (134 mg; 36%) in the Form of a White Solid $^1$H NMR (400 MHz, DMSO-d6) δ 8.01 (d, J=8.1 Hz, 1H), 7.76-7.57 (m, 2H), 7.30-7.10 (m, 2H), 7.07-6.86 (m, 2H), 5.65 (dd, J=5.9, 4.8 Hz, 1H), 4.60 (dd, J=5.3, 3.3 Hz, 2H), 3.95-3.74 (m, 1H), 3.33 (d, J=3.1 Hz, 2H), 2.94 (dd, J=13.2, 9.4 Hz, 1H), 2.69-2.55 (m, 2H), 2.12 (dq, J=15.5, 5.7, 4.0 Hz, 1H), 1.86 (ddd, J=13.1, 3.9, 2.1 Hz, 1H), 1.63-1.47 (m, 1H), 1.50-1.19 (m, 2H), 1.16 (t, J=7.6 Hz, 3H), 0.84 (d, J=6.7 Hz, 6H).

Retention time (chiral SFC) of 2.92 minutes

Part VIII: Synthesis of Sulfur-Based Sulfonamides Via Reaction Scheme 8

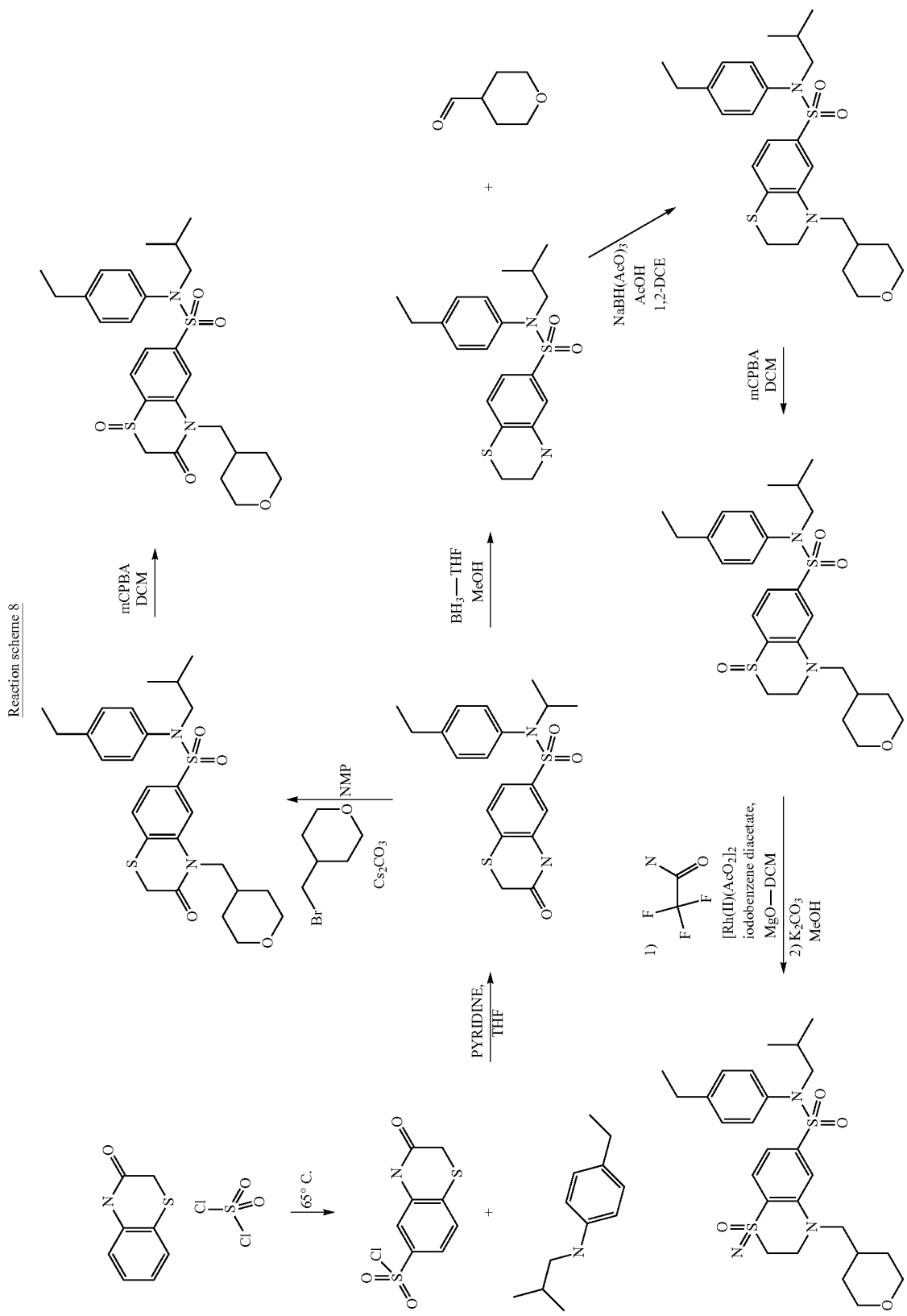

Example 128: Synthesis of 3-oxo-3,4-dihydro-2H-benzo[1,4]thiazine-6-sulfonic Acid (4-ethylphenyl)isobutylamide

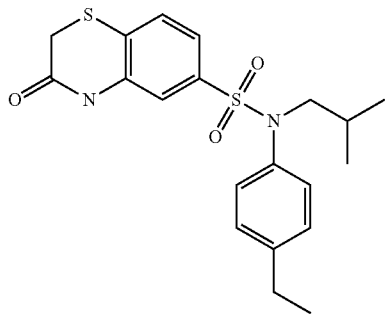

Compound 10

1. Synthesis of Intermediate 128.1

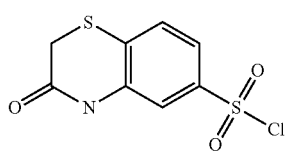 [SMILES: O=C1CSc2ccc(S(=O)(=O)Cl)cc2N1]

3-oxo-3,4-dihydro-2H-benzo[1,4]thiazine-6-sulfonyl chloride

4H-Benzo[1,4]thiazin-3-one (4.0 g; 24.21 mmol) is added slowly to chlorosulfonic acid (6.5 ml; 96.84 mmol) cooled to 10° C. The temperature is maintained below 20° C. The reaction medium is stirred at room temperature for 1 hour and then heated to a temperature of 65° C., poured slowly onto ice and then extracted with ethyl acetate. The organic phases are combined, washed with brine, dried over sodium sulfate and concentrated. The residue is taken up in ether and suction-filtered.

The 3-oxo-3,4-dihydro-2H-benzo[1,4]thiazine-6-sulfonyl chloride (4.88 g; 76%) is obtained in the form of an ocher-colored powder.

MS: [M+H]=262

2. Synthesis of Compound 10 According to the Invention

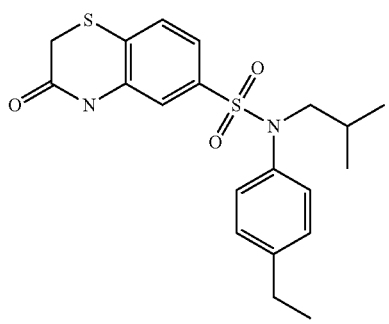 [SMILES: CCc1ccc(N(CC(C)C)S(=O)(=O)c2ccc3c(c2)NC(=O)CS3)cc1]

3-Oxo-3,4-dihydro-2H-benzo[1,4]thiazine-6-sulfonyl chloride (3.27 g; 12.41 mmol) is added to (4-ethylphenyl)isobutylamine (2 g; 11.28 mmol) and pyridine (40 ml; 495.56 mmol) dissolved in tetrahydrofuran (5.4 ml). The reaction medium is stirred at room temperature for 2 hours, hydrolyzed and extracted with ethyl acetate. The organic phases are combined, washed with 1N hydrochloric acid solution, with brine, dried over sodium sulfate and concentrated.

The crude product is chromatographed on silica gel (eluent: heptane/ethyl acetate, from 0 to 50% of ethyl acetate). The 3-oxo-3,4-dihydro-2H-benzo[1,4]thiazine-6-sulfonic acid (4-ethylphenyl)isobutylamide (2.53 g; 55%) is obtained in the form of a yellow solid.

$^1$H NMR (Chloroform-d) δ: 0.93 (d, J=6.7 Hz, 7H), 1.25 (td, J=7.6, 4.3 Hz, 4H), 1.53-1.67 (m, 2H), 2.67 (q, J=7.6 Hz, 2H), 3.32 (d, J=7.4 Hz, 2H), 3.50 (s, 2H), 6.94-7.04 (m, 2H), 7.07 (d, J=1.9 Hz, 1H), 7.12-7.20 (m, 2H), 7.22 (dd, J=8.2, 1.8 Hz, 1H), 7.41 (d, J=8.2 Hz, 1H), 8.28 (s, 1H).

MS: [M+H]=405

Example 129: Synthesis of 3,4-dihydro-2H-benzo[1,4]thiazine-6-sulfonic Acid (4-ethylphenyl)isobutylamide

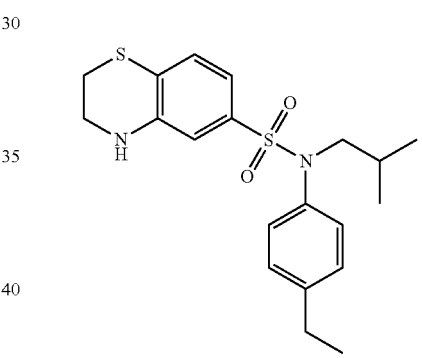

Compound 9

3-Oxo-3,4-dihydro-2H-benzo[1,4]thiazine-6-sulfonic acid (4-ethylphenyl)isobutylamide (500 mg; 1.28 mmol) is dissolved in the 1M borane-tetrahydrofuran complex with 5 mmol NaBH$_4$ (35 ml). The reaction medium is refluxed for 30 minutes and then cooled to a temperature of 0° C. and poured slowly into methanol (35 ml).

The solvents are concentrated and the residue is chromatographed on silica gel (eluent: heptane/ethyl acetate, from 0 to 40% of ethyl acetate).

The 3,4-dihydro-2H-benzo[1,4]thiazine-6-sulfonic acid (4-ethylphenyl)isobutylamide (437 mg; 86%) is obtained in the form of a white crystalline solid after recrystallization from an ethyl acetate/heptane mixture.

$^1$H NMR (DMSO-d6) δ: 0.82 (d, J=6.7 Hz, 6H), 1.17 (t, J=7.6 Hz, 3H), 1.31-1.47 (m, 1H), 2.59 (q, J=7.6 Hz, 2H), 2.97-3.05 (m, 2H), 3.25 (d, J=7.3 Hz, 2H), 3.48 (dt, J=7.0, 3.0 Hz, 2H), 6.48-6.56 (m, 2H), 6.75 (d, J=2.0 Hz, 1H), 6.95-7.04 (m, 3H), 7.14-7.21 (m, 2H).

MS: [M+H]=391

Example 130: Synthesis of 4-(tetrahydropyran-4-ylmethyl)-3,4-dihydro-2H-benzo[1,4]thiazine-6-sulfonic Acid (4-ethylphenyl)isobutylamide Compound 6

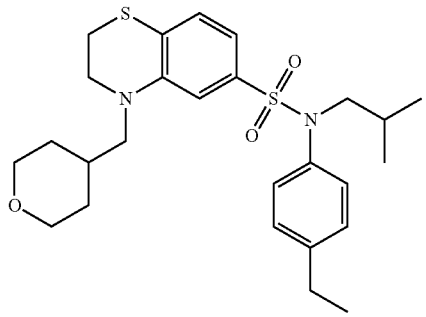

Sodium triacetoxyborohydride (33 mg; 0.15 mmol) is added at a temperature of 0° C. to 3,4-dihydro-2H-benzo[1,4]thiazine-6-sulfonic acid (4-ethylphenyl)isobutylamide (20 mg; 0.05 mmol), 4-formyltetrahydropyran (29 mg; 0.26 mmol) and acetic acid (0.15 μl) dissolved in 1,2-dichloroethane. The reaction medium is stirred at room temperature for a period of 24 hours, water is added and the resulting mixture is extracted with ethyl acetate. The organic phases are combined, washed with brine, dried over sodium sulfate and concentrated.

The crude product is chromatographed on silica gel (eluent: heptane/ethyl acetate, from 0 to 50% of ethyl acetate). The 4-(tetrahydropyran-4-ylmethyl)-3,4-dihydro-2H-benzo[1,4]thiazine-6-sulfonic acid (4-ethylphenyl) isobutylamide (15 mg; 59%) is obtained in the form of a beige-colored solid.

1H NMR (DMSO-d6) δ: 0.84 (d, J=6.6 Hz, 7H), 1.06-1.27 (m, 6H), 1.40-1.48 (m, 3H), 1.68-1.79 (m, 1H), 2.55-2.66 (m, 2H), 3.01 (d, J=6.9 Hz, 2H), 3.08 (t, J=4.8 Hz, 2H), 3.19 (t, J=11.5 Hz, 2H), 3.26 (d, J=7.3 Hz, 2H), 3.62 (t, J=4.8 Hz, 2H), 3.82 (dd, J=11.0, 4.2 Hz, 2H), 6.54 (s, 1H), 6.71 (d, J=7.9 Hz, 1H), 7.02 (d, J=8.0 Hz, 2H), 7.13 (d, J=8.1 Hz, 1H), 7.21 (d, J=7.9 Hz, 2H).

MS: [M+H]=489

Example 131: Synthesis of 1-oxo-4-(tetrahydropyran-4-ylmethyl)-1,2,3,4-tetrahydro-1λ⁴-benzo[1,4]thiazine-7-sulfonic Acid (4-ethylphenyl)isobutylamide Compound 3

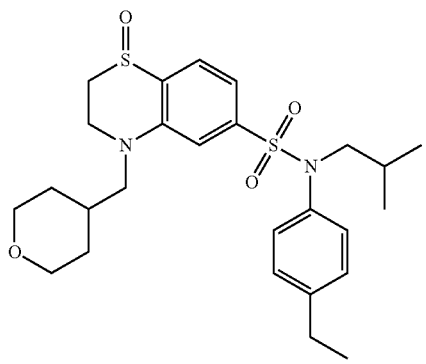

3-Chloroperbenzoic acid (124 mg; 0.55 mmol) is added, at a temperature of 0° C., to 4-(tetrahydropyran-4-ylmethyl)-3,4-dihydro-2H-benzo[1,4]thiazine-7-sulfonic acid (4-ethylphenyl)isobutylamide (300 mg; 0.61 mmol) dissolved in dichloromethane (6 ml). The reaction medium is stirred at room temperature for 30 minutes, hydrolyzed with aqueous 10% Na₂S₂O₃ solution and extracted with dichloromethane. The organic phases are combined, washed with 0.1N sodium hydroxide solution, with brine, dried over sodium sulfate and concentrated.

The crude product is chromatographed on silica gel (eluent: dichloromethane/methanol, from 0 to 10% of methanol). The 1-oxo-4-(tetrahydropyran-4-ylmethyl)-1,2,3,4-tetrahydro-1λ⁴-benzo[1,4]thiazine-7-sulfonic acid (4-ethylphenyl)isobutylamide (274 mg; 88%) is obtained in the form of a white solid by crystallization from a water/acetone mixture.

1H NMR (DMSO-d6) δ: 0.85 (dd, J=6.6, 1.3 Hz, 6H), 1.12-1.28 (m, 5H), 1.44 (dt, J=12.8, 9.6 Hz, 3H), 1.71-1.88 (m, 1H), 2.61 (q, J=7.6 Hz, 2H), 2.85 (td, J=13.6, 3.4 Hz, 1H), 3.09-3.36 (m, 12H), 3.64 (dt, J=14.0, 3.8 Hz, 1H), 3.78-3.90 (m, 3H), 6.81 (d, J=7.3 Hz, 2H), 7.01-7.08 (m, 2H), 7.19-7.26 (m, 2H), 7.70 (d, J=8.2 Hz, 1H).

MS: [M+H]=505

Example 132: Synthesis of 1-imino-1-oxo-4-(tetrahydropyran-4-ylmethyl)-1,2,3,4-tetrahydro-1λ⁶-benzo[1,4]thiazine-6-sulfonic Acid (4-ethylphenyl)isobutylamide Compound 1

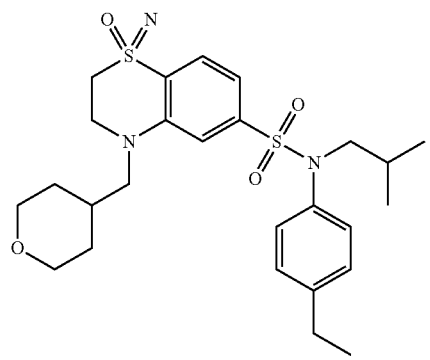

2,2,2-Trifluoroacetamide (109 mg; 0.97 mmol), rhodium (II) acetate (26 mg; 0.06 mmol), magnesium oxide (78 mg; 1.93 mmol) and iodobenzene diacetate (249 mg; 0.77 mmol) are added to a solution, degassed beforehand with argon, of 1-oxo-4-(tetrahydropyran-4-ylmethyl)-1,2,3,4-tetrahydro-1λ⁴-benzo[1,4]thiazine-6-sulfonic acid (4-ethylphenyl) isobutylamide (195.00 mg; 0.39 mmol) in dichloromethane (10 ml). The reaction medium is stirred at room temperature for 16 hours, filtered through Celite and concentrated. The residue obtained is diluted in methanol (10 ml), and potassium carbonate (267 mg; 1.93 mmol) is added.

The reaction medium is stirred for 30 minutes and then hydrolyzed and extracted with ethyl acetate. The organic phases are combined, washed with brine and dried over sodium sulfate. The solvents are evaporated off. The crude product is chromatographed on silica gel (eluent: dichloromethane/methanol, from 0 to 5% of methanol).

The 1-imino-1-oxo-4-(tetrahydropyran-4-ylmethyl)-1,2,3,4-tetrahydro-1$\lambda^6$-benzo[1,4]thiazine-6-sulfonic acid (4-ethylphenyl)isobutylamide (44.50 mg; 21.97%) is obtained in the form of a white solid.

1H NMR (DMSO-d6) δ: 0.86 (t, J=4.9 Hz, 8H), 1.09-1.33 (m, 9H), 1.36-1.49 (m, 3H), 1.75 (qd, J=8.6, 7.9, 4.2 Hz, 1H), 2.61 (q, J=7.6 Hz, 2H), 3.17 (dd, J=15.8, 9.0 Hz, 4H), 3.34-3.46 (m, 3H), 3.85 (ddd, J=23.1, 9.5, 4.1 Hz, 4H), 4.74 (s, 1H), 6.68 (s, 1H), 6.88 (d, J=8.1 Hz, 1H), 7.05 (d, J=8.2 Hz, 2H), 7.23 (d, J=7.9 Hz, 2H), 7.84 (d, J=8.1 Hz, 1H).

MS: [M+H]=519

Example 133: Synthesis of 3-oxo-4-(tetrahydropyran-4-ylmethyl)-3,4-dihydro-2H-benzo[1,4]thiazine-7-sulfonic Acid (4-ethylphenyl)isobutylamide Compound 70

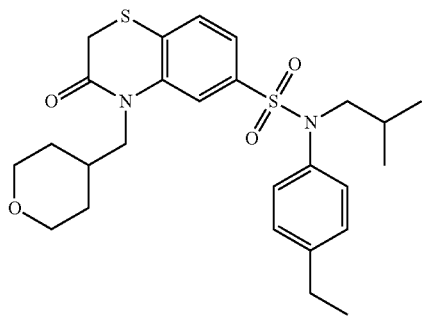

4-(Bromomethyl)tetrahydropyran (18 mg; 0.10 mmol) is added to 3-oxo-3,4-dihydro-2H-benzo[1,4]thiazine-7-sulfonic acid (4-ethylphenyl)isobutylamide (20 mg; 0.05 mmol) and cesium carbonate (24 mg; 0.07 mmol) dissolved in 1-methyl-2-pyrrolidone (0.4 ml).

The reaction medium is heated at 80° C. for 24 hours, hydrolyzed and then extracted with ethyl acetate. The organic phases are combined, washed with brine and dried over sodium sulfate.

The solvents are evaporated off and the crude product is chromatographed on silica gel (eluent: heptane/ethyl acetate, from 0 to 50% of ethyl acetate).

The 3-oxo-4-(tetrahydropyran-4-ylmethyl)-3,4-dihydro-2H-benzo[1,4]thiazine-7-sulfonic acid (4-ethylphenyl)isobutylamide (10.4 mg; 40%) is obtained in the form of a beige-colored solid.

1H NMR (DMSO-d6) δ: 0.85 (d, J=6.8 Hz, 7H), 1.17 (t, J=7.6 Hz, 3H), 1.25 (d, J=6.5 Hz, 2H), 1.37-1.67 (m, 10H), 1.68-1.77 (m, 5H), 2.44 (dt, J=11.1, 4.0 Hz, 10H), 2.60 (q, J=7.6 Hz, 2H), 3.17 (s, 1H), 3.33-3.38 (m, 5H), 3.80 (dt, J=11.3, 3.7 Hz, 7H), 3.92 (s, 1H), 7.02 (d, J=7.8 Hz, 2H), 7.18 (dd, J=18.5, 8.4 Hz, 3H), 7.42 (d, J=8.4 Hz, 1H), 7.60 (d, J=2.1 Hz, 1H), 12.17 (s, 2H)

MS: [M+H]=503

Example 134: Synthesis of 1,3-dioxo-4-(tetrahydropyran-4-ylmethyl)-1,2,3,4-tetrahydro-1$\lambda^4$-benzo[1,4]thiazine-6-sulfonic Acid (4-ethylphenyl)isobutylamide Compound 4

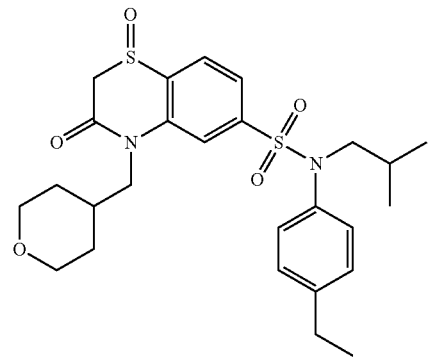

3-Chloroperbenzoic acid (161 mg; 0.72 mmol) is added, at 0° C., to 3-oxo-4-(tetrahydropyran-4-ylmethyl)-3,4-dihydro-2H-benzo[1,4]thiazine-6-sulfonic acid (4-ethylphenyl)isobutylamide (400 mg; 0.80 mmol) dissolved in dichloromethane (8 ml).

The reaction medium is stirred at room temperature for 1 hour, hydrolyzed with aqueous 10% $Na_2S_2O_3$ solution and extracted with dichloromethane. The organic phases are combined, washed with 0.1N sodium hydroxide solution and then with brine, and dried over sodium sulfate. The solvents are concentrated and the crude product is chromatographed on silica gel (eluent: heptane/ethyl acetate, from 0 to 80% of ethyl acetate). The 1,3-dioxo-4-(tetrahydropyran-4-ylmethyl)-1,2,3,4-tetrahydro-1$\lambda^4$-benzo[1,4]thiazine-6-sulfonic acid (4-ethylphenyl)isobutylamide (358 mg; 87%) is obtained in the form of a white solid.

1H NMR (DMSO-d6) δ: 0.87 (d, J=6.6 Hz, 6H), 1.01-1.23 (m, 5H), 1.37-1.53 (m, 3H), 1.62-1.83 (m, 1H), 2.62 (q, J=7.6 Hz, 2H), 3.05-3.22 (m, 2H), 3.33-3.49 (m, 2H), 3.72-3.89 (m, 3H), 4.04 (dd, J=14.8, 8.5 Hz, 1H), 4.29-4.39 (m, 2H), 7.01-7.08 (m, 2H), 7.21-7.28 (m, 2H), 7.43 (dd, J=7.8, 1.5 Hz, 1H), 7.50 (d, J=1.6 Hz, 1H), 8.08 (d, J=7.8 Hz, 1H).

MS: [M+H]=519

Part IX: Synthesis of Sulfur-Based Sulfonamides
Via Reaction Scheme 9
Reaction scheme 9
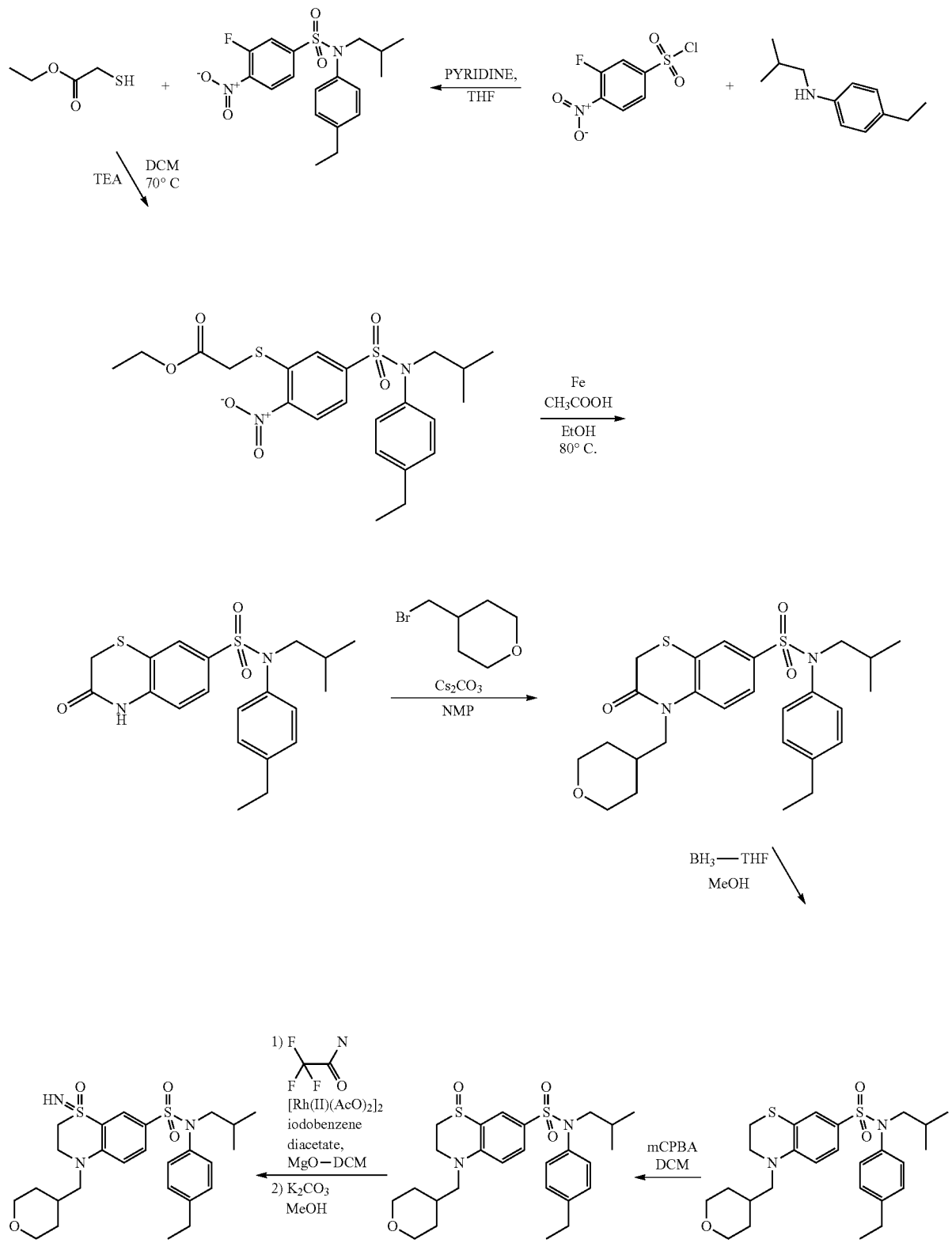

Example 135: Synthesis of 1-oxo-4-(tetrahydropyran-4-ylmethyl)-1,2,3,4-tetrahydro-1λ⁴-benzo[1,4]thiazine-7-sulfonic Acid (4-ethylphenyl)isobutylamide Compound 71

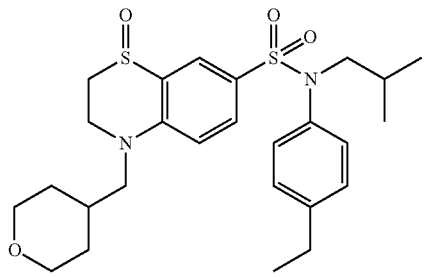

1. Synthesis of Intermediate 135.1

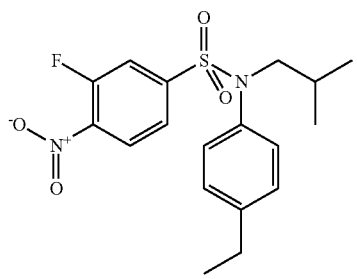

3-bromo-N-(4-ethylphenyl)-N-isobutyl-4-methoxybenzenesulfonamide

3-Fluoro-4-nitrobenzenesulfonyl chloride (5.57 g; 22.56 mmol) is added to a solution of (4-ethylphenyl)isobutylamine (4.0 g; 22.56 mmol) and pyridine (11 ml; 135.37 mmol) in tetrahydrofuran (80 ml). The reaction medium is stirred for 16 hours at room temperature, hydrolyzed and extracted with ethyl acetate. The organic phases are combined, washed with saturated NH₄Cl solution and then with brine, dried (Na₂SO₄) and concentrated.

The crude product is chromatographed on silica gel (eluent: heptane/ethyl acetate, from 0 to 10% of ethyl acetate). The 3-bromo-N-(4-ethylphenyl)-N-isobutyl-4-methoxybenzenesulfonamide (7.02 g; 82%) is obtained in the form of a flaky white solid with a compliant ¹H NMR.

MS: [M+H]=381

2. Synthesis of Intermediate 135.2

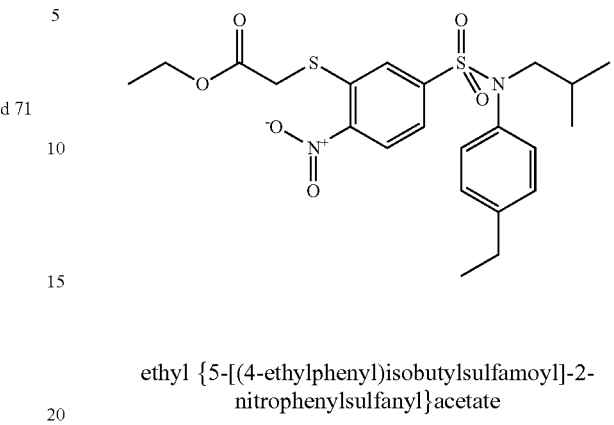

ethyl {5-[(4-ethylphenyl)isobutylsulfamoyl]-2-nitrophenylsulfanyl}acetate

Ethyl thioglycolate (0.86 ml; 7.89 mmol) is added slowly to a solution of N-(4-ethylphenyl)-3-fluoro-N-isobutyl-4-nitrobenzenesulfonamide (3.0 g; 7.89 mmol) and triethylamine (1.31 ml; 9.46 mmol) in tetrahydrofuran (75 ml). The reaction medium is stirred for 16 hours at room temperature.

The crude product is chromatographed on silica gel (eluent: heptane/ethyl acetate, from 0 to 30% of ethyl acetate).

The ethyl {5-[(4-ethylphenyl)isobutylsulfamoyl]-2-nitrophenylsulfanyl}acetate (3.49 g; 92%) is obtained in the form of a bright yellow solid with a compliant ¹H NMR.

MS: [M+H]=481.

3. Synthesis of Intermediate 135.3

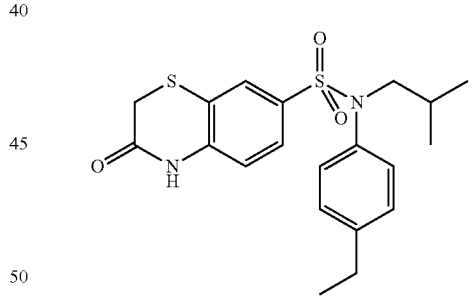

3-Oxo-3,4-dihydro-2H-benzo[1,4]thiazine-7-sulfonic Acid (4-ethylphenyl)isobutylamide Iron powder (1.16 g; 20.81 mmol) is added to a solution of ethyl {5-[(4-ethylphenyl)isobutylsulfamoyl]-2-nitrophenylsulfanyl}acetate (2.00 g; 4.16 mmol) in ethanol (20 ml) and acetic acid (5 ml).

The reaction medium is stirred for 2 hours at a temperature of 80° C., returned to room temperature, diluted with ethyl acetate and then filtered through Celite. The filtrate is washed with saturated NaHCO₃ solution and then with brine, dried (Na₂SO₄) and concentrated.

The crude product is chromatographed on silica gel (eluent: heptane/ethyl acetate, from 0 to 40% of ethyl acetate). The 3-oxo-3,4-dihydro-2H-benzo[1,4]thiazine-7-sulfonic acid (4-ethylphenyl)isobutylamide (0.98 g; 58%) is obtained in the form of a white powder with a compliant $^1$H NMR.

MS: [M+H]=405

4. Synthesis of Intermediate 135.4

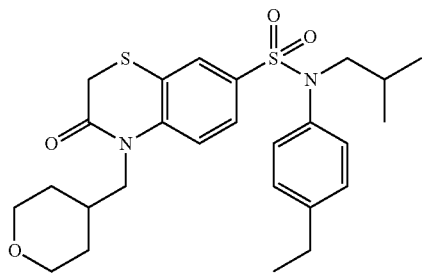 [SMILES: CCc1ccc(N(CC(C)C)S(=O)(=O)c2ccc3c(c2)SCC(=O)N3CC2CCOCC2)cc1]

3-Oxo-4-(tetrahydropyran-4-ylmethyl)-3,4-dihydro-2H-benzo[1,4]thiazine-7-sulfonic Acid (4-ethylphenyl)isobutylamide 4-(Bromomethyl)tetrahydropyran (797 mg; 4.45 mmol) is added to a mixture of 3-oxo-3,4-dihydro-2H-benzo[1,4]thiazine-7-sulfonic acid (4-ethylphenyl)isobutylamide (900 mg; 2.22 mmol) and cesium carbonate (1.09 g; 3.34 mmol) in 1-methyl-2-pyrrolidone (20 ml).

The reaction medium is stirred for 4 hours at a temperature of 110° C., hydrolyzed and extracted with ethyl acetate. The organic phases are combined, washed with brine, dried (Na$_2$SO$_4$) and concentrated.

The crude product is chromatographed on silica gel (eluent: heptane/ethyl acetate, from 0 to 60% of ethyl acetate). The 3-oxo-4-(tetrahydropyran-4-ylmethyl)-3,4-dihydro-2H-benzo[1,4]thiazine-7-sulfonic acid (4-ethylphenyl)isobutylamide (1.11 g; 99%) is obtained in the form of a white solid with a compliant $^1$H NMR.

MS: [M+H]=503

5. Synthesis of Intermediate 135.5

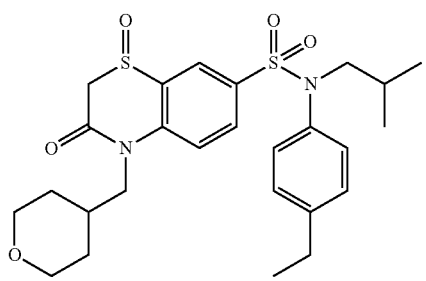 [SMILES: CCc1ccc(N(CC(C)C)S(=O)(=O)c2ccc3c(c2)S(=O)CC(=O)N3CC2CCOCC2)cc1]

1,3-Dioxo-4-(tetrahydropyran-4-ylmethyl)-1,2,3,4-tetrahydro-1λ$^4$-benzo[1,4]thiazine-7-sulfonic Acid (4-ethylphenyl)isobutylamide 3-Chloroperoxybenzoic acid (223 mg; 0.99 mmol) is added, at a temperature of 0° C., to 3-oxo-4-(tetrahydropyran-4-ylmethyl)-3,4-dihydro-2H-benzo[1,4]thiazine-7-sulfonic acid (4-ethylphenyl)isobutylamide (500 mg; 0.99 mmol) dissolved in dichloromethane (10 ml). The reaction medium is stirred for 30 minutes at room temperature, hydrolyzed with aqueous 10% Na$_2$S$_2$O$_3$ solution and extracted with dichloromethane. The organic phases are combined, washed with 0.1N sodium hydroxide solution and with brine, and then dried (Na$_2$SO$_4$) and concentrated.

The crude product is chromatographed on silica gel (eluent: heptane/ethyl acetate, from 0 to 80% of ethyl acetate). The 1,3-dioxo-4-(tetrahydropyran-4-ylmethyl)-1,2,3,4-tetrahydro-1λ$^4$-benzo[1,4]thiazine-7-sulfonic acid (4-ethylphenyl)isobutylamide (310 mg; 60%) is obtained in the form of a white crystalline powder after crystallization from an ethanol/heptane mixture.

MS: [M+H]=519

6. Synthesis of Intermediate 135.6

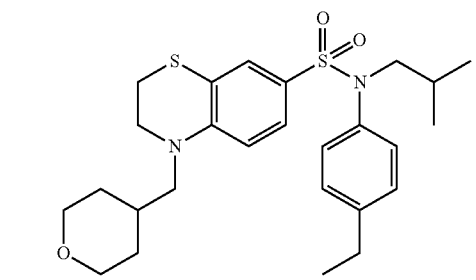 [SMILES: CCc1ccc(N(CC(C)C)S(=O)(=O)c2ccc3c(c2)SCCN3CC2CCOCC2)cc1]

4-(Tetrahydropyran-4-ylmethyl)-3,4-dihydro-2H-benzo[1,4]thiazine-7-sulfonic Acid (4-ethylphenyl)isobutylamide 3-Oxo-4-(tetrahydropyran-4-ylmethyl)-3,4-dihydro-2H-benzo[1,4]thiazine-7-sulfonic acid (4-ethylphenyl)isobutylamide (500 mg; 0.99 mmol) is added to a 1M solution of stabilized borane/tetrahydrofuran complex in tetrahydrofuran (35 ml). The reaction medium is stirred at reflux, cooled and poured at 0° C. into methanol (35 ml). The solvents are concentrated.

The crude product is chromatographed on silica gel (eluent: heptane/ethyl acetate, from 0 to 50% of ethyl acetate). The 4-(tetrahydropyran-4-ylmethyl)-3,4-dihydro-2H-benzo[1,4]thiazine-7-sulfonic acid (4-ethylphenyl)isobutylamide (466 mg; 95%) is obtained in the form of a white crystalline solid after recrystallization from ether, with a compliant $^1$H NMR.

MS: [M+H]=489

7. Synthesis of Compound 71 According to the Invention

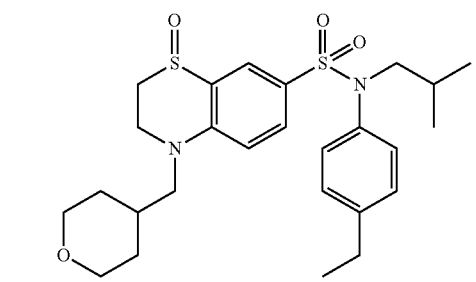 [SMILES: CCc1ccc(N(CC(C)C)S(=O)(=O)c2ccc3c(c2)S(=O)CCN3CC2CCOCC2)cc1]

3-Chloroperoxybenzoic acid (175.4 mg; 0.78 mmol) is added, at a temperature of 0° C., to 4-(tetrahydropyran-4-ylmethyl)-3,4-dihydro-2H-benzo[1,4]thiazine-7-sulfonic acid (4-ethylphenyl)isobutylamide (425.0 mg; 0.87 mmol) dissolved in dichloromethane (8.5 ml). The reaction medium is stirred for 15 minutes at room temperature, hydrolyzed with aqueous 10% $Na_2S_2O_3$ solution and then extracted with dichloromethane. The organic phases are combined, washed with 0.1N sodium hydroxide solution and then with brine, dried ($Na_2SO_4$) and concentrated.

The crude product is chromatographed on silica gel (eluent: heptane/ethyl acetate, from 0 to 100% of ethyl acetate and then dichloromethane/methanol, from 0 to 10% of methanol). The 1-oxo-4-(tetrahydropyran-4-ylmethyl)-1,2,3,4-tetrahydro-1λ$^4$-benzo[1,4]thiazine-7-sulfonic acid (4-ethylphenyl)isobutylamide (379 mg; 86%) is obtained in the form of a white crystalline powder after crystallization from an ether/heptane mixture.

1H NMR (DMSO-d6) δ: 0.84 (d, J=6.7 Hz, 6H), 1.19 (t, J=7.6 Hz, 3H), 1.35 (dddd, J=34.9, 26.9, 14.1, 8.5 Hz, 3H), 1.53-1.61 (m, 2H), 2.02 (ddd, J=11.6, 7.6, 3.7 Hz, 1H), 2.61 (q, J=7.6 Hz, 2H), 2.87 (td, J=13.7, 3.4 Hz, 1H), 3.14 (ddd, J=13.9, 4.1, 2.3 Hz, 1H), 3.20-3.33 (m, 8H), 3.42-3.50 (m, 2H), 3.69 (dt, J=14.1, 3.7 Hz, 1H), 3.82-3.98 (m, 3H), 6.97-7.04 (m, 2H), 7.09 (d, J=9.1 Hz, 1H), 7.16-7.23 (m, 2H), 7.35 (dd, J=9.1, 2.3 Hz, 1H), 7.54 (d, J=2.3 Hz, 1H)

MS: [M+H]=505

Example 136: Synthesis of 1-imino-1-oxo-4-(tetrahydropyran-4-ylmethyl)-1,2,3,4-tetrahydro-1λ$^6$-benzo[1,4]thiazine-7-sulfonic Acid (4-ethylphenyl)isobutylamide

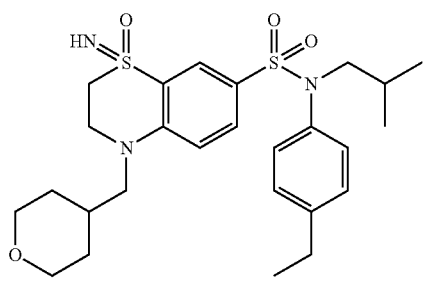 [SMILES: CCc1ccc(N(CC(C)C)S(=O)(=O)c2ccc3c(c2)S(=N)(=O)CCN3CC2CCOCC2)cc1]

2,2,2-Trifluoroacetamide (185 mg; 1.63 mmol), rhodium (II) acetate dimer (44 mg; 0.10 mmol), magnesium oxide (132 mg; 3.27 mmol) and iodobenzene diacetate (421 mg; 1.31 mmol) are added to a solution, degassed beforehand with argon, of 1-oxo-4-(tetrahydropyran-4-ylmethyl)-1,2,3,4-tetrahydro-1λ$^4$-benzo[1,4]thiazine-7-sulfonic acid (4-ethylphenyl)isobutylamide (330 mg; 0.65 mmol) in dichloromethane (16.5 ml).

The reaction medium is stirred for 16 hours at room temperature, filtered through Celite and concentrated. The residue is diluted in methanol (16.50 ml) and potassium carbonate (452 mg; 3.27 mmol) is added. The reaction medium is stirred for 30 minutes, hydrolyzed and extracted with ethyl acetate. The organic phases are combined, washed with brine, dried ($Na_2SO_4$) and concentrated.

The crude product is purified by preparative HPLC (C18 column, eluent: acetonitrile in water/0.1% of formic acid).

The 1-imino-1-oxo-4-(tetrahydropyran-4-ylmethyl)-1,2,3,4-tetrahydro-1λ$^6$-benzo[1,4]thiazine-7-sulfonic acid (4-ethylphenyl)isobutylamide (44.5 mg; 13%) is obtained in the form of a cream-colored crystalline powder after recrystallization from a heptane/dichloromethane mixture.

1H NMR (DMSO-d6) δ: 0.73-0.94 (m, 7H), 1.19 (t, J=7.6 Hz, 3H), 1.22-1.36 (m, 4H), 1.42 (dt, J=13.6, 6.8 Hz, 1H), 1.58 (d, J=13.1 Hz, 2H), 1.85-2.10 (m, 1H), 2.61 (q, J=7.6 Hz, 2H), 3.20-3.32 (m, 4H), 3.34-3.51 (m, 3H), 3.86 (dd, J=11.4, 4.0 Hz, 2H), 3.94 (p, J=3.7 Hz, 2H), 4.68 (s, 1H), 7.00 (dd, J=15.4, 8.7 Hz, 3H), 7.20 (d, J=8.1 Hz, 2H), 7.27 (dd, J=9.2, 2.4 Hz, 1H), 7.86 (d, J=2.4 Hz, 1H).

MS: [M+H]=520

Part X: Synthesis of Sulfur-Based Sulfonamides Via Reaction Scheme 10

Reaction scheme 10

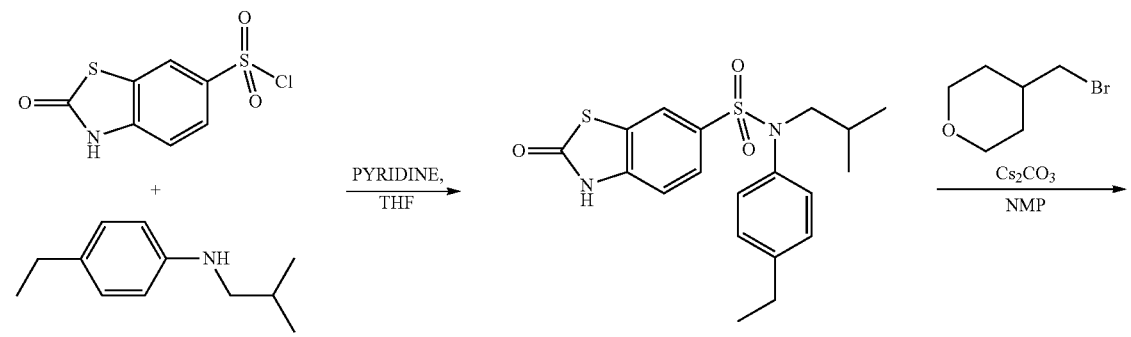

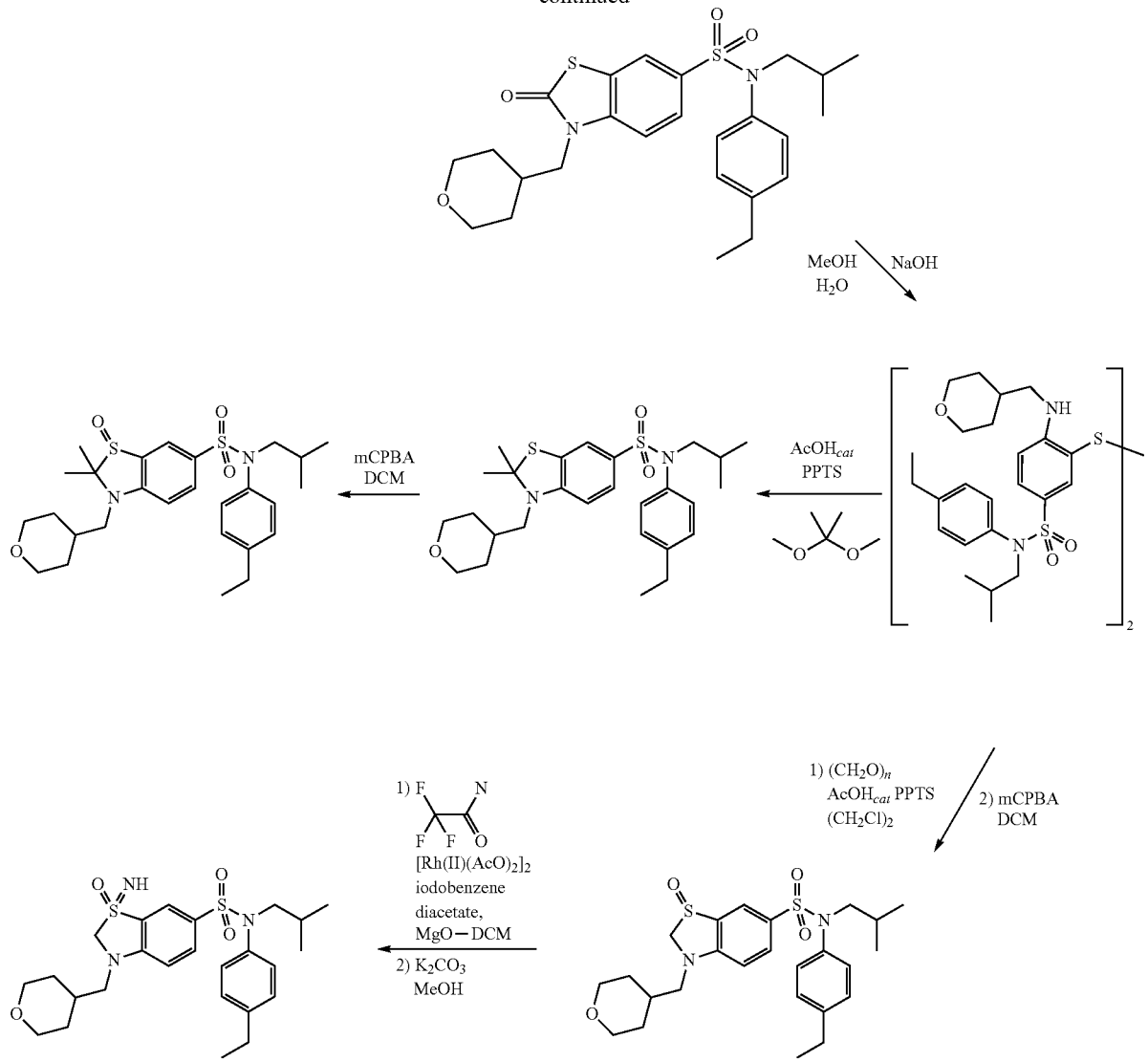
1. Synthesis of Intermediate 137.1
2-Oxo-2,3-dihydrobenzothiazole-6-sulfonic Acid (4-ethylphenyl)isobutylamide
2-Oxo-2,3-dihydrobenzothiazole-6-sulfonyl chloride (2.97 g; 11.28 mmol) is added to (4-ethylphenyl)isobutylam-
Example 137: Synthesis of 3-oxo-4-(tetrahydropyran-4-ylmethyl)-3,4-dihydro-2H-benzo[1,4]thiazine-7-sulfonic Acid (4-ethylphenyl)isobutylamide
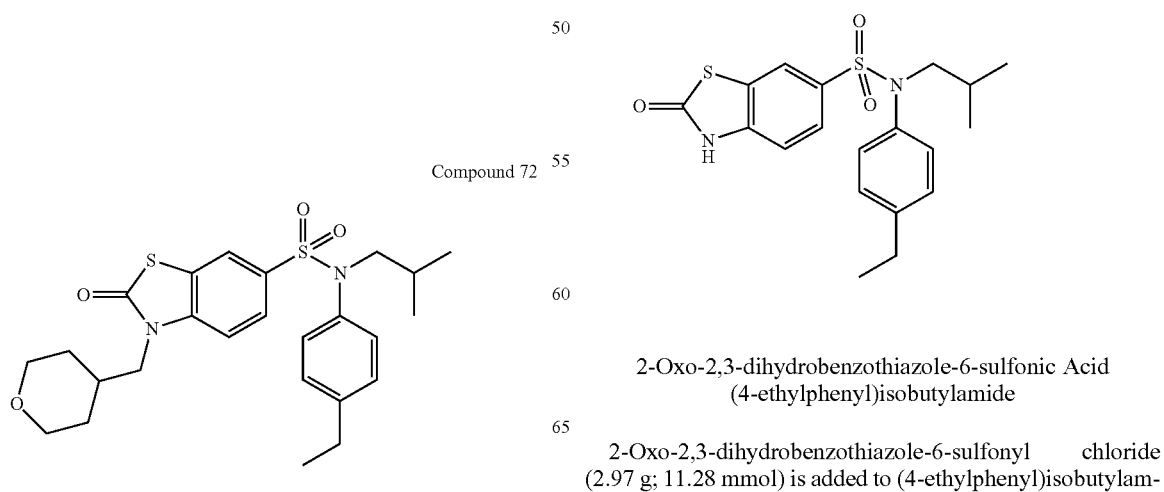
Compound 72 ine (2.00 g; 11.28 mmol) and pyridine (5.5 ml; 67.69 mmol) dissolved in tetrahydrofuran (40 ml). The reaction medium is stirred for 16 hours at room temperature, hydrolyzed and extracted with ethyl acetate. The organic phases are combined, washed with saturated NH$_4$Cl solution and then with brine, dried (MgSO$_4$) and concentrated.

The crude product is chromatographed on silica gel (eluent: heptane/ethyl acetate, from 0 to 10% of ethyl acetate). The 2-oxo-2,3-dihydrobenzothiazole-6-sulfonic acid (4-ethylphenyl)isobutylamide (2.67 g; 61%) is obtained in the form of a flaky white solid with a compliant $^1$H NMR.

MS: [M+H]=391

2. Synthesis of Compound 72 According to the Invention

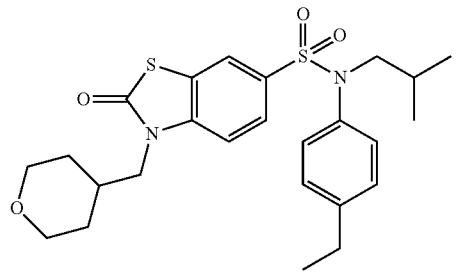 [SMILES: CCc1ccc(N(CC(C)C)S(=O)(=O)c2ccc3c(c2)sc(=O)n3CC2CCOCC2)cc1]

4-(Bromomethyl)tetrahydropyran (2.25 g; 12.55 mmol) is added to 2-oxo-2,3-dihydrobenzothiazole-6-sulfonic acid (4-ethylphenyl)isobutylamide (2.45 g; 6.27 mmol) and cesium carbonate (3.07 g; 9.41 mmol) dissolved in 1-methyl-2-pyrrolidone (50 ml). The reaction medium is stirred for 4 hours at 90° C., hydrolyzed and extracted with ethyl acetate. The organic phases are combined and then washed with brine, dried (Na$_2$SO$_4$) and concentrated.

The crude product is chromatographed on silica gel (eluent: heptane/ethyl acetate, from 0 to 60% of ethyl acetate). The 3-oxo-4-(tetrahydropyran-4-ylmethyl)-3,4-dihydro-2H-benzo[1,4]thiazine-7-sulfonic acid (4-ethylphenyl)isobutylamide (2.19 g; 72%) is obtained in the form of a white crystalline solid.

1H NMR (DMSO-d6) δ: 0.85 (d, J=6.6 Hz, 7H), 1.13-1.22 (m, 4H), 1.24-1.55 (m, 6H), 2.03 (ddt, J=10.8, 6.9, 3.4 Hz, 1H), 2.50-2.66 (m, 3H), 3.23 (td, J=11.6, 2.1 Hz, 2H), 3.34 (s, 1H), 3.83 (ddd, J=11.3, 4.4, 1.9 Hz, 2H), 3.90 (d, J=7.3 Hz, 2H), 6.96-7.04 (m, 2H), 7.14-7.22 (m, 2H), 7.42 (dd, J=8.6, 1.9 Hz, 1H), 7.57 (s, 1H), 8.05 (d, J=1.9 Hz, 1H)

MS: [M+H]=489

Example 138: Synthesis of 2,2-dimethyl-3-(tetrahydropyran-4-ylmethyl)-2,3-dihydrobenzothiazole-6-sulfonic Acid (4-ethylphenyl)isobutylamide Compound 73

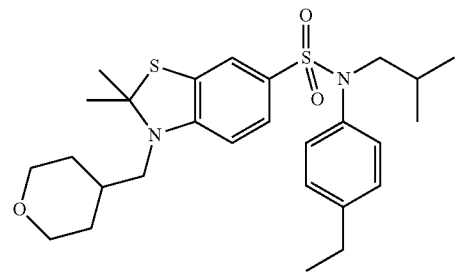

1. Synthesis of Intermediate 138.1

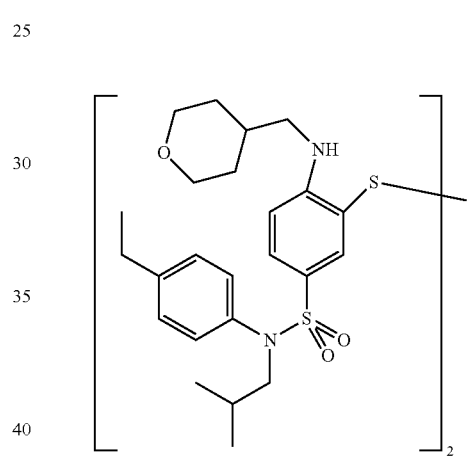

3,3'-disulfanediylbis(N-(4-ethylphenyl)-N-isobutyl-4-(((tetrahydro-2H-pyran-4-yl)methyl)amino)benzenesulfonamide A mixture of 2-oxo-3-(tetrahydropyran-4-ylmethyl)-2,3-dihydrobenzothiazole-6-sulfonic acid (4-ethylphenyl)isobutylamide (500 mg; 1.02 mmol) and sodium hydroxide (410 mg; 10.23 mmol), methanol (6 ml) and water (100 µl) is stirred for 16 hours at a temperature of 80° C. The reaction medium is diluted with 20 ml of ethyl acetate.

The organic phase is washed with 20 ml of saturated NH$_4$Cl solution, 20 ml of saturated NaHCO$_3$ solution and 20 ml of water, dried (MgSO$_4$), filtered and concentrated to dryness. The 3,3'-disulfanediylbis(N-(4-ethylphenyl)-N-isobutyl-4-(((tetrahydro-2H-pyran-4-yl)methyl)amino)benzenesulfonamide (500 mg; 53%) is obtained in the form of a yellow oil with a compliant $^1$H NMR.

MS: [M+H]=923

2. Synthesis of Compound 73 According to the Invention

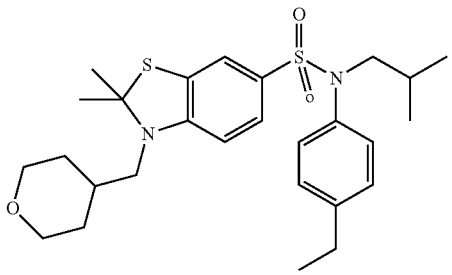

2,2-dimethyl-3-(tetrahydropyran-4-ylmethyl)-2,3-dihydrobenzothiazole-6-sulfonic Acid (4-ethylphenyl)isobutylamide 2,2-Dimethoxypropane (1.0 ml; 8.35 mmol) and pyridinium p-toluenesulfonate (245 mg; 0.97 mmol) are added to 3,3'-disulfanediylbis(N-(4-ethylphenyl)-N-isobutyl-4-(((tetrahydro-2H-pyran-4-yl)methyl)amino)benzenesulfonamide (300 mg; 0.32 mmol). The reaction medium is stirred for 16 hours at a temperature of 80° C. 3 drops of acetic acid are then added and the reaction medium is stirred for 2 hours at 80° C.

The crude product is purified by preparative HPLC (C18 column, eluent: acetonitrile in water/0.1% of formic acid). The 2,2-dimethyl-3-(tetrahydropyran-4-ylmethyl)-2,3-dihydrobenzothiazole-6-sulfonic acid (4-ethylphenyl)isobutylamide (70 mg; 40%) is obtained in the form of a clear yellow oil.

1H NMR (DMSO-d6) δ: 0.83 (d, J=6.7 Hz, 6H), 1.18 (t, J=7.6 Hz, 3H), 1.21-1.33 (m, 2H), 1.31-1.47 (m, 1H), 1.63 (s, 8H), 1.80 (s, 1H), 2.60 (q, J=7.6 Hz, 2H), 3.08 (d, J=7.2 Hz, 2H), 3.22-3.30 (m, 4H), 3.87 (dd, J=11.5, 3.8 Hz, 2H), 6.47 (d, J=8.4 Hz, 1H), 6.99-7.03 (m, 2H), 7.07 (dq, J=8.3, 2.1 Hz, 1H), 7.12 (d, J=2.0 Hz, 1H), 7.16-7.21 (m, 2H).

MS: [M+H]=503

Example 139: Synthesis of 2,2-dimethyl-1-oxo-3-(tetrahydropyran-4-ylmethyl)-2,3-dihydro-1H-1λ⁴-benzothiazole-6-sulfonic Acid (4-ethylphenyl)isobutylamide Compound 74

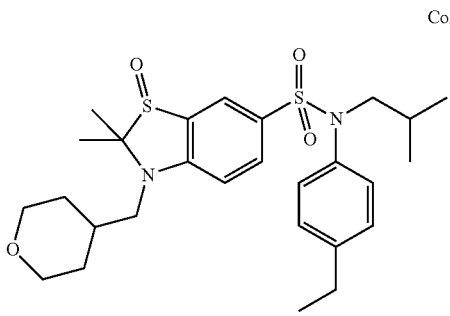

3-Chloroperoxybenzoic acid (30 mg; 0.15 mmol) is added to a solution of 2,2-dimethyl-3-(tetrahydropyran-4-ylmethyl)-2,3-dihydrobenzothiazole-6-sulfonic acid (4-ethylphenyl)isobutylamide (70 mg; 0.14 mmol) in dichloromethane (2 ml). The reaction medium is stirred for 45 minutes at room temperature, diluted with dichloromethane (10 ml) and water (5 ml), and extracted.

The organic phases are combined, dried (MgSO₄), filtered and concentrated.

The crude product is purified by preparative HPLC (C18 column, eluent: acetonitrile in water/0.1% of formic acid). The 2,2-dimethyl-1-oxo-3-(tetrahydropyran-4-ylmethyl)-2,3-dihydro-1H-1λ⁴-benzothiazole-6-sulfonic acid (4-ethylphenyl)isobutylamide (20 mg; 28%) is obtained in the form of a pale yellow solid.

1H NMR (DMSO-d6) δ: 0.85 (d, J=6.7 Hz, 6H), 1.19 (dd, J=15.7, 8.1 Hz, 6H), 1.25-1.49 (m, 3H), 1.56 (d, J=12.1 Hz, 2H), 1.64 (s, 3H), 1.90 (s, 1H), 2.60 (q, J=7.6 Hz, 2H), 3.18-3.28 (m, 2H), 3.87 (dt, J=10.6, 4.9 Hz, 2H), 7.00 (t, J=8.9 Hz, 3H), 7.19 (d, J=8.1 Hz, 2H), 7.46 (dd, J=8.5, 2.1 Hz, 1H), 8.00 (d, J=2.0 Hz, 1H).

MS: [M+H]=519

Example 140: Synthesis of the Compound 1-oxo-3-(tetrahydropyran-4-ylmethyl)-2,3-dihydro-1H-1)⁴-benzothiazole-6-sulfonic Acid (4-ethylphenyl)isobutylamide Compound 75

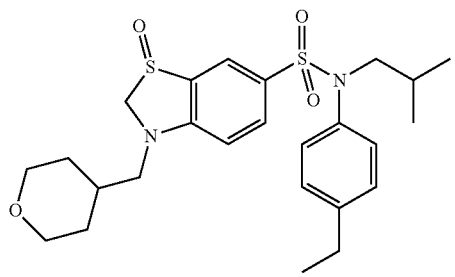

Paraformaldehyde (473 ml; 1.08 mmol), pyridinium p-toluenesulfonate (163 mg; 0.65 mmol) and 1,2-dichloroethane (3 ml) are added to 3,3'-disulfanediylbis(N-(4-ethylphenyl)-N-isobutyl-4-(((tetrahydro-2H-pyran-4-yl)methyl)amino)benzenesulfonamide (200 mg; 0.22 mmol).

The reaction medium is stirred for 16 hours at 80° C., filtered, diluted with dichloromethane, dried (MgSO₄) and filtered. 3-Chloroperoxybenzoic acid (107 mg; 0.48 mmol) is added to the filtrate. The reaction medium is stirred for 30 minutes at room temperature, diluted with dichloromethane (20 ml) and water (10 ml), and extracted. The organic phase is washed with a sodium sulfite solution (20 ml) and with water (20 ml), dried (MgSO₄), filtered and concentrated.

The crude product is purified by preparative HPLC (C18 column, eluent: acetonitrile in water/0.1% of formic acid). The 1-oxo-3-(tetrahydropyran-4-ylmethyl)-2,3-dihydro-1H-1λ⁴-benzothiazole-6-sulfonic acid (4-ethylphenyl)isobutylamide (70 mg; 66%) is obtained in the form of a white solid.

1H NMR (DMSO-d6) δ: 0.85 (dd, J=6.7, 3.5 Hz, 6H), 1.18 (t, J=7.6 Hz, 3H), 1.22-1.34 (m, 2H), 1.42 (dt, J=13.6, 6.9 Hz, 1H), 1.55 (t, J=13.0 Hz, 2H), 1.87-2.09 (m, 1H), 2.61 (q, J=7.5 Hz, 2H), 3.27 (ddt, J=12.1, 9.7, 6.3 Hz, 4H), 3.40 (dd, J=14.5, 7.4 Hz, 1H), 3.54 (dd, J=14.5, 7.2 Hz, 1H), 3.81-3.89 (m, 2H), 4.49 (d, J=13.6 Hz, 1H), 4.76 (d, J=13.6 Hz, 1H), 6.95-7.04 (m, 2H), 7.11 (d, J=9.0 Hz, 1H), 7.19 (d, J=8.3 Hz, 2H), 7.43 (dd, J=8.8, 2.0 Hz, 1H), 8.02 (d, J=2.0 Hz, 1H). MS: [M+H]=491

Example 141: Synthesis of 1-imino-1-oxo-3-(tetrahydropyran-4-ylmethyl)-2,3-dihydro-1H-1λ$^6$-benzothiazole-6-sulfonic Acid (4-ethylphenyl)isobutylamide Compound 76

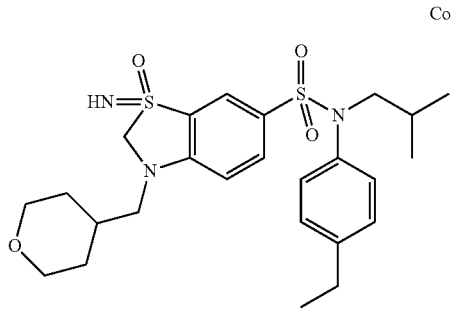

2,2,2-Trifluoroacetamide (40.3 mg; 0.36 mmol), rhodium (II) acetate dimer (9.5 mg; 0.02 mmol), magnesium oxide (30 mg; 0.71 mmol) and iodobenzene acetate (92 mg; 0.29 mmol) are added to a solution, degassed beforehand with argon, of 1-oxo-3-(tetrahydropyran-4-ylmethyl)-2,3-dihydro-1H-1λ$^4$-benzothiazole-6-sulfonic acid (4-ethylphenyl)isobutylamide (70 mg; 0.14 mmol) in dichloromethane (2 ml). The reaction medium is stirred for 3 days at room temperature, filtered through Celite and concentrated to dryness. The residue is taken up in methanol (1 ml), to which is added potassium carbonate (100 mg; 0.71 mol). The reaction medium is stirred for 1 hour, diluted with ethyl acetate (20 ml) and extracted.

The organic phase is washed with saturated NH$_4$Cl solution (20 ml), with saturated NaHCO$_3$ solution (20 ml) and with water (20 ml), dried (MgSO$_4$), filtered and concentrated.

The crude product is purified by preparative HPLC (C18 column, eluent: acetonitrile in water/0.1% of formic acid). The 1-imino-1-oxo-3-(tetrahydropyran-4-ylmethyl)-2,3-dihydro-1H-1λ$^6$-benzothiazole-6-sulfonic acid (4-ethylphenyl)isobutylamide (25 mg; 33.34%) is obtained in the form of a beige-colored solid.

1H NMR (DMSO-d6) δ: 0.84 (d, J=6.4 Hz, 6H), 1.18 (t, J=7.6 Hz, 3H), 1.29 (ddd, J=18.9, 11.8, 7.0 Hz, 2H), 1.42 (p, J=6.9 Hz, 1H), 1.48-1.65 (m, 2H), 1.93 (d, J=11.7 Hz, 1H), 2.61 (q, J=7.5 Hz, 2H), 3.25 (m, 4H), 3.46 (t, J=7.0 Hz, 2H), 3.86 (d, J=9.7 Hz, 2H), 4.49 (t, J=4.3 Hz, 2H), 7.01 (d, J=8.0 Hz, 2H), 7.08-7.24 (m, 4H), 7.37 (dd, J=9.4, 2.3 Hz, 1H), 7.50 (d, J=2.4 Hz, 1H), 8.23 (d, J=4.9 Hz, 1H).

MS: [M+H]=506

The invention claimed is:

1. A compound of formula (II), or a pharmaceutically acceptable addition salt thereof:

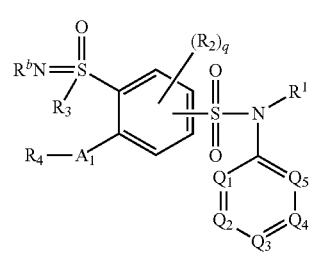

(II)

in which:
q denotes zero or a natural integer ranging from 1 to 3,
R$^1$ represents a linear or branched C$_3$-C$_5$ alkyl radical, a C$_3$-C$_5$ cycloalkyl radical, a linear or branched C$_2$-C$_5$ alkenyl radical,
R$_2$ represents a hydrogen atom or a halogen atom, a linear or branched C$_1$-C$_5$ alkyl radical, a linear or branched C$_2$-C$_4$ alkenyl radical, a C$_1$-C$_4$ alkoxy radical, a cyano group —CN; the alkyl, alkenyl and alkoxy radicals optionally being substituted with one or more halogen atoms,
R$^3$ represents a C$_1$-C$_3$ alkyl radical,
R$^4$ represents a hydrogen atom or a (CHR$^5$)$_n$—(Z)$_o$—(CHR'$^5$)$_p$—R$^6$ group,
n, o and p, which are identical or different, denote zero or a natural integer ranging from 1 to 3,
Z represents a divalent group chosen from —CH$_2$—, —NH— and —O—,
R$^5$ and R'$^5$, which are identical or different, represent a hydrogen atom, a methyl radical —CH$_3$, a hydroxyl radical —OH, a C$_1$ hydroxyalkyl radical, a carboxylic radical —COOH,
R$^6$ represents:
a hydrogen or halogen atom,
a heterocyclic radical optionally substituted with one or more halogen atoms, one or more linear or branched C$_1$-C$_3$ alkyl groups, one or more —OH groups, one or more carbonyl functions =O, one or more linear or branched C$_1$-C$_4$ hydroxyalkyl groups, a pyrrolidine ring, one or more amino groups, one or more —C(=O)R7 groups, one or more S(=O)$_2$R$^7$ groups; wherein the heterocyclic radical is a monocyclic heterocyclic ring having 2-6 carbon atoms and 1 to 4 heteroatoms selected from the group consisting of a sulfur atom, a nitrogen atom, and an oxygen atom; R$^7$ representing a linear or branched C$_1$-C$_3$ alkyl radical, a hydroxyl radical —OH, a linear or branched C$_1$-C$_4$ alkoxy radical, or an amino radical N(R$^{7a}$)(R$^{7b}$); with R$^{7a}$ and R$^{7b}$, which are identical or different, denoting a hydrogen atom, a linear or branched C$_1$-C$_3$ alkyl radical or a cyclopropyl radical,
a C$_3$-C$_6$ cycloalkyl radical optionally substituted with one or more —OH groups;
an aromatic or heteroaromatic radical optionally substituted with one or more halogen atoms, one or more linear or branched C$_1$-C$_3$ alkyl groups optionally substituted with one or more halogen atoms, one or more C$_1$-C$_3$ alkoxy groups, one or more amino groups —NR$^{11}$R$^{12}$, one or more —COR$^{11}$ groups, one or more —OR$^{11}$ groups, one or more C$_1$-C$_4$ hydroxyalkyl groups, one or more —COOR$^{11}$ groups, one or more amido —CONR$^{11}$R$^{12}$ groups, one or more —SOR$^{11}$ groups, one or more —SO$_2$R$^{11}$ groups, one or more —NHCOR$^{11}$ groups, one or more —NHCOOR$^{11}$ groups, one or more —SO$_2$NR$^{11}$R$^{12}$ groups or one or more —CN groups; wherein the heteroaromatic radical is a 5- or 6-membered monocyclic heteroaromatic ring having 1 to 3 heteroatoms selected from the group consisting of a sulfur atom, a nitrogen atom, and an oxygen atom; R$^{11}$ and R$^{12}$, which are identical or different, representing a hydrogen atom or a linear or branched C$_1$-C$_3$ alkyl radical optionally substituted with one or more halogen atoms;

A$_1$ represents a divalent group selected from the group consisting of —NR$^a$, —O—, —S—, —SO—, —SO$_2$—, —SO(=NH)—, —CH$_2$—, —C=C—, and —CH(R$^a$)—;

given that:

R$^a$ represents a hydrogen atom, a linear or branched C$_1$-C$_3$ alkyl radical or an acetyl radical —C(=O)CH$_3$, R$^b$ represents a hydrogen atom, a linear or branched C$_1$-C$_3$ alkyl radical or a cyclopropyl group, Q$_1$, Q$_2$, Q$_3$, Q$_4$ and Q$_5$ each represent a —CR'$_2$ group, R'$_2$ represents a hydrogen atom or a linear or branched C$_1$-C$_5$ alkyl radical, R$^a$ and R$^3$ can form, together with the carbon atoms to which they are attached, a C$_3$-C$_4$ heterocycloalkyl group comprising one sulfur atom and 0 to 1 nitrogen atom, which are optionally substituted with one or more carbonyl functions, one or more C$_1$-C$_3$ alkyl radicals, when A$_1$ represents —NR$^a$—, then R$^a$ and R$^4$ can form, together with the nitrogen atom to which they are attached, a C$_2$-C$_{10}$ heterocycloalkyl group optionally comprising 1 to 3 heteroatoms selected from the group consisting of a sulfur atom, a nitrogen atom and an oxygen atom; said heterocycloalkyl group being optionally substituted with at least one radical R$^{14}$, and R$^{14}$ represents a linear or branched C$_1$-C$_3$ alkyl radical, a linear or branched C$_1$-C$_3$ alkoxy radical, a halogen atom, a hydroxyl group —OH, a cyano group —CN, a —CONR$^{15}$R$^{16}$ group, a —SO$_2$R$^{16}$ group, a —COR$^{15}$ group or an amino group —CONR$^{15}$R$^{16}$ group, a —SO$_2$R$^{16}$ group, a —COR$^{15}$ group or an amino group —NR$^{15}$R$^{16}$; R$^{15}$ and R$^{16}$, which are identical or different, representing a hydrogen atom or a linear or branched C$_1$-C$_3$ alkyl radical.

2. The compound of formula (II) as defined by claim 1, or the pharmaceutically acceptable addition salt thereof, wherein R$^6$ represents a heterocyclic radical selected from the group consisting of:

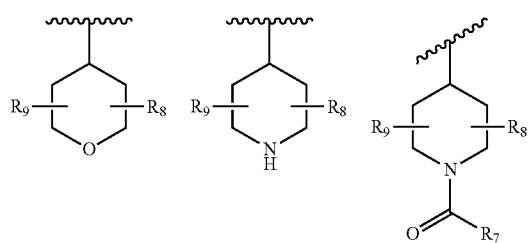

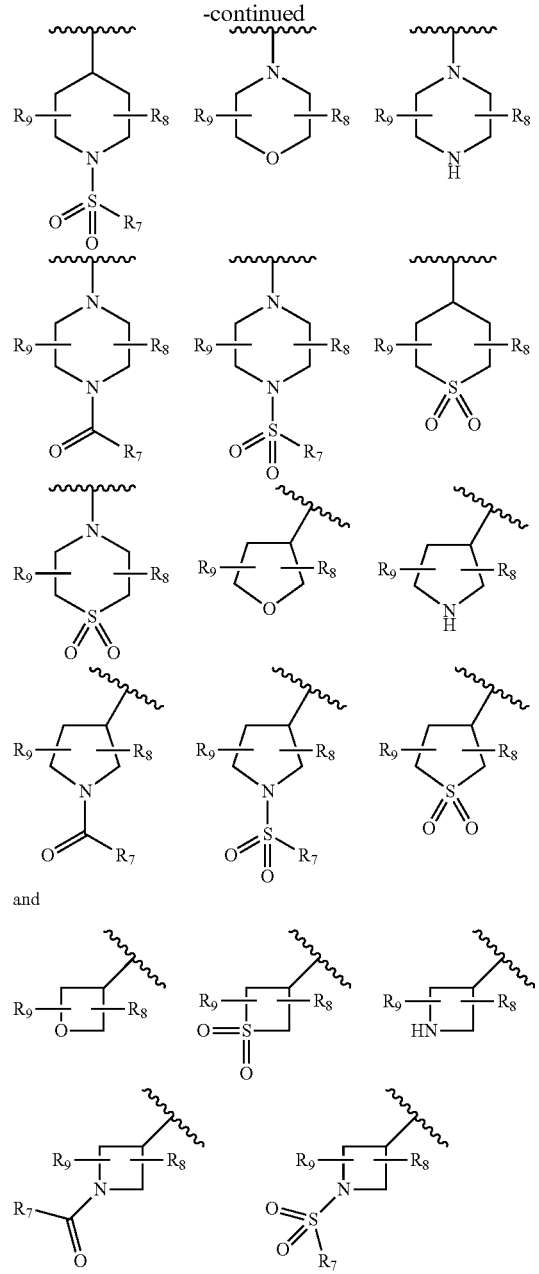

and in which:

R$_7$ represents a linear or branched C$_1$-C$_3$ alkyl radical, a hydroxyl radical —OH, a C$_1$-C$_3$ alkoxy radical or an amino radical N(R$^{7a}$)(R$^{7b}$), R$^{7a}$ and R$^{7b}$, which are identical or different, denote a hydrogen atom, a linear or branched C$_1$-C$_3$ alkyl radical or a cyclopropyl radical, R$^8$ and R$^9$, which are identical or different, represent a hydrogen atom, a linear or branched C$_1$-C$_3$ alkyl radical, a hydroxyl group —OH, a carbonyl group, a (C$_1$)hydroxyalkyl radical (CH$_2$OH), an amino group —NH$_2$, R$^8$ and R$^9$ can form, together with the carbon atoms to which they are attached, a 5- to 7-membered carbocyclic ring.

3. The compound of formula (II) as defined by claim 1, or the pharmaceutically acceptable addition salt thereof, wherein R⁶ represents an aromatic or heteroaromatic radical selected from the group consisting of

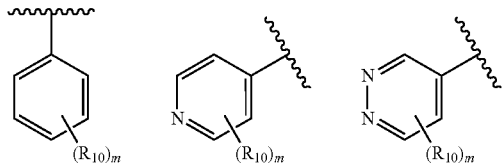

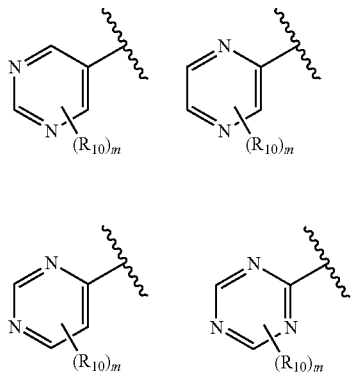

and

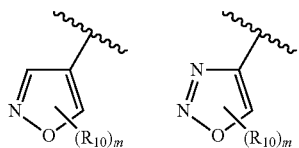

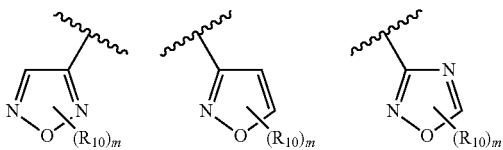

in which:

R$_{10}$ represents a hydrogen atom or a halogen atom; a linear or branched C$_1$-C$_3$ alkyl radical optionally substituted with one or more halogen atoms; a carbonyl function (=O), a group OR$^{11}$, a C$_1$-C$_4$ hydroxyalkyl group, an amino group —NR$^{11}$R$^{12}$, a —COR$^{11}$ group, a —COOR$^{11}$ group, an amido group —CONR$^{11}$R$^{12}$, a —SOR$^{11}$ group, a —SO$_2$R$^{11}$ group, a —NHCOR$^{11}$ group, a —NHCOOR$^{11}$ group, a —SO$_2$NR$^{11}$R$^{12}$ group or a cyano group —CN, R$^{11}$ and R$^{12}$, which are identical or different, represent a hydrogen atom or a linear or branched C$_1$-C$_3$ alkyl radical optionally substituted with one or more halogen atoms, m denotes zero or a natural integer ranging from 1 to 3.

4. The compound as defined by claim 1, wherein the compound is selected from the group consisting of the following compounds:

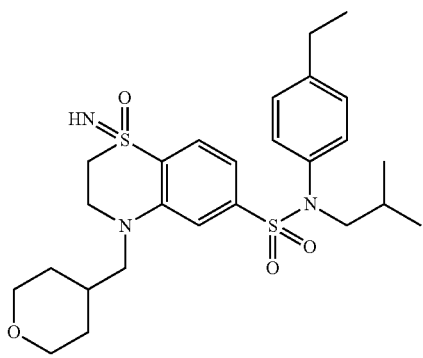 [SMILES: CCc1ccc(N(CC(C)C)S(=O)(=O)c2ccc3c(c2)N(CC2CCOCC2)CCS3(=N)=O)cc1]

imino-1-oxo-4-(tetrahydropyran-4-ylmethyl)-1,2,3,4-tetrahydro-1λ⁶-benzo[1,4]thiazine-7-sulfonic acid (4-ethylphenyl)isobutylamide
Compound 1

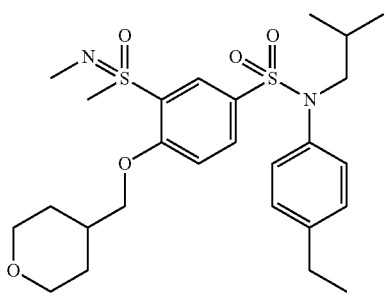

N-(4-ethylphenyl)-N-isobutyl-3-methanesulfinyl-4-(tetrahydropyran-4-ylmethoxy)benzene-N-methylsulfoximine
Compound 2

-continued

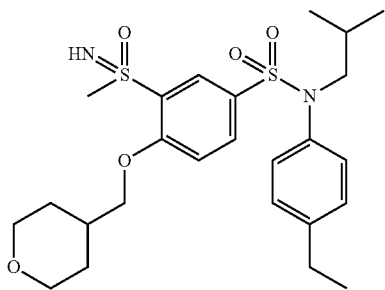 [SMILES: CCc1ccc(N(CC(C)C)S(=O)(=O)c2ccc(OCC3CCOCC3)c(S(C)(=N)=O)c2)cc1]

N-(4-ethylphenyl)-N-isobutyl-3-(S-methylsulfonimidoyl)-4-((tetrahydro-2H-pyran-4-yl)methoxy)benzenesulfonamide
Compound 26

Chiral

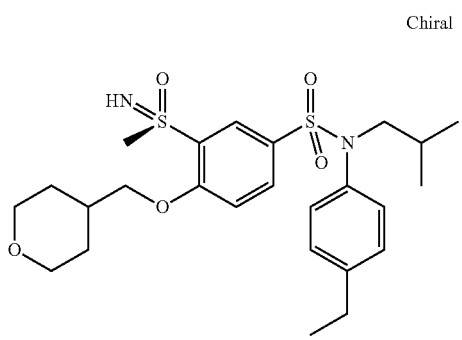 [SMILES: CCc1ccc(N(CC(C)C)S(=O)(=O)c2ccc(OCC3CCOCC3)c([S@](C)(=N)=O)c2)cc1]

N-(4-ethylphenyl)-N-isobutyl-3-(S-methylsulfonimidoyl)-4-((tetrahydro-2H-pyran-4-yl)methoxy)benzenesulfonamide
compound 7
(enantiomer A)

Chiral

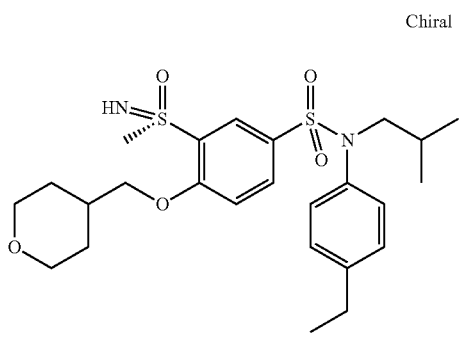 [SMILES: CCc1ccc(N(CC(C)C)S(=O)(=O)c2ccc(OCC3CCOCC3)c([S@@](C)(=N)=O)c2)cc1]

N-(4-ethylphenyl)-N-isobutyl-3-(S-methylsulfonimidoyl)-4-((tetrahydro-2H-pyran-4-yl)methoxy)benzenesulfonamide
compound 8
(enantiomer B)

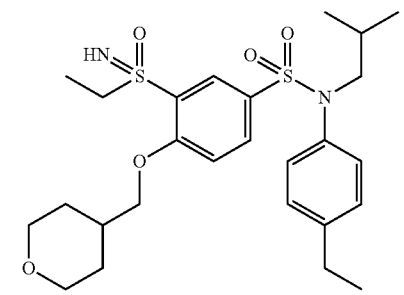 [SMILES: CCc1ccc(N(CC(C)C)S(=O)(=O)c2ccc(OCC3CCOCC3)c(S(=N)(=O)CC)c2)cc1]

N-(4-ethylphenyl)-N-isobutyl-3-ethanesulfoximino-4-(tetrahydropyran-4-ylmethoxy)benzenesulfonamide
Compound 18

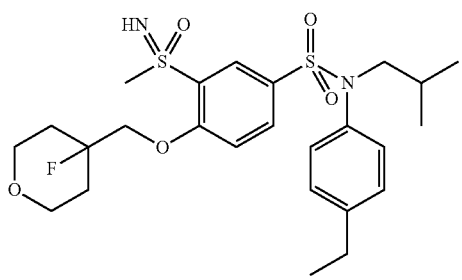

N-(4-ethylphenyl)-4-((4-fluorotetrahydro-2H-pyran-4-yl)methoxy)-N-isobutyl-3-(S-methylsulfonimidoyl)benzenesulfonamide
Compound 30

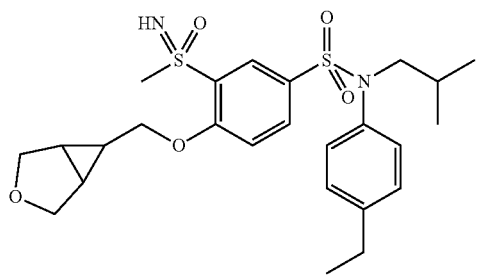 [SMILES: CCc1ccc(N(CC(C)C)S(=O)(=O)c2ccc(OCC3C4COCC43)c(S(C)(=N)=O)c2)cc1]

4-(3-oxabicyclo[3.1.0]hexan-6-yl)methoxy)-N-(4-ethylphenyl)-N-isobutyl-3-(S-methylsulfonimidoyl)benzenesulfonamide
Compound 31

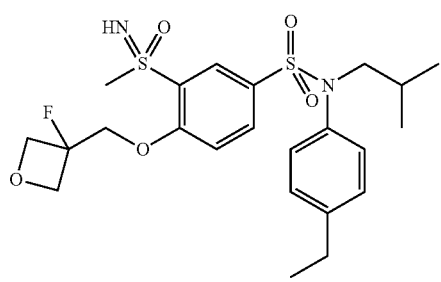 [SMILES: CCc1ccc(N(CC(C)C)S(=O)(=O)c2ccc(OCC3(F)COC3)c(S(C)(=N)=O)c2)cc1]

N-(4-ethylphenyl)-4-(3-fluorooxetan-3-yl)methoxy)-N-isobutyl-3-(S-methylsulfonimidoyl)benzenesulfonamide
Compound 32

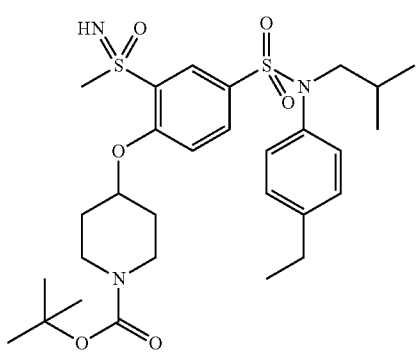 [SMILES: CCc1ccc(N(CC(C)C)S(=O)(=O)c2ccc(OC3CCN(C(=O)OC(C)(C)C)CC3)c(S(C)(=N)=O)c2)cc1]

tert-butyl 4-(4-(N-(4-ethylphenyl)-N-isobutylsulfamoyl)-2-(S-methylsulfonimidoyl)phenoxy)piperidine-1-carboxylate
Compound 33

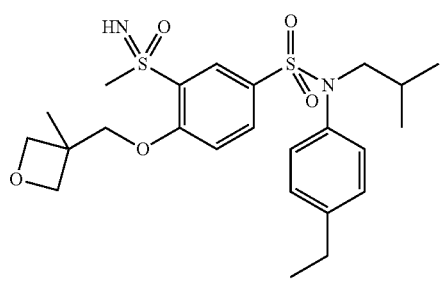 [SMILES: CCc1ccc(N(CC(C)C)S(=O)(=O)c2ccc(OCC3(C)COC3)c(S(C)(=N)=O)c2)cc1]

N-(4-ethylphenyl)-N-isobutyl-4-((3-methyloxetan-3-yl)methoxy)-3-(S-methylsulfonimidoyl)benzenesulfonamide
Compound 34

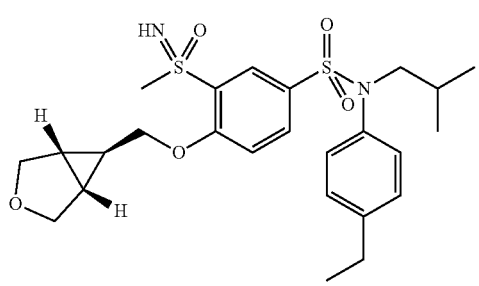 [SMILES: CCc1ccc(N(CC(C)C)S(=O)(=O)c2ccc(OC[C@H]3[C@@H]4COC[C@@H]43)c(S(C)(=N)=O)c2)cc1]

4-((((1R,5S,6R)-3-oxabicyclo[3.1.0]hexan-6-yl)methoxy)-N-(4-ethylphenyl)-N-isobutyl-3-(S-methylsulfonimidoyl)benzenesulfonamide
Compound 35

-continued

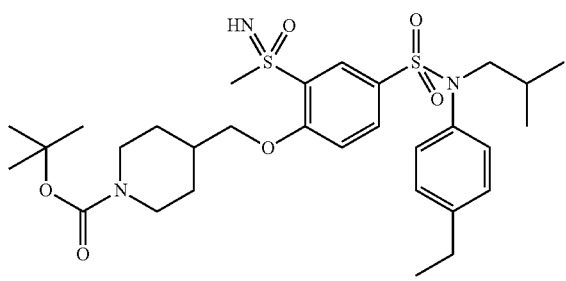 [SMILES: CCc1ccc(N(CC(C)C)S(=O)(=O)c2ccc(OCC3CCN(C(=O)OC(C)(C)C)CC3)c(S(C)(=N)=O)c2)cc1]

tert-butyl 4-((4-(N-(4-ethylphenyl)-N-isobutylsulfamoyl)-2-(S-methylsulfonimidoyl)phenoxy)methyl)piperidine-1-carboxylate
Compound 36

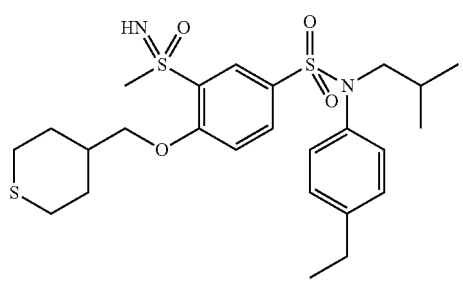 [SMILES: CCc1ccc(N(CC(C)C)S(=O)(=O)c2ccc(OCC3CCSCC3)c(S(C)(=N)=O)c2)cc1]

N-(4-ethylphenyl)-N-isobutyl-3-(S-methylsulfonimidoyl)-4-(pyridin-4-ylmethoxy)benzenesulfonamide
Compound 37

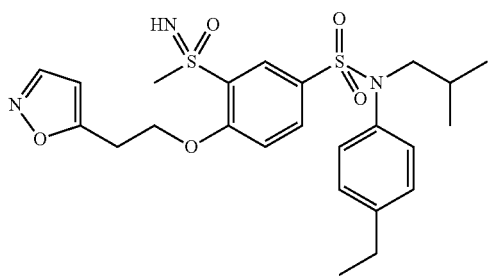 [SMILES: CCc1ccc(N(CC(C)C)S(=O)(=O)c2ccc(OCCc3ccno3)c(S(C)(=N)=O)c2)cc1]

N-(4-ethylphenyl)-N-isobutyl-4-(2-(isoxazol-5-yl)ethoxy)-3-(S-methylsulfonimidoyl)benzenesulfonamide
Compound 38

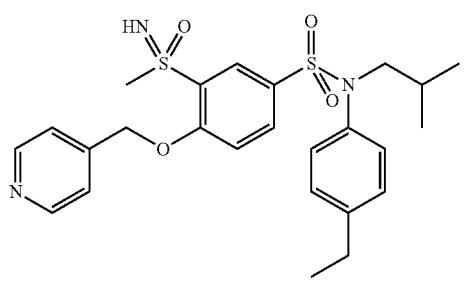 [SMILES: CCc1ccc(N(CC(C)C)S(=O)(=O)c2ccc(OCc3ccncc3)c(S(C)(=N)=O)c2)cc1]

N-(4-ethylphenyl)-N-isobutyl-3-(S-methylsulfonimidoyl)-4-(pyridin-4-ylmethoxy)benzenesulfonamide
Compound 39

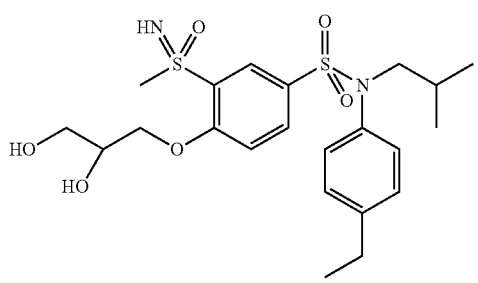 [SMILES: CCc1ccc(N(CC(C)C)S(=O)(=O)c2ccc(OCC(O)CO)c(S(C)(=N)=O)c2)cc1]

4-(2,3-dihydroxypropoxy)-N-(4-ethylphenyl)-N-isobutyl-3-(S-methylsulfonimidoyl)benzenesulfonamide
Compound 40

-continued

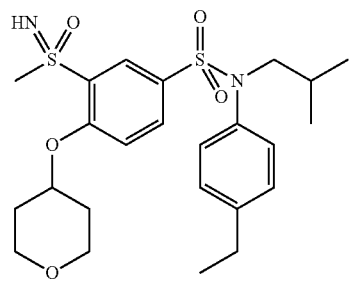 [SMILES: CCc1ccc(N(CC(C)C)S(=O)(=O)c2ccc(OC3CCOCC3)c(S(C)(=N)=O)c2)cc1]

N-(4-ethylphenyl)-N-isobutyl-3-(S-methylsulfonimidoyl)-4-((tetrahydro-2H-pyran-4-yl)oxy)benzenesulfonamide
Compound 42

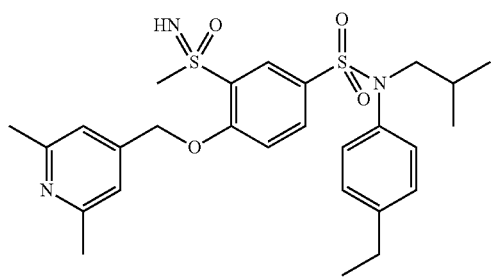 [SMILES: CCc1ccc(N(CC(C)C)S(=O)(=O)c2ccc(OCc3cc(C)nc(C)c3)c(S(C)(=N)=O)c2)cc1]

4-((2,6-dimethylpyridin-4-yl)methoxy)-N-(4-ethylphenyl)-N-isobutyl-3-(S-methylsulfonimidoyl)benzenesulfonamide
Compound 43

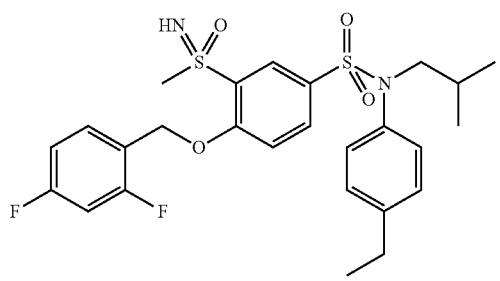 [SMILES: CCc1ccc(N(CC(C)C)S(=O)(=O)c2ccc(OCc3ccc(F)cc3F)c(S(C)(=N)=O)c2)cc1]

4-((2,4-difluorobenzyl)oxy)-N-(4-ethylphenyl)-N-isobutyl-3-(S-methylsulfonimidoyl)benzenesulfonamide
Compound 45

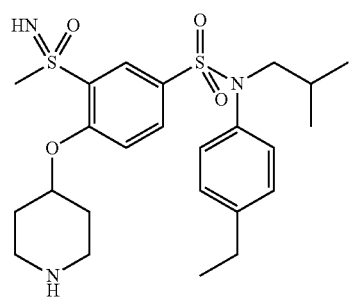 [SMILES: CCc1ccc(N(CC(C)C)S(=O)(=O)c2ccc(OC3CCNCC3)c(S(C)(=N)=O)c2)cc1]

N-(4-ethylphenyl)-N-isobutyl-3-(S-methylsulfonimidoyl)-4-(piperidin-4-ylmethoxy)benzenesulfonamide
Compound 46

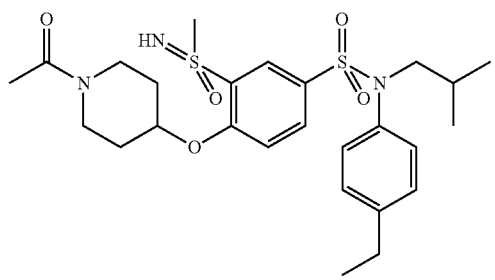 [SMILES: CCc1ccc(N(CC(C)C)S(=O)(=O)c2ccc(OC3CCN(C(C)=O)CC3)c(S(C)(=N)=O)c2)cc1]

4-((1-acetylpiperidin-4-yl)oxy)-N-(4-ethylphenyl)-N-isobutyl-3-(S-methylsulfonimidoyl)benzenesulfonamide
Compound 47

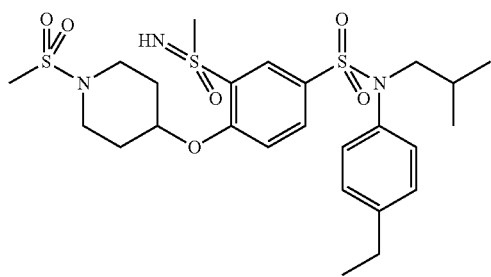 [SMILES: CCc1ccc(N(CC(C)C)S(=O)(=O)c2ccc(OC3CCN(S(C)(=O)=O)CC3)c(S(C)(=N)=O)c2)cc1]

N-(4-ethylphenyl)-N-isobutyl-3-(S-methylsulfonimidoyl)-4-((1-(methylsulfonyl)piperidin-4-yl)oxy)benzenesulfonamide
Compound 48

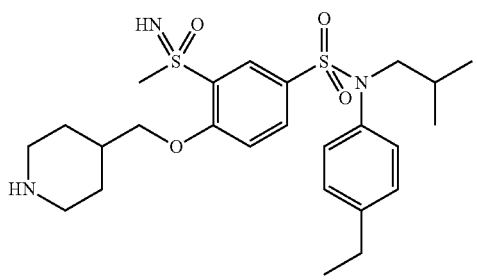 [SMILES: CCc1ccc(N(CC(C)C)S(=O)(=O)c2ccc(OCC3CCNCC3)c(S(C)(=N)=O)c2)cc1]

N-(4-ethylphenyl)-N-isobutyl-3-(S-methylsulfonimidoyl)-4-(piperidin-4-ylmethoxy)benzenesulfonamide
Compound 49

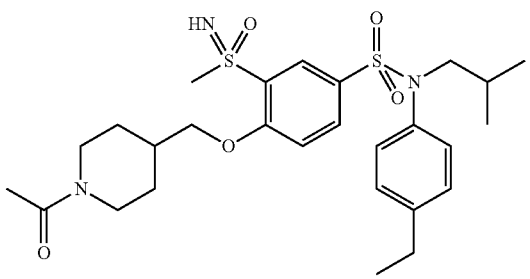 [SMILES: CCc1ccc(N(CC(C)C)S(=O)(=O)c2ccc(OCC3CCN(C(C)=O)CC3)c(S(C)(=N)=O)c2)cc1]

4-((1-acetylpiperidin-4-yl)methoxy)-N-(4-ethylphenyl)-N-isobutyl-3-(S-methylsulfonimidoyl)benzenesulfonamide
Compound 50

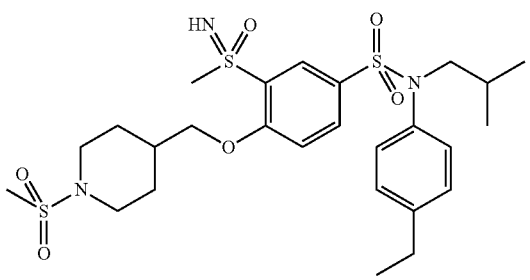 [SMILES: CCc1ccc(N(CC(C)C)S(=O)(=O)c2ccc(OCC3CCN(S(C)(=O)=O)CC3)c(S(C)(=N)=O)c2)cc1]

N-(4-ethylphenyl)-N-isobutyl-3-(S-methylsulfonimidoyl)-4-((1-(methylsulfonylpiperidin-4-yl)methoxy)benzenesulfonamide
Compound 51

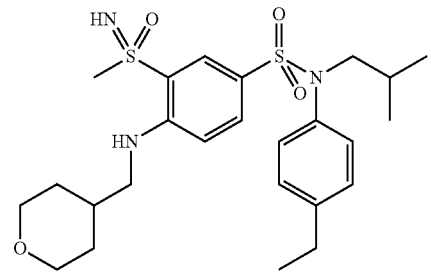 [SMILES: CCc1ccc(N(CC(C)C)S(=O)(=O)c2ccc(NCC3CCOCC3)c(S(C)(=N)=O)c2)cc1]

N-(4-ethylphenyl)-N-isobutyl-3-(S-methylsulfonimidoyl)-4-[(tetrahydropyran-4-ylmethyl)amino]benzenesulfonamide
Compound 52

-continued

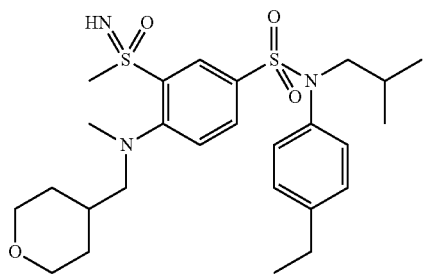 [SMILES: CCc1ccc(N(CC(C)C)S(=O)(=O)c2ccc(N(C)CC3CCOCC3)c(S(C)(=N)=O)c2)cc1]

N-(4-ethylphenyl)-N-isobutyl-4-(methyl((tetrahydro-2H-pyran-4-yl)methyl)amino)-3-(S-methylsulfonimidoyl)benzenesulfonamide
Compound 53

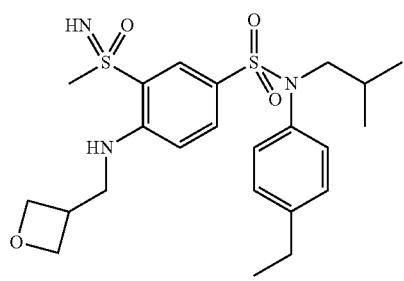 [SMILES: CCc1ccc(N(CC(C)C)S(=O)(=O)c2ccc(NCC3COC3)c(S(C)(=N)=O)c2)cc1]

N-(4-ethylphenyl)-N-isobutyl-3-(S-methylsulfonimidoyl)-4-((oxetan-3-ylmethyl)amino)benzenesulfonamide
Compound 54

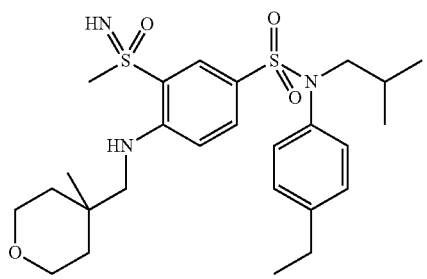 [SMILES: CCc1ccc(N(CC(C)C)S(=O)(=O)c2ccc(NCC3(C)CCOCC3)c(S(C)(=N)=O)c2)cc1]

N-(4-ethylphenyl)-N-isobutyl-3-(S-methylsulfonimidoyl)-4-(((4-methyltetrahydro-2H-pyran-4-yl)methyl)amino)benzenesulfonamide
Compound 55

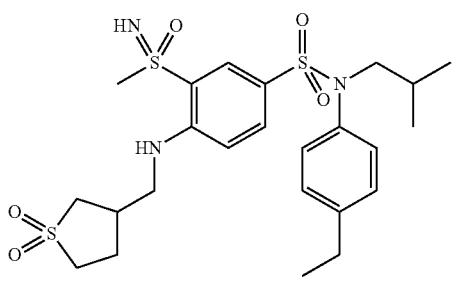 [SMILES: CCc1ccc(N(CC(C)C)S(=O)(=O)c2ccc(NCC3CCS(=O)(=O)C3)c(S(C)(=N)=O)c2)cc1]

4-(((1,1-dioxidotetrahydrothiophen-3-yl)methyl)amino)-N-(4-ethylphenyl)-N-isobutyl-3-(S-methylsulfonimidoyl)benzenesulfonamide
Compound 56

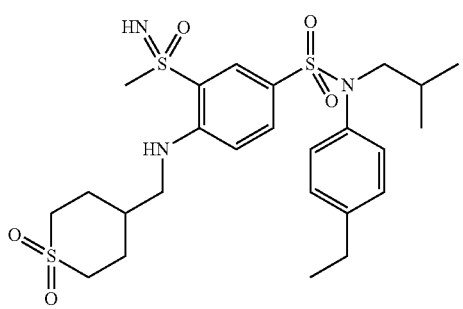 [SMILES: CCc1ccc(N(CC(C)C)S(=O)(=O)c2ccc(NCC3CCS(=O)(=O)CC3)c(S(C)(=N)=O)c2)cc1]

4-(((1,1-dioxidotetrahydro-2H-thiopyran-4-yl)methyl)amino)-N-(4-ethylphenyl)-N-isobutyl-3-(S-methylsulfonimidoyl)benzenesulfonamide
Compound 57

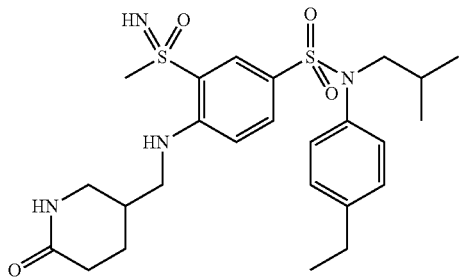 [SMILES: CCc1ccc(N(CC(C)C)S(=O)(=O)c2ccc(NCC3CCC(=O)NC3)c(S(C)(=N)=O)c2)cc1]

N-(4-ethylphenyl)-N-isobutyl-3-(S-methylsulfonimidoyl)-
4-(((6-oxopiperidin-3-yl)methyl)amino)benzenesulfonamide
Compound 58

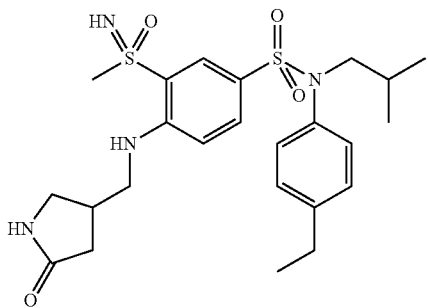 [SMILES: CCc1ccc(N(CC(C)C)S(=O)(=O)c2ccc(NCC3CNC(=O)C3)c(S(C)(=N)=O)c2)cc1]

N-(4-ethylphenyl)-N-isobutyl-3-(S-methylsulfonimidoyl)-
4-(((5-oxopyrrolidin-3-yl)methyl)amino)benzenesulfonamide
Compound 59

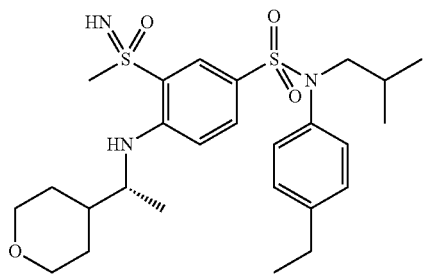 [SMILES: CCc1ccc(N(CC(C)C)S(=O)(=O)c2ccc(N[C@H](C)C3CCOCC3)c(S(C)(=N)=O)c2)cc1]

N-(4-ethylphenyl)-N-isobutyl-3-(S-methylsulfonimidoyl)-
4-(((R)-1-(tetrahydro-2H-pyran-4-yl)ethyl)amino)
benzenesulfonamide
Compound 60

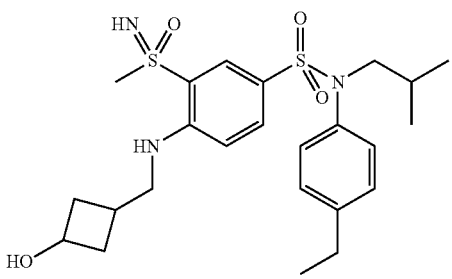 [SMILES: CCc1ccc(N(CC(C)C)S(=O)(=O)c2ccc(NCC3CC(O)C3)c(S(C)(=N)=O)c2)cc1]

N-(4-ethylphenyl)-4-(((3-
hydroxycyclobutyl)methyl)amino)-N-isobutyl-3-
(S-methylsulfonimidoyl)benzenesulfonamide
Compound 61

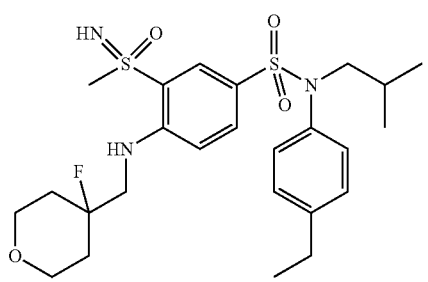 [SMILES: CCc1ccc(N(CC(C)C)S(=O)(=O)c2ccc(NCC3(F)CCOCC3)c(S(C)(=N)=O)c2)cc1]

N-(4-ethylphenyl)-4-(((4-fluorotetrahydro-2H-pyran-4-
yl)methyl)amino)-N-isobutyl-3-(S-methylsulfonimidoyl)
benzenesulfonamide
Compound 62

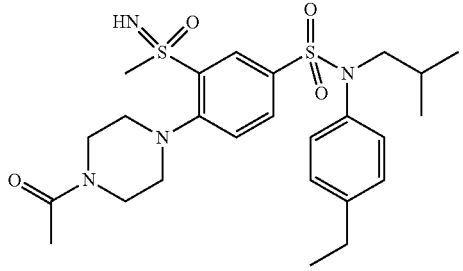 [SMILES: CCc1ccc(N(CC(C)C)S(=O)(=O)c2ccc(N3CCN(C(C)=O)CC3)c(S(C)(=N)=O)c2)cc1]

4-(4-acetylpiperazin-1-yl)-N-(4-ethylphenyl)-N-isobutyl-3-(S-methylsulfonimidoyl)benzenesulfonamide
Compound 63

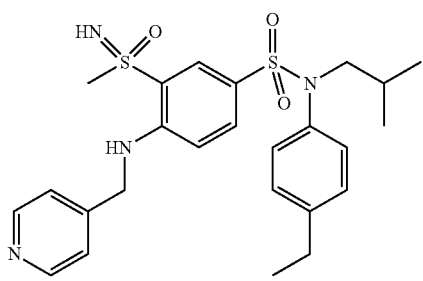

N-(4-ethylphenyl)-N-isobutyl-3-(S-methylsulfonimidoyl)-4-((pyridin-4-ylmethyl)amino)benzenesulfonamide
Compound 64

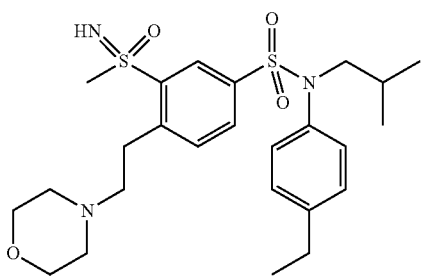 [SMILES: CCc1ccc(N(CC(C)C)S(=O)(=O)c2ccc(CCN3CCOCC3)c(S(C)(=N)=O)c2)cc1]

N-(4-ethylphenyl)-N-isobutyl-3-(S-methylsulfonimidoyl)-4-(2-morpholinoethyl)benzenesulfonamide
Compound 65

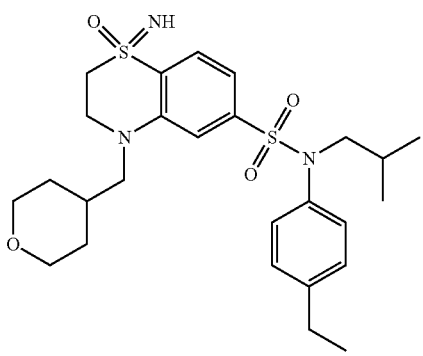 [SMILES: CCc1ccc(N(CC(C)C)S(=O)(=O)c2ccc3c(c2)N(CC2CCOCC2)CCS3(=N)=O)cc1]

1-imino-1-oxo-4-(tetrahydropyran-4-ylmethyl)-1,2,3,4-tetrahydro-1$\lambda^6$-benzo[1,4]thiazine-6-sulfonic acid (4-ethylphenyl)isobutylamide
Compound 69

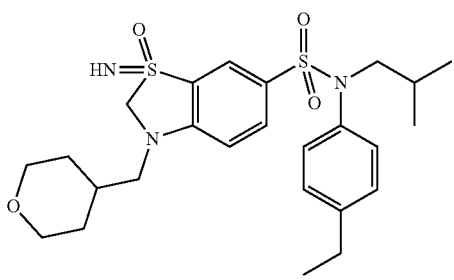 [SMILES: CCc1ccc(N(CC(C)C)S(=O)(=O)c2ccc3c(c2)S(=N)(=O)CN3CC2CCOCC2)cc1]

1-imino-1-oxo-3-(tetrahydropyran-4-ylmethyl)-2,3-dihydro-1H-1$\lambda^6$-benzothiazole-6-sulfonic acid (4-ethylphenyl)isobutylamide
Compound 76

-continued

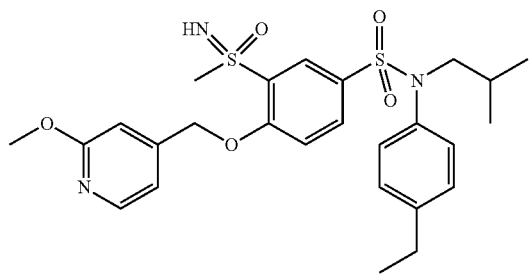 [SMILES: CCc1ccc(N(CC(C)C)S(=O)(=O)c2ccc(OCc3ccnc(OC)c3)c(S(C)(=N)=O)c2)cc1]

N-(4-ethylphenyl)-N-isobutyl-4-((2-methoxypyridin-4-yl)methoxy)-3-(S-methylsulfonimidoyl)benzenesulfonamide
Compound 77

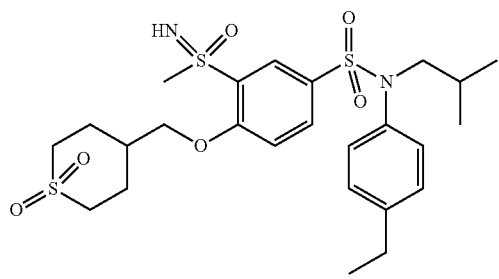

N-(4-ethylphenyl)-N-isobutyl-4-((2-methoxypyridin-4-yl)methoxy)-3-(S-methylsulfonimidoyl)benzenesulfonamide
Compound 78

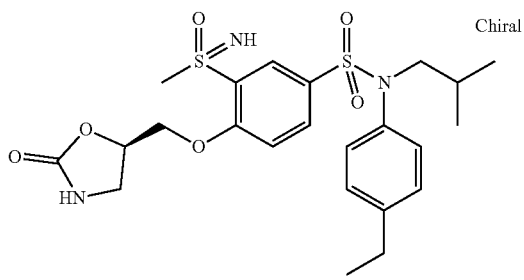 [SMILES: CCc1ccc(N(CC(C)C)S(=O)(=O)c2ccc(OC[C@H]3CNC(=O)O3)c(S(C)(=N)=O)c2)cc1]

Chiral

N-(4-ethylphenyl)-N-isobutyl-3-(S-methylsulfonimidoyl)-4-(((R)-2-oxooxazolidin-5-yl)methoxy)benzenesulfonamide
Compound 79

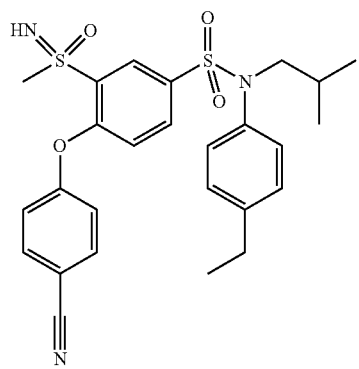 [SMILES: CCc1ccc(N(CC(C)C)S(=O)(=O)c2ccc(Oc3ccc(C#N)cc3)c(S(C)(=N)=O)c2)cc1]

4-(4-cyanophenoxy)-N-(4-ethylphenyl)-N-isobutyl-3-(S-methylsulfonimidoyl)benzenesulfonamide
Compound 80

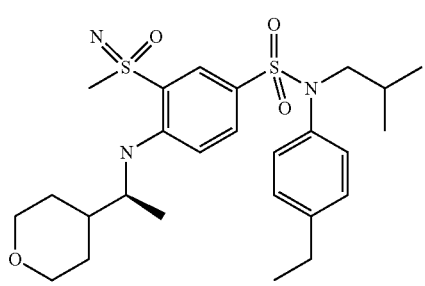 [SMILES: CCc1ccc(N(CC(C)C)S(=O)(=O)c2ccc(N[C@@H](C)C3CCOCC3)c(S(C)(=N)=O)c2)cc1]

N-(4-ethylphenyl)-N-isobutyl-3-(S-methylsulfonimidoyl)-4-(((S)-1-(tetrahydro-2H-pyran-4-yl)ethyl)amino)benzenesulfonamide
Compound 81

-continued

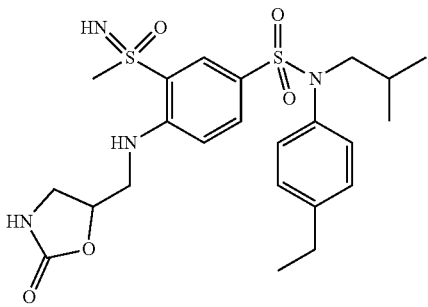 [SMILES: CCc1ccc(N(CC(C)C)S(=O)(=O)c2ccc(NCC3CNC(=O)O3)c(S(C)(=N)=O)c2)cc1]

N-(4-ethylphenyl)-N-isobutyl-3-(S-methylsulfonimidoyl)-4-(((2-oxooxazolidin-5-yl)methyl)amino)benzenesulfonamide
Compound 82

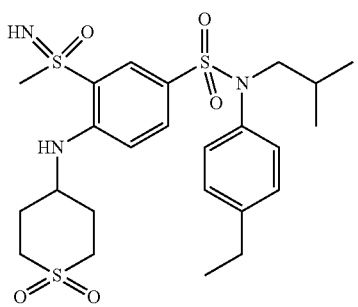 [SMILES: CCc1ccc(N(CC(C)C)S(=O)(=O)c2ccc(NC3CCS(=O)(=O)CC3)c(S(C)(=N)=O)c2)cc1]

4-((1,1-dioxidotetrahydro-2H-thiopyran-4-yl)amino)-N-(4-ethylphenyl)-N-isobutyl-3-(5-methylsulfonimidoyl)benzenesulfonamide
Compound 83

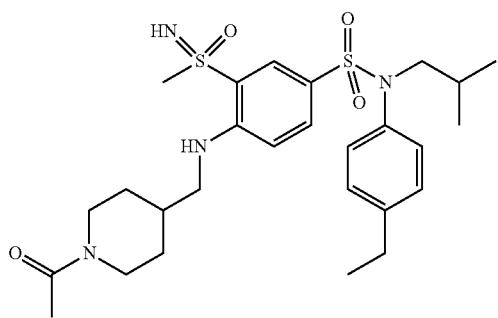 [SMILES: CCc1ccc(N(CC(C)C)S(=O)(=O)c2ccc(NCC3CCN(C(C)=O)CC3)c(S(C)(=N)=O)c2)cc1]

4-(((1-acetylpiperidin-4-yl)methyl)amino)-N-(4-ethylphenyl)-N-isobutyl-3-(S-methylsulfonimidoyl)benzenesulfonamide
Compound 84

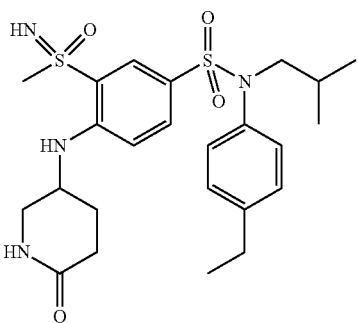 [SMILES: CCc1ccc(N(CC(C)C)S(=O)(=O)c2ccc(NC3CCC(=O)NC3)c(S(C)(=N)=O)c2)cc1]

N-(4-ethylphenyl)-N-isobutyl-3-(S-methylsulfonimidoyl)-4-((6-oxopiperidin-3-yl)amino)benzenesulfonamide
Compound 85

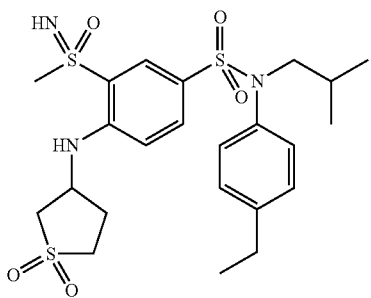 [SMILES: CCc1ccc(N(CC(C)C)S(=O)(=O)c2ccc(NC3CCS(=O)(=O)C3)c(S(C)(=N)=O)c2)cc1]

4-((1,1-dioxidotetrahydrothiophen-3-yl)amino)-N-(4-ethylphenyl)-N-isobutyl-3-(S-methylsulfonimidoyl)benzenesulfonamide
Compound 86

-continued

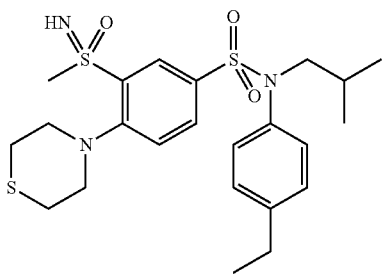 [SMILES: CCc1ccc(N(CC(C)C)S(=O)(=O)c2ccc(N3CCSCC3)c(S(C)(=N)=O)c2)cc1]

N-(4-ethylphenyl)-N-isobutyl-3-(S-methylsulfonimidoyl)-4-thiomorpholinobenzenesulfonamide
Compound 87

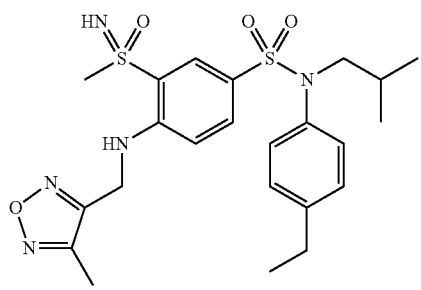 [SMILES: CCc1ccc(N(CC(C)C)S(=O)(=O)c2ccc(NCc3nonc3C)c(S(C)(=N)=O)c2)cc1]

N-(4-ethylphenyl)-N-isobutyl-4-(((4-methyl-1,2,5-oxadiazol-3-yl(methyl)amino)-3-(S-methylsulfonimidoyl)benzenesulfonamide
Compound 88

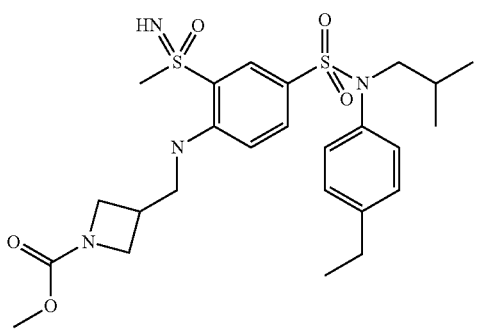 [SMILES: CCc1ccc(N(CC(C)C)S(=O)(=O)c2ccc(NCC3CN(C(=O)OC)C3)c(S(C)(=N)=O)c2)cc1]

methyl 3-(((4-(N-(4-ethylphenyl)-N-isobutylsulfamoyl)-2-(S-methylsulfonimidoyl)phenyl)amino)methyl)azetidine-1-carboxylate
Compound 89

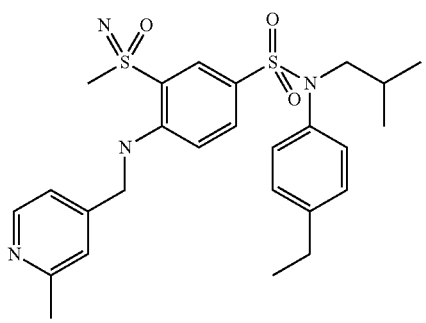 [SMILES: CCc1ccc(N(CC(C)C)S(=O)(=O)c2ccc(NCc3ccnc(C)c3)c(S(C)(=N)=O)c2)cc1]

N-(4-ethylphenyl)-N-isobutyl-4-(((2-methylpyridin-4-yl)methyl)amino)-3-(S-methylsulfonimidoyl)benzenesulfonamide
Compound 90

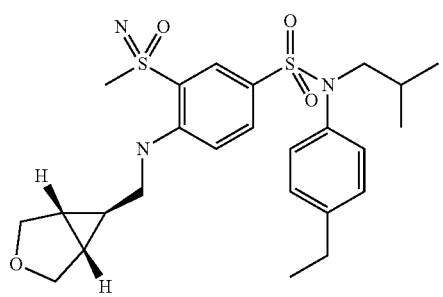 [SMILES: CCc1ccc(N(CC(C)C)S(=O)(=O)c2ccc(NC[C@@H]3[C@H]4COC[C@@H]34)c(S(C)(=N)=O)c2)cc1]

4-((((1R,5S,6S)-3-oxabicyclo[3.1.0]hexan-6-yl)methyl)amino)-N-(4-ethylphenyl)-N-isobutyl-3-(S-methylsulfonimidoyl)benzenesulfonamide
Compound 91

-continued

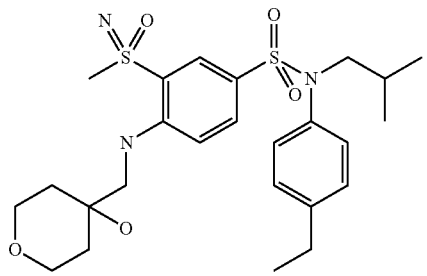 [SMILES: CCc1ccc(N(CC(C)C)S(=O)(=O)c2ccc(NCC3(O)CCOCC3)c(S(C)(=N)=O)c2)cc1]

N-(4-ethylphenyl)-4-(((4-hydroxytetrahydro-2H-pyran-4-yl)
methyl)amino)-N-isobutyl-3-(S-methylsulfonimidoyl)
benzenesulfonamide
Compound 92

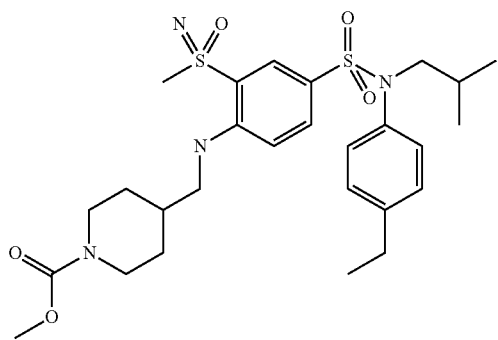 [SMILES: CCc1ccc(N(CC(C)C)S(=O)(=O)c2ccc(NCC3CCN(C(=O)OC)CC3)c(S(C)(=N)=O)c2)cc1]

methyl 4-(((4-(N-(4-ethylphenyl)-N-isobutylsulfamoyl)-2-
(S-methylsulfonimidoyl)phenyl)amino)methyl)
piperidine-1-carboxylate
Compound 93

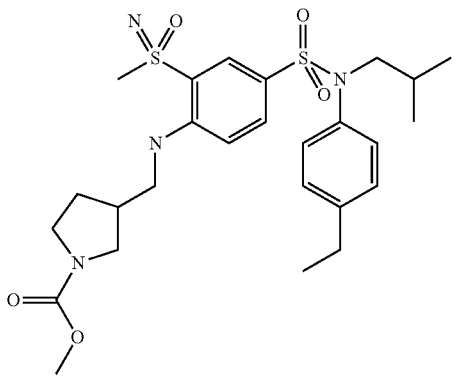 [SMILES: CCc1ccc(N(CC(C)C)S(=O)(=O)c2ccc(NCC3CCN(C(=O)OC)C3)c(S(C)(=N)=O)c2)cc1]

methyl 3-(((4-(N-(4-ethylphenyl)-N-isobutylsulfamoyl)-2-(S-
methylsulfonimidoyl)phenyl)amino)methyl)
pyrrolidine-1-carboxylate
Compound 94

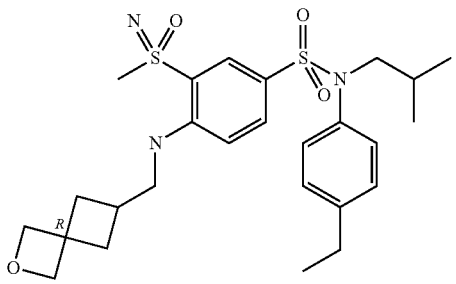

4-(((2-oxaspiro[3.3]heptan-6-yl)methyl)amino)-N-(4-
ethylphenyl)-N-isobutyl-3-(S-methylsulfonimidoyl)
benzenesulfonamide
Compound 95

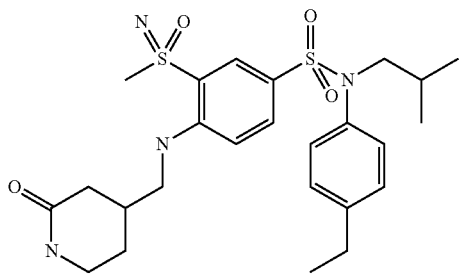 [SMILES: CCc1ccc(N(CC(C)C)S(=O)(=O)c2ccc(NCC3CCNC(=O)C3)c(S(C)(=N)=O)c2)cc1]

4-N-(4-ethylphenyl)-N-isobutyl-3-(S-methylsulfonimidoyl)-4-
(((2-oxopiperidin-4-yl)methyl)amino)benzenesulfonamide
Compound 96

-continued

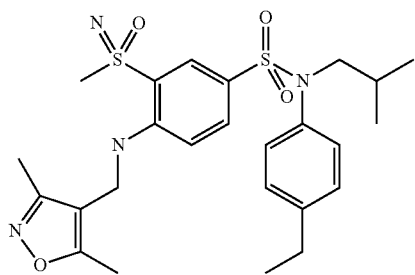 [SMILES: CCc1ccc(N(CC(C)C)S(=O)(=O)c2ccc(NCc3c(C)noc3C)c(S(C)(=N)=O)c2)cc1]

4-(((3,5-dimethylisoxazol-4-yl)methyl)amino)-N-(4-ethylphenyl)-N-isobutyl-3-(S-methylsulfonimidoyl)benzenesulfonamide
Compound 97

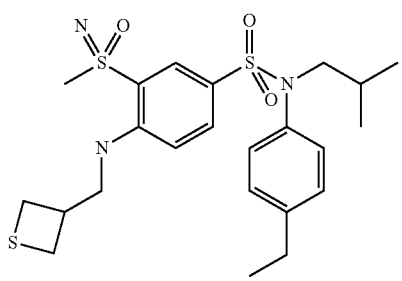 [SMILES: CCc1ccc(N(CC(C)C)S(=O)(=O)c2ccc(NCC3CSC3)c(S(C)(=N)=O)c2)cc1]

N-(4-ethylphenyl)-N-isobutyl-3-(S-methylsulfonimidoyl)-4-((thietan-3-ylmethyl)amino)benzenesulfonamide
Compound 99

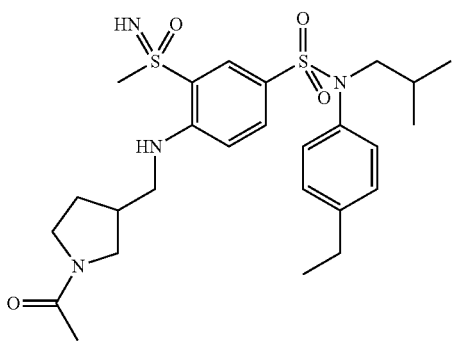 [SMILES: CCc1ccc(N(CC(C)C)S(=O)(=O)c2ccc(NCC3CCN(C(C)=O)C3)c(S(C)(=N)=O)c2)cc1]

4-(((1-acetylpyrrolidin-3-yl)methyl)amino)-N-(4-ethylphenyl)-N-isobutyl-3-(S-methylsulfonimidoyl)benzenesulfonamide
Compound 100

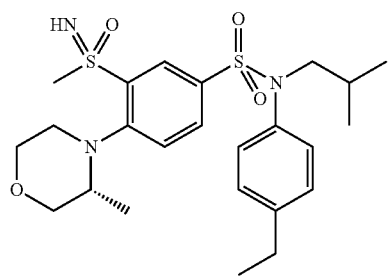 [SMILES: CCc1ccc(N(CC(C)C)S(=O)(=O)c2ccc(N3CCOC[C@H]3C)c(S(C)(=N)=O)c2)cc1]

N-(4-ethylphenyl)-N-isobutyl-4-((R)-3-methylmorpholino)-3-(S-methylsulfonimidoyl)benzenesulfonamide
Compound 103

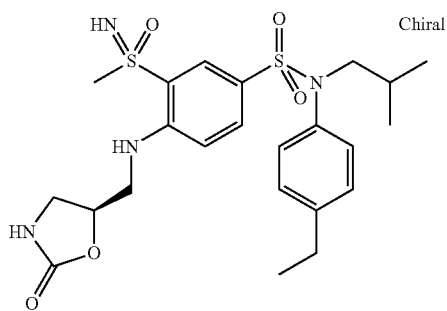 [SMILES: CCc1ccc(N(CC(C)C)S(=O)(=O)c2ccc(NC[C@@H]3CNC(=O)O3)c(S(C)(=N)=O)c2)cc1]

N-(4-ethylphenyl)-N-isobutyl-3-(S-methylsulfonimidoyl)-4-((((R)-2-oxooxazolidin-5-yl)methyl)amino)benzenesulfonamide
Compound 105

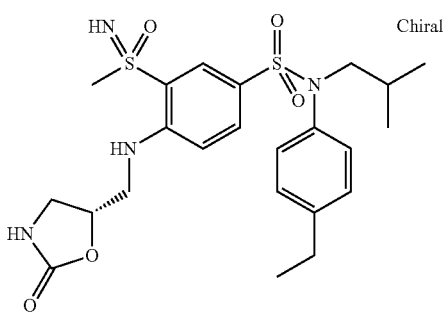 [SMILES: CCc1ccc(N(CC(C)C)S(=O)(=O)c2ccc(NC[C@H]3CNC(=O)O3)c(S(C)(=N)=O)c2)cc1]

N-(4-ethylphenyl)-N-isobutyl-3-(S-methylsulfonimidoyl)-4-((((S)-2-oxooxazolidin-5-yl)methyl)amino)benzenesulfonamide
Compound 106

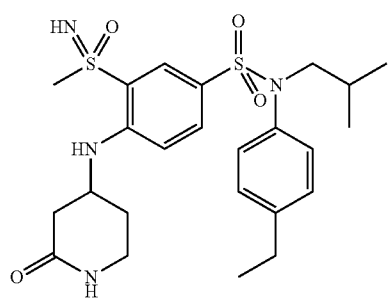 [SMILES: CCc1ccc(N(CC(C)C)S(=O)(=O)c2ccc(NC3CCNC(=O)C3)c(S(C)(=N)=O)c2)cc1]

N-(4-ethylphenyl)-N-isobutyl-3-(S-methylsulfonimidoyl)-4-((2-oxopiperidin-4-yl)amino)benzenesulfonamide
Compound 107

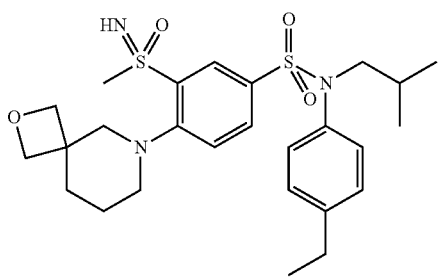 [SMILES: CCc1ccc(N(CC(C)C)S(=O)(=O)c2ccc(N3CCCC4(COC4)C3)c(S(C)(=N)=O)c2)cc1]

N-(4-ethylphenyl)-N-isobutyl-3-(S-methylsulfonimidoyl)-4-(2-oxa-6-azaspiro[3.5]nonan-6-yl)benzenesulfonamide
Compound 109

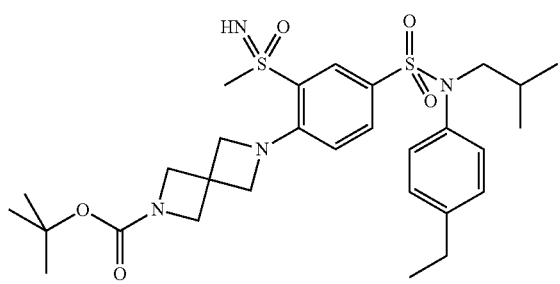 [SMILES: CCc1ccc(N(CC(C)C)S(=O)(=O)c2ccc(N3CC4(CN(C(=O)OC(C)(C)C)C4)C3)c(S(C)(=N)=O)c2)cc1]

tert-butyl 6-(4-(N-(4-ethylphenyl)-N-isobutylsulfamoyl)-2-(S-diazaspiro[3.3]heptane-2-carboxylate
Compound 110

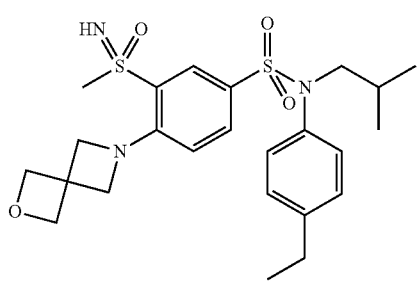 [SMILES: CCc1ccc(N(CC(C)C)S(=O)(=O)c2ccc(N3CC4(COC4)C3)c(S(C)(=N)=O)c2)cc1]

N-(4-ethylphenyl)-N-isobutyl-3-(S-methylsulfonimidoyl)-4-(2-oxa-6-azaspiro[3.3]heptan-6-yl)benzenesulfonamide
Compound 111

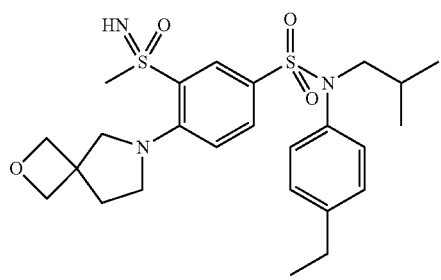 [SMILES: CCc1ccc(N(CC(C)C)S(=O)(=O)c2ccc(N3CCC4(COC4)C3)c(S(C)(=N)=O)c2)cc1] N-(4-ethylphenyl)-N-isobutyl-3-(S-methylsulfonimidoyl)-4-(2-oxa-6-azaspiro[3.4]octan-6-1)benzenesulfonamide
Compound 112

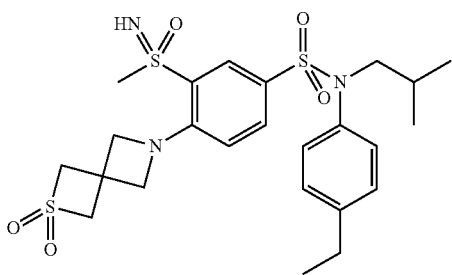 [SMILES: CCc1ccc(N(CC(C)C)S(=O)(=O)c2ccc(N3CC4(C3)CS(=O)(=O)C4)c(S(C)(=N)=O)c2)cc1] 4-(2,2-dioxido-2-thia-6-azaspiro[3.3]heptan-6-yl)-N-(4-ethylphenyl)-N-isobutyl-3-(S-methylsulfonimidoyl)benzenesulfonamide
Compound 113

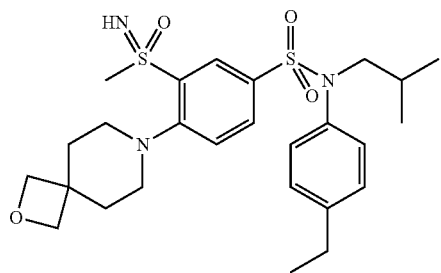 [SMILES: CCc1ccc(N(CC(C)C)S(=O)(=O)c2ccc(N3CCC4(CC3)COC4)c(S(C)(=N)=O)c2)cc1] N-(4-ethylphenyl)-N-isobutyl-3-(S-methylsulfonimidoyl)-4-(2-oxa-7-azaspiro[3.5]nonan-7-yl)benzenesulfonamide
Compound 114

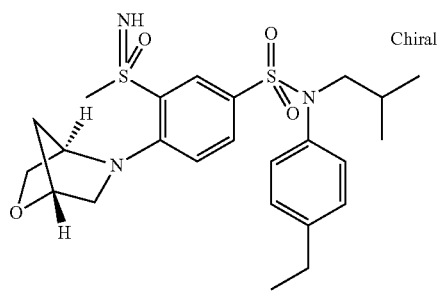 [SMILES: CCc1ccc(N(CC(C)C)S(=O)(=O)c2ccc(N3C[C@H]4C[C@@H]3CO4)c(S(C)(=N)=O)c2)cc1] Chiral 4-((1R,4R)-2-oxa-5-azabicyclo[2.2.1]heptan-5-yl)-N-(4-ethylphenyl)-N-isobutyl-3-(S-methylsulfonimidoyl)benzenesulfonamide
Compound 115

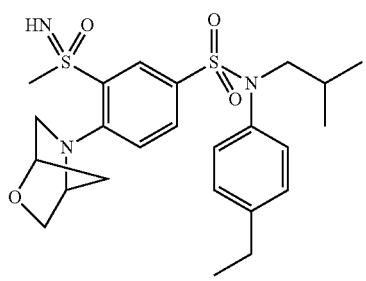 [SMILES: CCc1ccc(N(CC(C)C)S(=O)(=O)c2ccc(N3CC4CC3CO4)c(S(C)(=N)=O)c2)cc1] 4-((1R,4R)-2-oxa-5-azabicyclo[2.2.1]heptan-5-yl)-N-(4-ethylphenyl)-N-isobutyl-3-(S-methylsulfonimidoyl)benzenesulfonamide
Compound 117

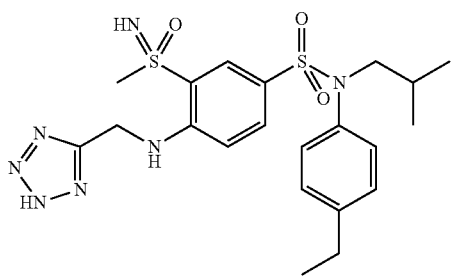 [SMILES: CCc1ccc(N(CC(C)C)S(=O)(=O)c2ccc(NCc3nn[nH]n3)c(S(C)(=N)=O)c2)cc1]

4-(((2H-tetrazol-5-yl)methyl)amino)-N-(4-ethylphenyl)-N-isobutyl-3-(S-methylsulfonimidoyl)benzenesulfonamide
Compound 118

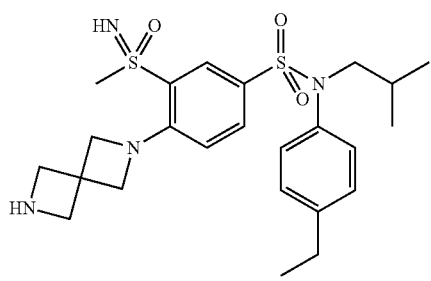 [SMILES: CCc1ccc(N(CC(C)C)S(=O)(=O)c2ccc(N3CC4(CNC4)C3)c(S(C)(=N)=O)c2)cc1]

-(4-ethylphenyl)-N-isobutyl-3-(S-methylsulfonimidoyl)-4-(2,6-diazaspiro[3.3]heptan-2-yl)benzenesulfonamide
Compound 121

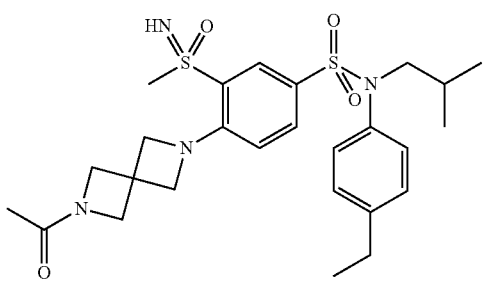 [SMILES: CCc1ccc(N(CC(C)C)S(=O)(=O)c2ccc(N3CC4(CN(C(C)=O)C4)C3)c(S(C)(=N)=O)c2)cc1]

4-(6-acetyl-2,6-diazaspiro[3.3]heptan-2-yl)-N-(4-ethylphenyl)-N-isobutyl-3-(S-methylsulfonimidoyl)benzenesulfonamide
Compound 122

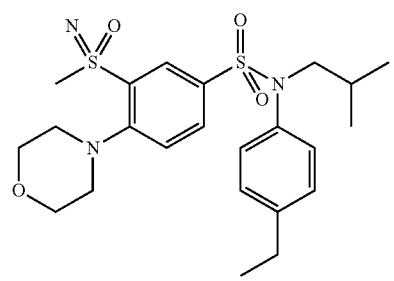 [SMILES: CCc1ccc(N(CC(C)C)S(=O)(=O)c2ccc(N3CCOCC3)c(S(C)(=N)=O)c2)cc1]

N-(4-ethylphenyl)-N-isobutyl-3-(S-methylsulfonimidoyl)-4-morpholinobenzenesulfonamide
Compound 123

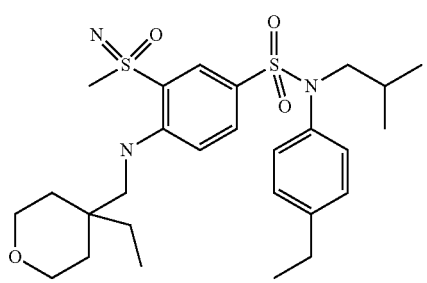 [SMILES: CCc1ccc(N(CC(C)C)S(=O)(=O)c2ccc(NCC3(CC)CCOCC3)c(S(C)(=N)=O)c2)cc1]

N-(4-ethylphenyl)-4-(((4-ethyltetrahydro-2H-pyran-4-yl)methyl)amino)-N-isobutyl-3-(S-methylsulfonimidoyl)benzenesulfonamide
Compound 124

-continued

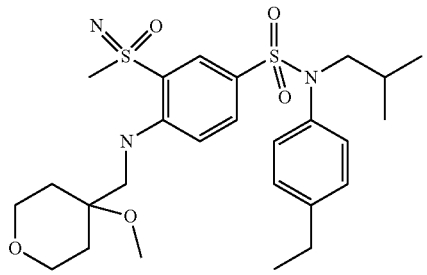 [SMILES: CCc1ccc(N(CC(C)C)S(=O)(=O)c2ccc(NCC3(OC)CCOCC3)c(S(C)(=N)=O)c2)cc1]

N-(4-ethylphenyl)-N-isobutyl-4-(((4-methoxytetrahydro-2H-pyran-4-yl)methyl)amino)-3-(S-methylsulfonimidoyl)benzenesulfonamide
Compound 125

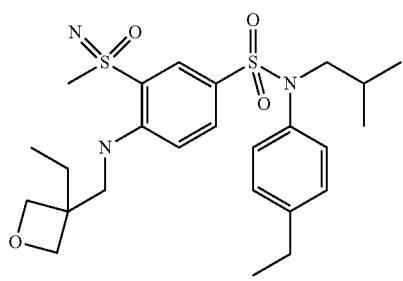 [SMILES: CCc1ccc(N(CC(C)C)S(=O)(=O)c2ccc(NCC3(CC)COC3)c(S(C)(=N)=O)c2)cc1]

4-(((3-ethyloxetan-3-yl)methyl)amino)-N-(4-ethylphenyl)-N-isobutyl-3-(S-methylsulfonimidoyl)benzenesulfonamide
Compound 126

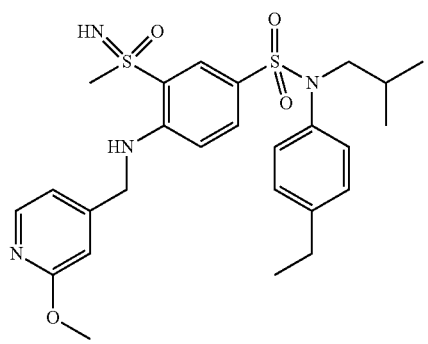 [SMILES: CCc1ccc(N(CC(C)C)S(=O)(=O)c2ccc(NCc3ccnc(OC)c3)c(S(C)(=N)=O)c2)cc1]

N-(4-ethylphenyl)-N-isobutyl-4-(((2-methoxypyridin-4-yl)methyl)amino)-3-(S-methylsulfonimidoyl)benzenesulfonamide
Compound 127

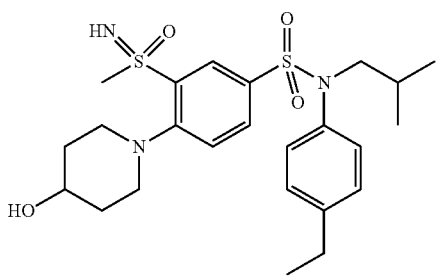 [SMILES: CCc1ccc(N(CC(C)C)S(=O)(=O)c2ccc(N3CCC(O)CC3)c(S(C)(=N)=O)c2)cc1]

N-(4-ethylphenyl)-4-(4-hydroxypiperidin-1-yl)-N-isobutyl-3-(S-methylsulfonimidoyl)benzenesulfonamide
Compound 128

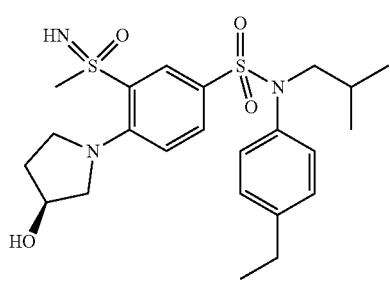 [SMILES: CCc1ccc(N(CC(C)C)S(=O)(=O)c2ccc(N3CC[C@H](O)C3)c(S(C)(=N)=O)c2)cc1]

N-(4-ethylphenyl)-4-((S)-3-hydroxypyrrolidin-1-yl)-N-isobutyl-3-(S-methylsulfonimidoyl)benzenesulfonamide
Compound 129

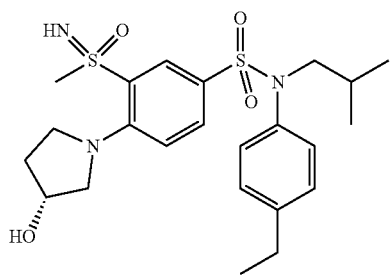 [SMILES: CCc1ccc(N(CC(C)C)S(=O)(=O)c2ccc(N3CC[C@@H](O)C3)c(S(C)(=N)=O)c2)cc1]

N-(4-ethylphenyl)-4-((R)-3-hydroxypyrrolidin-1-yl)-N-isobutyl-3-(S-methylsulfonimidoyl)benzenesulfonamide
Compound 130

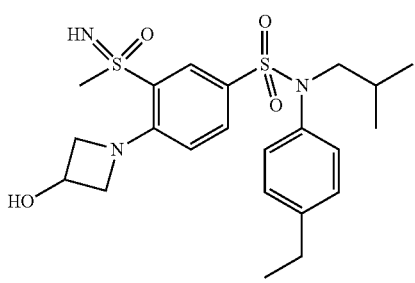 [SMILES: CCc1ccc(N(CC(C)C)S(=O)(=O)c2ccc(N3CC(O)C3)c(S(C)(=N)=O)c2)cc1]

N-(4-ethylphenyl)-4-(3-hydroxyazetidin-1-yl)-N-isobutyl-3-(S-methylsulfonimidoyl)benzenesulfonamide
Compound 131

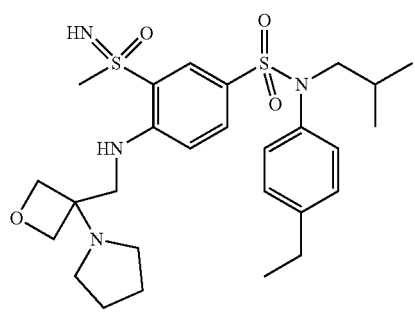 [SMILES: CCc1ccc(N(CC(C)C)S(=O)(=O)c2ccc(NCC3(N4CCCC4)COC3)c(S(C)(=N)=O)c2)cc1]

N-(4-ethylphenyl)-N-isobutyl-3-(S-methylsulfonimidoyl)-4-(((3-(pyrrolidin-1-yl)oxetan-3-yl)methyl)amino)benzenesulfonamide
Compound 132

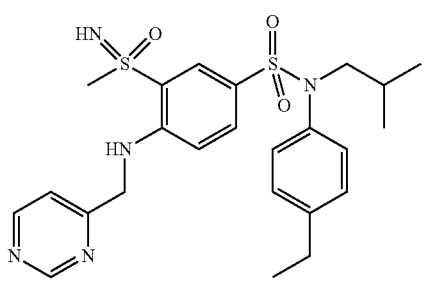 [SMILES: CCc1ccc(N(CC(C)C)S(=O)(=O)c2ccc(NCc3ccncn3)c(S(C)(=N)=O)c2)cc1]

N-(4-ethylphenyl)-N-isobutyl-3-(S-methylsulfonimidoyl)-4-((pyrimidin-4-ylmethyl)amino)benzenesulfonamide
Compound 133

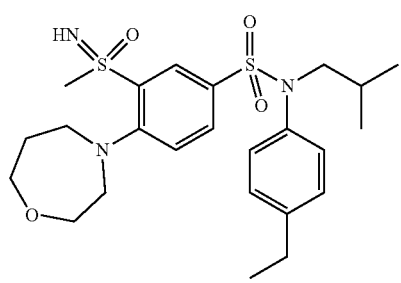 [SMILES: CCc1ccc(N(CC(C)C)S(=O)(=O)c2ccc(N3CCCOCC3)c(S(C)(=N)=O)c2)cc1]

N-(4-ethylphenyl)-N-isobutyl-3-(S-methylsulfonimidoyl)-4-(1,4-oxazepan-4-yl)benzenesulfonamide
Compound 137

-continued

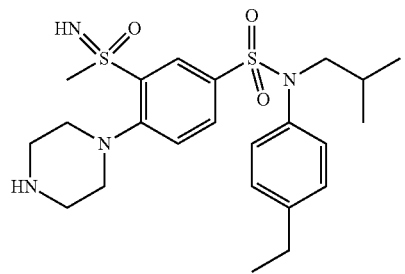 [SMILES: CCc1ccc(N(CC(C)C)S(=O)(=O)c2ccc(N3CCNCC3)c(S(C)(=N)=O)c2)cc1]

N-(4-ethylphenyl)-N-isobutyl-3-(S-methylsulfonimidoyl)-
4-(piperazin-1-yl)benzenesulfonamide
Compound 140

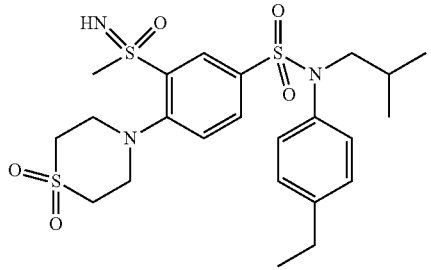 [SMILES: CCc1ccc(N(CC(C)C)S(=O)(=O)c2ccc(N3CCS(=O)(=O)CC3)c(S(C)(=N)=O)c2)cc1]

N-(4-ethylphenyl)-4-(((3-
hydroxycyclobutyl)methyl)amino)-N-isobutyl-3-(S-
methylsulfonimidoyl)benzenesulfonamide
Compound 141

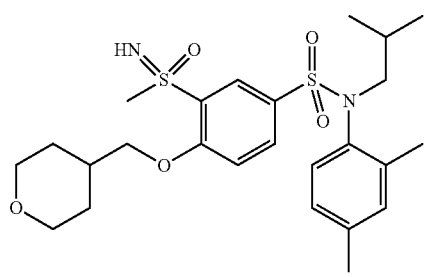 [SMILES: Cc1ccc(N(CC(C)C)S(=O)(=O)c2ccc(OCC3CCOCC3)c(S(C)(=N)=O)c2)c(C)c1]

N-(2,4-dimethylphenyl)-N-isobutyl-3-(S-methylsulfonimidoyl)-
4-((tetrahydro-2H-pyran-4-yl)methoxy)benzenesulfonamide
Compound 142 and

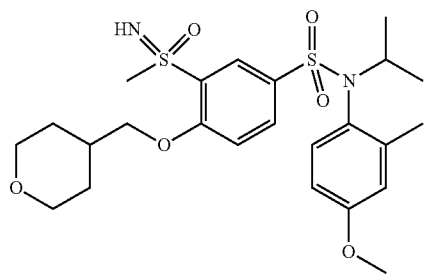 [SMILES: COc1ccc(N(C(C)C)S(=O)(=O)c2ccc(OCC3CCOCC3)c(S(C)(=N)=O)c2)c(C)c1]

N-isopropyl-N-(4-methoxy-2-methylphenyl)-3-(S-methylsulfonimidoyl)-
4-((tetrahydro-2H-pyran-4-yl)methoxy)benzenesulfonamide
Compound 143 or the pharmaceutically acceptable addition salt thereof.

5. The compound as defined by claim 1, wherein the compound is selected from the group consisting of:

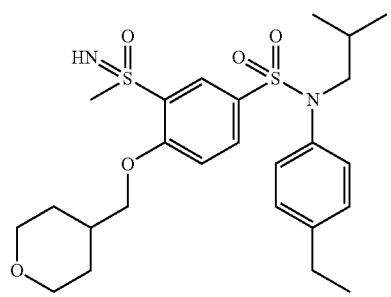

N-(4-ethylphenyl)-N-isobutyl-3-(S-
methylsulfonimidoyl)-4-((tetrahydro-2H-pyran-4-
yl)methoxy)benzenesulfonamide
Compound 26

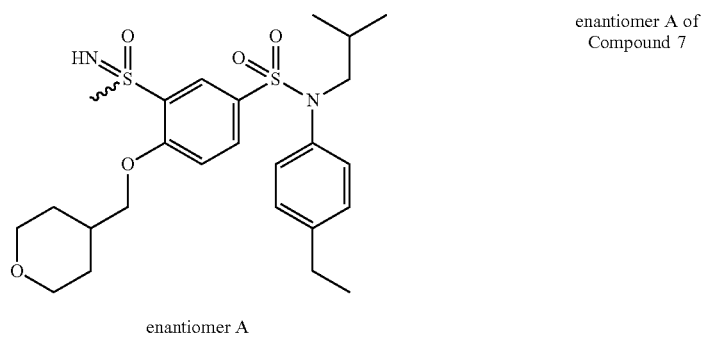

enantiomer A of Compound 7 enantiomer A

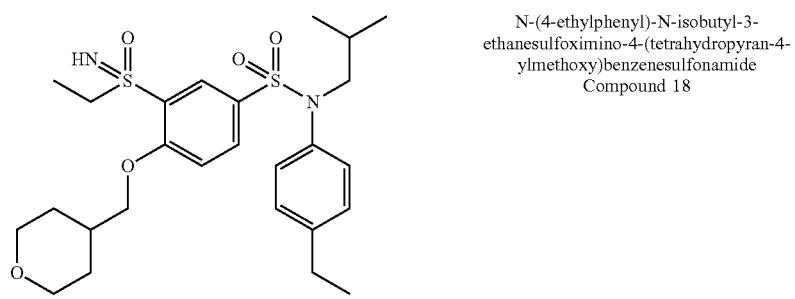

N-(4-ethylphenyl)-N-isobutyl-3-ethanesulfoximino-4-(tetrahydropyran-4-ylmethoxy)benzenesulfonamide
Compound 18

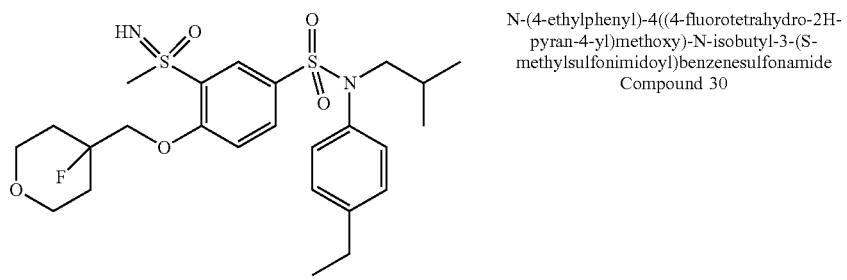

N-(4-ethylphenyl)-4-((4-fluorotetrahydro-2H-pyran-4-yl)methoxy)-N-isobutyl-3-(S-methylsulfonimidoyl)benzenesulfonamide
Compound 30

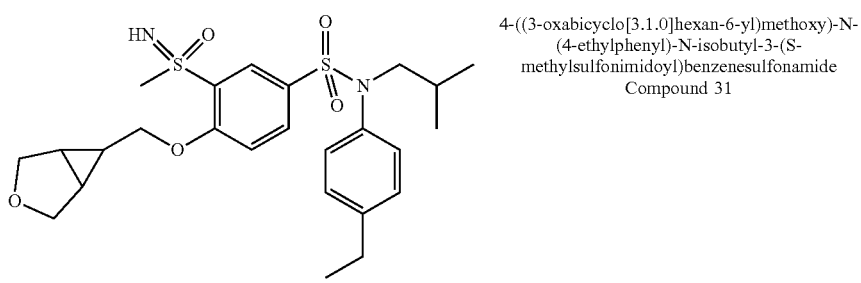

4-((3-oxabicyclo[3.1.0]hexan-6-yl)methoxy)-N-(4-ethylphenyl)-N-isobutyl-3-(S-methylsulfonimidoyl)benzenesulfonamide
Compound 31

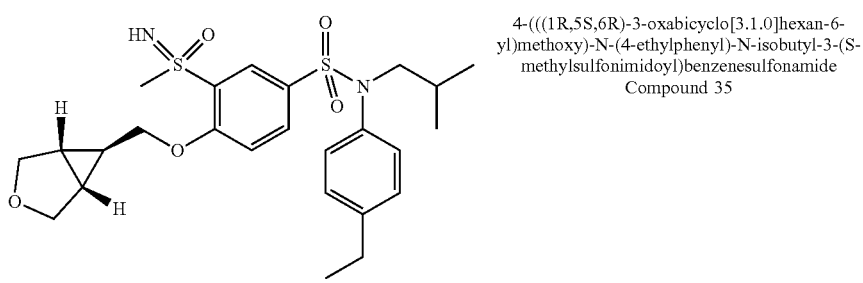

4-(((1R,5S,6R)-3-oxabicyclo[3.1.0]hexan-6-yl)methoxy)-N-(4-ethylphenyl)-N-isobutyl-3-(S-methylsulfonimidoyl)benzenesulfonamide
Compound 35

-continued

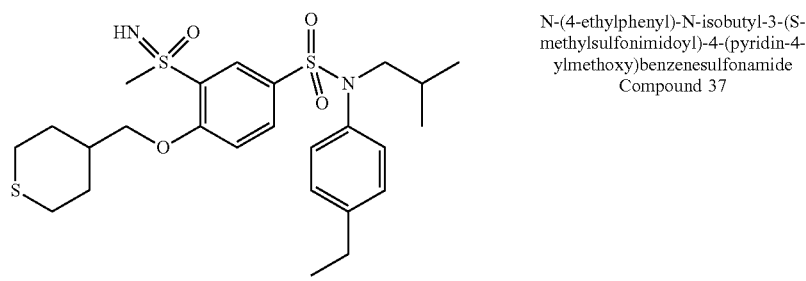

N-(4-ethylphenyl)-N-isobutyl-3-(S-methylsulfonimidoyl)-4-(pyridin-4-ylmethoxy)benzenesulfonamide
Compound 37

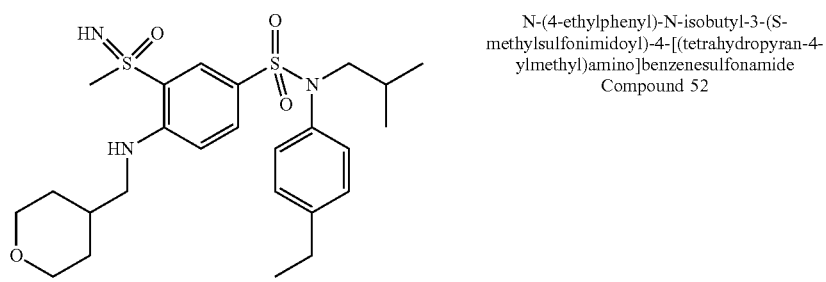

N-(4-ethylphenyl)-N-isobutyl-3-(S-methylsulfonimidoyl)-4-[(tetrahydropyran-4-ylmethyl)amino]benzenesulfonamide
Compound 52

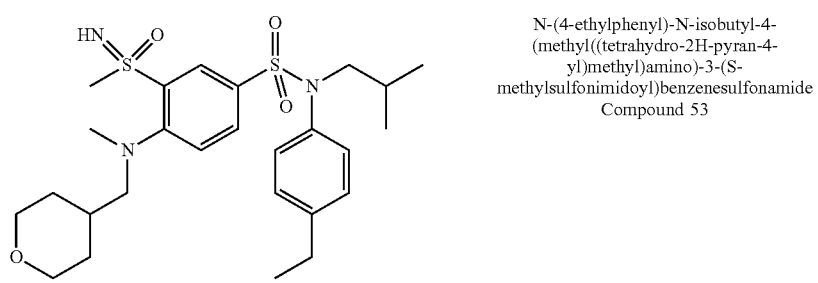

N-(4-ethylphenyl)-N-isobutyl-4-(methyl((tetrahydro-2H-pyran-4-yl)methyl)amino)-3-(S-methylsulfonimidoyl)benzenesulfonamide
Compound 53

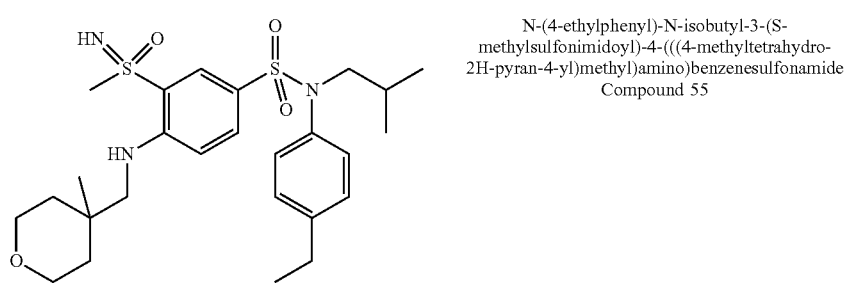

N-(4-ethylphenyl)-N-isobutyl-3-(S-methylsulfonimidoyl)-4-(((4-methyltetrahydro-2H-pyran-4-yl)methyl)amino)benzenesulfonamide
Compound 55

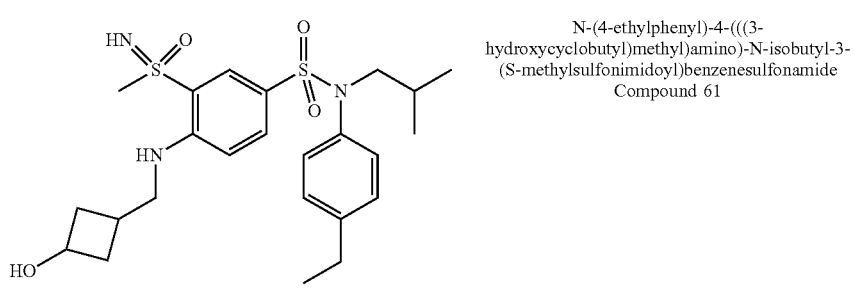

N-(4-ethylphenyl)-4-(((3-hydroxycyclobutyl)methyl)amino)-N-isobutyl-3-(S-methylsulfonimidoyl)benzenesulfonamide
Compound 61

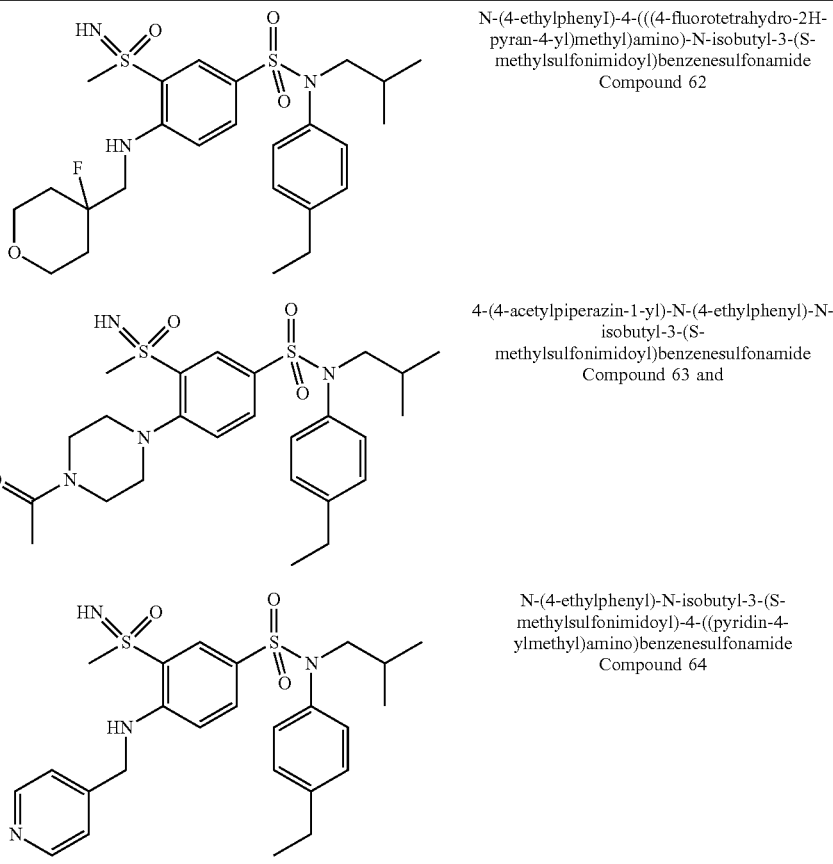
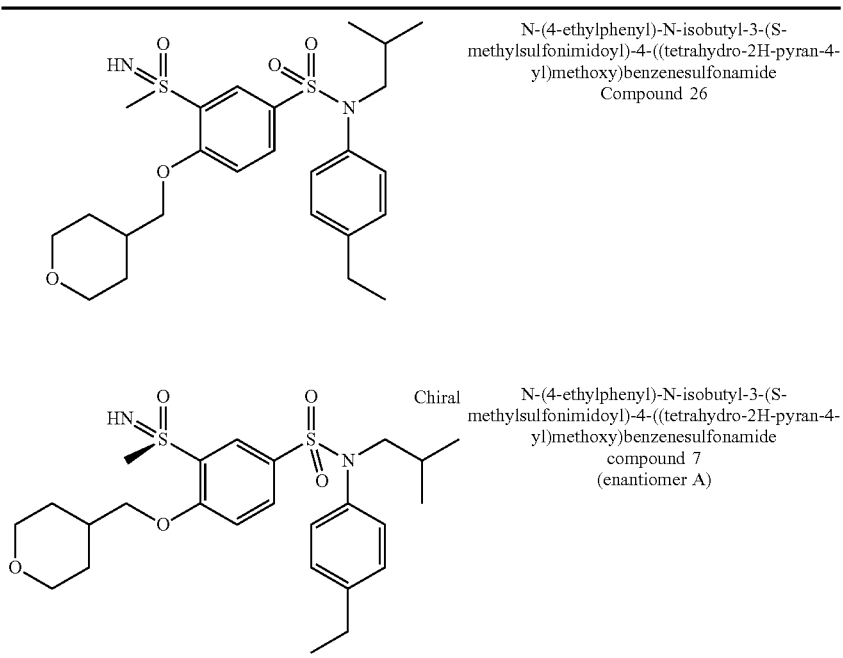
or the pharmaceutically acceptable addition salt thereof.
6. The compound as defined by claim 1, wherein the compound is selected from the group consisting of:

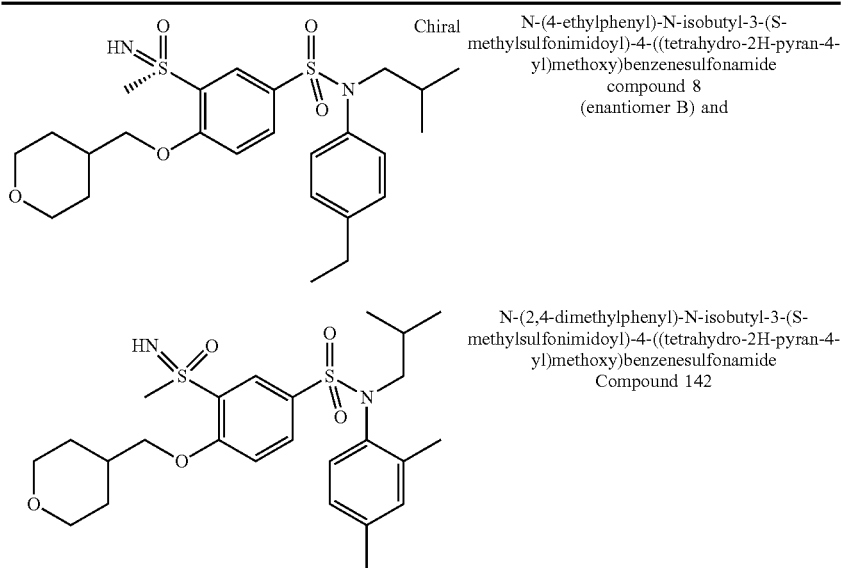

| | |
|---|---|
| | N-(4-ethylphenyl)-N-isobutyl-3-(S-methylsulfonimidoyl)-4-((tetrahydro-2H-pyran-4-yl)methoxy)benzenesulfonamide compound 8 (enantiomer B) and |
| | N-(2,4-dimethylphenyl)-N-isobutyl-3-(S-methylsulfonimidoyl)-4-((tetrahydro-2H-pyran-4-yl)methoxy)benzenesulfonamide Compound 142 | or the pharmaceutically acceptable addition salt thereof.

7. A method of treating an inflammatory disorder and/or autoimmune disease, the method comprising administering an effective amount of the compound as defined by claim 1, or the pharmaceutically acceptable addition salt thereof, to an individual subject in need thereof, wherein the inflammatory disorder and/or autoimmune disease is acne, atopic dermatitis and/or psoriasis.

8. A method of treating acne, the method comprising administering an effective amount of the compound as defined by claim 1, or the pharmaceutically acceptable addition salt thereof, to an individual subject in need thereof.

9. A method of treating psoriasis, the method comprising administering an effective amount of the compound as defined by claim 1, or a pharmaceutically acceptable addition salt thereof, to an individual subject in need thereof.

10. A pharmaceutical composition comprising one or more compounds as defined by claim 1 or a pharmaceutically acceptable addition salt thereof, and a pharmaceutically acceptable carrier.

11. The pharmaceutical composition as defined by claim 10, wherein the composition is formulated for treating is acne, atopic dermatitis and/or psoriasis.

12. The pharmaceutical composition as defined by claim 11, wherein the composition is formulated for treating acne.

13. The pharmaceutical composition as defined by claim 11, wherein the composition is formulated for treating atopic dermatitis.

14. The pharmaceutical composition as defined by claim 11, wherein the composition is formulated for treating psoriasis.

15. A method of treating atopic dermatitis, the method comprising administering an effective amount of the compound as defined by claim 1, or the pharmaceutically acceptable addition salt thereof, to an individual subject in need thereof.

* * * * *